US012773431B2

(12) United States Patent
Olle et al.

(10) Patent No.: US 12,773,431 B2
(45) Date of Patent: Oct. 27, 2026

(54) COMPOSITIONS AND METHODS FOR SUPPRESSING PATHOGENIC ORGANISMS

(71) Applicant: Vedanta Biosciences, Inc., Cambridge, MA (US)

(72) Inventors: Bernat Olle, Cambridge, MA (US); Silvia Caballero, Cambridge, MA (US)

(73) Assignee: Vedanta Biosciences, Inc., Cambridge, MA (US)

( * ) Notice: Subject to any disclaimer, the term of this patent is extended or adjusted under 35 U.S.C. 154(b) by 404 days.

(21) Appl. No.: 18/277,572

(22) PCT Filed: Feb. 18, 2022

(86) PCT No.: PCT/US2022/017043
§ 371 (c)(1),
(2) Date: Aug. 16, 2023

(87) PCT Pub. No.: WO2022/178292
PCT Pub. Date: Aug. 25, 2022

(65) Prior Publication Data

US 2024/0316119 A1 Sep. 26, 2024

Related U.S. Application Data

(60) Provisional application No. 63/151,003, filed on Feb. 18, 2021.

(51) Int. Cl.
*A61K 35/74* (2015.01)
*A61K 9/19* (2006.01)
*A61K 31/095* (2006.01)
*A61P 31/04* (2006.01)

(52) U.S. Cl.
CPC ................ *A61K 35/74* (2013.01); *A61K 9/19* (2013.01); *A61K 31/095* (2013.01); *A61P 31/04* (2018.01)

(58) Field of Classification Search
CPC ...................................................... A61K 35/74
See application file for complete search history.

(56) References Cited

U.S. PATENT DOCUMENTS 9,999,641 B2 6/2018 Schneider et al.
11,633,433 B2 4/2023 Honda et al.
12,053,495 B2 8/2024 Caballero et al.
2013/0266539 A1 10/2013 Borody
2014/0147425 A1 5/2014 Henn et al.
2016/0158294 A1 6/2016 Von Maltzahn et al.
2016/0158295 A1 6/2016 Afeyan et al.
2016/0193258 A1 7/2016 Berry et al.
2016/0199424 A1 7/2016 Berry et al.
2016/0271188 A1 9/2016 Berry et al.
2017/0143775 A1 5/2017 Mulder et al.
2017/0209502 A1 7/2017 Honda et al.
2017/0319633 A1 11/2017 Allen-Vercoe et al.
2018/0000872 A1 1/2018 Hamilton et al.
2019/0160114 A1 5/2019 Madsen, II et al.
2020/0405775 A1 12/2020 Caballero et al.
2022/0118030 A1 * 4/2022 Goodman .............. A61K 45/06
2022/0409674 A1 12/2022 Caballero et al.
2025/0009811 A1 1/2025 Caballero et al.

FOREIGN PATENT DOCUMENTS

CA 3027917 A1 12/2017
CN 101198252 A 6/2008
CN 109640688 A 4/2019
WO WO 2007/075186 A2 7/2007
WO WO 2012/142605 A1 10/2012
WO WO 2013/080561 A9 6/2013
WO WO 2014/182635 A1 11/2014
WO WO 2015/156419 A1 10/2015
WO WO 2016/209806 A1 12/2016
WO WO 2017/075098 A1 5/2017
WO WO 2017/079450 A1 5/2017
WO WO 2017/160711 A1 9/2017
WO WO 2017/218680 A1 12/2017
WO WO 2018/136884 A1 7/2018
WO WO 2019/036510 A1 2/2019
WO WO 2019/094837 A1 5/2019
WO WO 2019/118515 A2 6/2019
WO WO-2020172492 A2 * 8/2020 ............. A61K 40/11
WO WO 2021/016083 A1 1/2021
WO WO 2022/178292 A1 8/2022

OTHER PUBLICATIONS

Antunes et al., Antivirulence activity of the human gut metabolome. mBio. Jul. 29, 2014;5(4):e01183-14. doi: 10.1128/mBio.01183-14. 13 pages.
Atarashi et al., Ectopic colonization of oral bacteria in the intestine drives TH1 cell induction and inflammation. Science. Oct. 20, 2017;358(6361):359-365. doi: 10.1126/science.aan4526. Author Manuscript. 16 pages.
Atarashi et al., Treg induction by a rationally selected mixture of Clostridia strains from the human microbiota. Nature. Aug. 8, 2013;500(7461):232-6. doi: 10.1038/nature12331. Epub Jul. 10, 2013.
Caballero et al., Distinct but Spatially Overlapping Intestinal Niches for Vancomycin-Resistant Enterococcus faecium and Carbapenem-Resistant Klebsiella pneumoniae. PLoS Pathog. Sep. 3, 2015;11(9):e1005132. doi: 10.1371/journal.ppat.1005132. 20 pages.
Cassone et al., Colonization with Multi-Drug Resistant Organisms in Nursing Homes: Scope, Importance, and Management. Curr Geriatr Rep. Author manuscript; available in PMC Mar. 1, 2016. Published in final edited form as: Curr Geriatr Rep. Mar. 2015; 4(1): 87-95. Published online Jan. 23, 2015. doi: 10.1007/s13670-015-0120-2.

(Continued)

*Primary Examiner* — Ruth A Davis
(74) *Attorney, Agent, or Firm* — Wolf, Greenfield & Sacks, P.C.

(57) ABSTRACT

Provided herein are compositions and methods for suppressing infection by pathogenic organisms. Also provided herein are compositions and methods for reducing or preventing colonization by pathogenic organisms and methods of treating infection by a pathogenic organism. Also provided herein are compositions comprising taurine and methods of using such compositions for suppressing infection by pathogenic organisms, preventing colonization by pathogenic organisms, and methods of treating infection pathogenic organisms.

9 Claims, 6 Drawing Sheets

Specification includes a Sequence Listing.

(56) References Cited

OTHER PUBLICATIONS

Dewhirst et al., The human oral microbiome. J Bacteriol. Oct. 2010;192(19):5002-17. doi: 10.1128/JB.00542-10. Epub Jul. 23, 2010.
Edgar, Updating the 97% identity threshold for 16S ribosomal RNA OTUs. Bioinformatics. Jul. 15, 2018;34(14):2371-2375. doi: 10.1093/bioinformatics/bty113.
Genbank Accession No. AB215084 sequence. Bakir et al.; May 27, 2005.
Genbank Accession No. LT223618 sequence. Urmite et al.; Feb. 6, 2013.
Kulkarni et al., Roles of putative type II secretion and type IV pilus systems in the virulence of uropathogenic *Escherichia coli*. PLoS One. 2009;4(3):e4752. doi: 10.1371/journal.pone.0004752. Epub Mar. 9, 2009. 9 pages.
Morrison et al., Formation of short chain fatty acids by the gut microbiota and their impact on human metabolism. Gut Microbes. May 3, 2016;7(3):189-200. doi: 10.1080/19490976.2015.1134082. Epub Mar. 10, 2016.
Reijnders et al., Effects of Gut Microbiota Manipulation by Antibiotics on Host Metabolism in Obese Humans: A Randomized Double-Blind Placebo-Controlled Trial. Cell Metab. Jul. 12, 2016;24(1):63-74. doi: 10.1016/j.cmet.2016.06.016.
Ridaura et al., Gut Microbiota from Twins Discordant for Obesity Modulate Metabolism in Mice. Science. Sep. 6, 2013;341(6150):1241214. doi: 10.1126/science.1241214.
Schirmer et al., Compositional and Temporal Changes in the Gut Microbiome of Pediatric Ulcerative Colitis Patients Are Linked to Disease Course. Cell Host Microbe. Oct. 10, 2018;24(4):600-610.e4 and Supplemental Information. doi: 10.1016/j.chom.2018.09.009. 20 pages.
Seekatz et al., Restoration of short chain fatty acid and bile acid metabolism following fecal microbiota transplantation in patients with recurrent Clostridium difficile infection. Anaerobe. Oct. 2018;53:64-73. doi: 10.1016/j.anaerobe.2018.04.001. Epub Apr. 12, 2018.
Sirbu et al., Vancomycin Taper and Pulse Regimen With Careful Follow-up for Patients With Recurrent Clostridium difficile Infection. Clin Infect Dis. Oct. 15, 2017;65(8):1396-1399. doi: 10.1093/cid/cix529.
Stacy et al., Infection trains the host for microbiota-enhanced resistance to pathogens. Cell. Feb. 4, 2021;184(3):P615-627. doi: 10.1016/j.cell.2020.12.011. Epub Jan. 15, 2021.
Ubeda et al., Vancomycin-resistant Enterococcus domination of intestinal microbiota is enabled by antibiotic treatment in mice and precedes bloodstream invasion in humans. J Clin Invest. Dec. 2010;120(12):4332-41. doi: 10.1172/JCI43918. Epub Nov. 22, 2010.
Wang et al., The value of serum PCT test in the treatment of gynecological infectious diseases. Chinese Journal of Public Health Engineering, China Sanitary Engineering. Apr. 20, 2017; 16(2):215-216. DOI:10.19937/j.issn.1671-4199.2017.02.034.
Wu et al., Phascolarctobacterium faecium abundant colonization in human gastrointestinal tract. Exp Ther Med. Oct. 2017;14(4):3122-3126. doi: 10.3892/etm.2017.4878. Epub Aug. 3, 2017.
Xiao et al., Bacterial diversity and community structure of supragingival plaques in adults with dental health or caries revealed by 16S pyrosequencing. Frontiers in microbiology. Jul. 22, 2016;7:1145. 15 pages.
Yoneda et al., Oral Bacteria and Bowel Diseases—Mini Review. J Gastrointest Dig Syst. 2016; 6(2): 1-4. DOI: 10.4172/2161-069X.1000404.
Yu et al., Effects of taurine on gut microbiota and metabolism in mice. Amino Acids. Jul. 2016;48(7):1601-17. doi: 10.1007/s00726-016-2219-y. Epub Mar. 30, 2016.
[No Author Listed], Bacteroides eggerthii 10128 is an anaerobe, mesophilic bacterium that was isolated from human faeces. BacDive ID: 1583. Accessible at https://bacdive.dsmz.de/strain/1583. Last updated Sep. 12, 2024. 6 pages.
[No Author Listed], Clostridioides difficile 1780 is an anaerobe, spore-forming, mesophilic human pathogen that produces toxins and was isolated from Human feces. BacDive ID: 2582. Accessible at https://bacdive.dsmz.de/strain/2582. Last updated Sep. 12, 2024. 6 pages.
[No Author Listed], Clostridium leptum DSM 753 is an anaerobe, mesophilic bacterium that was isolated from human faeces. BacDive ID: 2612. Accessible at https://bacdive.dsmz.de/strain/2612. Last updated Sep. 12, 2024. 6 pages.
[No Author Listed], *Escherichia coli* U5/41 is a facultative anaerobe, mesophilic, Gram-negative human pathogen that has multiple antibiotic resistances and was isolated from urine. BacDive ID: 4907. Accessible at https://bacdive.dsmz.de/strain/4907. Last updated Sep. 12, 2024. 6 pages.
[No Author Listed], Fusobacterium mortiferum strain DSM 19809 16S ribosomal RNA, partial sequence. NCBI Ref Seq ID: NR_117734.1. Accessible at https://www.ncbi.nlm.nih.gov/nuccore/NR_117734.1/. Mar. 12, 2019. 2 pages.
[No Author Listed], *Fusobacterium nucleatum* subsp. *nucleatum* 1612A is an anaerobe, mesophilic, Gram-negative bacterium that was isolated from cervico-facial lesion. BacDive ID: 5765. Accessible at https://bacdive.dsmz.de/strain/5765. Last updated Sep. 12, 2024. 6 pages.
[No Author Listed], *Klebsiella pneumoniae* subsp. *pneumoniae* 298-53 is an aerobe, mesophilic, Gram-negative human pathogen of the family Enterobacteriaceae. BacDive ID: 4959. Accessible at https://bacdive.dsmz.de/strain/4959. Last updated Sep. 12, 2024. 6 pages.
Bengoechea et al., Klebsiella pneumoniae infection biology: living to counteract host defences. FEMS Microbiol Rev. Mar. 1, 2019;43(2):123-144. doi: 10.1093/femsre/fuy043.
Brook et al., The relationship between *Fusobacterium* species and other flora in mixed infection. J Med Microbiol. Mar. 1986;21(2):93-100. doi: 10.1099/00222615-21-2-93.
Budič et al., *Escherichia coli* bacteriocins: antimicrobial efficacy and prevalence among isolates from patients with bacteraemia. PLoS One. 2011;6(12):e28769. doi: 10.1371/journal.pone.0028769. Epub Dec. 19, 2011.
Coyte et al., Understanding Competition and Cooperation within the Mammalian Gut Microbiome. Curr Biol. Jun. 3, 2019;29(11):R538-R544. doi: 10.1016/j.cub.2019.04.017. Author Manuscript. 15 pages.
Fathi et al., Isolation, Detection, and Characterization of Enterotoxigenic Bacteroides fragilis in Clinical Samples. Open Microbiol J. Apr. 14, 2016;10:57-63. doi: 10.2174/1874285801610010057.
Geva-Zatorsky et al., Mining the Human Gut Microbiota for Immunomodulatory Organisms. Cell. Feb. 23, 2017;168(5):928-943.e11. doi: 10.1016/j.cell.2017.01.022. Epub Feb. 16, 2017.
Jyothsna et al., *Paraclostridium benzoelyticum* gen. nov., sp. nov., isolated from marine sediment and reclassification of *Clostridium bifermentans* as *Paraclostridium bifermentans* comb. nov. Proposal of a new genus *Paeniclostridium* gen. nov. to accommodate *Clostridium sordellii* and *Clostridium ghonii*. Int J Syst Evol Microbiol. Mar. 2016;66(3):1268-1274. doi: 10.1099/ijsem.0.000874. Epub Jan. 5, 2016. Erratum in: Int J Syst Evol Microbiol. Jun. 2016;66(6):2459. doi: 10.1099/ijsem.0.001144. 8 pages.
Konstantinidis et al., Towards a genome-based taxonomy for prokaryotes. J Bacteriol. Sep. 2005;187(18):6258-64. doi: 10.1128/JB.187.18.6258-6264.2005.
Mccarville et al., Novel perspectives on therapeutic modulation of the gut microbiota. Therap Adv Gastroenterol. Jul. 2016;9(4):580-93. doi: 10.1177/1756283X16637819. Epub Apr. 4, 2016.
Mysara et al., Reconciliation between operational taxonomic units and species boundaries. FEMS Microbiol Ecol. Apr. 1, 2017;93(4):fix029. doi: 10.1093/femsec/fix029.
Schober et al., BacDive in 2025: the core database for prokaryotic strain data. Nucleic Acids Res. Jan. 6, 2025;53(D1):D748-D756. doi: 10.1093/nar/gkae959.
Sefik et all., Individual intestinal symbionts induce a distinct population of $ROR\gamma^{+}$ regulatory T cells. Science. Aug. 28, 2015;349(6251):993-7. doi: 10.1126/science.aaa9420. Epub Aug. 13, 2015.
Stackebrandt et al., Report of the ad hoc committee for the re-evaluation of the species definition in bacteriology. Int J Syst Evol Microbiol. May 2002;52(Pt 3):1043-1047. doi: 10.1099/00207713-52-3-1043.

(56) References Cited

OTHER PUBLICATIONS

Weiss et al., In vitro interaction network of a synthetic gut bacterial community. Isme J. Apr. 2022;16(4):1095-1109. doi: 10.1038/s41396-021-01153-z. Epub Dec. 2, 2021.
[No Author Listed], Ecogenomics/GTDBTk. Github. Retrieved from https://github.com/Ecogenomics/GTDBTk/releases/tag/1.0.0. Dec. 5, 2019. 1 page.
[No Author Listed], Fusobacterium Knorr 1922 (Approved Lists 1980). Retrieved from lpsn.dsmz.de/genus/fusobacterium on May 4, 2026. LPSN Record No. 515666. doi: 10.83108/rn.515666/. 3 pages.
[No Author Listed], Fusobacterium mortiferum. ATCC Acc. No. ATCC® 25557™. Retrieved from https://genomes.atcc.org/genomes/4a4de2c8308b499d?tab=related-genomes-tab. Accessed Mar. 10, 2026. 1 page.
[No Author Listed], Fusobacterium_A mortiferum. GTDB Acc. No. GCF_000158195.2. Retrieved from https://gtdb.ecogenomic.org/genome?gid=GCF_000158195.2. Jul. 27, 2011. 2 pages.
[No Author Listed], List of /releases/release89/89.0/. GTDB Data. Retrieved from https://data.gtdb.ecogenomic.org/releases/release89/89.0. Jun. 17, 2019. 1 page.
[No Author Listed], Taxon History. GTDB. Retrieved from https://gtdb.ecogenomic.org/taxon-history?from=R80&to=R95&query=g_Fusobacterium_A. Accessed on Mar. 10, 2026. 1 page.
Jain et al., High throughput ANI analysis of 90K prokaryotic genomes reveals clear species boundaries. Nat Commun. Nov. 30, 2018;9(1):5114. doi: 10.1038/s41467-018-07641-9.
Parker et al., International Code of Nomenclature of Prokaryotes. Int J Syst Evol Microbiol. Jan. 2019;69(1A):S1-S111. doi: 10.1099/ijsem.0.000778. Epub Jan. 11, 2019.
Parks et al., A complete domain-to-species taxonomy for Bacteria and Archaea. Nat Biotechnol. Sep. 2020;38(9):1079-1086. doi: 10.1038/s41587-020-0501-8. Epub Apr. 27, 2020. Erratum in: Nat Biotechnol. Sep. 2020;38(9):1098. doi: 10.1038/s41587-020-0539-7.
Parks et al., A standardized bacterial taxonomy based on genome phylogeny substantially revises the tree of life. Nat Biotechnol. Nov. 2018;36(10):996-1004. doi: 10.1038/nbt.4229. Epub Aug. 27, 2018.
Skerman et al., Approved Lists of Bacterial Names. Int J Syst Bacteriol. 1980;30:225-420.

* cited by examiner

| 47-mix Phylum | 47-mix Family | 47-mix Species/strain ID |
|---|---|---|
| **Actinobacteria** | Coriobacteriaceae | *Collinsella aerofaciens_F P323F6* |
| | Bifidobacteriaceae | *Bifidobacterium longum P454C6* |
| | | *Bifidobacterium pseudocatenulatum P566D7* |
| | | *Bifidobacterium adolescentis P567E11* |
| **Bacteroidetes** | Bacteroidaceae | *Bacteroides caccae P350A5* |
| | | *Bacteroides xylanisolvens P324A11* |
| | | *Bacteroides cellulosilyticus P346C5* |
| | | *Bacteroides uniformis P346D2* |
| | | *Bacteroides_B vulgatus P347B6* |
| | | *Bacteroides fragilis P349H3* |
| | | *Bacteroides thetaiotaomicron P453B7* |
| | | *Bacteroides faecis P563A4* |
| | | *Bacteroides ovatus P563G11* |
| | Marinifilaceae | *Odoribacter splanchnicus P344D6* |
| | Tannerellaceae | *Parabacteroides distasonis P453D4* |
| | | *Parabacteroides merdae P455C10* |
| | Rikenellaceae | *Alistipes putredinis P326A5* |
| | | *Alistipes shahii P326F6* |
| | Porphyromonadaceae | *Barnesiella intestinihomins* |
| | Odoribacteraceae | *Butyricimonas synergistica* |
| | Prevotellaceae | *Prevotella copri* |

FIG. 3

| 47-mix Phylum | 47-mix Family | 47-mix Species/strain ID |
|---|---|---|
| **Firmicutes** | Peptostreptococcaceae | *Paraclostridium massiliensis P351C5* |
| | | *Paeniclostridium sordellii P350D9* |
| | Erysipelatotrichiaceae | *Absiella innocuum P454F4* |
| | | *Absiella innocuum P351A7* |
| | | *Erysipelatoclostridium ramosum P562A4* |
| | Lachnospiraceae | *Clostridium_M citroniae P562A3* |
| | | *Clostridium_M clostridioforme P351A11* |
| | | *Eubacterium_E hallii P327B8* |
| | | *Agathobacter rectale P476A3* |
| | | *Blautia producta P351A5* |
| | | *Blautia_A obeum P327F6* |
| | | *Dorea longicatena_B P451G4* |
| | | *Coprococcus_B comes P473C9* |
| | | *Anaerostipes caccae MUR_MP3C12* |
| | | *Blautia luti* |
| | | *Blautia faecis* |
| | | *Blautia wexlerae* |
| | Ruminococcaceae | *Agathobaculum sp MUR_P3C8a* |
| | | *Ruminococcus faecis* |
| | Acidaminococcaceae | *Phascolarctobacterium faecium MUR_P6E9* |
| | Clostridiaceae | *Clostridium bolteae* |
| **Proteobacteria** | Enterobacteriaceae | *Escherichia coli P453D11* |
| | Desulfovibrionaceae | *Bilophila wadsworthia* |
| | Alcaligenaceae | *Parasutterella excrementihominis* |
| **Fusobacteria** | Fusobacteriaceae | *Fusobacterium_A sp P455B12* |
| **Verrucomicrobia** | Akkermansia | *Akkermansia muciniphila* |

FIG. 3
CONTINUED

SEQUENCE LISTING

```
<160> NUMBER OF SEQ ID NOS: 83

<210> SEQ ID NO 1
<211> LENGTH: 1464
<212> TYPE: DNA
<213> ORGANISM: Unknown
<220> FEATURE:
<223> OTHER INFORMATION: Collinsella aerofaciens_F

<400> SEQUENCE: 1

agagttcgat cctggctcag gatgaacgct ggcggcgcgc ctaacacatg caagtcgaac     60

ggcacccctc tccggaggga agcgagtggc gaacggctga gtaacacgtg gagaacctgc    120

cccctccccc gggatagccg cccgaaagga cgggtaatac cggatacccc ggggtgccgc    180

atggcacccc ggctaaagcc ccgacgggag gggatggctc cgcggcccat caggtagacg    240

gcggggtgac ggcccaccgt gccgacaacg ggtagccggg ttgagagacc gaccggccag    300

attgggactg agacacggcc cagactccta cgggaggcag cagtggggaa tcttgcgcaa    360

tgggggggaac cctgacgcag cgacgccgcg tgcgggacgg aggccttcgg gtcgtaaacc    420

gctttcagca gggaagagtc aagactgtac ctgcagaaga agccccggct aactacgtgc    480

cagcagccgc ggtaatacgt agggggcgag cgttatccgg attcattggg cgtaaagcgc    540

gcgtaggcgg cccggcaggc cgggggtcga agcggggggc tcaacccccc gaagcccccg    600

gaacctccgc ggcttgggtc cggtagggga gggtggaaca cccggtgtag cggtggaatg    660

cgcagatatc gggtggaaca ccggtggcga aggcggccct ctgggccgag accgacgctg    720

aggcgcgaaa gctgggggag cgaacaggat tagataccct ggtagtccca gccgtaaacg    780

atggacgcta ggtgtggggg gacgatcccc ccgtgccgca gccaacgcat taagcgtccc    840

gcctggggag tacggccgca aggctaaaac tcaaaggaat tgacgggggc ccgcacaagc    900

agcggagcat gtggcttaat tcgaagcaac gcgaagaacc ttaccagggc ttgacatatg    960

ggtgaagcgg gggagacccc gtggccgaga ggagcccata caggtggtgc atggctgtcg   1020

tcagctcgtg tcgtgagatg ttgggttaag tcccgcaacg agcgcaaccc ccgccgcgtg   1080

ttgccatcgg gtgatgccgg gaacccacgc gggaccgccg ccgtcaaggc ggaggagggc   1140

ggggacgacg tcaagtcatc atgcccctta tgccctgggc tgcacacgtg ctacaatggc   1200

cggtacagag ggatgccacc ccgcgagggg gagcggatcc cggaaagccg gccccagttc   1260

ggattggggg ctgcaacccg cccccatgaa gtcggagttg ctagtaatcg cggatcagca   1320

tgccgcggtg aatgcgttcc cgggccttgt acacaccgcc cgtcacacca cccgagtcgt   1380

ctgcacccga agtcgccggc ccaaccgaga ggggggaggc gccgaaggtg tggagggtga   1440

ggggggtgaa gtcgtaacaa ggta                                          1464

<210> SEQ ID NO 2
<211> LENGTH: 1517
<212> TYPE: DNA
```

<213> ORGANISM: Unknown
<220> FEATURE:
<223> OTHER INFORMATION: Bacteroides xylanisolvens

<400> SEQUENCE: 2
agagtttgat cctggctcag gatgaacgct agctacaggc ttaacacatg caagtcgagg 60
ggcagcattt tagtttgctt gcaaactaaa gatggcgacc ggcgcacggg tgagtaacac 120
gtatccaacc tgccgataac tcggggatag cctttcgaaa gaaagattaa tatccgatag 180
tatattaaaa ccgcatggtt ttactattaa agaatttcgg ttatcgatgg ggatgcgttc 240
cattagtttg ttggcggggt aacggcccac caagactacg atggataggg gttctgagag 300
gaaggtcccc cacattggaa ctgagacacg gtccaaactc ctacgggagg cagcagtgag 360
gaatattggt caatggacga gagtctgaac cagccaagta gcgtgaagga tgactgccct 420
atgggttgta aacttctttt atatgggaat aaagtattcc acgtgtggga ttttgtatgt 480
accatatgaa taaggatcgg ctaactccgt gccagcagcc gcggtaatac ggaggatccg 540
agcgttatcc ggatttattg ggtttaaagg gagcgtaggt ggattgttaa gtcagttgtg 600
aaagtttgcg gctcaaccgt aaaattgcag ttgaaactgg cagtcttgag tacagtagag 660
gtgggcggaa ttcgtggtgt agcggtgaaa tgcttagata tcacgaagaa ctccgattgc 720
gaaggcagct cactagactg caactgacac tgatgctcga aagtgtgggt atcaaacagg 780
attagatacc ctggtagtcc acacagtaaa cgatgaatac tcgctgtttg cgatatacag 840
taagcggcca agcgaaagca ttaagtattc cacctgggga gtacgccggc aacggtgaaa 900
ctcaaaggaa ttgacggggg cccgcacaag cggaggaaca tgtggtttaa ttcgatgata 960
cgcgaggaac cttacccggg cttaaattgc atttgaataa tctggaaaca ggttagccgc 1020
aaggcaaatg tgaaggtgct gcatggttgt cgtcagctcg tgccgtgagg tgtcggctta 1080
agtgccataa cgagcgcaac ccttatcttt agttactaac aggttatgct gaggactcta 1140
gagagactgc cgtcgtaaga tgtgaggaag gtggggatga cgtcaaatca gcacggccct 1200
tacgtccggg gctacacacg tgttacaatg gggggtacag aaggcagcta cctggcgaca 1260
ggatgctaat cccaaaaacc tctctcagtt cggatcgaag tctgcaaccc gacttcgtga 1320
agctggattc gctagtaatc gcgcatcagc catggcgcgg tgaatacgtt cccgggcctt 1380
gtacacaccg cccgtcaagc catgaaagcc gggggtacct gaagtacgta accgcaagga 1440
gcgtcctagg gtaaaactgg taattggggc taagtcgtaa caaggtagcc gtaccggaag 1500
gtgcggctgg aacacct 1517

<210> SEQ ID NO 3
<211> LENGTH: 1485
<212> TYPE: DNA
<213> ORGANISM: Unknown
<220> FEATURE:
<223> OTHER INFORMATION: Alistipes putredinis

<400> SEQUENCE: 3
agagtttgat cctggctcag gatgaacgct agcggcaggc ttaacacatg caagtcgagg 60
ggcagcataa tggatagcaa tatctatggt ggcgaccggc gcacgggtgc gtaacgcgta 120
tgcaacctac ctttaacagg gggataacac tgagaaattg gtactaatac cccataatat 180
catagaaggc atcttttatg gttgaaaatt ccgatggtta gagatgggca tgcgttgtat 240
tagctagttg gtggggtaac ggctcaccaa ggcgacgata catagggggga ctgagaggtt 300 aacccccccac actggtactg agacacggac cagactccta cgggaggcag cagtgaggaa 360

```
tattggtcaa tggacgcaag tctgaaccag ccatgccgcg tgcaggatga cggctctatg    420
agttgtaaac tgcttttgta cgagggtaaa cgcagatacg tgtatctgtc tgaaagtatc    480
gtacgaataa ggatcggcta actccgtgcc agcagccgcg gtaatacgga ggattcaagc    540
gttatccgga tttattgggt ttaaagggtg cgtaggcggt ttgataagtt agaggtgaaa    600
tttcggggct caaccctgaa cgtgcctcta atactgttga gctagagagt agttgcggta    660
ggcggaatgt atggtgtagc ggtgaaatgc ttagagatca tacagaacac cgattgcgaa    720
ggcagcttac caaactatat ctgacgttga ggcacgaaag cgtggggagc aaacaggatt    780
agataccctg gtagtccacg cagtaaacga tgataactcg ttgtcggcga tacacagtcg    840
gtgactaagc gaaagcgata agttatccac ctggggagta cgttcgcaag aatgaaactc    900
aaaggaattg acgggggccc gcacaagcgg aggaacatgt ggtttaattc gatgatacgc    960
gaggaacctt acccgggctt gaaagttagc gacgattctt gaaagaggat ttcccttcgg   1020
ggcgcgaaac taggtgctgc atggttgtcg tcagctcgtg ccgtgaggtg tcgggttaag   1080
tcccataacg agcgcaaccc ctaccgttag ttgccatcag gtgaagctgg gcactctggc   1140
gggactgccg gtgtaagccg agaggaaggt ggggatgacg tcaaatcagc acggccctta   1200
cgtccggggc tacacacgtg ttacaatggt aggtacagag ggcagctacc cagcgatggg   1260
atgcgaatct cgaaagccta tctcagttcg gattggaggc tgaaacccgc ctccatgaag   1320
ttggattcgc tagtaatcgc gcatcagcca tggcgcggtg aatacgttcc cgggccttgt   1380
acacaccgcc cgtcaagcca tgggagccgg gggtgcctga agttcgtgac cgcaaggagc   1440
gacctagggc aaaactggtg actggggcta agtcgtaaca aggta                   1485
```

<210> SEQ ID NO 4
<211> LENGTH: 1512
<212> TYPE: DNA
<213> ORGANISM: Unknown
<220> FEATURE:
<223> OTHER INFORMATION: Alistipes shahii

<400> SEQUENCE: 4

```
agagtttgat cctggctcag gatgaacgct agcggcaggc ctaacacatg caagtcgagg     60
ggcagcacgg tgtagcaata cactggtggc gaccggcgca cgggtgcgta acgcgtatgc    120
aacctaccca taacaggggg ataacactga gaaattggta ctaatacccc ataacatcag    180
gaccggcatc ggttctggtt gaaaactccg gtggttatgg atgggcatgc gttgtattag    240
ctggttggtg aggtaacggc tcaccaaggc aacgatacat agggggactg agaggttaac    300
cccccacatt ggtactgaga cacggaccaa actcctacgg gaggcagcag tgaggaatat    360
tggtcaatgg acgcaagtct gaaccagcca tgccgcgtgc aggaagacgg ctctatgagt    420
tgtaaactgc ttttgtacga gagtaaacgc tcttacgtgt aagagcctga aagtatcgta    480
cgaataagga tcggctaact ccgtgccagc agccgcggta atacggagga tccaagcgtt    540
atccggattt attgggttta aagggtgcgt aggcggtttg ataagttaga ggtgaaatac    600
cggtgcttaa caccggaact gcctctaata ctgttgaact agagagtagt tgcggtaggc    660
ggaatgtatg gtgtagcggt gaaatgctta gagatcatac agaacaccga ttgcgaaggc    720
agcttaccaa actatatctg acgttgaggc acgaaagcgt ggggagcaaa caggattaga    780
taccctggta gtccacgcag taaacgatga taactcgctg tcggcgatac acagtcggcg    840
gctaagcgaa agcgataagt tatccacctg ggagtacgt tcgcaagaat gaaactcaaa     900
```

```
ggaattgacg gggcccgca caagcggagg aacatgtggt ttaattcgat gatacgcgag    960

gaaccttacc cgggcttgaa agttactgac gattctggaa acaggatttc ccttcggggc   1020

aggaaactag gtgctgcatg gttgtcgtca gctcgtgccg tgaggtgtcg ggttaagtcc   1080

cataacgagc gcaaccccta ccgttagttg ccatcaggtc aagctgggca ctctggcggg   1140

actgccggtg taagccgaga ggaaggtggg gatgacgtca aatcagcacg gcccttacgt   1200

ccggggctac acacgtgtta caatggtagg tacagagggc agctacccag tgatgggatg   1260

cgaatctcga aagcctatct cagttcggat cggaggctga aacccgcctc cgtgaagttg   1320

gattcgctag taatcgcgca tcagccatgg cgcggtgaat acgttcccgg gccttgtaca   1380

caccgcccgt caagccatgg aagctggggg tgcctgaagt tcgtgaccgc aaggagcgac   1440

ctagggcaaa accggtgact ggggctaagt cgtaacaagg tagccgtacc ggaaggtgcg   1500

gctggaacac ct                                                       1512
```

<210> SEQ ID NO 5
<211> LENGTH: 1472
<212> TYPE: DNA
<213> ORGANISM: Unknown
<220> FEATURE:
<223> OTHER INFORMATION: Eubacterium_E hallii

<400> SEQUENCE: 5

```
ctcaggatga acgctagcta caggcttaac acatgcaagt cgaggggcag cattccagtt     60

tgcttgcaaa ctggagatgg cgaccggcgc acgggtgagt aacacgtatc caacctgccg    120

ataactcggg gatagccttt cgaaagaaag attaataccc gatggcataa tagaaccgca    180

tggtttgatt attaaagaat ttcggttatc gatggggatg cgttccatta ggcagttggt    240

ggggtaacgg cccaccaaac cttcgatgga taggggttct gagaggaagg tcccccacat    300

tggaactgag acacggtcca aactcctacg ggaggcagca gtgaggaata ttggtcaatg    360

gacgagagtc tgaaccagcc aagtagcgtg aaggatgact gccctatggg ttgtaaactt    420

cttttatatg ggaataaagt ggtccacgtg tggatttttg tatgtaccat atgaataagg    480

atcggctaac tccgtgccag cagccgcggt aatacggagg atccgagcgt tatccggatt    540

tattgggttt aaagggagcg taggtggaca gttaagtcag ttgtgaaagt ttgcggctca    600

accgtaaaat tgcagttgat actggctgtc ttgagtacag tagaggcggg cggaattcgt    660

ggtgtagcgg tgaaatgctt agatatcacg aagaactccg attgcgaagg cagctcactg    720

gactgcaact gacactgatg ctcgaaagtg tgggtatcaa acaggattag ataccctggt    780

agtccacaca gtaaacgatg aatactcgct gtttgcgata tacagtaagc ggccaagcga    840

aagcattaag tattccacct ggggagtacg ccggcaacgg tgaaactcaa aggaattgac    900

gggggcccgc acaagcggag gaacatgtgg tttaattcga tgatacgcga ggaaccttac    960

ccgggcttaa attgcatttg aatatattgg aaacagtata gtcgtaagac aaatgtgaag   1020

gtgctgcatg gttgtcgtca gctcgtgccg tgaggtgtcg gcttaagtgc cataacgagc   1080

gcaaccctta tctttagtta ctaacaggtc atgctgagga ctctggagag actgccgtcg   1140

taagatgtga ggaaggtggg gatgacgtca aatcagcacg gcccttacgt ccggggctac   1200

acacgtgtta caatgggggg tacagaaggc cgctacctgg tgacaggatg ctaatcccaa   1260

aagcctctct cagttcggat cgaagtctgc aacccgactt cgtgaagctg gattcgctag   1320

taatcgcgca tcagccatgg cgcggtgaat acgttcccgg gccttgtaca caccgcccgt   1380

caagccatga aagccggggg tacctgaagt acgtaaccgc aaggagcgtc ctagggtaaa   1440
```

actggtaatt ggggctaagt cgtaacaagg ta 1472

<210> SEQ ID NO 6
<211> LENGTH: 1488
<212> TYPE: DNA
<213> ORGANISM: Unknown
<220> FEATURE:
<223> OTHER INFORMATION: Blautia_A obeum

<400> SEQUENCE: 6
agagtttgat cctggctcag gatgaacgct ggcggcgtgc ttaacacatg caagtcgaac 60
gggaaacctt ttattgaagc ttcggcagat ttagctggtt tctagtggcg gacgggtgag 120
taacgcgtgg gtaacctgcc ttatacaggg ggataacaac cagaaatggt tgctaatacc 180
gcataagcgc acaggaccgc atggtccggt gtgaaaaact ccggtggtat aagatggacc 240
cgcgttggat tagctagttg gcagggtaac ggcctaccaa ggcgacgatc catagccggc 300
ctgagagggt gaacggccac attgggactg agacacggcc cagactccta cgggaggcag 360
cagtggggaa tattgcacaa tgggggaaac cctgatgcag cgacgccgcg tgaaggaaga 420
agtatctcgg tatgtaaact tctatcagca gggaagatag tgacggtacc tgactaagaa 480
gccccggcta actacgtgcc agcagccgcg gtaatacgta gggggcaagc gttatccgga 540
tttactgggt gtaaagggag cgtagacgga ctggcaagtc tgatgtgaaa ggcgggggct 600
caacccctgg actgcattgg aaactgttag tcttgagtgc cggagaggta agcggaattc 660
ctagtgtagc ggtgaaatgc gtagatatta ggaggaacac cagtggcgaa ggcggcttac 720
tggacggtaa ctgacgttga ggctcgaaag cgtggggagc aaacaggatt agataccctg 780
gtagtccacg ccgtaaacga tgaatactag gtgttgggga gcaaagctct tcggtgccgc 840
cgcaaacgca ttaagtattc cacctgggga gtacgttcgc aagaatgaaa ctcaaaggaa 900
ttgacgggga cccgcacaag cggtggagca tgtggtttaa ttcgaagcaa cgcgaagaac 960
cttaccaagt cttgacatcc ctctgaccgt tccttaaccg gaactttcct tcgggacagg 1020
ggagacaggt ggtgcatggt tgtcgtcagc tcgtgtcgtg agatgttggg ttaagtcccg 1080
caacgagcgc aacccctatc cccagtagcc agcagtccgg ctgggcactc tgaggagact 1140
gccagggata acctggagga aggcggggat gacgtcaaat catcatgccc cttatgattt 1200
gggctacaca cgtgctacaa tggcgtaaac aaagggaagc aagcctgcga aggtaagcaa 1260
atcccaaaaa taacgtccca gttcggactg cagtctgcaa ctcgactgca cgaagctgga 1320
atcgctagta atcgcggatc agaatgccgc ggtgaatacg ttcccgggtc ttgtacacac 1380
cgcccgtcac accatgggag tcagtaacgc ccgaagtcag tgacctaact gcaaagaagg 1440
agctgccgaa ggcgggaccg atgactgggg tgaagtcgta acaaggta 1488

<210> SEQ ID NO 7
<211> LENGTH: 1512
<212> TYPE: DNA
<213> ORGANISM: Unknown
<220> FEATURE:
<223> OTHER INFORMATION: Odoribacter splanchnicus

<400> SEQUENCE: 7
agagtttgat cctggctcag gatgaacgct agcgacaggc ttaacacatg caagtcgagg 60
ggcatcatga ggtagcaata ccttgatggc gaccggcgca cgggtgagta acgcgtatgc 120
aacctgcctg ataccggggt atagcccatg gaaacgtgga ttaacacccc atagtacttt 180

```
tatcctgcat gggatgtgag ttaaatgttt aaggtatcgg atgggcatgc gtcctattag    240
ttagttggcg gggtaacagc ccaccaagac gatgataggt aggggttctg agaggaaggt    300
cccccacatt ggaactgaga cacggtccaa actcctacgg gaggcagcag tgaggaatat    360
tggtcaatgg acgagagtct gaaccagcca agtcgcgtga gggaagactg ccctatgggt    420
tgtaaacctc ttttataagg gaagaataag ttctacgtgt agaatgatgc ctgtacctta    480
tgaataagca tcggctaact ccgtgccagc agccgcggta atacggagga tgcgagcgtt    540
atccggattt attgggttta aagggtgcgt aggcggttta ttaagttagt ggttaaatat    600
ttgagctaaa ctcaattgtg ccattaatac tggtaaactg gagtacagac gaggtaggcg    660
gaataagtta agtagcggtg aaatgcatag atataactta gaactccgat agcgaaggca    720
gcttaccaga ctgtaactga cgctgatgca cgagagcgtg ggtagcgaac aggattagat    780
accctggtag tccacgccgt aaacgatgct cactggttct gtgcgatata ttgtacggga    840
ttaagcgaaa gtattaagtg agccacctgg ggagtacgtc ggcaacgatg aaactcaaag    900
gaattgacgg gggcccgcac aagcggagga acatgtggtt taattcgatg atacgcgagg    960
aaccttacct gggtttaaat gggaaatgtc gtatttggaa acagatattc tcttcggagc   1020
gtttttcaag gtgctgcatg gttgtcgtca gctcgtgccg tgaggtgtcg ggttaagtcc   1080
cataacgagc gcaaccctta ccgttagttg ctagcatgta atgatgagca ctctaacggg   1140
actgccaccg taaggtgaga ggaaggcggg gatgacgtca aatcagcacg gcccttacac   1200
ccagggctac acacgtgtta caatggccgg tacagagggc cgctaccagg tgactggatg   1260
ccaatctcaa aagccggtcg tagttcggat tggagtctgt aacccgactc catgaagttg   1320
gattcgctag taatcgcgca tcagccatgg cgcggtgaat acgttcccgg gccttgtaca   1380
caccgcccgt caagccatgg aagccggggg tgcctgaagt ccgtaaccgc gaggatcggc   1440
ctagggcaaa actggtaact ggggctaagt cgtaacaagg tagccgtacc ggaaggtgcg   1500
gctggaacac ct                                                       1512
```

<210> SEQ ID NO 8
<211> LENGTH: 1473
<212> TYPE: DNA
<213> ORGANISM: Unknown
<220> FEATURE:
<223> OTHER INFORMATION: Bacteroides cellulosilyticus

<400> SEQUENCE: 8

```
agagtttgat cctggctcag gatgaacgct agctacaggc ttaacacatg caagtcgagg     60
ggcagcatga cctagcaata ggttgatggc gaccggcgca cgggtgagta acacgtatcc    120
aacctaccgg ttattccggg atagcctttc gaaagaaaga ttaataccgg atagtataac    180
gagaaggcat ctttttgtta ttaaagaatt tcgataaccg atggggatgc gttccattag    240
tttgttggcg gggtaacggc ccaccaagac atcgatggat aggggttctg agaggaaggt    300
cccccacatt ggaactgaga cacggtccaa actcctacgg gaggcagcag tgaggaatat    360
tggtcaatgg acgagagtct gaaccagcca agtagcgtga aggatgactg ccctatgggt    420
tgtaaacttc ttttatatgg gaataaagtg agccacgtgt ggctttttgt atgtaccata    480
cgaataagga tcggctaact ccgtgccagc agccgcggta atacggagga tccgagcgtt    540
atccggattt attgggttta aagggagcgt aggcggacta ttaagtcagc tgtgaaagtt    600
tgcggctcaa ccgtaaaatt gcagttgata ctggtcgtct tgagtgcagt agaggtaggc    660
ggaattcgtg gtgtagcggt gaaatgctta gatatcacga agaactccga ttgcgaaggc    720
```

```
agcttactgg actgtaactg acgctgatgc tcgaaagtgt gggtatcaaa caggattaga    780

taccctggta gtccacacag taaacgatga atactcgctg tttgcgatat acggcaagcg    840

gccaagcgaa agcattaagt attccacctg gggagtacgc cggcaacggt gaaactcaaa    900

ggaattgacg gggcccgca caagcggagg aacatgtggt ttaattcgat gatacgcgag    960

gaaccttacc cgggcttaaa ttgcaaatga atatagtgga aacattatag ccgcaaggca   1020

tttgtgaagg tgctgcatgg ttgtcgtcag ctcgtgccgt gaggtgtcgg cttaagtgcc   1080

ataacgagcg caacccttat ctttagttac taacaggtca tgctgaggac tctagagaga   1140

ctgccgtcgt aagatgtgag gaaggtgggg atgacgtcaa atcagcacgg cccttacgtc   1200

cggggctaca cacgtgttac aatggggggt acagaaggca gctacacagc gatgtgatgc   1260

taatcccaaa agcctctctc agttcggatt ggagtctgca acccgactcc atgaagctgg   1320

attcgctagt aatcgcgcat cagccacggc gcggtgaata cgttcccggg ccttgtacac   1380

accgcccgtc aagccatgaa agccgggggt acctgaagtc cgtaaccgta aggagcggcc   1440

tagggtaaaa ctggtaattg gggctaagtc gta                                1473
```

<210> SEQ ID NO 9
<211> LENGTH: 1474
<212> TYPE: DNA
<213> ORGANISM: Bacteroides uniformis

<400> SEQUENCE: 9

```
ctggctcagg atgaacgcta gctacaggct taacacatgc aagtcgaggg gcagcatgaa     60

cttagcttgc taagtttgat ggcgaccggc gcacgggtga gtaacacgta tccaacctgc    120

cgatgactcg ggatagcct ttcgaaagaa agattaatac ccgatggcat agttcttccg    180

catggtagaa ctattaaaga atttcggtca tcgatgggga tgcgttccat taggttgttg    240

gcggggtaac ggcccaccaa gccttcgatg gatagggggtt ctgagaggaa ggtcccccac    300

attggaactg agacacggtc caaactccta cgggaggcag cagtgaggaa tattggtcaa    360

tggacgagag tctgaaccag ccaagtagcg tgaaggatga ctgccctatg ggttgtaaac    420

ttcttttata cgggaataaa gtgaggcacg tgtgcctttt tgtatgtacc gtatgaataa    480

ggatcggcta actccgtgcc agcagccgcg gtaatacgga ggatccgagc gttatccgga    540

tttattgggt ttaaagggag cgtaggcgga cgcttaagtc agttgtgaaa gtttgcggct    600

caaccgtaaa attgcagttg atactgggtg tcttgagtac agtagaggca ggcggaattc    660

gtggtgtagc ggtgaaatgc ttagatatca cgaagaactc cgattgcgaa ggcagcttgc    720

tggactgtaa ctgacgctga tgctcgaaag tgtgggtatc aaacaggatt agataccctg    780

gtagtccaca cagtaaacga tgaatactcg ctgtttgcga tatacagtaa gcggccaagc    840

gaaagcgtta agtattccac ctggggagta cgccggcaac ggtgaaactc aaaggaattg    900

acgggggccc gcacaagcgg aggaacatgt ggtttaattc gatgatacgc gaggaacctt    960

acccgggctt gaattgcaac tgaatgatgt ggagacatgt cagccgcaag gcagttgtga   1020

aggtgctgca tggttgtcgt cagctcgtgc cgtgaggtgt cggcttaagt gccataacga   1080

gcgcaaccct tatcgatagt taccatcagg ttatgctggg gactctgtcg agactgccgt   1140

cgtaagatgt gaggaaggtg gggatgacgt caaatcagca cggcccttac gtccggggct   1200

acacacgtgt tacaatgggg ggtacagaag gcagctacac ggcgacgtga tgctaatccc   1260

taaagcctct ctcagttcgg attggagtct gcaacccgac tccatgaagc tggattcgct   1320
```

agtaatcgcg catcagccac ggcgcggtga atacgttccc gggccttgta cacaccgccc 1380
gtcaagccat gaaagccggg ggtacctgaa gtgcgtaacc gcgaggagcg ccctagggta 1440
aaactggtga ttggggctaa gtcgtaacaa ggta 1474

<210> SEQ ID NO 10
<211> LENGTH: 1503
<212> TYPE: DNA
<213> ORGANISM: Unknown
<220> FEATURE:
<223> OTHER INFORMATION: Bacteroides_B vulgatus

<400> SEQUENCE: 10
atgaagagtt tgatcctggc tcaggatgaa cgctagctac aggcttaaca catgcaagtc 60
gaggggcagc atggtcttag cttgctaagg ccgatggcga ccggcgcacg ggtgagtaac 120
acgtatccaa cctgccgtct actcttggac agccttctga aaggaagatt aatacaagat 180
ggcatcatga gtccgcatgt tcacatgatt aaaggtattc cggtagacga tggggatgcg 240
ttccattaga tagtaggcgg ggtaacggcc cacctagtct tcgatggata ggggttctga 300
gaggaaggtc ccccacattg gaactgagac acggtccaaa ctcctacggg aggcagcagt 360
gaggaatatt ggtcaatggg cgagagcctg aaccagccaa gtagcgtgaa ggatgactgc 420
cctatgggtt gtaaacttct tttataaagg aataaagtcg ggtatggata cccgtttgca 480
tgtactttat gaataaggat cggctaactc cgtgccagca gccgcggtaa tacggaggat 540
ccgagcgtta tccggattta ttgggtttaa agggagcgta gatggatgtt taagtcagtt 600
gtgaaagttt gcggctcaac cgtaaaattg cagttgatac tggatatctt gagtgcagtt 660
gaggcaggcg gaattcgtgg tgtagcggtg aaatgcttag atatcacgaa gaactccgat 720
tgcgaaggca gcctgctaag ctgcaactga cattgaggct cgaaagtgtg ggtatcaaac 780
aggattagat accctggtag tccacacggt aaacgatgaa tactcgctgt ttgcgatata 840
cagcaagcgg ccaagcgaaa gcgttaagta ttccacctgg ggagtacgcc ggcaacggtg 900
aaactcaaag gaattgacgg gggcccgcac aagcggagga acatgtggtt taattcgatg 960
atacgcgagg aaccttaccc gggcttaaat tgcagatgaa ttacggtgaa agccgtaagc 1020
cgcaaggcat ctgtgaaggt gctgcatggt tgtcgtcagc tcgtgccgtg aggtgtcggc 1080
ttaagtgcca taacgagcgc aacccttgtt gtcagttact aacaggttcc gctgaggact 1140
ctgacaagac tgccatcgta agatgtgagg aaggtgggga tgacgtcaaa tcagcacggc 1200
ccttacgtcc ggggctacac acgtgttaca atgggggta cagagggccg ctaccacgcg 1260
agtggatgcc aatcccaaaa acctctctca gttcggactg gagtctgcaa cccgactcca 1320
cgaagctgga ttcgctagta atcgcgcatc agccacggcg cggtgaatac gttcccgggc 1380
cttgtacaca ccgcccgtca agccatggga gccgggggta cctgaagtgc gtaaccgcga 1440
ggagcgccct agggtaaaac tggtgactgg ggctaagtcg taacaaggta gccgtaccgg 1500
aag 1503

<210> SEQ ID NO 11
<211> LENGTH: 1525
<212> TYPE: DNA
<213> ORGANISM: Bacteroides fragilis

<400> SEQUENCE: 11
atgaagagtt tgatcctggc tcaggatgaa cgctagctac aggcttaaca catgcaagtc 60
gaggggcatc aggaagaaag cttgctttct ttgctggcga ccggcgcacg ggtgagtaac 120

```
acgtatccaa cctgcccttt actcggggat agcctttcga aagaaagatt aatacccgat    180

ggcataatga ttccgcatgg tttcattatt aaaggattcc ggtaaaggat ggggatgcgt    240

tccattaggt tgttggtgag gtaacggctc accaagcctt cgatggatag gggttctgag    300

aggaaggtcc cccacattgg aactgagaca cggtccaaac tcctacggga ggcagcagtg    360

aggaatattg gtcaatgggc gctagcctga accagccaag tagcgtgaag gatgaaggct    420

ctatgggtcg taaacttctt ttatataaga ataaagtgca gtatgtatac tgttttgtat    480

gtattatatg aataaggatc ggctaactcc gtgccagcag ccgcggtaat acggaggatc    540

cgagcgttat ccggatttat tgggtttaaa gggagcgtag gtggactggt aagtcagttg    600

tgaaagtttg cggctcaacc gtaaaattgc agttgatact gtcagtcttg agtacagtag    660

aggtgggcgg aattcgtggt gtagcggtga aatgcttaga tatcacgaag aactccgatt    720

gcgaaggcag ctcactggac tgcaactgac actgatgctc gaaagtgtgg gtatcaaaca    780

ggattagata ccctggtagt ccacacagta aacgatgaat actcgctgtt tgcgatatac    840

agtaagcggc caagcgaaag cattaagtat tccacctggg gagtacgccg gcaacggtga    900

aactcaaagg aattgacggg ggcccgcaca agcggaggaa catgtggttt aattcgatga    960

tacgcgagga accttacccg ggcttaaatt gcagtggaat gatgtggaaa catgtcagtg   1020

agcaatcacc gctgtgaagg tgctgcatgg ttgtcgtcag ctcgtgccgt gaggtgtcgg   1080

cttaagtgcc ataacgagcg caacccttat ctttagttac taacaggtta tgctgaggac   1140

tctagagaga ctgccgtcgt aagatgtgag gaaggtgggg atgacgtcaa atcagcacgg   1200

cccttacgtc cggggctaca cacgtgttac aatgggggt acagaaggca gctagcgggt    1260

gaccgtatgc taatcccaaa agcctctctc agttcggatc gaagtctgca acccgacttc   1320

gtgaagctgg attcgctagt aatcgcgcat cagccacggc gcggtgaata cgttcccggg   1380

ccttgtacac accgcccgtc aagccatggg agccgggggt acctgaagta cgtaaccgca   1440

aggatcgtcc tagggtaaaa ctggtgactg gggctaagtc gtaacaaggt agccgtaccg   1500

gaaggtgcgg ctggaacacc tcctt                                        1525
```

<210> SEQ ID NO 12
<211> LENGTH: 1475
<212> TYPE: DNA
<213> ORGANISM: Bacteroides caccae

<400> SEQUENCE: 12

```
tggctcagga tgaacgctag ctacaggctt aacacatgca agtcgagggg catcagtttg     60

gtttgcttgc aaaccaaagc tggcgaccgg cgcacgggtg agtaacacgt atccaacctg    120

cctcatactc ggggatagcc tttcgaaaga aagattaata tccgatagca tatatttccc    180

gcatgggttt tatattaaag aaattcggta tgagatgggg atgcgttcca ttagtttgtt    240

ggggggtaa cggcccacca agactacgat ggataggggt tctgagagga aggtccccca     300

cattggaact gagacacggt ccaaactcct acgggaggca gcagtgagga atattggtca    360

atggacgcga gtctgaacca gccaagtagc gtgaaggatg actgccctat gggttgtaaa    420

cttcttttat atgggaataa agttgtccac gtgtggattt ttgtatgtac catatgaata    480

aggatcggct aactccgtgc cagcagccgc ggtaatacgg aggatccgag cgttatccgg    540

atttattggg tttaaaggga gcgtaggcgg attgttaagt cagttgtgaa agtttgcggc    600

tcaaccgtaa aattgcagtt gatactggca gtcttgagtg cagtagaggt gggcggaatt    660
```

```
cgtggtgtag cggtgaaatg cttagatatc acgaagaact ccgattgcga aggcagctca    720

ctggagtgta actgacgctg atgctcgaaa gtgtgggtat caaacaggat tagataccct    780

ggtagtccac acagtaaacg atgaatactc gctgtttgcg atatacagta agcggccaag    840

cgaaagcatt aagtattcca cctggggagt acgccggcaa cggtgaaact caaaggaatt    900

gacgggggcc cgcacaagcg gaggaacatg tggtttaatt cgatgatacg cgaggaacct    960

tacccgggct taaattgcaa atgaattatg ggaaacccca taggccgcaa ggcatttgtg   1020

aaggtgctgc atggttgtcg tcagctcgtg ccgtgaggtg tcggcttaag tgccataacg   1080

agcgcaaccc ttatcttcag ttactaacag gtcatgctga ggactctgga gagactgccg   1140

tcgtaagatg tgaggaaggt ggggatgacg tcaaatcagc acggccctta cgtccggggc   1200

tacacacgtg ttacaatggg gggtacagaa ggccgctacc tggtgacagg atgccaatcc   1260

caaaaacctc tctcagttcg gatcgaagtc tgcaacccga cttcgtgaag ctggattcgc   1320

tagtaatcgc gcatcagcca tggcgcggtg aatacgttcc cgggccttgt acacaccgcc   1380

cgtcaagcca tgaaagccgg gggtacctga agtacgtaac cgcaaggagc gtcctagggt   1440

aaaactggta attggggcta agtcgtaaca aggta                              1475
```

<210> SEQ ID NO 13
<211> LENGTH: 1492
<212> TYPE: DNA
<213> ORGANISM: Unknown
<220> FEATURE:
<223> OTHER INFORMATION: Paeniclostridium sordellii

<400> SEQUENCE: 13

```
gtttgatcct ggctcaggat gaacgctggc ggcgtgccta acacatgcaa gtcgagcgaa     60

cccttcgggg tgagcggcgg acgggtgagt aacgcgtggg taacctgccc tgtacacacg    120

gataacatac cgaaaggtat gctaatacgg gataatatat gagagtcgca tggcttttgt    180

atcaaagctc tggcggtaca ggatggaccc gcgtctgatt agctagttgg taaggtaacg    240

gcttaccaag gcaacgatca gtagccgacc tgagagggtg atcggccaca ttggaactga    300

gacacggtcc aaactcctac gggaggcagc agtggggaat attgcacaat gggcgaaagc    360

ctgatgcagc aacgccgcgt gagcgatgaa ggccttcggg tcgtaaagct ctgtcctcaa    420

ggaagataat gacggtactt gaggaggaag ccccggctaa ctacgtgcca gcagccgcgg    480

taatacgtag gggctagcg ttatccggaa ttactgggcg taaagggtgc gtaggcggtc    540

tttcaagcca gaagtgaaag gctacggctc aaccgtagta agcttttgga actgtaggac    600

ttgagtgcag gagaggagag tggaattcct agtgtagcgg tgaaatgcgt agatattagg    660

aggaacacca gtagcgaagg cggctctctg gactgtaact gacgctgagg cacgaaagcg    720

tggggagcaa acaggattag ataccctggt agtccacgcc gtaaacgatg agtactaggt    780

gtcgggggtt accccccctcg gtgccgcagc taacgcatta agtactccgc ctgggaagta    840

cgctcgcaag agtgaaactc aaaggaattg acggggaccc gcacaagtag cggagcatgt    900

ggtttaattc gaagcaacgc gaagaacctt acctaagctt gacatcccac tgacctctcc    960

ctaatcggag atttcccttc ggggacagtg gtgacaggtg gtgcatggtt gtcgtcagct   1020

cgtgtcgtga gatgttgggt taagtcccgc aacgagcgca acccttgcct ttagttgcca   1080

gcattaagtt gggcactcta gagggactgc cgaggataac tcggaggaag gtggggatga   1140

cgtcaaatca tcatgcccct tatgcttagg gctacacacg tgctacaatg ggtggtacag   1200

agggttgcca agccgtgagg tggagctaat cccttaaagc cattctcagt tcggattgta   1260
```

ggctgaaact cgcctacatg aagctggagt tactagtaat cgcagatcag aatgctgcgg 1320
tgaatgcgtt cccgggtctt gtacacaccg cccgtcacac catgggagtt gggggcgccc 1380
gaagccggtt agctaacctt ttaggaagcg gccgtcgaag gtgaaaccaa tgactggggt 1440
gaagtcgtaa caaggtagcc gtatcggaag gtgcggctgg atcacctcct tt 1492

<210> SEQ ID NO 14
<211> LENGTH: 1490
<212> TYPE: DNA
<213> ORGANISM: Unknown
<220> FEATURE:
<223> OTHER INFORMATION: Blautia producta

<400> SEQUENCE: 14
agagtttgat cctggctcag gatgaacgct ggcggcgtgc ttaacacatg caagtcgagc 60
gaagcactaa gacagatttc ttcggattga agtctttgtg actgagcggc ggacgggtga 120
gtaacgcgtg ggtaacctgc ctcatacagg gggataacag ttagaaatga ctgctaatac 180
cgcataagcg cacaggaccg catggtctgg tgtgaaaaac tccggtggta tgagatggac 240
ccgcgtctga ttagctagtt ggaggggtaa cggcccacca aggcgacgat cagtagccgg 300
cctgagaggg tgaacggcca cattgggact gagacacggc ccagactcct acgggaggca 360
gcagtgggga atattgcaca atgggggaaa ccctgatgca gcgacgccgc gtgaaggaag 420
aagtatctcg gtatgtaaac ttctatcagc agggaagaaa atgacggtac ctgactaaga 480
agccccggct aactacgtgc cagcagccgc ggtaatacgt agggggcaag cgttatccgg 540
atttactggg tgtaaaggga gcgtagacgg aagagcaagt ctgatgtgaa aggctggggc 600
ttaaccccag gactgcattg gaaactgttg ttctagagtg ccggagaggt aagcggaatt 660
cctagtgtag cggtgaaatg cgtagatatt aggaggaaca ccagtggcga aggcggctta 720
ctggacggta actgacgttg aggctcgaaa gcgtggggag caaacaggat tagataccct 780
ggtagtccac gccgtaaacg atgaatacta ggtgtcgggt ggcaaagcca ttcggtgccg 840
cagcaaacgc aataagtatt ccacctgggg agtacgttcg caagaatgaa actcaaagga 900
attgacgggg acccgcacaa gcggtggagc atgtggttta attcgaagca acgcgaagaa 960
ccttaccaag tcttgacatc cctctgaccg tcccgtaacg gggcttccc ttcggggcag 1020 aggagacagg tggtgcatgg ttgtcgtcag ctcgtgtcgt gagatgttgg gttaagtccc 1080
gcaacgagcg caacccttat ccttagtagc cagcacatga tggtgggcac tctagggaga 1140
ctgccgggga taacccggag gaaggcgggg acgacgtcaa atcatcatgc cccttatgat 1200
ttgggctaca cacgtgctac aatggcgtaa acaaagggaa gcgagacagc gatgttgagc 1260
gaatcccaaa aataacgtcc cagttcggac tgcagtctgc aactcgactg cacgaagctg 1320
gaatcgctag taatcgcgga tcagaatgcc gcggtgaata cgttcccggg tcttgtacac 1380
accgcccgtc acaccatggg agtcagtaac gcccgaagtc agtgacctaa ccgaaaggaa 1440
ggagctgccg aaggcgggac cgataactgg ggtgaagtcg taacaaggta 1490

<210> SEQ ID NO 15
<211> LENGTH: 1475
<212> TYPE: DNA
<213> ORGANISM: Unknown
<220> FEATURE:
<223> OTHER INFORMATION: Absiella innocuum

<400> SEQUENCE: 15

```
atggagagtt tgatcctggc tcaggatgaa cgctggcggc atgcctaata catgcaagtc     60
gaacgaagtt tcgaggaagc ttgcttccaa agagacttag tggcgaacgg gtgagtaaca    120
cgtaggtaac ctgcccatgt gtccgggata actgctggaa acggtagcta aaaccggata    180
ggtatacaga gcgcatgctc agtatattaa agcgcccatc aaggcgtgaa catggatgga    240
cctgcggcgc attagctagt tggtgaggta acggcccacc aaggcgatga tgcgtagccg    300
gcctgagagg gtaaacggcc acattgggac tgagacacgg cccaaactcc tacgggaggc    360
agcagtaggg aattttcgtc aatgggggaa accctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatggaaac tggtatgctg    660
gagtgcagaa gagggcgatg gaattccatg tgtagcggta aaatgcgtag atatatggag    720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctggggag tatgcacgca    900
agtgtgaaac tcaaaggaat tgacgggggc ccgcacaagc ggtggagtat gtggtttaat    960
tcgaagcaac gcgaagaacc ttaccaggcc ttgacatgga aacaaatacc ctagagatag   1020
gggataatt atggatcaca caggtggtgc atggttgtcg tcagctcgtg tcgtgagatg   1080
ttgggttaag tcccgcaacg agcgcaaccc ttgtcgcatg ttaccagcat caagttgggg   1140
actcatgcga gactgccggt gacaaaccgg aggaaggtgg ggatgacgtc aaatcatcat   1200
gccccttatg gcctgggcta cacacgtact acaatggcga ccacaaagag cagcgacaca   1260
gtgatgtgaa gcgaatctca taaaggtcgt ctcagttcgg attgaagtct gcaactcgac   1320
ttcatgaagt cggaatcgct agtaatcgca gatcagcatg ctgcggtgaa tacgttctcg   1380
ggccttgtac acaccgcccg tcaaaccatg ggagtcagta atacccgaag ccggtggcat   1440
aaccgtaagg agtgagccgt cgaaggtagg accga                              1475
```

<210> SEQ ID NO 16
<211> LENGTH: 1496
<212> TYPE: DNA
<213> ORGANISM: Unknown
<220> FEATURE:
<223> OTHER INFORMATION: Clostridium_M clostridioforme

<400> SEQUENCE: 16

```
agagtttgat cctggctcag gatgaacgct ggcggcgtgc ctaacacatg caagtcgaac     60
gaagcaatta agatgaagtt ttcggatgga atcttgattg actgagtggc ggacgggtga    120
gtaacgcgtg gataacctgc ctcacactgg gggataacag ttagaaatga ctgctaatac    180
cgcataagcg cacagtgccg catggcagtg tgtgaaaaac tccggtggtg tgagatggat    240
ccgcgtctga ttagccagtt ggcggggtaa cggcccacca aagcgacgat cagtagccga    300
cctgagaggg tgaccggcca cattgggact gagacacggc ccaaactcct acgggaggca    360
gcagtgggga atattgcaca atgggcgaaa gcctgatgca gcgacgccgc gtgagtgaag    420
aagtatttcg gtatgtaaag ctctatcagc agggaagaaa atgacggtac ctgactaaga    480
agccccggct aactacgtgc cagcagccgc ggtaatacgt agggggcaag cgttatccgg    540
atttactggg tgtaaaggga gcgtagacgg cgaagcaagt ctgaagtgaa aacccggggc    600
```

tcaaccctgg gactgctttg gaaactgttt tgctagagtg tcggagaggt aagtggaatt 660
cctagtgtag cggtgaaatg cgtagatatt aggaggaaca ccagtggcga aggcggctta 720
ctggacgata actgacgttg aggctcgaaa gcgtggggag caaacaggat tagataccct 780
ggtagtccac gccgtaaacg atgaatgcta ggtgttgggg ggcaaagccc ttcggtgccg 840
ccgcaaacgc agtaagcatt ccacctgggg agtacgttcg caagaatgaa actcaaagga 900
attgacgggg acccgcacaa gcggtggagc atgtggttta attcgaagca acgcgaagaa 960
ccttaccaag tcttgacatc cccctgacgg gccggtaacg cggcctttcc ttcgggacag 1020
gggagacagg tggtgcatgg ttgtcgtcag ctcgtgtcgt gagatgttgg gttaagtccc 1080
gcaacgagcg caacccttat ccttagtagc cagcaggtag agccgggcac tctagggaga 1140
ctgccaggga taacctggag gaaggtgggg atgacgtcaa atcatcatgc cccttatgat 1200
ttgggctaca cacgtgctac aatggcgtaa acaaagggaa gcgagacagt gatgtggagc 1260
aaatcccaaa aataacgtcc cagttcggac tgtagtctgc aacccgacta cacgaagctg 1320
gaatcgctag taatcgcgaa tcagaatgtc gcggtgaata cgttcccggg tcttgtacac 1380
accgcccgtc acaccatggg agtcagcaac gcccgaagtc agtgacccaa ccgaaaggag 1440
ggagctgccg aaggcggggc aggtaactgg ggtgaagtcg taacaaggta gccgta 1496

<210> SEQ ID NO 17
<211> LENGTH: 1490
<212> TYPE: DNA
<213> ORGANISM: Unknown
<220> FEATURE:
<223> OTHER INFORMATION: Paraclostridium massiliensis

<400> SEQUENCE: 17
agagtttgat cctggctcag gatgaacgct ggcggcgtgc ctaacacatg caagtcgagc 60
gatctcttcg gagagagcgg cggacgggtg agtaacgcgt gggtaacctg ccctgtacac 120
acggataaca taccgaaagg tatactaata cgggataaca tacgaaagtc gcatggcttt 180
tgtatcaaag ctccggcggt acaggatgga cccgcgtctg attagctagt tggtaaggta 240
atggcttacc aaggcaacga tcagtagccg acctgagagg gtgatcggcc acactggaac 300
tgagacacgg tccagactcc tacgggaggc agcagtgggg aatattgcac aatgggcgaa 360
agcctgatgc agcaacgccg cgtgagcgat gaaggccttc gggtcgtaaa gctctgtcct 420
caaggaagat aatgacggta cttgaggagg aagccccggc taactacgtg ccagcagccg 480
cggtaatacg taggggggcta gcgttatccg gaattactgg gcgtaaaggg tgcgtaggtg 540 gtttttaag tcagaagtga aaggctacgg ctcaaccgta gtaagctttt gaaactagag 600
aacttgagtg caggagagga gagtagaatt cctagtgtag cggtgaaatg cgtagatatt 660
aggaggaata ccagtagcga aggcggctct ctggactgta actgacactg aggcacgaaa 720
gcgtggggag caaacaggat tagataccct ggtagtccac gccgtaaacg atgagtacta 780
ggtgtcgggg gttacccccc tcggtgccgc agctaacgca ttaagtactc cgcctgggaa 840
gtacgctcgc aagagtgaaa ctcaaaggaa ttgacgggga cccgcacaag tagcggagca 900
tgtggtttaa ttcgaagcaa cgcgaagaac cttacctaag cttgacatcc cactgacctc 960
tccctaatcg gagatttccc ttcggggaca gtggtgacag gtggtgcatg gttgtcgtca 1020
gctcgtgtcg tgagatgttg ggttaagtcc cgcaacgagc gcaacccttg cctttagttg 1080
ccagcattaa gttgggcact ctagagggac tgccgaggat aactcggagg aaggtgggga 1140
tgacgtcaaa tcatcatgcc ccttatgctt agggctacac acgtgctaca atgggtggta 1200
cagagggttg ccaagccgcg aggtggagct aatcccttaa agccattctc agttcggatt 1260
gtaggctgaa actcgcctac atgaagctgg agttactagt aatcgcagat cagaatgctg 1320
cggtgaatgc gttcccgggt cttgtacaca ccgcccgtca caccatggaa gttgggggcg 1380
cccgaagccg gttagctaac cttttaggaa gcggccgtcg aaggtgaaac caatgactgg 1440
ggtgaagtcg taacaaggta gccgtatcgg aaggtgcggc tggatcacct 1490

<210> SEQ ID NO 18
<211> LENGTH: 1524
<212> TYPE: DNA
<213> ORGANISM: Unknown
<220> FEATURE:
<223> OTHER INFORMATION: Dorea longicatena B

<400> SEQUENCE: 18
agagtttgat cctggctcag gatgaacgct ggcggcgtgc ttaacacatg caagtcgagc 60
gaagcactta agtctgattc ttcggatgaa gacttttgtg actgagcggc ggacgggtga 120
gtaacgcgtg ggtaacctgc ctcatacagg gggataacag ttagaaatga ctgctaatac 180
cgcataagac cacggtaccg catggtacag tggtaaaaac tccggtggta tgagatggac 240
ccgcgtctga ttaggtagtt ggtggggtaa cggcctacca agccgacgat cagtagccga 300
cctgagaggg tgaccggcca cattgggact gagacacggc ccagactcct acgggaggca 360
gcagtgggga atattgcaca atggaggaaa ctctgatgca gcgacgccgc gtgaaggatg 420
aagtatttcg gtatgtaaac ttctatcagc agggaagaaa atgacggtac ctgactaaga 480
agccccggct aactacgtgc cagcagccgc ggtaatacgt agggggcaag cgttatccgg 540
atttactggg tgtaaaggga gcgtagacgg cacggcaagc cagatgtgaa agcccggggc 600
tcaaccccgg gactgcattt ggaactgctg agctagagtg tcggagaggc aagtggaatt 660
cctagtgtag cggtgaaatg cgtagatatt aggaggaaca ccagtggcga aggcggcttg 720
ctggacgatg actgacgttg aggctcgaaa gcgtggggag caaacaggat tagataccct 780
ggtagtccac gccgtaaacg atgactgcta ggtgtcgggt ggcaaagcca ttcggtgccg 840
cagctaacgc aataagcagt ccacctgggg agtacgttcg caagaatgaa actcaaagga 900
attgacgggg acccgcacaa gcggtggagc atgtggttta attcgaagca acgcgaagaa 960
ccttacctga tcttgacatc ccgatgaccg cttcgtaatg gaagcttttc ttcggaacat 1020
cggtgacagg tggtgcatgg ttgtcgtcag ctcgtgtcgt gagatgttgg gttaagtccc 1080
gcaacgagcg caacccctat cttcagtagc cagcaggtta agctgggcac tctggagaga 1140
ctgccaggga taacctggag gaaggtgggg atgacgtcaa atcatcatgc cccttatgac 1200
cagggctaca cacgtgctac aatggcgtaa acaaagagaa gcgaactcgc gagggtaagc 1260
aaatctcaaa aataacgtct cagttcggat tgtagtctgc aactcgacta catgaagctg 1320
gaatcgctag taatcgcaga tcagaatgct gcggtgaata cgttcccggg tcttgtacac 1380
accgcccgtc acaccatggg agtcagtaac gcccgaagtc agtgacccaa ccgtaaggag 1440
ggagctgccg aaggtgggac cgataactgg ggtgaagtcg taacaaggta gccgtatcgg 1500
aaggtgcggc tggatcacct cctt 1524

<210> SEQ ID NO 19
<211> LENGTH: 1474
<212> TYPE: DNA
<213> ORGANISM: Bacteroides thetaiotaomicron

<400> SEQUENCE: 19

```
atgaagagtt tgatcctggc tcaggatgaa cgctagctac aggcttaaca catgcaagtc      60
gaggggcagc atttcagttt gcttgcaaac tggagatggc gaccggcgca cgggtgagta     120
acacgtatcc aacctgccga taactcgggg atagcctttc gaaagaaaga ttaatacccg     180
atggcataat agaaccgcat ggttttttta ttaaagaatt tcggttatcg atggggatgc     240
gttccattag gcagttggtg aggtaacggc tcaccaaacc ttcgatggat aggggttctg     300
agaggaaggt cccccacatt ggaactgaga cacggtccaa actcctacgg gaggcagcag     360
tgaggaatat tggtcaatgg acgagagtct gaaccagcca agtagcgtga aggatgactg     420
ccctatgggt tgtaaacttc ttttatatgg gaataaagtt ttccacgtgt ggaattttgt     480
atgtaccata tgaataagga tcggctaact ccgtgccagc agccgcggta atacggagga     540
tccgagcgtt atccggattt attgggttta aagggagcgt aggtggacag ttaagtcagt     600
tgtgaaagtt tgcggctcaa ccgtaaaatt gcagttgata ctggctgtct tgagtacagt     660
agaggtgggc ggaattcgtg gtgtagcggt gaaatgctta gatatcacga agaactccga     720
ttgcgaaggc agctcactgg actgcaactg acactgatgc tcgaaagtgt gggtatcaaa     780
caggattaga taccctggta gtccacacag taaacgatga atactcgctg tttgcgatat     840
acagtaagcg gccaagcgaa agcattaagt attccacctg ggagtacgcc ggcaacggt      900
gaaactcaaa ggaattgacg gggcccgca caagcggagg aacatgtggt ttaattcgat      960
gatacgcgag gaaccttacc cgggcttaaa ttgcatttga atatattgga aacagtatag    1020
tcgtaagaca aatgtgaagg tgctgcatgg ttgtcgtcag ctcgtgccgt gaggtgtcgg    1080
cttaagtgcc ataacgagcg caacccttat ctttagttac taacaggtca tgctgaggac    1140
tctagagaga ctgccgtcgt aagatgtgag gaaggtgggg atgacgtcaa atcagcacgg    1200
cccttacgtc cggggctaca cacgtgttac aatgggggt acagaaggca gctacctggt     1260
gacaggatgc taatcccaaa agcctctctc agttcggatc gaagtctgca acccgacttc    1320
gtgaagctgg attcgctagt aatcgcgcat cagccatggc gcggtgaata cgttcccggg    1380
ccttgtacac accgcccgtc aagccatgaa agccgggggt acctgaagta cgtaaccgca    1440
aggagcgtcc tagggtaaaa ctggtaattg gggc                                1474
```

<210> SEQ ID NO 20
<211> LENGTH: 1483
<212> TYPE: DNA
<213> ORGANISM: Parabacteroides distasonis

<400> SEQUENCE: 20

```
cgaagagttt gatcctggct caggatgaac gctagcgaca ggcttaacac atgcaagtcg      60
aggggcagca caggtagcaa taccgggtgg cgaccggcgc acgggtgagt aacgcgtatg     120
caacttgcct atcagagggg gataacccgg cgaaagtcgg actaataccg catgaagcag     180
ggatcccgca tgggaatatt tgctaaagat tcatcgctga tagataggca tgcgttccat     240
taggcagttg gcggggtaac agcccaccaa accgacgatg gataggggtt ctgagaggaa     300
ggtcccccac attggtactg agacacggac caaactccta cgggaggcag cagtgaggaa     360
tattggtcaa tggccgagag gctgaaccag ccaagtcgcg tgagggatga aggttctatg     420
gatcgtaaac ctcttttata agggaataaa gtgcgggacg tgtcccgttt tgtatgtacc     480
ttatgaataa ggatcggcta actccgtgcc agcagccgcg gtaatacgga ggatccgagc     540
```

```
gttatccgga tttattgggt ttaaagggtg cgtaggcggc cttttaagtc agcggtgaaa    600
gtctgtggct caaccataga attgccgttg aaactggggg gcttgagtat gtttgaggca    660
ggcggaatgc gtggtgtagc ggtgaaatgc atagatatca cgcagaaccc cgattgcgaa    720
ggcagcctgc caagccatga ctgacgctga tgcacgaaag cgtggggatc aaacaggatt    780
agataccctg gtagtccacg cagtaaacga tgatcactag ctgtttgcga tacactgtaa    840
gcggcacagc gaaagcgtta agtgatccac ctggggagta cgccggcaac ggtgaaactc    900
aaaggaattg acgggggccc gcacaagcgg aggaacatgt ggtttaattc gatgatacgc    960
gaggaacctt acccgggttt gaacgcattc ggaccgaggt ggaaacacct tttctagcaa   1020
tagccgtttg cgaggtgctg catggttgtc gtcagctcgt gccgtgaggt gtcggcttaa   1080
gtgccataac gagcgcaacc cttgccacta gttactaaca ggtaaagctg aggactctgg   1140
tgggactgcc agcgtaagct gcgaggaagg cggggatgac gtcaaatcag cacggccctt   1200
acatccgggg cgacacacgt gttacaatgg cgtggacaaa gggaagccac ctggcgacag   1260
ggagcgaatc cccaaaccac gtctcagttc ggatcggagt ctgcaacccg actccgtgaa   1320
gctggattcg ctagtaatcg cgcatcagcc atggcgcggt gaatacgttc ccgggccttg   1380
tacacaccgc ccgtcaagcc atgggagccg gggtacctg aagtccgtaa ccgcgaggat    1440
cggcctaggg taaaactggt gactggggct aagtcgtaac aag                     1483
```

<210> SEQ ID NO 21
<211> LENGTH: 1538
<212> TYPE: DNA
<213> ORGANISM: Escherichia coli

<400> SEQUENCE: 21

```
ttgaagagtt tgatcatggc tcagattgaa cgctggcggc aggcctaaca catgcaagtc     60
gaacggtaac aggaagcagc ttgctgcttt gctgacgagt ggcggacggg tgagtaatgt    120
ctgggaaact gcctgatgga gggggataac tactggaaac ggtagctaat accgcataac    180
gtcgcaagac caaagagggg gaccttcggg cctcttgcca tcggatgtgc ccagatggga    240
ttagctagta ggtggggtaa cggctcacct aggcgacgat ccctagctgg tctgagagga    300
tgaccagcca cactggaact gagacacggt ccagactcct acgggaggca gcagtgggga    360
atattgcaca atgggcgcaa gcctgatgca gccatgccgc gtgtatgaag aaggccttcg    420
ggttgtaaag tactttcagc ggggaggaag ggagtaaagt taataccttt gctcattgac    480
gttacccgca gaagaagcac cggctaactc cgtgccagca gccgcggtaa tacggagggt    540
gcaagcgtta atcggaatta ctgggcgtaa agcgcacgca ggcggtttgt taagtcagat    600
gtgaaatccc cgggctcaac ctgggaactg catctgatac tggcaagctt gagtctcgta    660
gaggggggta gaattccagg tgtagcggtg aaatgcgtag agatctggag gaataccggt    720
ggcgaaggcg gccccctgga cgaagactga cgctcaggtg cgaaagcgtg gggagcaaac    780
aggattagat accctggtag tccacgccgt aaacgatgtc gacttggagg ttgtgccctt    840
gaggcgtggc ttccggagct aacgcgttaa gtcgaccgcc tggggagtac ggccgcaagg    900
ttaaaactca aatgaattga cgggggcccg cacaagcggt ggagcatgtg gtttaattcg    960
atgcaacgcg aagaacctta cctggtcttg acatccacgg aagttttcag agatgagaat   1020
gtgccttcgg gaaccgtgag acaggtgctg catggctgtc gtcagctcgt gttgtgaaat   1080
gttgggttaa gtcccgcaac gagcgcaacc cttatccttt gttgccagcg gtccggccgg   1140
gaactcaaag gagactgcca gtgataaact ggaggaaggt ggggatgacg tcaagtcatc   1200
```

atggccctta cgaccagggc tacacacgtg ctacaatggc gcatacaaag agaagcgacc 1260
tcgcgagagc aagcggacct cataaagtgc gtcgtagtcc ggattggagt ctgcaactcg 1320
actccatgaa gtcggaatcg ctagtaatcg tggatcagaa tgccacggtg aatacgttcc 1380
cgggccttgt acacaccgcc cgtcacacca tgggagtggg ttgcaaaaga agtaggtagc 1440
ttaaccttcg ggagggcgct taccactttg tgattcatga ctggggtgaa gtcgtaacaa 1500
ggtaaccgta ggggaacctg cggttggatc acctcctt 1538

<210> SEQ ID NO 22
<211> LENGTH: 1506
<212> TYPE: DNA
<213> ORGANISM: Bifidobacterium longum

<400> SEQUENCE: 22
tggctcagga tgaacgctgg cggcgtgctt aacacatgca agtcgaacgg gatccatcag 60
gctttgcttg gtggtgagag tggcgaacgg gtgagtaatg cgtgaccgac ctgccccata 120
caccggaata gctcctggaa acgggtggta atgccggatg ctccagttga tcgcatggtc 180
ttctgggaaa gctttcgcgg tatgggatgg ggtcgcgtcc tatcagcttg acggcggggt 240
aacggcccac cgtggcttcg acgggtagcc ggcctgagag ggcgaccggc cacattggga 300
ctgagatacg gcccagactc ctacgggagg cagcagtggg gaatattgca caatgggcgc 360
aagcctgatg cagcgacgcc gcgtgaggga tggaggcctt cgggttgtaa acctctttta 420
tcggggagca agcgagagtg agtttacccg ttgaataagc accggctaac tacgtgccag 480
cagccgcggt aatacgtagg gtgcaagcgt tatccggaat tattgggcgt aaagggctcg 540
taggcggttc gtcgcgtccg gtgtgaaagt ccatcgctta acggtggatc cgcgccgggt 600
acgggcgggc ttgagtgcgg taggggagac tggaattccc ggtgtaacgg tggaatgtgt 660
agatatcggg aagaacacca atggcgaagg caggtctctg ggccgttact gacgctgagg 720
agcgaaagcg tggggagcga acaggattag ataccctggt agtccacgcc gtaaacggtg 780
gatgctggat gtggggcccg ttccacgggt tccgtgtcgg agctaacgcg ttaagcatcc 840
cgcctgggga gtacggccgc aaggctaaaa ctcaaagaaa ttgacggggg cccgcacaag 900
cggcggagca tgcggattaa ttcgatgcaa cgcgaagaac cttacctggg cttgacatgt 960
tcccgacggt cgtagagata cggcttccct tcggggcggg ttcacaggtg gtgcatggtc 1020
gtcgtcagct cgtgtcgtga gatgttgggt taagtcccgc aacgagcgca accctcgccc 1080
cgtgttgcca gcggattatg ccgggaactc acgggggacc gccggggtta actcggagga 1140
aggtggggat gacgtcagat catcatgccc cttacgtcca gggcttcacg catgctacaa 1200
tggccggtac aacgggatgc gacgcggcga cgcggagcgg atccctgaaa accggtctca 1260
gttcggatcg cagtctgcaa ctcgactgcg tgaaggcgga gtcgctagta atcgcgaatc 1320
agcaacgtcg cggtgaatgc gttcccgggc cttgtacaca ccgcccgtca agtcatgaaa 1380
gtgggcagca cccgaagccg gtggcctaac cccttgtggg atggagccgt ctaaggtgag 1440
gctcgtgatt gggactaagt cgtaacaagg tagccgtacc ggaaggtgcg gctggatcac 1500
ctcctt 1506

<210> SEQ ID NO 23
<211> LENGTH: 1475
<212> TYPE: DNA
<213> ORGANISM: Unknown
<220> FEATURE:

<223> OTHER INFORMATION: Absiella innocuum

<400> SEQUENCE: 23
atggagagtt tgatcctggc tcaggatgaa cgctggcggc atgcctaata catgcaagtc 60
gaacgaagtt tcgaggaagc ttgcttccaa agagacttag tggcgaacgg gtgagtaaca 120
cgtaggtaac ctgcccatgt gtccgggata actgctggaa acggtagcta aaaccggata 180
ggtatacaga gcgcatgctc agtatattaa agcgcccatc aaggcgtgaa catggatgga 240
cctgcggcgc attagctagt tggtgaggta acggcccacc aaggcgatga tgcgtagccg 300
gcctgagagg gtaaacggcc acattgggac tgagacacgg cccaaactcc tacgggaggc 360
agcagtaggg aattttcgtc aatgggggaa accctgaacg agcaatgccg cgtgagtgaa 420
gaaggtcttc ggatcgtaaa gctctgttgt aagtgaagaa cggctcatag aggaaatgct 480
atgggagtga cggtagctta ccagaaagcc acggctaact acgtgccagc agccgcggta 540
atacgtaggt ggcaagcgtt atccggaatc attgggcgta aagggtgcgt aggtggcgta 600
ctaagtctgt agtaaaaggc aatggctcaa ccattgtaag ctatggaaac tggtatgctg 660
gagtgcagaa gagggcgatg gaattccatg tgtagcggta aaatgcgtag atatatggag 720
gaacaccagt ggcgaaggcg gtcgcctggt ctgtaactga cactgaggca cgaaagcgtg 780
gggagcaaat aggattagat accctagtag tccacgccgt aaacgatgag aactaagtgt 840
tggaggaatt cagtgctgca gttaacgcaa taagttctcc gcctggggag tatgcacgca 900
agtgtgaaac tcaaaggaat tgacgggggc ccgcacaagc ggtggagtat gtggtttaat 960
tcgaagcaac gcgaagaacc ttaccaggcc ttgacatgga aacaaatacc ctagagatag 1020
ggggataatt atggatcaca caggtggtgc atggttgtcg tcagctcgtg tcgtgagatg 1080
ttgggttaag tcccgcaacg agcgcaaccc ttgtcgcatg ttaccagcat caagttgggg 1140
actcatgcga gactgccggt gacaaaccgg aggaaggtgg ggatgacgtc aaatcatcat 1200
gccccttatg gcctgggcta cacacgtact acaatggcgg ccacaaagag cagcgacaca 1260
gtgatgtgaa gcgaatctca taaaggtcgt ctcagttcgg attgaagtct gcaactcgac 1320
ttcatgaagt cggaatcgct agtaatcgca gatcagcatg ctgcggtgaa tacgttctcg 1380
ggccttgtac acaccgcccg tcaaaccatg ggagtcagta atacccgaag ccggtggcat 1440
aaccgtaagg agtgagccgt cgaaggtagg accga 1475

<210> SEQ ID NO 24
<211> LENGTH: 1500
<212> TYPE: DNA
<213> ORGANISM: Unknown
<220> FEATURE:
<223> OTHER INFORMATION: Fusobacterium_A sp

<400> SEQUENCE: 24
agagtttgat cctggctcag gatgaacgct gacagaatgc ttaacacatg caagtctact 60
tgatccttcg ggtgatggtg gcggacgggt gagtaacgcg taaagaactt gccctgcagt 120
ctgggacaac atttggaaac gaatgctaat accggatatt atgtatttct cgcatgagtt 180
ttacatgaaa gctatatgcg ctgcaggaga gctttgcgtc ctattagcta gttggtgagg 240
taacggctca ccaaggccat gataggtagc cggcctgaga gggtgaacgg ccacaagggg 300
actgagacac ggcccttact cctacgggag gcagcagtgg ggaatattgg acaatggacc 360
aaaagtctga tccagcaatt ctgtgtgcac gatgaagttt ttcggaatgt aaagtgcttt 420
cagttgggac gaagtaagtg acggtaccaa cagaagaagc gacggctaaa tacgtgccag 480
cagccgcggt aatacgtatg tcgcaagcgt tatccggatt tattgggcgt aaagcgcgtc 540
taggcggttt ggtaagtctg atgtgaaaat gcggggctca actccgtatt gcgttggaaa 600
ctgctaaact agagtactgg agaggtgggc ggaactacaa gtgtagaggt gaaattcgta 660
gatatttgta ggaatgccga tggggaagcc agcccactgg acagatactg acgctaaagc 720
gcgaaagcgt gggtagcaaa caggattaga taccctggta gtccacgccg taaacgatga 780
ttactaggtg ttggggggtcg aacctcagcg cccaagctaa cgcgataagt aatccgcctg 840
gggagtacgt acgcaagtat gaaactcaaa ggaattgacg gggacccgca caagcggtgg 900
agcatgtggt ttaattcgac gcaacgcgag gaaccttacc agcgtttgac atcctaagaa 960
attagcagag atgcttttgt gccccttcgg gggaacttag tgacaggtgg tgcatggctg 1020
tcgtcagctc gtgtcgtgag atgttgggtt aagtcccgca acgagcgcaa cccctttcgt 1080
atgttgccat cattaagttg ggcactcatg cgatactgcc tgcgatgagc aggaggaagg 1140
tggggatgac gtcaagtcat catgcccctt atacgctggg ctacacacgt gctacaatgg 1200
gtagtacaga gagtcgcaaa cctgcgaggg ggagctaatc tcagaaaact attctcagtt 1260
cggattgtac tctgcaactc gagtacatga agttggaatc gctagtaatc gcaaatcagc 1320
tatgttgcgg tgaatacgtt ctcgggtctt gtacacaccg cccgtcacac cacgagagtt 1380
ggttgcacct gaagtagcag gcctaaccgc aaggagggat gctccgaggg tgtgattagc 1440
gattggggtg aagtcgtaac aaggtatccg tacgggaacg tgcggatgga tcacctcctt 1500

<210> SEQ ID NO 25
<211> LENGTH: 1489
<212> TYPE: DNA
<213> ORGANISM: Unknown
<220> FEATURE:
<223> OTHER INFORMATION: Parabacteroides merdae

<400> SEQUENCE: 25
agagtttgat cctggctcag gatgaacgct agcgacaggc ttaacacatg caagtcgagg 60
ggcagcatga tttgtagcaa tacagattga tggcgaccgg cgcacgggtg agtaacgcgt 120
atgcaactta cctatcagag gggatagcc cggcgaaagt cggattaata ccccataaaa 180
caggggtccc gcatgggaat atttgttaaa gattcatcgc tgatagatag gcatgcgttc 240
cattaggcag ttggcggggt aacggcccac caaaccgacg atggataggg gttctgagag 300
gaaggtcccc cacattggta ctgagacacg gaccaaactc ctacgggagg cagcagtgag 360
gaatattggt caatggccga gaggctgaac cagccaagtc gcgtgaagga agaaggatct 420
atggtttgta aacttctttt ataggggaat aaagtggagg acgtgtcctt ttttgtatgt 480
accctatgaa taagcatcgg ctaactccgt gccagcagcc gcggtaatac ggaggatgcg 540
agcgttatcc ggatttattg ggtttaaagg gtgcgtaggt ggtgatttaa gtcagcggtg 600
aaagtttgtg gctcaaccat aaaattgccg ttgaaactgg gttacttgag tgtgtttgag 660
gtaggcggaa tgcgtggtgt agcggtgaaa tgcatagata tcacgcagaa ctccgattgc 720
gaaggcagct tactaaacca taactgacac tgaagcacga aagcgtgggg atcaaacagg 780
attagatacc ctggtagtcc acgcagtaaa cgatgattac taggagtttg cgatacaatg 840
taagctctac agcgaaagcg ttaagtaatc cacctgggga gtacgccggc aacggtgaaa 900
ctcaaaggaa ttgacggggg cccgcacaag cggaggaaca tgtggtttaa ttcgatgata 960
cgcgaggaac cttacccggg tttgaacgta gtctgaccgg agtggaaaca ctctttctag 1020

```
caatagcaga ttacgaggtg ctgcatggtt gtcgtcagct cgtgccgtga ggtgtcggct   1080

taagtgccat aacgagcgca acccttatca ctagttacta acaggtgaag ctgaggactc   1140

tggtgagact gccagcgtaa gctgtgagga aggtggggat gacgtcaaat cagcacggcc   1200

cttacatccg ggcgacacac cgtgttacaa tggcatggac aaagggcagc tacctggtga   1260

caggatgcta atctccaaac catgtctcag ttcggatcgg agtctgcaac tcgactccgt   1320

gaagctggat tcgctagtaa tcgcgcatca gccatggcgc ggtgaatacg ttcccgggcc   1380

ttgtacacac cgcccgtcaa gccatgggag ccgggggtac ctgaagtccg taaccgcaag   1440

gatcggccta gggtaaaact ggtgactggg gctaagtcgt aacaaggta               1489
```

```
<210> SEQ ID NO 26
<211> LENGTH: 1522
<212> TYPE: DNA
<213> ORGANISM: Unknown
<220> FEATURE:
<223> OTHER INFORMATION: Coprococcus_B comes

<400> SEQUENCE: 26

gagagtttga tcctggctca ggatgaacgc tggcggcgtg cttaacacat gcaagtcgaa     60

cgaagcactt acctttgatt cttcggatga aggtttttgt gactgagtgg cggacgggtg    120

agtaacgcgt gggtaacctg cctcatacag ggggataaca gttagaaatg actgctaata    180

ccgcataaga ccacagagct gcatggctca gtgggaaaaa ctccggtggt atgagatgga    240

cccgcgtctg attaggtagt tggtggggta acggcctacc aagccaacga tcagtagccg    300

acctgagagg gtgaccggcc acattgggac tgagacacgg cccaaactcc tacgggaggc    360

agcagtgggg aatattgcac aatgggggaa accctgatgc agcgacgccg cgtgagcgaa    420

gaagtatttc ggtatgtaaa gctctatcag cagggaagaa aatgacggta cctgactaag    480

aagcaccggc taaatacgtg ccagcagccg cggtaatacg tatggtgcaa gcgttatccg    540

gatttactgg gtgtaaaggg agcgtagacg gctgtgtaag tctgaagtga aagcccgggg    600

ctcaaccccg ggactgcttt ggaaactatg cagctagagt gtcggagagg taagtggaat    660

tcccagtgta gcggtgaaat gcgtagatat tgggaggaac accagtggcg aaggcggctt    720

actggacgat gactgacgtt gaggctcgaa agcgtgggga gcaaacagga ttagataccc    780

tggtagtcca cgccgtaaac gatgactact aggtgtcggg gagcagagct cttcggtgcc    840

gcagcaaacg caataagtag tccacctggg gagtacgttc gcaagaatga aactcaaagg    900

aattgacggg gacccgcaca agcggtggag catgtggttt aattcgaagc aacgcgaaga    960

accttacctg ctcttgacat cccggtgacc ggcatgtaat gatgcctttt cttcggaaca   1020

ccggtgacag gtggtgcatg gttgtcgtca gctcgtgtcg tgagatgttg ggttaagtcc   1080

cgcaacgagc gcaaccctta tcttcagtag ccagcaattc ggatgggcac tctggagaga   1140

ctgccaggga taacctggag gaaggtgggg atgacgtcaa atcatcatgc cccttatgag   1200

cagggctaca cacgtgctac aatgacgtaa acaaagggaa gcgagcctgc gagggtaagc   1260

aaatctcaaa aataacgtct cagttcggat tgtagtctgc aactcgacta catgaagctg   1320

gaatcgctag taatcgcgaa tcagcatgtc gcggtgaata cgttcccggg tcttgtacac   1380

accgcccgtc acaccatggg agttggtaac gcccgaagtc agtgacccaa ccgtaaggag   1440

ggagctgccg aaggtgggac cgataactgg ggtgaagtcg taacaaggta gccgtatcgg   1500

aaggtgcggc tggatcacct cc                                            1522
```

<210> SEQ ID NO 27
<211> LENGTH: 1521
<212> TYPE: DNA
<213> ORGANISM: Unknown
<220> FEATURE:
<223> OTHER INFORMATION: Agathobacter rectale

<400> SEQUENCE: 27

```
agagtttgat cctggctcag gatgaacgct ggcggcgtgc ttaacacatg caagtcgaac     60

gaagcacttt atttgatttc cttcgggact gattattttg tgactgagtg gcggacgggt    120

gagtaacgcg tgggtaacct gccttgtaca gggggataac agttggaaac ggctgctaat    180

accgcataag cgcacggcat cgcatgatgc agtgtgaaaa actccggtgg tataagatgg    240

acccgcgttg gattagctag ttggtgaggt aacggcccac caaggcgacg atccatagcc    300

gacctgagag ggtgaccggc cacattggga ctgagacacg gcccaaactc ctacgggagg    360

cagcagtggg gaatattgca caatgggcga aagcctgatg cagcgacgcc gcgtgagcga    420

agaagtattt cggtatgtaa agctctatca gcagggaaga taatgacggt acctgactaa    480

gaagcaccgg ctaaatacgt gccagcagcc gcggtaatac gtatggtgca agcgttatcc    540

ggatttactg ggtgtaaagg gagcgcaggc ggtgcggcaa gtctgatgtg aaagcccggg    600

gctcaacccc ggtactgcat tggaaactgt cgtactagag tgtcggaggg gtaagcggaa    660

ttcctagtgt agcggtgaaa tgcgtagata ttaggaggaa caccagtggc gaaggcggct    720

tactggacga taactgacgc tgaggctcga aagcgtgggg agcaaacagg attagatacc    780

ctggtagtcc acgccgtaaa cgatgaatac taggtgttgg gaagcattgc ttctcggtgc    840

cgtcgcaaac gcagtaagta ttccacctgg ggagtacgtt cgcaagaatg aaactcaaag    900

gaattgacgg ggacccgcac aagcggtgga gcatgtggtt taattcgaag caacgcgaag    960

aaccttacca agtcttgaca tccttctgac cggtacttaa ccgtaccttc tcttcggagc   1020

aggagtgaca ggtggtgcat ggttgtcgtc agctcgtgtc gtgagatgtt gggttaagtc   1080

ccgcaacgag cgcaaccctt atctttagta gccagcggtt cggccgggca ctctagagag   1140

actgccaggg ataacctgga ggaaggcggg gatgacgtca aatcatcatg ccccttatga   1200

cttgggctac acacgtgcta caatggcgta aacaaaggga agcaaagctg tgaagccgag   1260

caaatctcaa aaataacgtc tcagttcgga ctgtagtctg caacccgact acacgaagct   1320

ggaatcgcta gtaatcgcag atcagaatgc tgcggtgaat acgttcccgg gtcttgtaca   1380

caccgcccgt cacaccatgg gagttgggaa tgcccgaagc cagtgaccta accgaaagga   1440

aggagctgtc gaaggcaggc tcgataactg gggtgaagtc gtaacaaggt agccgtatcg   1500

gaaggtgcgg ctggatcacc t                                             1521
```

<210> SEQ ID NO 28
<211> LENGTH: 1509
<212> TYPE: DNA
<213> ORGANISM: Unknown
<220> FEATURE:
<223> OTHER INFORMATION: Erysipelatoclostridium ramosum

<400> SEQUENCE: 28

```
gagagtttga tcctggctca ggatgaacgc tggcggcgtg cctaatacat gcaagtcgaa     60

cgcgagcact tgtgctcgag tggcgaacgg gtgagtaata cataagtaac ctgccctaga    120

cagggggata actattggaa acgatagcta agaccgcata ggtacggaca ctgcatggtg    180

accgtattaa aagtgcctca aagcactggt agaggatgga cttatggcgc attagctggt    240
```

```
tggcggggta acggcccacc aaggcgacga tgcgtagccg acctgagagg gtgaccggcc    300

acactgggac tgagacacgg cccagactcc tacgggaggc agcagtaggg aattttcggc    360

aatgggggaa accctgaccg agcaacgccg cgtgaaggaa gaaggttttc ggattgtaaa    420

cttctgttat aaaggaagaa cggcggctac aggaaatggt agccgagtga cggtacttta    480

ttagaaagcc acggctaact acgtgccagc agccgcggta atacgtaggt ggcaagcgtt    540

atccggaatt attgggcgta aagagggagc aggcggcagc aagggtctgt ggtgaaagcc    600

tgaagcttaa cttcagtaag ccatagaaac caggcagcta gagtgcagga gaggatcgtg    660

gaattccatg tgtagcggtg aaatgcgtag atatatggag gaacaccagt ggcgaaggcg    720

acgatctggc ctgcaactga cgctcagtcc cgaaagcgtg gggagcaaat aggattagat    780

accctagtag tccacgccgt aaacgatgag tactaagtgt tggatgtcaa agttcagtgc    840

tgcagttaac gcaataagta ctccgcctga gtagtacgtt cgcaagaatg aaactcaaag    900

gaattgacgg gggcccgcac aagcggtgga gcatgtggtt taattcgaag caacgcgaag    960

aaccttacca ggtcttgaca tactcataaa ggctccagag atggagagat agctatatga   1020

gatacaggtg gtgcatggtt gtcgtcagct cgtgtcgtga gatgttgggt taagtcccgc   1080

aacgagcgca acccttatcg ttagttacca tcattaagtt ggggactcta gcgagactgc   1140

cagtgacaag ctggaggaag gcggggatga cgtcaaatca tcatgcccct atgacctggg   1200

ctacacgtgc tacaatggat ggtgcagaga gaggcgagcc gcgggcgaaa caaaagccca   1260

taaaaccatt tcagttccgg attgtagtct gcaactcgac tttattacat gagagttgga   1320

atcgctagta atcgcgaatc agcatgtcgc ggtttgaata cgttctcggg ccttaccgcc   1380

cgtcacacca aaggattgat aacacggcgg tggctaaccg caaggaaagg ctgtctaagg   1440

tgggattgat gattggggta aagtcgtaac gaaggtatcc ctacgggaac gtggggatgg   1500

atcacctcc                                                           1509
```

```
<210> SEQ ID NO 29
<211> LENGTH: 1496
<212> TYPE: DNA
<213> ORGANISM: Unknown
<220> FEATURE:
<223> OTHER INFORMATION: Clostridium_M citroniae

<400> SEQUENCE: 29

agagtttgat cctggctcag gatgaacgct ggcggcgtgc ctaacacatg caagtcgaac     60

gaagcaatta gaaagaagtt ttcggatgga tttctgattg actgagtggc ggacgggtga    120

gtaacgcgtg gataacctgc ctcacactgg gggataacag ttagaaatgg ctgctaatac    180

cgcataagcg cacagtaccg catggtacgg tgtgaaaaac tccggtggtg tgagatggat    240

ccgcgtctga ttagttagtt ggcggggtaa cggcccacca agacagcgat cagtagccga    300

cctgagaggg tgaccggcca cattgggact gagacacggc ccaaactcct acgggaggca    360

gcagtgggga atattgcaca atgggcgaaa gcctgatgca gcgacgccgc gtgagtgaag    420

aagtatttcg gtatgtaaag ctctatcagc agggaagaaa ctgacggtac ctgactaaga    480

agccccggct aactacgtgc cagcagccgc ggtaatacgt agggggcaag cgttatccgg    540

atttactggg tgtaaaggga gcgtagacgg cgaagcaagt ctggagtgaa aacccagggc    600

tcaaccctgg gactgctttg gaaactgttt tgctagagtg tcggagaggt aagtggaatt    660

cctagtgtag cggtgaaatg cgtagatatt aggaggaaca ccagtggcga aggcggctta    720

ctggacgata actgacgttg aggctcgaaa gcgtggggag caaacaggat tagataccct    780
```

```
ggtagtccac gccgtaaacg atgaatgcta ggtgttgggg ggcaaagccc ttcggtgccg    840

tcgcaaacgc aataagcatt ccacctgggg agtacgttcg caagaatgaa actcaaagga    900

attgacgggg acccgcacaa gcggtggagc atgtggttta attcgaagca acgcgaagaa    960

ccttaccaag tcttgacatc cccctgaccg gtcagtaaag tgacctttcc ttcgggacag   1020

gggagacagg tggtgcatgg ttgtcgtcag ctcgtgtcgt gagatgttgg gttaagtccc   1080

gcaacgagcg caacccttat ccttagtagc cagcaggtaa agctgggcac tctagggaga   1140

ctgccaggga taacctggag gaaggtgggg atgacgtcaa atcatcatgc cccttatgat   1200

ttgggctaca cacgtgctac aatggcgtaa acaaagggaa gcgaccctgc gaaggcaagc   1260

aaatcccaaa aataacgtcc cagttcggac tgtagtctgc aacccgacta cacgaagctg   1320

gaatcgctag taatcgcgaa tcagaatgtc gcggtgaata cgttcccggg tcttgtacac   1380

accgcccgtc acaccatggg agtcagcaac gcccgaagtc agtgacccaa ccgaaaggag   1440

ggagctgccg aaggcggggc aggtaactgg ggtgaagtcg taacaaggta gccgta       1496
```

<210> SEQ ID NO 30
<211> LENGTH: 1293
<212> TYPE: DNA
<213> ORGANISM: Unknown
<220> FEATURE:
<223> OTHER INFORMATION: Bacteroides faecis

<400> SEQUENCE: 30

```
atgaagagtt tgatcctggc tcaggatgaa cgctagctac aggcttaaca catgcaagtc     60

gaggggcatc aggaagaaag cttgctttct ttgctggcga ccggcgcacg ggtgagtaac    120

acgtatccaa cctgcccttt actcggggat agcctttcga aagaaagatt aatacccgat    180

ggcataatga ttccgcatgg tttcattatt aaaggattcc ggtaaaggat ggggatgcgt    240

tccattaggt tgttggtgag gtaacggctc accaagcctt cgatggatag ggttctgag    300

aggaaggtcc cccacattgg aactgagaca cggtccaaac tcctacggga ggcagcagtg    360

aggaatattg gtcaatgggc gatagcctga accagccaag tagcgtgaag gatgactgcc    420

ctatgggttg taaacttctt ttataaagga ataaagtcgg gtatgcatac ccgtttgcat    480

gtactttatg aataaggatc ggctaactcc gtgccagcag ccgcggtaat acggaggatc    540

cgagcgttat ccggatttat tgggtttaaa gggagcgtag gtggatgttt aagtcagttg    600

tgaaagtttg cggctcaacc gtaaaattgc agttgatact ggctgtcttg agtgcagttg    660

aggcaggcgg aattcgtggt gtagcggtga aatgcttaga tatcacgaag aactccgatt    720

gcgaaggcag cctgctaagc tgcaactgac attgaggctc gaaagtgtgg gtatcaaaca    780

ggattagata ccctggtagt ccacacggta aacgatgaat actcgctgtt tgcgatatac    840

ggcaagcggc caagcgaaag cgttaagtat tccacctggg gagtacgccg gcaacggtga    900

aactcaaagg aattgacggg ggcccgcaca agcggaggaa catgtggttt aattcgatga    960

tacgcgagga accttacccg ggcttaaatt gcagtggaat gatgtggaaa catgtcagtg   1020

agcaatcacc gctgtgaagg tgctgcatgg ttgtcgtcag ctcgtgccgt gaggtgtcgg   1080

cttaagtgcc ataacgagcg caacccttat ctttagttac taacaggtga tgctgaggac   1140

tctggagaga ctgccatcgt aagatgtgag gaaggtgggg atgacgtcaa atcagcacgg   1200

cccttacgtc cggggctaca cacgtgttac aatgggaggt acagaaggca gctacccggc   1260

gacgggatgc caatccccaa aacctctctc agt                                1293
```

<210> SEQ ID NO 31
<211> LENGTH: 1505
<212> TYPE: DNA
<213> ORGANISM: Bacteroides ovatus

<400> SEQUENCE: 31
atgaagagtt tgatcctggc tcaggatgaa cgctagctac aggcttaaca catgcaagtc 60
gaggggcagc atggtcttag cttgctaagg ctgatggcga ccggcgcacg ggtgagtaac 120
acgtatccaa cctgccgtct actcttggcc agccttctga aaggaagatt aatccaggat 180
gggatcatga gttcacatgt ccgcatgatt aaaggtattt tccggtagac gatggggatg 240
cgttccatta gatagttggc ggggtaacgg cccaccaaac cgacgatgga taggggttct 300
gagaggaagg tcccccacat tggtactgag acacggacca aactcctacg ggaggcagca 360
gtgaggaata ttggtcaatg ggcgagagcc tgaaccagcc aagtagcgtg aaggatgact 420
gccctatggg ttgtaaactt cttttataag ggaataaagt cgggtatgca tacccgtttg 480
catgtacttt atgaataagg atcggctaac tccgtgccag cagccgcggt aatacggagg 540
atccgagcgt tatccggatt tattgggttt aaagggagcg taggtggacg tttaagtcag 600
ttgtgaaagt ttgcggctca accgtaaaat tgcagttgat actggatgtc ttgagtgcag 660
ttgaggcagg cggaattcgt ggtgtagcgg tgaaatgctt agatatcacg aagaactccg 720
attgcgaagg cagcctgcta agctgcaact gacattgagg ctcgaaagtg tgggtatcaa 780
acaggattag ataccctggt agtccacacg gtaaacgatg aatactcgct gtttgcgata 840
tacggcaagc ggccaagcga aagcgttaag tattccacct ggggagtacg ccggcaacgg 900
tgaaactcaa aggaattgac gggggcccgc acaagcggag gaacatgtgg tttaattcga 960
tgatacgcga ggaaccttac ccgggcttaa attgcagacg aattacgagg aaacttgtaa 1020
gccgcaaggc gtctgtgaag gtgctgcatg gttgtcgtca gctcgtgccg tgaggtgtcg 1080
gcttaagtgc cataacgagc gcaaccctta tctttagtta ctaacaggtt atgctgagga 1140
ctctagagag actgccatcg taagatgtga ggaaggtggg gatgacgtca aatcagcacg 1200
gcccttacgt ccggggctac acacgtgtta caatgggggg tacagagggc cgctaccacg 1260
cgagtggatg ccaatcccta aaacccctct cagttcggac tggagtctgc aacccgactc 1320
cacgaagctg gattcgctag taatcgcgca tcagccacgg cgcggtgaat acgttcccgg 1380
gccttgtaca caccgcccgt caagccatgg gagccggggg tacctgaagt gcgtaaccgc 1440
gaggatcgcc ctagggtaaa actggtgact ggggctaagt cgtaacaagg tagccgtacc 1500
ggaag 1505

<210> SEQ ID NO 32
<211> LENGTH: 1511
<212> TYPE: DNA
<213> ORGANISM: Bifidobacterium pseudocatenulatum

<400> SEQUENCE: 32
ttcgattctg gctcaggatg aacgctggcg gcgtgcttaa cacatgcaag tcgaacggga 60
tccatcaggc tttgcttggt ggtgagagtg gcgaacgggt gagtaatgcg tgaccgacct 120
gccccataca ccggaatagc tcctggaaac gggtggtaat gccggatgct ccgactcctc 180
gcatggggtg tcgggaaaga tttcatcggt atgggatggg gtcgcgtcct atcaggtagt 240
cggcggggta acggcccacc gagcctacga cgggtagccg gcctgagagg gcgaccggcc 300
acattgggac tgagatacgg cccagactcc tacgggaggc agcagtgggg aatattgcac 360

```
aatgggcgca agcctgatgc agcgacgccg cgtgcgggat gacggccttc gggttgtaaa    420
ccgcttttga tcgggagcaa gccttcgggt gagtgtacct ttcgaataag caccggctaa    480
ctacgtgcca gcagccgcgg taatacgtag ggtgcaagcg ttatccggaa ttattgggcg    540
taaagggctc gtaggcggtt cgtcgcgtcc ggtgtgaaag tccatcgctt aacggtggat    600
ctgcgccggg tacgggcggg ctggagtgcg gtaggggaga ctggaattcc cggtgtaacg    660
gtggaatgtg tagatatcgg gaagaacacc aatggcgaag gcaggtctct gggccgttac    720
tgacgctgag gagcgaaagc gtggggagcg aacaggatta gataccctgg tagtccacgc    780
cgtaaacggt ggatgctgga tgtggggccc gttccacggg ttccgtgtcg gagctaacgc    840
gttaagcatc ccgcctgggg agtacggccg caaggctaaa actcaaagaa attgacgggg    900
gcccgcacaa gcggcggagc atgcggatta attcgatgca acgcgaagaa ccttacctgg    960
gcttgacatg ttcccgacag ccgtagagat atggcctccc ttcggggcgg gttcacaggt   1020
ggtgcatggt cgtcgtcagc tcgtgtcgtg agatgttggg ttaagtcccg caacgagcgc   1080
aaccctcgcc ctgtgttgcc agcacgtcat ggtgggaact cacgggggac cgccggggtc   1140
aactcggagg aaggtgggga tgacgtcaga tcatcatgcc ccttacgtcc agggcttcac   1200
gcatgctaca atggccggta caacgggatg cgacacggcg acgtggagcg gatccctgaa   1260
aaccggtctc agttcggatt ggagtctgca acccgactcc atgaaggcgg agtcgctagt   1320
aatcgcggat cagcaacgcc gcggtgaatg cgttcccggg ccttgtacac accgcccgtc   1380
aagtcatgaa agtgggtagc acccgaagcc ggtggcctaa ccctttgtgg atggagccgt   1440
ctaaggtgag actcgtgatt gggactaagt cgtaacaagg tagccgtacc ggaaggtgcg   1500
gctggatcac c                                                        1511
```

<210> SEQ ID NO 33
<211> LENGTH: 1452
<212> TYPE: DNA
<213> ORGANISM: Unknown
<220> FEATURE:
<223> OTHER INFORMATION: Anaerostipes caccae

<400> SEQUENCE: 33

```
gcttaacaca tgcaagtcga acgaagcatt taggattgaa gttttcggat ggatttccta     60
tatgactgag tggcggacgg gtgagtaacg cgtggggaac ctgccctata caggggggata   120
acagctggaa acggctgcta ataccgcata agcgcacaga atcgcatgat tcagtgtgaa    180
aagccctggc agtataggat ggtcccgcgt ctgattagct ggttggtgag gtaacggctc    240
accaaggcga cgatcagtag ccggcttgag agagtgaacg gccacattgg gactgagaca    300
cggcccaaac tcctacggga ggcagcagtg gggaatattg cacaatgggg gaaaccctga    360
tgcagcgacg ccgcgtgagt gaagaagtat ttcggtatgt aaagctctat cagcagggaa    420
gaaaacagac ggtacctgac taagaagccc cggctaacta cgtgccagca gccgcggtaa    480
tacgtagggg gcaagcgtta tccggaatta ctgggtgtaa agggtgcgta ggtggcatgg    540
taagtcagaa gtgaaagccc ggggcttaac cccgggactg cttttgaaac tgtcatgctg    600
gagtgcagga gaggtaagcg gaattcctag tgtagcggtg aaatgcgtag atattaggag    660
gaacaccagt ggcgaaggcg gcttactgga ctgtcactga cactgatgca cgaaagcgtg    720
gggagcaaac aggattagat accctggtag tccacgccgt aaacgatgaa tactaggtgt    780
cggggccgta gaggcttcgg tgccgcagca aacgcagtaa gtattccacc tggggagtac    840
```

```
gttcgcaaga atgaaactca aaggaattga cggggacccg cacaagcggt ggagcatgtg    900

gtttaattcg aagcaacgcg aagaacctta cctggtcttg acatcccaat gaccgaacct    960

taaccggttt ttctttcgga gacattggag acaggtggtg catggttgtc gtcagctcgt   1020

gtcgtgagat gttgggttaa gtcccgcaac gagcgcaacc cctatcttta gtagccagca   1080

tttaaggtgg gcactctaga gagactgcca gggataacct ggaggaaggt ggggacgacg   1140

tcaaatcatc atgcccctta tggccagggc tacacacgtg ctacaatggc gtaaacaaag   1200

ggaagcgaag tcgtgaggcg aagcaaatcc cagaaataac gtctcagttc ggattgtagt   1260

ctgcaactcg actacatgaa gctggaatcg ctagtaatcg tgaatcagaa tgtcacggtg   1320

aatacgttcc cgggtcttgt acacaccgcc cgtcacacca tgggagtcag taacgcccga   1380

agtcagtgac ccaaccgcaa ggagggagct gccgaaggtg ggaccgataa ctggggtgaa   1440

gtcgtaacaa gg                                                       1452
```

<210> SEQ ID NO 34
<211> LENGTH: 1436
<212> TYPE: DNA
<213> ORGANISM: Bifidobacterium adolescentis

<400> SEQUENCE: 34

```
gtgagagtgg cgaacgggtg agtaatgcgt gaccgacctg ccccatacac cggaatagct     60

cctggaaacg ggtggtaatg ccggatgctc cagttggatg catgtccttc tgggaaagat    120

tcatcggtat gggatggggt cgcgtcctat cagcttgatg gcggggtaac ggcccaccat    180

ggcttcgacg ggtagccggc ctgagagggc gaccggccac attgggactg agatacggcc    240

cagactccta cgggaggcag cagtggggaa tattgcacaa tgggcgcaag cctgatgcag    300

cgacgccgcg tgcgggatga cggccttcgg gttgtaaacc gcttttgact gggagcaagc    360

ccttcggggt gagtgtacct ttcgaataag caccggctaa ctacgtgcca gcagccgcgg    420

taatacgtag ggtgcaagcg ttatccggaa ttattgggcg taaagggctc gtaggcggtt    480

cgtcgcgtcc ggtgtgaaag tccatcgctt aacggtggat ccgcgccggg tacgggcggg    540

cttgagtgcg gtaggggaga ctggaattcc cggtgtaacg gtggaatgtg tagatatcgg    600

gaagaacacc aatggcgaag gcaggtctct gggccgtcac tgacgctgag gagcgaaagc    660

gtggggagcg aacaggatta gataccctgg tagtccacgc cgtaaacggt ggatgctgga    720

tgtggggacc attccacggt ctccgtgtcg gagccaacgc gttaagcatc ccgcctgggg    780

agtacggccg caaggctaaa actcaaagaa attgacgggg gcccgcacaa gcggcggagc    840

atgcggatta attcgatgca acgcgaagaa ccttacctgg gcttgacatg ttcccgacag    900

ccccagagat ggggcctccc ttcggggcgg gttcacaggt ggtgcatggt cgtcgtcagc    960

tcgtgtcgtg agatgttggg ttaagtcccg caacgagcgc aaccctcgcc ctgtgttgcc   1020

agcacgtcgt ggtgggaact cacgggggac cgccggggtc aactcggagg aaggtgggga   1080

tgacgtcaga tcatcatgcc ccttacgtcc agggcttcac gcatgctaca atggccggta   1140

caacgggatg cgacactgtg aggtggagcg gatcccttaa aaccggtctc agttcggatt   1200

ggagtctgca acccgactcc atgaaggcgg agtcgctagt aatcgcggat cagcaacgcc   1260

gcggtgaatg cgttcccggg ccttgtacac accgcccgtc aagtcatgaa agtgggtagc   1320

acccgaagcc ggtggcccaa ccttttttggg gggagccgtc taaggtgaga ctcgtgattg   1380

ggactaagtc gtaacaaggt agccgtaccg gaaggtgcgg ctggatcacc tccttt       1436
```

<210> SEQ ID NO 35
<211> LENGTH: 1476
<212> TYPE: DNA
<213> ORGANISM: Unknown
<220> FEATURE:
<223> OTHER INFORMATION: Agathobaculum sp MUR_P3C8a

<400> SEQUENCE: 35
agtttgatcc tggctcagga tgaacgctgg cggcgtgcct aacacatgca agtcgaacgg 60
ggttattttg gaaaatcctt cgggattgga attcttaacc tagtggcgga cgggtgagta 120
acgcgtgagc aatctgcctt taagaggggg ataacagtcg gaaacggctg ctaataccgc 180
ataaagcatt gaattcgcat gttttcgatg ccaaaggagc aatccgcttt tagatgagct 240
cgcgtctgat tagctagttg gcggggtaac ggcccaccaa ggcgacgatc agtagccgga 300
ctgagaggtt gaacggccac attgggactg agacacggcc cagactccta cgggaggcag 360
cagtggggaa tattgcgcaa tgggggaac cctgacgcag caacgccgcg tgattgaaga 420
aggccttcgg gttgtaaaga tctttaatca gggacgaaac atgacggtac ctgaagaata 480
agctccggct aactacgtgc cagcagccgc ggtaatacgt agggagcaag cgttatccgg 540
atttactggg tgtaaagggc gcgcaggcgg gccggcaagt tggaagtgaa atccgggggc 600
ttaacccccg aactgctttc aaaactgctg gtcttgagtg atggagaggc aggcggaatt 660
ccgtgtgtag cggtgaaatg cgtagatata cggaggaaca ccagtggcga aggcggcctg 720
ctggacatta actgacgctg aggcgcgaaa gcgtggggag caaacaggat tagataccct 780
ggtagtccac gccgtaaacg atggatacta ggtgtgggag gtattgaccc cttccgtgcc 840
gcagttaaca caataagtat cccacctggg gagtacggcc gcaaggttga aactcaaagg 900
aattgacggg ggcccgcaca agcagtggag tatgtggttt aattcgaagc aacgcgaaga 960
accttaccag gccttgacat cccgatgacc ggtctagaga tagaccttct cttcggagca 1020
tcggagacag gtggtgcatg gttgtcgtca gctcgtgtcg tgagatgttg ggttaagtcc 1080
cgcaacgagc gcaaccctta cggttagttg atacgcaaga tcactctagc cggactgccg 1140
ttgacaaaac ggaggaaggt ggggacgacg tcaaatcatc atgcccctta tggcctgggc 1200
tacacacgta ctacaatggc agtcatacag agggaagcaa aatcgcgagg tggagcaaat 1260
ccctaaaagc tgtcccagtt cagattgcag gctgcaaccc gcctgcatga agtcggaatt 1320
gctagtaatc gcggatcagc atgccgcggt gaatacgttc ccgggccttg tacacaccgc 1380
ccgtcacacc atgagagccg tcaatacccg aagtccgtag cctaaccgta aggagggcgc 1440
ggccgaaggt aggggtggta attagggtga agtcgt 1476

<210> SEQ ID NO 36
<211> LENGTH: 1511
<212> TYPE: DNA
<213> ORGANISM: Unknown
<220> FEATURE:
<223> OTHER INFORMATION: Phascolarctobacterium faecium MUR_P6E9

<400> SEQUENCE: 36
atcctggctc aggacgaacg ctggcggcgt gcctaacaca tgcaagtcga acggagaatt 60
ttatttcggt agaattctta gtggcgaacg ggtgagtaac gcgtaggcaa cctgcccttt 120
agacggggac aacattccga aaggagtgct aataccggat gtgatcatcg tgccgcatgg 180
caggatgaag aaagatggcc tctacaagta agctatcgct aaaggatggg cctgcgtctg 240
attagctagt tggtagtgta acggactacc aaggcgatga tcagtagccg gtctgagagg 300
atgaacggcc acattgggac tgagacacgg cccaaactcc tacgggaggc agcagtgggg 360
aatcttccgc aatggacgaa agtctgacgg agcaacgccg cgtgagtgat gaaggatttc 420
ggtctgtaaa gctctgttgt ttatgacgaa cgtgcagtgt gtgaacaatg cattgcaatg 480
acggtagtaa acgaggaagc cacggctaac tacgtgccag cagccgcggt aatacgtagg 540
tggcgagcgt tgtccggaat tattgggcgt aaagagcatg taggcggctt aataagtcga 600
gcgtgaaaat gcggggctca accccgtatg gcgctggaaa ctgttaggct tgagtgcagg 660
agaggaaagg ggaattccca gtgtagcggt gaaatgcgta gatattggga ggaacaccag 720
tggcgaaggc gcctttctgg actgtgtctg acgctgagat gcgaaagcca gggtagcgaa 780
cgggattaga taccccggta gtcctggccg taaacgatgg gtactaggtg taggaggtat 840 cgacccctto tgtgccggag ttaacgcaat aagtaccccg cctggggagt acggccgcaa 900
ggttgaaact caaaggaatt gacgggggcc cgcacaagcg gtggagtatg tggtttaatt 960
cgacgcaacg cgaagaacct taccaaggct tgacattgat tgaacgctct agagatagag 1020
ctttcccttc ggggacaaga aaacaggtgg tgcatggctg tcgtcagctc gtgtcgtgag 1080
atgttgggtt aagtcccgca acgagcgcaa cccctatcct atgttaccag caagtaaagt 1140
tggggactca tgggagactg ccagggacaa cctggaggaa ggcggggatg acgtcaagtc 1200
atcatgcccc ttatgtcttg ggctacacac gtactacaat ggtcggaaac agagggaagc 1260
gaagccgcga ggcagagcaa accccagaaa cccgatctca gttcggatcg caggctgcaa 1320
cccgcctgcg tgaagtcgga atcgctagta atcgcaggtc agcatactgc ggtgaatacg 1380
ttcccgggcc ttgtacacac cgcccgtcac accacgaaag ttggtaacac ccgaagccgg 1440
tgaggtaacc tataaggagc cagccgtcta aggtggggcc gatgattggg gtgaagtcgt 1500
aacaaggtag c 1511

<210> SEQ ID NO 37
<211> LENGTH: 1505
<212> TYPE: DNA
<213> ORGANISM: Unknown
<220> FEATURE:
<223> OTHER INFORMATION: Akkermansia muciniphila

<400> SEQUENCE: 37
agagtttgat tctggctcag aacgaacgct ggcggcgtgg ataagacatg caagtcgaac 60
gagagaattg ctagcttgct aataattctc tagtggcgca cgggtgagta acacgtgagt 120
aacctgcccc caagagtggg atagccccgg gaaactggga ttaataccgc ataaaatcgc 180
aagattaaag cagcaatgcg cttggggatg ggctcgcgtc ctattagtta gttggtgagg 240
taacggctca ccaaggcgat gacgggtagc cggtctgaga ggatgtccgg ccacactgga 300
actgagacac ggtccagaca cctacgggtg gcagcagtcg agaatcattc acaatggggg 360
aaaccctgat ggtgcgacgc cgcgtggggg aatgaaggtc ttcggattgt aaacccctgt 420
catgtgggag caaattaaaa agatagtacc acaagaggaa gagacggcta actctgtgcc 480
agcagccgcg gtaatacaga ggtctcaagc gttgttcgga atcactgggc gtaaagcgtg 540
cgtaggcggt ttcgtaagtc gtgtgtgaaa ggcgggggct caacccccgg actgcacatg 600
atactgcgag actagagtaa tggaggggga accggaattc tcggtgtagc agtgaaatgc 660
gtagatatcg agaggaacac tcgtggcgaa ggcgggttcc tggacattaa ctgacgctga 720
ggcacgaagg ccaggggagc gaaagggatt agatacccct gtagtcctgg cagtaaacgg 780
tgcacgcttg gtgtgcgggg aatcgacccc ctgcgtgccg gagctaacgc gttaagcgtg 840

```
ccgcctgggg agtacggtcg caagattaaa actcaaagaa attgacgggg acccgcacaa    900

gcggtggagt atgtggctta attcgatgca acgcgaagaa ccttacctgg gcttgacatg    960

taatgaacaa catgtgaaag catgcgactc ttcggaggcg ttacacaggt gctgcatggc   1020

cgtcgtcagc tcgtgtcgtg agatgtttgg ttaagtccag caacgagcgc aacccctgtt   1080

gccagttacc agcacgtaaa ggtggggact ctggcgagac tgcccagatc aactgggagg   1140

aaggtgggga cgacgtcagg tcagtatggc ccttatgccc agggctgcac acgtactaca   1200

atgcccagta cagagggggc cgaagccgcg aggcggagga aatcctaaaa actgggccca   1260

gttcggactg taggctgcaa cccgcctaca cgaagccgga atcgctagta atggcgcatc   1320

agctacggcg ccgtgaatac gttcccgggt cttgtacaca ccgcccgtca catcatggaa   1380

gccggtcgca cccgaagtat ctgaagccaa ccgcaaggag gcagggtcct aaggtgagac   1440

tggtaactgg gatgaagtcg taacaaggta gccgtagggg aacctgcggc tggatcacct   1500

ccttt                                                               1505
```

<210> SEQ ID NO 38
<211> LENGTH: 1484
<212> TYPE: DNA
<213> ORGANISM: Unknown
<220> FEATURE:
<223> OTHER INFORMATION: Barnesiella intestinihomins

<400> SEQUENCE: 38

```
gatgaacgct agcgacaggc ctaacacatg caagtcgagg ggcagcgaag aggtagcaat     60

acctctgtcg gcgaccggcg cacgggtgag taacacgtat gcaatccacc tgtaacaggg    120

ggataacccg gagaaatccg gactaatacc ccataatatg ggcgctccgc atggagagtt    180

cattaaagag agcaattttg gttacagacg agcatgcgct ccattagcca gttggcgggg    240

taacggccca ccaaagcgac gatggatagg ggttctgaga ggaaggtccc ccacattgga    300

actgagacac ggtccaaact cctacgggag gcagcagtga ggaatattgg tcaatggtcg    360

gcagactgaa ccagccaagt cgcgtgaggg aagacggccc tacgggttgt aaacctcttt    420

tgtcggagag taaagtacgc tacgtgtagc gtattgcaag tatccgaaga aaaagcatcg    480

gctaactccg tgccagcagc cgcggtaata cggaggatgc gagcgttatc cggatttatt    540

gggtttaaag ggtgcgtagg cggcacgcca agtcagcggt gaaatttccg ggctcaaccc    600

ggagtgtgcc gttgaaactg gcgagctaga gtgcacaaga ggcaggcgga atgcgtggtg    660

tagcggtgaa atgcatagat atcacgcaga accccgattg cgaaggcagc ctgctagggt    720

gaaacagacg ctgaggcacg aaagcgtggg tatcgaacag gattagatac cctggtagtc    780

cacgcagtaa acgatgaata ctaactgttt gcgatacaat gtaagcggta cagcgaaagc    840

gttaagtatt ccacctgggg agtacgccgg caacggtgaa actcaaagga attgacgggg    900

gcccgcacaa gcggaggaac atgtggttta attcgatgat acgcgaggaa ccttacccgg    960

gctcaaacgc agggggaatg tcggtgaaag ccggcagcta gtaatagtca cctgcgaggt   1020

gctgcatggt tgtcgtcagc tcgtgccgtg aggtgtcggc ttaagtgcca taacgagcgc   1080

aacccctatc gacagttact aacgggtgaa gccgaggact ctgtcgagac tgccggcgca   1140

agccgcgagg aaggtgggga tgacgtcaaa tcagcacggc ccttacgtcc ggggcgacac   1200

acgtgttaca atggcaggta cagaaggcag ccagtcagca atgacgcgcg aatcccgaaa   1260

acctgtctca gttcggattg gagtctgcaa cccgactcca tgaagctgga ttcgctagta   1320
```

atcgcgcatc agccatggcg cggtgaatac gttcccgggc cttgtacaca ccgcccgtca 1380
agccatggaa gccgggagta cctgaagcat gcaaccgcaa ggagcgtacg aaggtaatac 1440
cggtaactgg ggctaagtcg taacaaggta gccgtaccgg aagg 1484

<210> SEQ ID NO 39
<211> LENGTH: 1543
<212> TYPE: DNA
<213> ORGANISM: Bilophila wadsworthia

<400> SEQUENCE: 39
agagtttgat tctggctcag attgaacgct ggcggcgtgc ttaacacatg caagtcgaac 60
gtgaaagtcc ttcggggcga gtaaagtggc gcacgggtga gtaacgcgtg gataatctac 120
ccttaagatg ggataacgg ctggaaacgg tcgctaatac cgaatacgct cccgatttta 180
tcgttggggg gaaagatggc ctctgcttgc aagctatcgc ttaaggatga gtccgcgtcc 240
cattagctag ttggcggggt aacggcccac caaggcaacg atgggtagcc ggtctgagag 300
gatgaccggc cacactggaa ctggaacacg gtccagactc ctacgggagg cagcagtggg 360
gaatattgcg caatgggcga aagcctgacg cagcgacgcc gcgtgaggga tgaaggttct 420
cggatcgtaa acctctgtca ggggggaaga aaccccctcg tgtgaataat gcgagggctt 480
gacggtaccc ccaaaggaag caccggctaa ctccgtgcca gcagccgcgg taatacggag 540
ggtgcaagcg ttaatcggaa tcactgggcg taaagcgcac gtaggcggct tggtaagtca 600
ggggtgaaat cccacagccc aactgtggaa ctgcctttga tactgccagg cttgagtacc 660
ggagagggtg gcggaattcc aggtgtagga gtgaaatccg tagatatctg gaggaacacc 720
ggtggcgaag gcggccacct ggacggtaac tgacgctgag gtgcgaaagc gtgggtagca 780
aacaggatta gataccctgg tagtccacgc tgtaaacgat gggtgctggg tgctgggatg 840
tatgtctcgg tgccgtagct aacgcgataa gcaccccgcc tggggagtac ggtcgcaagg 900
ctgaaactca aagaaattga cgggggcccg cacaagcggt ggagtatgtg gtttaattcg 960
atgcaacgcg aagaacctta cccaggcttg acatctaggg aacccttcgg aaatgaaggg 1020
gtgcccttcg gggagcccta agacaggtgc tgcatggctg tcgtcagctc gtgccgtgag 1080
gtgttgggtt aagtcccgca acgagcgcaa cccctatctt cagttgccag caggtaaggc 1140
tgggcactct ggagagaccg ccccggtcaa cggggaggaa ggtggggacg acgtcaagtc 1200
atcatggccc ttacgcctgg ggctacacac gtactacaat ggcgcgcaca aagggtagcg 1260
agaccgcgag gtggagccaa tcccaaaaaa cgcgtcccag tccggattgg agtctgcaac 1320
tcgactccat gaagtcggaa tcgctagtaa ttcgagatca gcatgctcgg gtgaatgcgt 1380
tcccgggcct tgtacacacc gcccgtcaca ccacgaaagt cggttttacc cgaagccggt 1440
gagctaactc gcaagagaag cagccgtcta cggtagggcc gatgattggg gtgaagtcgt 1500
aacaaggtag ccgtagggga acctgcggct ggatcacctc ctt 1543

<210> SEQ ID NO 40
<211> LENGTH: 1487
<212> TYPE: DNA
<213> ORGANISM: Unknown
<220> FEATURE:
<223> OTHER INFORMATION: Blautia faecis

<400> SEQUENCE: 40
agagtttgat cctggctcag gatgaacgct ggcggcgtgc ttaacacatg caagtcgaac 60
gggaaatact ttattgaaac ttcggtcgat ttaatttatt tctagtggcg gacgggtgag 120

```
taacgcgtgg gtaacctgcc ttataccggg ggataacagc cagaaatggc tgctaatacc    180
gcataagcgc acagaaccgc atggttcggt gtgaaaaact ccggtggtat aagatggacc    240
cgcgttggat tagctagttg gcagggcagc ggcctaccaa ggcgacgatc catagccggc    300
ctgagagggt gaacggccac attgggactg agacacggcc cagactccta cgggaggcag    360
cagtggggaa tattgcacaa tggggggaaac cctgatgcag cgacgccgcg tgaaggaaga    420
agtatctcgg tatgtaaact tctatcagca gggaagataa tgacggtacc tgactaagaa    480
gccccggcta actacgtgcc agcagccgcg gtaatacgta gggggcaagc gttatccgga    540
tttactgggt gtaaagggag cgtagacggc gcagcaagtc tgatgtgaaa ggcaggggct    600
taacccctgg actgcattgg aaactgctgt gcttgagtgc cggaggggta agcggaattc    660
ctagtgtagc ggtgaaatgc gtagatatta ggaggaacac cagtggcgaa ggcggcttac    720
tggacggtaa ctgacgttga ggctcgaaag cgtggggagc aaacaggatt agataccctg    780
gtagtccacg ccgtaaacga tgaatactag gtgtcaggga gcacagctct ttggtgccgc    840
cgcaaacgca ttaagtattc cacctgggga gtacgttcgc aagaatgaaa ctcaaaggaa    900
ttgacgggga cccgcacaag cggtggagca tgtggtttaa ttcgaagcaa cgcgaagaac    960
cttaccaaat cttgacatcc ctctgaccgg gacttaaccg tccctttcct tcgggacagg   1020
ggagacaggt ggtgcatggt tgtcgtcagc tcgtgtcgtg agatgttggg ttaagtcccg   1080
caacgagcgc aacccctatc cttagtagcc agcacgatgg tgggcactct gaggagactg   1140
ccagggataa cctggaggaa ggcggggatg acgtcaaatc atcatgcccc ttatgatttg   1200
ggctacacac gtgctacaat ggcgtaaaca aagggaagcg aacctgtgag ggtgggcaaa   1260
tctcaaaaat aacgtcccag ttcggactgc agtctgcaac tcgactgcac gaagctggaa   1320
tcgctagtaa tcgcggatca gaatgccgcg gtgaatacgt tcccgggtct tgtacacacc   1380
gcccgtcaca ccatgggagt cagtaacgcc cgaagtcagt gacctaaccg caagggagga   1440
gctgccgaag gcgggaccga tgactggggt gaagtcgtaa caaggta                1487
```

```
<210> SEQ ID NO 41
<211> LENGTH: 1488
<212> TYPE: DNA
<213> ORGANISM: Unknown
<220> FEATURE:
<223> OTHER INFORMATION: Blautia wexlerae

<400> SEQUENCE: 41

agagtttgat cctggctcag gatgaacgct ggcggcgtgc ttaacacatg caagtcgaac     60
gggaattact ttattgaagc ttcggcagat ttagctggtt tctagtggcg gacgggtgag    120
taacgcgtgg gtaacctgcc ttgtacaggg ggataacagt cagaaatgac tgctaatacc    180
gcataagcgc acaggaccgc atggtccggt gtgaaaaact ccggtggtat aagatggacc    240
cgcgttggat tagcttgttg gtggggtaac ggcccaccaa ggcgacgatc catagccggc    300
ctgagagggt gaacggccac attgggactg agacacggcc cagactccta cgggaggcag    360
cagtggggaa tattgcacaa tgggggaaac cctgatgcag cgacgccgcg tgaaggaaga    420
agtatctcgg tatgtaaact tctatcagca gggaagaaaa tgacggtacc tgactaagaa    480
gccccggcta actacgtgcc agcagccgcg gtaatacgta gggggcaagc gttatccgga    540
tttactgggt gtaaagggag cgtagacgga tggacaagtc tgatgtgaaa ggctggggct    600
caaccccggg actgcattgg aaactgcccg tcttgagtgc cggagaggta agcggaattc    660
```

```
ctagtgtagc ggtgaaatgc gtagatatta ggaggaacac cagtggcgaa ggcggcttac     720

tggacggtaa ctgacgttga ggctcgaaag cgtggggagc aaacaggatt agataccctg     780

gtagtccacg cggtaaacga tgaatgctag gtgtcgggtg acaaagtcat tcggtgccgc     840

cgcaaacgca ttaagcattc cacctgggga gtacgttcgc aagaatgaaa ctcaaaggaa     900

ttgacgggga cccgcacaag cggtggagca tgtggtttaa ttcgaagcaa cgcgaagaac     960

cttaccaagt cttgacatcc ctctgaccgg aacttaaccg ttccttccct tcggggcaga    1020

ggagacaggt ggtgcatggt tgtcgtcagc tcgtgtcgtg agatgttggg ttaagtcccg    1080

caacgagcgc aacccctatc cccagtagcc agcatttaag gtgggcactc tggggagact    1140

gccagggata acctggagga aggcggggat gacgtcaaat catcatgccc cttatgattt    1200

gggctacaca cgtgctacaa tggcgtaaac aaagggaagc gaacccgcga gggtgggcaa    1260

atcccaaaaa taacgtccca gttcggactg tagtctgcaa cccgactaca cgaagctgga    1320

atcgctagta atcgcggatc agaatgccgc ggtgaatacg ttcccgggtc ttgtacacac    1380

cgcccgtcac accatgggag tcagtaacgc ccgaagtcag tgacctaacc gtaaggaggg    1440

agctgccgaa ggcgggaccg atgactgggg tgaagtcgta acaaggta                 1488
```

<210> SEQ ID NO 42
<211> LENGTH: 1477
<212> TYPE: DNA
<213> ORGANISM: Unknown
<220> FEATURE:
<223> OTHER INFORMATION: Blautia luti

<400> SEQUENCE: 42

```
ctggctcagg atgaacgctg gcggcgtgct taacacatgc aagtcgaacg ggaaatattt      60

cattgagact tcggtggatt tgatctattt ctagtggcgg acgggtgagt aacgcgtggg     120

taacctgcct tatacagggg gataacagtc agaaatggct gctaataccg cataagcgca     180

cagagctgca tggctcagtg tgaaaaactc cggtggtata agatggaccc gcgttggatt     240

agctggttgg tggggtaacg gcccaccaag gcgacgatcc atagccggcc tgagagggtg     300

aacggccaca ttgggactga gacacggccc agactcctac gggaggcagc agtggggaat     360

attgcacaat gggggaaacc ctgatgcagc gacgccgcgt gaaggaagaa gtatctcggt     420

atgtaaactt ctatcagcag ggaagatagt gacggtacct gactaagaag ccccggctaa     480

ctacgtgcca gcagccgcgg taatacgtag ggggcaagcg ttatccggat ttactgggtg     540

taaagggagc gtagacggtg tggcaagtct gatgtgaaag gcatgggctc aacctgtgga     600

ctgcattgga aactgtcata cttgagtgcc ggaggggtaa gcggaattcc tagtgtagcg     660

gtgaaatgcg tagatattag gaggaacacc agtggcgaag gcggcttact ggacggtaac     720

tgacgttgag gctcgaaagc gtggggagca aacaggatta gataccctgg tagtccacgc     780

cgtaaacgat gaatactagg tgtcggggag tatggctctt cggtgccgtc gcaaacgcag     840

taagtattcc acctggggag tacgttcgca agaatgaaac tcaaaggaat tgacggggac     900

ccgcacaagc ggtggagcat gtggtttaat tcgaagcaac gcgaagaacc ttaccaagtc     960

ttgacatccg cctgaccggt ccttaaccgg acctttcctt cgggacagga gagacaggtg    1020

gtgcatggtt gtcgtcagct cgtgtcgtga gatgttgggt taagtcccgc aacgagcgca    1080

acccctatcc tcagtagcca gcatttaagg tgggcactct ggggagactg ccagggataa    1140

cctggaggaa ggcggggatg acgtcaaatc atcatgcccc ttatgatttg ggctacacac    1200

gtgctacaat ggcgtaaaca aagggaagcg agatcgtgag atggagcaaa tcccaaaaat    1260
```

aacgtcccag ttcggactgt agtctgcaac ccgactacac gaagctggaa tcgctagtaa 1320
tcgcggatca gaatgccgcg gtgaatacgt tcccgggtct tgtacacacc gcccgtcaca 1380
ccatgggagt cagtaacgcc cgaagtcagt gacctaactg caaagaagga gctgccgaag 1440
gcgggaccga tgactggggt gaagtcgtaa caaggta 1477

<210> SEQ ID NO 43
<211> LENGTH: 1483
<212> TYPE: DNA
<213> ORGANISM: Unknown
<220> FEATURE:
<223> OTHER INFORMATION: Butyricimonas synergistica

<400> SEQUENCE: 43
agagtttgat cctggctcag gatgaacgct agcgacaggc ttaacacatg caagtcgagg 60
ggcagcacgg tgtagcaata cactggtggc gaccggcgca cgggtgagta acacgtgtgc 120
aaccaacccc gtaccgggag ataacccgcg gaaacgtgga ctaacatccc ataagactct 180
agagccgcat ggctctggat ttaaaattcc ggtggtacgg gacgggcacg cgcgacatta 240
ggtagttggc ggggtaacgg cccaccaagc cgacgatgtc taggggttct gagaggaagg 300
tcccccacac tggaactgag acacggtcca gactcctacg ggaggcagca gtgaggaata 360
ttggtcaatg ggcgcgagcc tgaaccagcc aagtcgcgtg agggaagaat ggtctatggc 420
ctgtaaacct cttttgtcaa ggaagaataa aaggtacgtg taccttcttg ccagtacttg 480
acgaataagc atcggctaac tccgtgccag cagccgcggt aatacggggg atgcgagcgt 540
tatccggatt tattgggttt aaagggcgcg taggcgggac gccaagtcag cggtaaaaga 600
ctgcagctaa actgtagcac gccgttgaaa ctggcgacct ggagacgaga cgagggaggc 660
ggaacaagtg aagtagcggt gaaatgctta gatatcactt ggaaccccga tagcgaaggc 720
agcttcccag gctcgatctg acgctgatgc gcgagagcgt gggtagcgaa caggattaga 780
taccctggta gtccacgccg taaacgatgc tcactggatc ttggcgatac actgccaggg 840
ttcaagcgaa agtattaagt gagccacctg gggagtacgt cggcaacgat gaaactcaaa 900
ggaattgacg gggcccgca caagcggagg aacatgtggt ttaattcgat gatacgcgag 960
gaaccttacc cgggtttaaa tgtattttgc atttcttgga aacaggaatt cccttcgggg 1020
ctagatacaa ggtgctgcat ggttgtcgtc agctcgtgcc gtgaggtgtc gggttaagtc 1080
ccataacgag cgcaacccct atcgccagtt gccatcggtt gaagccgggc actctgtcga 1140
gactgccacc gtaaggtgcg aggaaggcgg ggatgacgtc aaatcagcac ggcccttaca 1200
cccggggcga cacacgtgtt acaatggccg gtacagaggg cagccacggg gtgacccgga 1260
gcgaatctct aaagccggtc gtagttcgga ctggagtctg caacccgact ccacgaagtt 1320
ggattcgcta gtaatcgcgc atcagccatg gcgcggtgaa tacgttcccg ggccttgtac 1380
acaccgcccg tcaagccatg gaagccggga gtacctgaag atcgtgaccg cgaggaacgg 1440
gctagggtaa taccggtaac tggggctaag tcgtaacaag gta 1483

<210> SEQ ID NO 44
<211> LENGTH: 1496
<212> TYPE: DNA
<213> ORGANISM: Unknown
<220> FEATURE:
<223> OTHER INFORMATION: Clostridium bolteae

<400> SEQUENCE: 44

```
agagtttgat cctggctcag gatgaacgct ggcggcgtgc ctaacacatg caagtcgaac     60
gaagcaatta aaggaagttt tcggatggaa tttgattgac tgagtggcgg acgggtgagt    120
aacgcgtgga taacctgcct cacactgggg gataacagtt agaaatgact gctaataccg    180
cataagcgca cagtaccgca tggtacggtg tgaaaaactc cggtggtgtg agatggatcc    240
gcgtctgatt agccagttgg cggggtaacg gcccaccaaa gcgacgatca gtagccgacc    300
tgagagggtg accggccaca ttgggactga gacacggccc aaactcctac gggaggcagc    360
agtggggaat attgcacaat gggcgaaagc ctgatgcagc gacgccgcgt gagtgaagaa    420
gtatttcggt atgtaaagct ctatcagcag ggaagaaaat gacggtacct gactaagaag    480
ccccggctaa ctacgtgcca gcagccgcgg taatacgtag ggggcaagcg ttatccggat    540
ttactgggtg taaagggagc gtagacggcg aagcaagtct gaagtgaaaa cccagggctc    600
aaccctggga ctgctttgga aactgttttg ctagagtgtc ggagaggtaa gtggaattcc    660
tagtgtagcg gtgaaatgcg tagatattag gaggaacacc agtggcgaag gcggcttact    720
ggacgataac tgacgttgag gctcgaaagc gtggggagca aacaggatta gataccctgg    780
tagtccacgc cgtaaacgat gaatgctagg tgttgggggg caaagccctt cggtgccgtc    840
gcaaacgcag taagcattcc acctggggag tacgttcgca agaatgaaac tcaaaggaat    900
tgacggggac ccgcacaagc ggtggagcat gtggtttaat tcgaagcaac gcgaagaacc    960
ttaccaagtc ttgacatcct cttggccggc gtgtaacggc gccttccctt cggggcaaga   1020
gagacaggtg gtgcatggtt gtcgtcagct cgtgtcgtga gatgttgggt taagtcccgc   1080
aacgagcgca acccttatcc ttagtagcca gcaggtagag ctgggcactc tagggagact   1140
gccagggata acctggagga aggtggggat gacgtcaaat catcatgccc cttatgattt   1200
gggctacaca cgtgctacaa tggcgtaaac aaagggaagc aagacagtga tgtggagcaa   1260
atcccaaaaa taacgtccca gttcggactg tagtctgcaa cccgactaca cgaagctgga   1320
atcgctagta atcgcgaatc agaatgtcgc ggtgaatacg ttcccgggtc ttgtacacac   1380
cgcccgtcac accatgggag tcagcaacgc ccgaagtcag tgacccaact cgcaagagag   1440
ggagctgccg aaggcggggc aggtaactgg ggtgaagtcg taacaaggta gccgta       1496
```

<210> SEQ ID NO 45
<211> LENGTH: 1494
<212> TYPE: DNA
<213> ORGANISM: Unknown
<220> FEATURE:
<223> OTHER INFORMATION: Parasutterella excrementihominis

<400> SEQUENCE: 45

```
attgaacgct ggcggaacgc tttacacatg caagtcgaac ggtaacgtgg ggaggagctt     60
gctccacccc gacgacgagt ggcgaacggg tgagtaatac atcggaacgt gtccgcttgt    120
gggggacaac cagccgaaag gttggctaat accgcatgag ttctacggaa gaaagagggg    180
gacccgcaag ggcctctcgc gagcggagcg gccgatgact gattagccgg ttggtgaggt    240
aacggctcac caaagcaacg atcagtagct ggtctgagag gacgaccagc cacactggga    300
ctgagacacg gcccagactc ctacgggagg cagcagtggg gaattttgga caatgggcgc    360
aagcctgatc cagctattcc gcgtgtggga tgaaggccct cgggttgtaa accacttttg    420
tagagaacga aaagacacca tcgaataaat ggtgttgctg acggtactct aagaataagc    480
accggctaac tacgtgccag cagccgcggt aatacgtagg gtgcgagcgt taatcggaat    540
tactgggcgt aaagggtgcg caggcggttg agtaagacag atgtgaaatc cccgagctta    600
```

```
actcgggaat ggcatatgtg actgctcgac tagagtgtgt cagagggagg tggaattcca    660

cgtgtagcag tgaaatgcgt agatatgtgg aagaacaccg atggcgaagg cagcctcctg    720

ggacataact gacgctcagg cacgaaagcg tggggagcaa acaggattag ataccctggt    780

agtccacgcc ctaaacgatg ttaactagtt gttgggatgt aacaatctca gtaacgcagc    840

caacgcgaga agttaaccgc ctgggaagta cggtcgcaag actaaaactc aaaggaattg    900

acggggaccc gcacaagcgg tggatgatgt ggattaattc gatgcaacgc gaaaaacctt    960

acctaccctt gacatgtcag gaagctcttg taatgagagc gtgcccgcaa gggagcctga   1020

acacaggtgc tgcatggctg tcgtcagctc gtgtcgtgag atgttgggtt aagtcccgca   1080

acgagcgcaa cccttgtcac tagttgctac gaaagggcac tctagtgaga ctgccggtga   1140

caaaccggag gaaggtgggg atgacgtcaa gtcctcatgg cccttatggg tagggcttca   1200

cacgtcatac aatggtcgga acagagggca gcgaagccgt gaggcggagc caatcccaga   1260

aaaccgatcg tagtccggat tgcagtctgc aactcgactg catgaagtcg gaatcgctag   1320

taatcgcgga tcagcatgcc gcggtgaata cgttcccggg tcttgtacac accgcccgtc   1380

aaacaatggg agtggtgttt accagaagtc gttagcctaa ccgcaaggag ggcggcgacc   1440

acggtgagca ccgtgactaa tgttaagtcg taacaaggta gccgtaccgg aagg         1494


<210> SEQ ID NO 46
<211> LENGTH: 1490
<212> TYPE: DNA
<213> ORGANISM: Unknown
<220> FEATURE:
<223> OTHER INFORMATION: Prevotella copri

<400> SEQUENCE: 46

agagtttgat cctggctcag gatgaacgct agctacaggc ttaacacatg caagtcgagg     60

ggaaacgata ttggaagctt gcttccgata ggcgtcgacc ggcgcacggg tgagtaacgc    120

gtatccaacc tgcccaccac ttggggataa ccttgcgaaa gtaagactaa tacccaatga    180

tatctctaga agacatctga aagagattaa agatttatcg gtgatggatg gggatgcgtc    240

tgattagctt gttggcgggg taacggccca ccaaggcgac gatcagtagg ggttctgaga    300

ggaaggtccc ccacattgga actgagacac ggtccaaact cctacgggag gcagcagtga    360

ggaatattgg tcaatgggcg agagcctgaa ccagccaagt agcgtgcagg atgacggccc    420

tatgggttgt aaactgcttt tataagggaa taaagtgaga gtcgtgactc tttttgcatg    480

taccttatga ataaggaccg gctaattccg tgccagcagc cgcggtaata cggaaggtcc    540

gggcgttatc cggatttatt gggtttaaag ggagcgtagg ccggagatta agcgtgttgt    600

gaaatgtaga cgctcaacgt ctgcactgca gcgcgaactg gtttccttga gtacgcacaa    660

agtgggcgga attcgtggtg tagcggtgaa atgcttagat atcacgaaga actccgattg    720

cgaaggcagc tcactggagc gcaactgacg ctgaagctcg aaagtgcggg tatcgaacag    780

gattagatac cctggtagtc cgcacggtaa acgatggatg cccgctgttg gtctgaatag    840

gtcagcggcc aagcgaaagc attaagcatc ccacctgggg agtacgccgg caacggtgaa    900

actcaaagga attgacgggg gcccgcacaa gcggaggaac atgtggttta attcgatgat    960

acgcgaggaa ccttacccgg gcttgaattg cagaggaagg atttggagac aatgacgccc   1020

ttcggggcct ctgtgaaggt gctgcatggt tgtcgtcagc tcgtgccgtg aggtgtcggc   1080

ttaagtgcca taacgagcgc aacccctctc cttagttgcc atcaggttaa gctgggcact   1140
```

```
ctgggggcac tgccaccgta aggtgtgagg aaggtgggga tgacgtcaaa tcagcacggc   1200

ccttacgtcc ggggctacac acgtgttaca atggcaggta cagagagatg gtcccttgca   1260

aaacggatca aatccttaaa gcctgtctca gttcggactg gggtctgcaa cccgacccca   1320

cgaagctgga ttcgctagta atcgcgcatc agccatggcg cggtgaatac gttcccgggc   1380

cttgtacaca ccgcccgtca agccatgaaa gccgggggcg cctaaagtcc gtgaccgtaa   1440

ggagcggcct agggcgaaac tggtaattgg ggctaagtcg taacaaggta              1490
```

<210> SEQ ID NO 47
<211> LENGTH: 1520
<212> TYPE: DNA
<213> ORGANISM: Unknown
<220> FEATURE:
<223> OTHER INFORMATION: Ruminococcus faecis

<400> SEQUENCE: 47

```
tttgatcctg gctcaggatg aacgctggcg gcgtgcttaa cacatgcaag tcgaacgaag     60

caccttgatt tgattcttcg gatgaagatc ctggtgactg agtggcggac gggtgagtaa    120

cgcgtgggta acctgcctca tacaggggga taacagttag aaatgactgc taataccgca    180

taagaccaca gcaccgcatg gtgcaggggt aaaaactccg gtggtatgag atggacccgc    240

gtctgattag gtagttggtg gggtaacggc ctaccaagcc gacgatcagt agccgacctg    300

agagggtgac cggccacatt gggactgaga cacggcccaa actcctacgg gaggcagcag    360

tggggaatat tgcacaatgg gggaaaccct gatgcagcga cgccgcgtga gcgatgaagt    420

atttcggtat gtaaagctct atcagcaggg aagaaaatga cggtacctga ctaagaagca    480

ccggctaaat acgtgccagc agccgcggta atacgtatgg tgcaagcgtt atccggattt    540

actgggtgta aagggagcgt agacggagtg gcaagtctga tgtgaaaacc cggggctcaa    600

ccccgggact gcattggaaa ctgtcaatct agagtaccgg agaggtaagc ggaattccta    660

gtgtagcggt gaaatgcgta gatattagga ggaacaccag tggcgaaggc ggcttactgg    720

acggtaactg acgttgaggc tcgaaagcgt ggggagcaaa caggattaga taccctggta    780

gtccacgccg taaacgatga ctactaggtg tcgggcagca aagctgttcg gtgccgcagc    840

aaacgcaata agtagtccac ctggggagta cgttcgcaag aatgaaactc aaaggaattg    900

acggggaccc gcacaagcgg tggagcatgt ggtttaattc gaagcaacgc gaagaacctt    960

acctgctctt gacatctccc tgaccggcaa gtaatgttgc ctttccttcg ggacagggat   1020

gacaggtggt gcatggttgt cgtcagctcg tgtcgtgaga tgttgggtta agtcccgcaa   1080

cgagcgcaac ccctatcttt agtagccagc ggtcaggccg ggcactctag agagactgcc   1140

agggataacc tggaggaagg tggggatgac gtcaaatcat catgcccctt atgagcaggg   1200

ctacacacgt gctacaatgg cgtaaacaaa gggaggcaga accgcgaggt cgagcaaatc   1260

ccaaaaataa cgtctcagtt cggattgtag tctgcaactc gactacatga agctggaatc   1320

gctagtaatc gcgaatcaga atgtcgcggt gaatacgttc ccgggtcttg tacacaccgc   1380

ccgtcacacc atgggagtca gtaacgcccg aagtcagtga cccaaccgta aggagggagc   1440

tgccgaaggt gggaccgata actggggtga agtcgtaaca aggtagccgt atcggaaggt   1500

gcggctggat cacctccttt                                                1520
```

<210> SEQ ID NO 48
<211> LENGTH: 1474
<212> TYPE: DNA
<213> ORGANISM: Bacteroides caccae

<400> SEQUENCE: 48
tggctcagga tgaacgctag ctacaggctt aacacatgca agtcgagggg catcagtttg 60
gtttgcttgc aaaccaaagc tggcgaccgg cgcacgggtg agtaacacgt atccaacctg 120
cctcatactc ggggatagcc tttcgaaaga aagattaata tccgatagca tatatttccc 180
gcatgggttt tatattaaag aaattcggta tgagatgggg atgcgttcca ttagtttgtt 240
ggggggggtaa cggcccacca agactacgat ggataggggt tctgagagga aggtccccca 300
cattggaact gagacacggt ccaaactcct acgggaggca gcagtgagga atattggtca 360
atggacgcga gtctgaacca gccaagtagc gtgaaggatg actgccctat gggttgtaaa 420
cttcttttat atgggaataa agttgtccac gtgtggattt ttgtatgtac catatgaata 480
aggatcggct aactccgtgc cagcagccgc ggtaatacgg aggatccgag cgttatccgg 540
atttattggg tttaaaggga gcgtaggcgg attgttaagt cagttgtgaa agtttgcggc 600
tcaaccgtaa aattgcagtt gatactggca gtcttgagtg cagtagaggt gggcggaatt 660
cgtggtgtag cggtgaaatg cttagatatc acgaagaact ccgattgcga aggcagccac 720
tggagtgtaa ctgacgctga tgctcgaaag tgtgggtatc aaacaggatt agataccctg 780
gtagtccaca cagtaaacga tgaatactcg ctgtttgcga tatacagtaa gcggccaagc 840
gaaagcatta agtattccac ctggggagta cgccggcaac ggtgaaactc aaaggaattg 900
acgggggccc gcacaagcgg aggaacatgt ggtttaattc gatgatacgc gaggaacctt 960
acccgggctt aaattgcaaa tgaattatgg ggaaacccat aggccgcaag gcatttgtga 1020
aggtgctgca tggttgtcgt cagctcgtgc cgtgaggtgt cggcttaagt gccataacga 1080
gcgcaaccct tatcttcagt tactaacagg tcatgctgag gactctggag agactgccgt 1140
cgtaagatgt gaggaaggtg gggatgacgt caaatcagca cggcccttac gtccggggct 1200
acacacgtgt tacaatgggg ggtacagaag gccgctacct ggtgacagga tgccaatccc 1260
aaaaacctct ctcagttcgg atcgaagtct gcaacccgac ttcgtgaagc tggattcgct 1320
agtaatcgcg catcagccat ggcgcggtga atacgttccc gggccttgta cacaccgccc 1380
gtcaagccat gaaagccggg ggtacctgaa gtacgtaacc gcaaggagcg tcctagggta 1440
aaactggtaa ttggggctaa gtcgtaacaa ggta 1474

<210> SEQ ID NO 49
<211> LENGTH: 1473
<212> TYPE: DNA
<213> ORGANISM: Unknown
<220> FEATURE:
<223> OTHER INFORMATION: Bacteroides cellulosilyticus/ Bacteroides intestinalis

<400> SEQUENCE: 49
agagtttgat cctggctcag gatgaacgct agctacaggc ttaacacatg caagtcgagg 60
ggcagcatga cctagcaata ggttgatggc gaccggcgca cgggtgagta acacgtatcc 120
aacctaccgg ttattccggg atagcctttc gaaagaaaga ttaataccgg atagtataac 180
gagaaggcat ctttttgtta ttaaagaatt tcgataaccg atggggatgc gttccattag 240
tttgttggcg gggtaacggc ccaccaagac atcgatggat aggggttctg agaggaaggt 300
cccccacatt ggaactgaga cacggtccaa actcctacgg gaggcagcag tgaggaatat 360
tggtcaatgg acgagagtct gaaccagcca agtagcgtga aggatgactg ccctatgggt 420
tgtaaacttc ttttatatgg gaataaagtg agccacgtgt ggctttttgt atgtaccata 480
cgaataagga tcggctaact ccgtgccagc agccgcggta atacggagga tccgagcgtt 540
atccggattt attgggttta aagggagcgt aggcggacta ttaagtcagc tgtgaaagtt 600
tgcggctcaa ccgtaaaatt gcagttgata ctggtcgtct tgagtgcagt agaggtaggc 660
ggaattcgtg gtgtagcggt gaaatgctta gatatcacga agaactccga ttgcgaaggc 720
agcttactgg actgtaactg acgctgatgc tcgaaagtgt gggtatcaaa caggattaga 780
taccctggta gtccacacag taaacgatga atactcgctg tttgcgatat acggcaagcg 840
gccaagcgaa agcattaagt attccacctg gggagtacgc cggcaacggt gaaactcaaa 900
ggaattgacg gggcccgca caagcggagg aacatgtggt ttaattcgat gatacgcgag 960
gaaccttacc cgggcttaaa ttgcaaatga atatagtgga aacattatag ccgcaaggca 1020
tttgtgaagg tgctgcatgg ttgtcgtcag ctcgtgccgt gaggtgtcgg cttaagtgcc 1080
ataacgagcg caacccttat ctttagttac taacaggtca tgctgaggac tctagagaga 1140
ctgccgtcgt aagatgtgag gaaggtgggg atgacgtcaa atcagcacgg cccttacgtc 1200
cggggctaca cacgtgttac aatgggggt acagaaggca gctacacagc gatgtgatgc 1260
taatcccaaa agcctctctc agttcggatt ggagtctgca acccgactcc atgaagctgg 1320
attcgctagt aatcgcgcat cagccacggc gcggtgaata cgttcccggg ccttgtacac 1380
accgcccgtc aagccatgaa agccgggggt acctgaagtc cgtaaccgta aggagcggcc 1440
tagggtaaaa ctggtaattg ggctaagtc gta 1473

<210> SEQ ID NO 50
<211> LENGTH: 1472
<212> TYPE: DNA
<213> ORGANISM: Unknown
<220> FEATURE:
<223> OTHER INFORMATION: Bacteroides faecis

<400> SEQUENCE: 50
ctcaggatga acgctagcta caggcttaac acatgcaagt cgaggggcag catttcagtt 60
tgcttgcaaa ctggagatgg cgaccggcgc acgggtgagt aacacgtatc caacctgccg 120
ataactcggg gatagccttt cgaaagaaag attaataccc gatggcataa tagaaccgca 180 tggtttttt attaaagaat ttcggttatc gatggggatg cgttccatta ggcagttggt 240
gaggtaacgg ctcaccaaac cttcgatgga taggggttct gagaggaagg tcccccacat 300
tggaactgag acacggtcca aactcctacg ggaggcagca gtgaggaata ttggtcaatg 360
gacgagagtc tgaaccagcc aagtagcgtg aaggatgact gccctatggg ttgtaaactt 420
cttttatatg ggaataaagt tttccacgtg tggaattttg tatgtaccat atgaataagg 480
atcggctaac tccgtgccag cagccgcggt aatacggagg atccgagcgt tatccggatt 540
tattgggttt aaagggagcg taggtggaca gttaagtcag ttgtgaaagt ttgcggctca 600
accgtaaaat tgcagttgat actggctgtc ttgagtacag tagaggtggg cggaattcgt 660
ggtgtagcgg tgaaatgctt agatatcacg aagaactccg attgcgaagg cagctcactg 720
gactgcaact gacactgatg ctcgaaagtg tgggtatcaa acaggattag ataccctggt 780
agtccacaca gtaaacgatg aatactcgct gtttgcgata tacagtaagc ggccaagcga 840
aagcattaag tattccacct ggggagtacg ccggcaacgg tgaaactcaa aggaattgac 900
gggggcccgc acaagcggag gaacatgtgg tttaattcga tgatacgcga ggaaccttac 960
ccgggcttaa attgcatttg aatatattgg aaacagtata gtcgtaagac aaatgtgaag 1020
gtgctgcatg gttgtcgtca gctcgtgccg tgaggtgtcg gcttaagtgc cataacgagc 1080
gcaaccctta tctttagtta ctaacaggtc atgctgagga ctctagagag actgccgtcg 1140
taagatgtga ggaaggtggg gatgacgtca aatcagcacg gcccttacgt ccggggctac 1200
acacgtgtta caatgggggg tacagaaggc agctacctgg tgacaggatg ctaatcccaa 1260
aagcctctct cagttcggat cgaagtctgc aacccgactt cgtgaagctg gattcgctag 1320
taatcgcgca tcagccatgg cgcggtgaat acgttcccgg gccttgtaca caccgcccgt 1380
caagccatga aagccggggg tacctgaagt acgtaaccgc aaggagcgtc ctagggtaaa 1440
actggtaatt ggggctaagt cgtaacaagg ta 1472

<210> SEQ ID NO 51
<211> LENGTH: 929
<212> TYPE: DNA
<213> ORGANISM: Bacteroides ovatus

<400> SEQUENCE: 51
cgatatccgg atttattgga gtttaaggga gcgtaggtgg attgttaagt cagttgtgaa 60
agtttgcggc tcaaccgtaa aattgcagtt gaaactggca gtcttgagta cagtagaggt 120
gggcggaatt cgtggtgtag cggtgaaatg cttagatatc acgaagaact ccgattgcga 180
aggcagctca ctagactgtc actgacactg atgctcgaaa gtgtgggtat caaacaggat 240
tagataccct ggtagtccac acagtaaacg atgaatactc gctgtttgcg atatacagta 300
agcggccaag cgaaagcatt aagtattcca cctggggagt acgccggcaa cggtgaaact 360
caaaggaatt gacgggggcc cgcacaagcg gaggaacatg tggtttaatt cgatgatacg 420
cgaggaacct tacccgggct taaattgcaa cagaatatat tggaaacagt atagccgtaa 480
ggctgttgtg aaggtgctgc atggttgtcg tcagctcgtg ccgtgaggtg tcggcttaag 540
tgccataacg agcgcaaccc ttatctttag ttactaacag gtkatgctga ggactctaga 600
gagactgccg tcgtaagatg tgaggaaggt ggggatgacg tcaaatcagc acggccctta 660
cgtccggggc tacacacgtg ttacaatggg gggtacagaa ggcsgctacc tggtgacagg 720
atgctaatcc caaaaacctc tctcagttcg gatcgaagtc tgcaacccga cttcgtgaag 780
ctggattcgc tagtaatcgc gcatcagcca tggcgcggtg aatacgttcc cgggccttgt 840
acacaccgcc cgtcaagcca tgaaagccgg gggtacctga agtacgtaac cgcaaggagc 900
gtcctagggg taaaactggt aattggggc 929

<210> SEQ ID NO 52
<211> LENGTH: 873
<212> TYPE: DNA
<213> ORGANISM: Bacteroides thetaiotaomicron

<400> SEQUENCE: 52
tttaagggag cgtaggtgga cagttaagtc agttgtgaaa gtttgcggct caaccgtaaa 60
attgcagttg atactggctg tcttgagtac agtagaggtg ggcggaattc gtggtgtagc 120
ggtgaaatgc ttagatatca cgaagaactc cgattgcgaa ggcagctcac tggactgcaa 180
ctgacactga tgctcgaaag tgtgggtatc aaacaggatt agataccctg gtagtccaca 240
cagtaaacga tgaatactcg ctgtttgcga tatacagtaa gcggccwagc gaaagcatta 300
agtattccac ctggggagta cgccggcaac ggtgaaactc aaaggaattg acgggggccc 360
gcacaagcgg aggaacatgt ggtttaattc gatgatacgc gaggaacctt acccgggctt 420
aaattgcaww tgaatawwyt ggaaacagkw tagycgyaag rcawwtgtga aggtgctgca 480
tggttgtcgt cagctcgtgc cgtgaggtgt cggcttaagt gccataacga gcgcaaccct 540
tatctttagt tactaacagg tcatgctgag gactctagag agactgccgt cgtaagatgt 600
gaggaaggtg gggatgacgt caaatcagca cggcccttac gtccggggct acacacgtgt 660
tacaatgggg ggtacagaag gcagctacct ggtgacagga tgctaatccc aaaagcctct 720
ctcagttcgg atcgaagtct gcaacccgac ttcgtgaagc tggattcgct agtaatcgcg 780
catcagccat ggcgcggtga atacgttccc gggccttgta cacaccgccc gtcaagccat 840
gaaagccggg ggtacctgaa gtacgtaacc gca 873

<210> SEQ ID NO 53
<211> LENGTH: 1474
<212> TYPE: DNA
<213> ORGANISM: Bacteroides uniformis

<400> SEQUENCE: 53
ctggctcagg atgaacgcta gctacaggct taacacatgc aagtcgaggg gcagcatgaa 60
cttagcttgc taagtttgat ggcgaccggc gcacgggtga gtaacacgta tccaacctgc 120
cgatgactcg ggatagcct ttcgaaagaa agattaatac ccgatggcat agttcttccg 180
catggtagaa ctattaaaga atttcggtca tcgatgggga tgcgttccat taggttgttg 240
gcggggtaac ggcccaccaa gccttcgatg gataggggtt ctgagaggaa ggtcccccac 300
attggaactg agacacggtc caaactccta cgggaggcag cagtgaggaa tattggtcaa 360
tggacgagag tctgaaccag ccaagtagcg tgaaggatga ctgccctatg ggttgtaaac 420
ttcttttata cgggaataaa gtgaggcacg tgtgcctttt tgtatgtacc gtatgaataa 480
ggatcggcta actccgtgcc agcagccgcg gtaatacgga ggatccgagc gttatccgga 540
tttattgggt ttaaagggag cgtaggcgga cgcttaagtc agttgtgaaa gtttgcggct 600
caaccgtaaa attgcagttg atactgggtg tcttgagtac agtagaggca ggcggaattc 660
gtggtgtagc ggtgaaatgc ttagatatca cgaagaactc cgattgcgaa ggcagcttgc 720
tggactgtaa ctgacgctga tgctcgaaag tgtgggtatc aaacaggatt agataccctg 780
gtagtccaca cagtaaacga tgaatactcg ctgtttgcga tatacagtaa gcggccaagc 840
gaaagcgtta agtattccac ctggggagta cgccggcaac ggtgaaactc aaaggaattg 900
acgggggccc gcacaagcgg aggaacatgt ggtttaattc gatgatacgc gaggaacctt 960
acccgggctt gaattgcaac tgaatgatgt ggagacatgt cagccgcaag gcagttgtga 1020
aggtgctgca tggttgtcgt cagctcgtgc cgtgaggtgt cggcttaagt gccataacga 1080
gcgcaaccct tatcgatagt taccatcagg ttatgctggg gactctgtcg agactgccgt 1140
cgtaagatgt gaggaaggtg gggatgacgt caaatcagca cggcccttac gtccggggct 1200
acacacgtgt tacaatgggg ggtacagaag gcagctacac ggcgacgtga tgctaatccc 1260
taaagcctct ctcagttcgg attggagtct gcaacccgac tccatgaagc tggattcgct 1320
agtaatcgcg catcagccac ggcgcggtga atacgttccc gggccttgta cacaccgccc 1380
gtcaagccat gaaagccggg ggtacctgaa gtgcgtaacc gcgaggagcg ccctagggta 1440
aaactggtga ttggggctaa gtcgtaacaa ggta 1474

<210> SEQ ID NO 54
<211> LENGTH: 1503
<212> TYPE: DNA
<213> ORGANISM: Bacteroides vulgatus

<400> SEQUENCE: 54
atgaagagtt tgatcctggc tcaggatgaa cgctagctac aggcttaaca catgcaagtc 60
gaggggcagc atggtcttag cttgctaagg ccgatggcga ccggcgcacg ggtgagtaac 120
acgtatccaa cctgccgtct actcttggac agccttctga aaggaagatt aatacaagat 180
ggcatcatga gttcacatgt tcacatgatt aaaggtattc cggtagacga tggggatgcg 240
ttccattaga tagtaggcgg ggtaacggcc cacctagtct tcgatggata ggggttctga 300
gaggaaggtc ccccacattg gaactgagac acggtccaaa ctcctacggg aggcagcagt 360
gaggaatatt ggtcaatggg cgagagcctg aaccagccaa gtagcgtgaa ggatgactgc 420
cctatgggtt gtaaacttct tttataaagg aataaagtcg ggtatgcata cccgtttgca 480
tgtactttat gaataaggat cggctaactc cgtgccagca gccgcggtaa tacggaggat 540
ccgagcgtta tccggattta ttgggtttaa agggagcgta gatggatgtt taagtcagtt 600
gtgaaagttt gcggctcaac cgtaaaattg cagttgatac tggatatctt gagtgcagtt 660
gaggcaggcg gaattcgtgg tgtagcggtg aaatgcttag atatcacgaa gaactccgat 720
tgcgaaggca gcctgctaag ctgcaactga cattgaggct cgaaagtgtg ggtatcaaac 780
aggattagat accctggtag tccacacggt aaacgatgaa tactcgctgt ttgcgatata 840
cggcaagcgg ccaagcgaaa gcgttaagta ttccacctgg ggagtacgcc ggcaacggtg 900
aaactcaaag gaattgacgg gggcccgcac aagcggagga acatgtggtt taattcgatg 960
atacgcgagg aaccttaccc gggcttaaat tgcagatgaa ttacggtgaa agccgtaagc 1020
cgcaaggcat ctgtgaaggt gctgcatggt tgtcgtcagc tcgtgccgtg aggtgtcggc 1080
ttaagtgcca taacgagcgc aaccccttgtt gtcagttact aacaggttcc gctgaggact 1140
ctgacaagac tgccatcgta agatgtgagg aaggtgggga tgacgtcaaa tcagcacggc 1200
ccttacgtcc ggggctacac acgtgttaca atggggggta cagagggccg ctaccacgcg 1260
agtggatgcc aatcccaaaa acctctctca gttcggactg gagtctgcaa cccgactcca 1320
cgaagctgga ttcgctagta atcgcgcatc agccacggcg cggtgaatac gttcccgggc 1380
cttgtacaca ccgcccgtca agccatggga gccgggggta cctgaagtgc gtaaccgcga 1440
ggagcgccct agggtaaaac tggtgactgg ggctaagtcg taacaaggta gccgtaccgg 1500
aag 1503

<210> SEQ ID NO 55
<211> LENGTH: 887
<212> TYPE: DNA
<213> ORGANISM: Bifidobacterium adolescentis

<400> SEQUENCE: 55
gggctcgtag kcggttcgtc gcgtccggtg tgaaagtcca ycgcttaacg gtggatccgc 60
gccgggtacg ggcgggcttg agtgcggtag gggagactgg aattcccggt gtaacggtgg 120
aatgtgtaga tatcgggaag aacaccaatg gcgaaggcag gtctctgggc cgtcactgac 180
gctgaggagc gaaagcgtgg ggagcgaaca ggattagata ccctggtagt ccacgccgta 240
aacggtggat gctggatgtg gggaccattc cacggtctcc gtgtcggagc caacgcgtta 300
agcatcccgc ctggggagta cggccgcaag gctaaaactc aaagaaattg acgggggccc 360
gcacaagcgg cggagcatgc ggattaattc gatgcaacgc gaagaacctt acctgggctt 420
gacatgttcc cgacagcccc agagatgggg cctcccttcg ggcgggttc acaggtggtg 480
catggtcgtc gtcagctcgt gtcgtgagat gttgggttaa gtcccgcaac gagcgcaacc 540

```
ctcgccctgt gttgccagca cgtcgtggtg ggaactcacg ggggaccgcc ggggtcaact    600

cggaggaagg tggggatgac gtcagatcat catgcccctt acgtccaggg cttcacgcat    660

gctacaatgg ccggtacaac gggatgcgac actgtgaggt ggagcggatc ccttaaaacc    720

ggtctcagtt cggattggag tctgcaaccc gactccatga aggcggagtc gctagtaatc    780

gcggatcagc aacgccgcgg tgaatgcgtt cccgggcctt gtacacaccg cccgtcaagt    840

catgaaagtg ggtagcaccc gaagccggtg gcccatcctt tttgggg                  887
```

<210> SEQ ID NO 56
<211> LENGTH: 1495
<212> TYPE: DNA
<213> ORGANISM: Bifidobacterium longum

<400> SEQUENCE: 56

```
tggctcagga tgaacgctgg cggcgtgctt aacacatgca agtcgaacgg gatccatcag     60

gctttgcttg gtggtgagag tggcgaacgg gtgagtaatg cgtgaccgac ctgccccata    120

caccggaata gctcctggaa acgggtggta atgccggatg ctccagttga tcgcatggtc    180

ttctgggaaa gctttcgcgg tatgggatgg ggtcgcgtcc tatcagcttg acggcggggt    240

aacggcccac cgtggcttcg acgggtagcc ggcctgagag ggcgaccggc cacattggga    300

ctgagatacg gcccagactc ctacgggagg cagcagtggg gaatattgca caatgggcgc    360

aagcctgatg cagcgacgcc gcgtgaggga tggaggcctt cgggttgtaa acctctttta    420

tcggggagca agcgagagtg agtttacccg ttgaataagc accggctaac tacgtgccag    480

cagccgcggt aatacgtagg gtgcaagcgt tatccggaat tattgggcgt aaagggctcg    540

taggcggttc gtcgcgtccg gtgtgaaagt ccatcgctta acggtggatc cgcgccgggt    600

acgggcgggc ttgagtgcgg taggggagac tggaattccc ggtgtaacgg tggaatgtgt    660

agatatcggg aagaacacca atggcgaagg caggtctctg ggccgttact gacgctgagg    720

agcgaaagcg tggggagcga acaggattag ataccctggt agtccacgcc gtaaacggtg    780

gatgctggat gtggggcccg ttccacgggt tccgtgtcgg agctaacgcg ttaagcatcc    840

cgcctgggga gtacggccgc aaggctaaaa ctcaaagaaa ttgacggggg cccgcacaag    900

cggcggagca tgcggattaa ttcgatgcaa cgcgaagaac cttacctggg cttgacatgt    960

tcccgacggt cgtagagata cggcttccct tcggggcggg ttcacaggtg gtgcatggtc   1020

gtcgtcagct cgtgtcgtga gatgttgggt taagtcccgc aacgagcgca accctcgccc   1080

cgtgttgcca gcggattatg ccgggaactc acgggggacc gccggggtta actcggagga   1140

aggtggggat gacgtcagat catcatgccc cttacgtcca gggcttcacg catgctacaa   1200

tggccggtac aacgggatgc gacgcggcga cgcggagcgg atccctgaaa accggtctca   1260

gttcggatcg cagtctgcaa ctcgactgcg tgaaggcgga gtcgctagta atcgcgaatc   1320

agcaacgtcg cggtgaatgc gttcccgggc cttgtacaca ccgcccgtca agtcatgaaa   1380

gtgggcagca cccgaagccg gtggcctaac cccttgtggg atggagccgt ctaaggtgag   1440

gctcgtgatt gggactaagt cgtaacaagg tagccgtacc ggaaggtgcg gctgg        1495
```

<210> SEQ ID NO 57
<211> LENGTH: 689
<212> TYPE: DNA
<213> ORGANISM: Bifidobacterium pseudocatenulatum

<400> SEQUENCE: 57

```
ggttcgtcgc gtccggtgtg aaagtccatc gtttaacggt ggatctgcgc cgggtacggg      60
cgggctggag tgcggtaggg gagactggaa ttcccggtgt aacggtggaa tgtgtagata     120
tcgggaagaa caccaatggc gaaggcaggt ctctgggccg ttactgacgc tgaggagcga     180
aagcgtgggg agcgaacagg attagatacc ctggtagtcc acgccgtaaa cggtggatgc     240
tggatgtggg gcccgttcca cgggttccgt gwcggagcta acgcgttaag catcccgcct     300
ggggagtacg gccgcaaggc taaaacwmaa akaaattgac gggggcccgc acaagcggcg     360
gagcatgcgg attaattcga tgcaacgcga agaaccttac ctgggcttga catgttcccg     420
acagccgtag agatatggcc tcccttcggg gcgggttcac aggtggtgca tggtcgtcgt     480
cagctcgtgt cgtgagatgt tgggttaagt cccgcaacga gcgcaaccct cgccctgtgt     540
tgccagcacg tcatggtggg aactcacggg ggaccgccgg ggtcaactcg gaggaaggtg     600
gggatgacgt cagatcatca tgccccttac gttcagggct tcacgcatgc tacaatggcc     660
ggtacaacgg gatgcgacac ggcgacgtg                                       689
```

```
<210> SEQ ID NO 58
<211> LENGTH: 1394
<212> TYPE: DNA
<213> ORGANISM: Unknown
<220> FEATURE:
<223> OTHER INFORMATION: Blautia coccoides/ Blautia producta

<400> SEQUENCE: 58

tgtgactgag cggcggacgg gtgagtaacg cgtgggtaac ctgcctcata caggggggata      60
acagttagaa atgactgcta ataccgcata agcgcacagg accgcatggt ctggtgtgaa     120
aaactccggt ggtatgagat ggacccgcgt ctgattagct agttggaggg gtaacggccc     180
accaaggcga cgatcagtag ccggcctgag agggtgaacg gccacattgg gactgagaca     240
cggcccagac tcctacggga ggcagcagtg gggaatattg cacaatgggg gaaaccctga     300
tgcagcgacg ccgcgtgaag gaagaagtat ctcggtatgt aaacttctat cagcagggaa     360
gaaaatgacg gtacctgact aagaagcccc ggctaactac gtgccagcag ccgcggtaat     420
acgtaggggg caagcgttat ccggatttac tgggtgtaaa gggagcgtag acggaagagc     480
aagtctgatg tgaaaggctg ggcttaacc ccaggactgc attggaaact gttgttctag     540
agtgccggag aggtaagcgg aattcctagt gtagcggtga aatgcgtaga tattaggagg     600
aacaccagtg gcgaaggcgg cttactggac ggtaactgac gttgaggctc gaaagcgtgg     660
ggagcaaaca ggattagata ccctggtagt ccacgccgta aacgatgaat actaggtgtc     720
gggtggcaaa gccattcggt gccgcagcaa acgcaataag tattccacct ggggagtacg     780
ttcgcaagaa tgaaactcaa aggaattgac ggggacccgc acaagcggtg gagcatgtgg     840
tttaattcga agcaacgcga agaaccttac caagtcttga catccctctg accgtcccgt     900
aacgggggct tcccttcggg gcagaggaga caggtggtgc atggttgtcg tcagctcgtg     960
tcgtgagatg ttgggttaag tcccgcaacg agcgcaaccc ttatccttag tagccagcac    1020
atgatggtgg gcactctagg gagactgccg gggataaccc ggaggaaggc ggggacgacg    1080
tcaaatcatc atgcccctta tgatttgggc tacacacgtg ctacaatggc gtaaacaaag    1140
ggaagcgaga cagcgatgtt gagcgaatcc caaaaataac gtcccagttc ggactgcagt    1200
ctgcaactcg actgcacgaa gctggaatcg ctagtaatcg cggatcagaa tgccgcggtg    1260
aatacgttcc cgggtcttgt acacaccgcc cgtcacacca tgggagtcag taacgcccga    1320
agtcagtgac ctaaccgaaa ggaaggagct gccgaaggcg ggaccgataa ctggggtgaa    1380
```

gtcgtaacaa ggta 1394

<210> SEQ ID NO 59
<211> LENGTH: 918
<212> TYPE: DNA
<213> ORGANISM: Unknown
<220> FEATURE:
<223> OTHER INFORMATION: Clostridium citroniae

<400> SEQUENCE: 59
tccggattta ctggagtagt aagggagcgt agacggcgaa gcaagtctgg agtgaaaacc 60
cagggctcaa ccctgggact gctttggaaa ctgttttgct agagtgtcgg agaggtaagt 120
ggaattccta gtgtagcggt gaaatgcgta gatattagga ggaacaccag tggcgaaggc 180
ggcttactgg acgataactg acgttgaggc tcgaaagcgt ggggagcaaa caggattaga 240
taccctggta gtccacgccg taaacgatga atgctaggtg ttgggggca aagcccttcg 300 gtgccgtcgc aaacgcaata agcattccac ctggggagta cgttcgcaag aatgaaactc 360
aaaggaattg acggggaccc gcacaagcgg tggagcatgt ggtttaattc gaagcaacgc 420
gaagaacctt accaagtctt gacatccccc tgaccggtca gtaaagtgac ctttccttcg 480
ggacagggga gacaggtggt gcatggttgt cgtcagctcg tgtcgtgaga tgttgggtta 540
agtcccgcaa cgagcgcaac ccttatcctt agtagccagc aggtaaagct gggcactcta 600
gggagactgc cagggataac ctggaggaag gtggggatga cgtcaaatca tcatgcccct 660
tatgatttgg gctacacacg tgctacaatg gcgtaaacaa agggaagcga ccctgcgaag 720
gcaagcaaat cccaaaaata acgtcccagt tcggactgta gtctgcaacc cgactacacg 780
aagctggaat cgctagtaat cgcgaatcag aatgtcgcgg tgaatacgtt cccgggtctt 840
gtacacaccg cccgtcacac catgggagtc agcaacgccc gaagtcagtg acccaaccga 900
aaggagggag ctgccgaa 918

<210> SEQ ID NO 60
<211> LENGTH: 1307
<212> TYPE: DNA
<213> ORGANISM: Unknown
<220> FEATURE:
<223> OTHER INFORMATION: Clostridium clostridioforme

<400> SEQUENCE: 60
taataccgca taagcgcaca gtgccgcatg gcagtgtgtg aaaaactccg gtggtgtgag 60
atggatccgc gtctgattag ccagttggcg gggtaacggc ccaccaaagc gacgatcagt 120
agccgacctg agagggtgac cggccacatt gggactgaga cacggcccaa actcctacgg 180
gaggcagcag tggggaatat tgcacaatgg gcgaaagcct gatgcagcga cgccgcgtga 240
gtgaagaagt atttcggtat gtaaagctct atcagcaggg aagaaaatga cggtacctga 300
ctaagaagcc ccggctaact acgtgccagc agccgcggta atacgtaggg ggcaagcgtt 360
atccggattt actgggtgta aagggagcgt agacggcgaa gcaagtctga agtgaaaacc 420
cggggctcaa ccctgggact gctttggaaa ctgttttgct agagtgtcgg agaggtaagt 480
ggaattccta gtgtagcggt gaaatgcgta gatattagga ggaacaccag tggcgaaggc 540
ggcttactgg acgataactg acgttgaggc tcgaaagcgt ggggagcaaa caggattaga 600
taccctggta gtccacgccg taaacgatga atgctaggtg ttgggggca aagcccttcg 660 gtgccgccgc aaacgcagta agcattccac ctggggagta cgttcgcaag aatgaaactc 720

```
aaaggaattg acggggaccc gcacaagcgg tggagcatgt ggtttaattc gaagcaacgc    780

gaagaacctt accaagtctt gacatccccc tgacgggccg gtaacgcggc ctttccttcg    840

ggacagggga gacaggtggt gcatggttgt cgtcagctcg tgtcgtgaga tgttgggtta    900

agtcccgcaa cgagcgcaac ccttatcctt agtagccagc aggtagagcc gggcactcta    960

gggagactgc cagggataac ctggaggaag gtggggatga cgtcaaatca tcatgcccct   1020

tatgatttgg gctacacacg tgctacaatg gcgtaaacaa agggaagcga gacagtgatg   1080

tggagcaaat cccaaaaata acgtcccagt tcggactgta gtctgcaacc cgactacacg   1140

aagctggaat cgctagtaat cgcgaatcag aatgtcgcgg tgaatacgtt cccgggtctt   1200

gtacacaccg cccgtcacac catgggagtc agcaacgccc gaagtcagtg acccaaccga   1260

aaggagggag ctgccgaagg cggggcaggt aactggggtg aagtcgt                 1307
```

```
<210> SEQ ID NO 61
<211> LENGTH: 1475
<212> TYPE: DNA
<213> ORGANISM: Clostridium innocuum

<400> SEQUENCE: 61

atggagagtt tgatcctggc tcaggatgaa cgctggcggc atgcctaata catgcaagtc     60

gaacgaagtt tcgaggaagc ttgcttccaa agagacttag tggcgaacgg gtgagtaaca    120

cgtaggtaac ctgcccatgt gtccgggata actgctggaa acggtagcta aaaccggata    180

ggtatacaga gcgcatgctc agtatattaa agcgcccatc aaggcgtgaa catggatgga    240

cctgcggcgc attagctagt tggtgaggta acggcccacc aaggcgatga tgcgtagccg    300

gcctgagagg gtaaacggcc acattgggac tgagacacgg cccaaactcc tacgggaggc    360

agcagtaggg aattttcgtc aatgggggaa accctgaacg agcaatgccg cgtgagtgaa    420

gaaggtcttc ggatcgtaaa gctctgttgt aagtgaagaa cggctcatag aggaaatgct    480

atgggagtga cggtagctta ccagaaagcc acggctaact acgtgccagc agccgcggta    540

atacgtaggt ggcaagcgtt atccggaatc attgggcgta aagggtgcgt aggtggcgta    600

ctaagtctgt agtaaaaggc aatggctcaa ccattgtaag ctatggaaac tggtatgctg    660

gagtgcagaa gagggcgatg gaattccatg tgtagcggta aaatgcgtag atatatggag    720

gaacaccagt ggcgaaggcg gtcgcctggt ctgtaactga cactgaggca cgaaagcgtg    780

gggagcaaat aggattagat accctagtag tccacgccgt aaacgatgag aactaagtgt    840

tggaggaatt cagtgctgca gttaacgcaa taagttctcc gcctggggag tatgcacgca    900

agtgtgaaac tcaaaggaat tgacgggggc ccgcacaagc ggtggagtat gtggtttaat    960

tcgaagcaac gcgaagaacc ttaccaggcc ttgacatgga aacaaatacc ctagagatag   1020

ggggataatt atggatcaca caggtggtgc atggttgtcg tcagctcgtg tcgtgagatg   1080

ttgggttaag tcccgcaacg agcgcaaccc ttgtcgcatg ttaccagcat caagttgggg   1140

actcatgcga gactgccggt gacaaaccgg aggaaggtgg ggatgacgtc aaatcatcat   1200

gccccttatg gcctgggcta cacacgtact acaatggcgg ccacaaagag cagcgacaca   1260

gtgatgtgaa gcgaatctca taaaggtcgt ctcagttcgg attgaagtct gcaactcgac   1320

ttcatgaagt cggaatcgct agtaatcgca gatcagcatg ctgcggtgaa tacgttctcg   1380

ggccttgtac acaccgcccg tcaaaccatg ggagtcagta atacccgaag ccggtggcat   1440

aaccgtaagg agtgagccgt cgaaggtagg accga                              1475
```

<210> SEQ ID NO 62
<211> LENGTH: 1475
<212> TYPE: DNA
<213> ORGANISM: Unknown
<220> FEATURE:
<223> OTHER INFORMATION: Clostridium innocuum / Erysipelotrichaceae bacterium 6_1_45

<400> SEQUENCE: 62

```
atggagagtt tgatcctggc tcaggatgaa cgctggcggc atgcctaata catgcaagtc     60
gaacgaagtt tcgaggaagc ttgcttccaa agagacttag tggcgaacgg gtgagtaaca    120
cgtaggtaac ctgcccatgt gtccgggata actgctggaa acggtagcta aaaccggata    180
ggtatacaga gcgcatgctc agtatattaa agcgcccatc aaggcgtgaa catggatgga    240
cctgcggcgc attagctagt tggtgaggta acggcccacc aaggcgatga tgcgtagccg    300
gcctgagagg gtaaacggcc acattgggac tgagacacgg cccaaactcc tacgggaggc    360
agcagtaggg aattttcgtc aatgggggaa accctgaacg agcaatgccg cgtgagtgaa    420
gaaggtcttc ggatcgtaaa gctctgttgt aagtgaagaa cggctcatag aggaaatgct    480
atgggagtga cggtagctta ccagaaagcc acggctaact acgtgccagc agccgcggta    540
atacgtaggt ggcaagcgtt atccggaatc attgggcgta aagggtgcgt aggtggcgta    600
ctaagtctgt agtaaaaggc aatggctcaa ccattgtaag ctatggaaac tggtatgctg    660
gagtgcagaa gagggcgatg gaattccatg tgtagcggta aaatgcgtag atatatggag    720
gaacaccagt ggcgaaggcg gtcgcctggt ctgtaactga cactgaggca cgaaagcgtg    780
gggagcaaat aggattagat accctagtag tccacgccgt aaacgatgag aactaagtgt    840
tggaggaatt cagtgctgca gttaacgcaa taagttctcc gcctggggag tatgcacgca    900
agtgtgaaac tcaaaggaat tgacgggggc ccgcacaagc ggtggagtat gtggtttaat    960
tcgaagcaac gcgaagaacc ttaccaggcc ttgacatgga aacaaatacc ctagagatag   1020
ggggataatt atggatcaca caggtggtgc atggttgtcg tcagctcgtg tcgtgagatg   1080
ttgggttaag tcccgcaacg agcgcaaccc ttgtcgcatg ttaccagcat caagttgggg   1140
actcatgcga gactgccggt gacaaaccgg aggaaggtgg ggatgacgtc aaatcatcat   1200
gccccttatg gcctgggcta cacacgtact acaatggcga ccacaaagag cagcgacaca   1260
gtgatgtgaa gcgaatctca taaaggtcgt ctcagttcgg attgaagtct gcaactcgac   1320
ttcatgaagt cggaatcgct agtaatcgca gatcagcatg ctgcggtgaa tacgttctcg   1380
ggccttgtac acaccgcccg tcaaaccatg ggagtcagta atacccgaag ccggtggcat   1440
aaccgtaagg agtgagccgt cgaaggtagg accga                               1475
```

<210> SEQ ID NO 63
<211> LENGTH: 906
<212> TYPE: DNA
<213> ORGANISM: Clostridium sordellii

<400> SEQUENCE: 63

```
acacatgcaa gtcgagcgaa cccttcgggg tgagcggcgg acgggtgagt aacgcgtggg     60
taacctgccc tgtacacacg gataacatac cgaaaggtat gctaatacgg gatrayatat    120
gagagtcgca tggcttttgt atcaaagctc cggcggtaca ggatggaccc gcgtctgatt    180
agctagttgg taaggtaacg gcttaccaag gcaacgatca gtagccgacc tgagagggtg    240
atcggccaca ttggaactga gacacggtcc aaactcmtac gggaggcagc agtggggaat    300
attgcacaat gggcgaaagc ctgatgcagc aacgccgcgt gagcgatgaa ggccttcggg    360
```

tcgtaaagct ctgtcctcaa ggaagataat gacggtactt gaggaggaag ccccggctaa 420
ctacgtgcca gcagccgcgg taatacgtag gggctagcg ttatccggaa ttactgggcg 480
taaagggtgc gtaggcggtc tttcaagcca gaagtgaaag gctacggctc aaccgtagta 540
agcttttgga actgtaggac ttgagtgcag gagaggagag tggaattcct agtgtagcgg 600
tgaaatgcgt agatattagg aggaacacca gtagcgaagg cggctctctg gactgtaact 660
gacgctgagg cacgaaagcg tggggagcaa acaggattag ataccctggt agtccacgcc 720
gtaaacgatg agtactaggt gtcgggggtt acccccctcg gtgccgcagc taacgcatta 780
agtactccgc ctgggaagta cgctcgcaag agtgaaactc aaaggaattg acggggaccc 840
gcacaagtag cggagcatgt ggtttaattc gaagcaacgc gaagaacctt atctaarctt 900
gacatc 906

<210> SEQ ID NO 64
<211> LENGTH: 380
<212> TYPE: DNA
<213> ORGANISM: Unknown
<220> FEATURE:
<223> OTHER INFORMATION: Coprococcus comes

<400> SEQUENCE: 64
acrggaggca gcagtgggga atattgcaca atgggggaaa ccctgatgca gcgacgccrc 60
gtgagcgaag aagtattkcg gtatgtaaag ctctatcagc agggaagaaa atgacggtac 120
ctgactaaga agcaccggct aaatacgtgc cagcagccgc ggtaatacgt atggtgcaag 180
cgttatccgg atttactggg tgtaaaggga gcgtagacgg ctgtgtaagt ctgaagtgaa 240
aggcgggggc tccccccgg ggactgcttt ggaaactatg cagctagact gtcggacagg 300
taagtggaat tcccagtgta gcggtgaaat gcgtagatat tgggaggaac agcaktgggt 360
aaggctsctt acaggacrat 380

<210> SEQ ID NO 65
<211> LENGTH: 1317
<212> TYPE: DNA
<213> ORGANISM: Unknown
<220> FEATURE:
<223> OTHER INFORMATION: Dorea longicatena

<400> SEQUENCE: 65
taacgcgtgg gtaacctgcc tcatacaggg ggataacagt tagaaatgac tgctaatacc 60
gcataagacc acggtaccgc atggtacagt ggtaaaaact ccggtggtat gagatggacc 120
cgcgtctgat taggtagttg gtggggtaac ggcctaccaa gccgacgatc agtagccgac 180
ctgagagggt gaccggccac attgggactg agacacggcc cagactccta cgggaggcag 240
cagtggggaa tattgcacaa tggaggaaac tctgatgcag cgacgccgcg tgaaggatga 300
agtatttcgg tatgtaaact tctatcagca gggaagaaaa tgacggtacc tgactaagaa 360
gccccggcta actacgtgcc agcagccgcg gtaatacgta gggggcaagc gttatccgga 420
tttactgggt gtaaagggag cgtagacggc acggcaagcc agatgtgaaa gcccggggct 480
caaccccggg actgcatttg gaactgctga gctagagtgt cggagaggca agtggaattc 540
ctagtgtagc ggtgaaatgc gtagatatta ggaggaacac cagtggcgaa ggcggcttgc 600
tggacgatga ctgacgttga ggctcgaaag cgtggggagc aaacaggatt agataccctg 660
gtagtccacg ccgtaaacga tgactgctag gtgtcgggtg gcaaagccat tcggtgccgc 720
agctaacgca ataagcagtc cacctgggga gtacgttcgc aagaatgaaa ctcaaaggaa 780
ttgacgggga cccgcacaag cggtggagca tgtggtttaa ttcgaagcaa cgcgaagaac 840
cttacctgat cttgacatcc cgatgaccgc ttcgtaatgg aagcttttct tcggaacatc 900
ggtgacaggt ggtgcatggt tgtcgtcagc tcgtgtcgtg agatgttggg ttaagtcccg 960
caacgagcgc aacccctatc ttcagtagcc agcaggttaa gctgggcact ctggagagac 1020
tgccagggat aacctggagg aaggtgggga tgacgtcaaa tcatcatgcc ccttatgacc 1080
agggctacac acgtgctaca atggcgtaaa caaagagaag cgaactcgcg agggtaagca 1140
aatctcaaaa ataacgtctc agttcggatt gtagtctgca actcgactac atgaagctgg 1200
aatcgctagt aatcgcagat cagaatgctg cggtgaatac gttcccgggt cttgtacaca 1260
ccgcccgtca caccatggga gtcagtaacg cccgaagtca gtgacccaac cgtaagg 1317

<210> SEQ ID NO 66
<211> LENGTH: 808
<212> TYPE: DNA
<213> ORGANISM: Unknown
<220> FEATURE:
<223> OTHER INFORMATION: Erysipelatoclostridium ramosum

<400> SEQUENCE: 66
gagggagcag gcggcagcaa gggtctgtgg tgaaagcctg aagttaaact tcagtaagcc 60
atagaaacca ggcagctaga gtgcaggaga ggakcgtgga attccatgtg tagcggtgaa 120
atgcgtagat atatggagga acaccagtgg cgaaggcgac gatctggcct gcaactgacg 180
ctcagtcccg aaagcgtggg gagcaaatag gattagatac cctagtagtc cacgccgtaa 240
acgatgagta ctragtgttg gatgtcaaag ttcagtgctg cagttaacgc aataagtact 300
ccgcctgagt agtacgttcg caagaatgaa actcaaagga attgacgggg gcccgcacaa 360
gcggtggagc atgtggttta attcgaagca acgcgaagaa ccttaccagg tcttgacata 420
ctcataaagg ctccagagat ggagagatag ctatatgaga tacaggtggt gcatggttgt 480
cgtcagctcg tgtcgtgaga tgttgggtta agtcccgcaa cgagcgcaac ccttatcgtt 540
agttaccatc attaagttgg ggactctagc gagactgcca gtgacaagct ggaggaargc 600
ggggatgacg tcaaatcatc atgcccctta tgacctgggc tacacacgtg ctacaatgga 660
tggtgcagag ggaagcgaag ccgcgaggtg aagcaaaacc cataaaacca ttctcagttc 720
ggattgtagt ctgcarctcg actacatgaa gttggaatcg ctagtaatcg cgaatcarca 780
tgtcgcgatg aatamgttct cgggcctt 808

<210> SEQ ID NO 67
<211> LENGTH: 1521
<212> TYPE: DNA
<213> ORGANISM: Eubacterium rectale

<400> SEQUENCE: 67
agagtttgat cctggctcag gatgaacgct ggcggcgtgc ttaacacatg caagtcgaac 60
gaagcacttt atttgatttc cttcgggact gattattttg tgactgagtg gcggacgggt 120
gagtaacgcg tgggtaacct gccttgtaca gggggataac agttggaaac ggctgctaat 180
accgcataag cgcacggcat cgcatgatgc agtgtgaaaa actccggtgg tataagatgg 240
acccgcgttg gattagctag ttggtgaggt aacggcccac caaggcgacg atccatagcc 300
gacctgagag ggtgaccggc cacattggga ctgagacacg gcccaaactc ctacgggagg 360
cagcagtggg gaatattgca caatgggcga aagcctgatg cagcgacgcc gcgtgagcga 420

```
agaagtattt cggtatgtaa agctctatca gcagggaaga taatgacggt acctgactaa    480

gaagcaccgg ctaaatacgt gccagcagcc gcggtaatac gtatggtgca agcgttatcc    540

ggatttactg ggtgtaaagg gagcgcaggc ggtgcggcaa gtctgatgtg aaagcccggg    600

gctcaacccc ggtactgcat tggaaactgt cgtactagag tgtcggaggg gtaagcggaa    660

ttcctagtgt agcggtgaaa tgcgtagata ttaggaggaa caccagtggc gaaggcggct    720

tactggacga taactgacgc tgaggctcga aagcgtgggg agcaaacagg attagatacc    780

ctggtagtcc acgccgtaaa cgatgaatac taggtgttgg gaagcattgc ttctcggtgc    840

cgtcgcaaac gcagtaagta ttccacctgg ggagtacgtt cgcaagaatg aaactcaaag    900

gaattgacgg ggacccgcac aagcggtgga gcatgtggtt taattcgaag caacgcgaag    960

aaccttacca agtcttgaca tccttctgac cggtacttaa ccgtaccttc tcttcggagc   1020

aggagtgaca ggtggtgcat ggttgtcgtc agctcgtgtc gtgagatgtt gggttaagtc   1080

ccgcaacgag cgcaaccctt atctttagta gccagcggtt cggccgggca ctctagagag   1140

actgccaggg ataacctgga ggaaggcggg gatgacgtca aatcatcatg ccccttatga   1200

cttgggctac acacgtgcta caatggcgta aacaaaggga agcaaagctg tgaagccgag   1260

caaatctcaa aaataacgtc tcagttcgga ctgtagtctg caacccgact acacgaagct   1320

ggaatcgcta gtaatcgcag atcagaatgc tgcggtgaat acgttcccgg gtcttgtaca   1380

caccgcccgt cacaccatgg gagttgggaa tgcccgaagc cagtgaccta accgaaagga   1440

aggagctgtc gaaggcaggc tcgataactg gggtgaagtc gtaacaaggt agccgtatcg   1500

gaaggtgcgg ctggatcacc t                                             1521


<210> SEQ ID NO 68
<211> LENGTH: 1482
<212> TYPE: DNA
<213> ORGANISM: Unknown
<220> FEATURE:
<223> OTHER INFORMATION: Odoribacter splanchnicus

<400> SEQUENCE: 68

agagtttgat cctggctcag gatgaacgct agcgacaggc ttaacacatg caagtcgagg     60

ggcatcatga ggtagcaata ccttgatggc gaccggcgca cgggtgagta acgcgtatgc    120

aacctgcccg ataccggggt atagcccatg gaaacgtgga ttaacacccc atagtacttt    180

tatcctgcat gggatgtgag ttaaatgttt aaggtatcgg atgggcatgc gtcctattag    240

ttagttggcg gggtaacagc ccaccaagac gatgataggt aggggttctg agaggaaggt    300

cccccacatt ggaactgaga cacggtccaa actcctacgg gaggcagcag tgaggaatat    360

tggtcaatgg acgagagtct gaaccagcca agtcgcgtga gggaagactg ccctatgggt    420

tgtaaacctc ttttataagg gaagaataag ttctacgtgt agaatgatgc ctgtacctta    480

tgaataagca tcggctaact ccgtgccagc agccgcggta atacggagga tgcgagcgtt    540

atccggattt attgggttta aagggtgcgt aggcggttta ttaagttagt ggttaaatat    600

ttgagctaaa ctcaattgtg ccattaatac tggtaaactg gagtacagac gaggtaggcg    660

gaataagtta agtagcggtg aaatgcatag atataactta gaactccgat agcgaaggca    720

gcttaccaga ctgtaactga cgctgatgca cgagagcgtg ggtagcgaac aggattagat    780

accctggtag tccacgccgt aaacgatgct cactggttct gtgcgatata ttgtacggga    840

ttaagcgaaa gtattaagtg agccacctgg ggagtacgtc ggcaacgatg aaactcaaag    900
```

gaattgacgg gggcccgcac aagcggagga acatgtggtt taattcgatg atacgcgagg 960
aaccttacct gggtttaaat gggaaatgtc gtatttggaa acagatattc tcttcggagc 1020
gtttttcaag gtgctgcatg gttgtcgtca gctcgtgccg tgaggtgtcg ggttaagtcc 1080
cataacgagc gcaaccctta ccgttagttg ctagcatgta atgatgagca ctctaacggg 1140
actgccaccg taaggtgaga ggaaggcggg gatgacgtca aatcagcacg gcccttacac 1200
ccagggctac acacgtgtta caatggccgg tacagagggc cgctaccagg tgactggatg 1260
ccaatctcaa aagccggtcg tagttcggat tggagtctgt aacccgactc catgaagttg 1320
gattcgctag taatcgcgca tcagccatgg cgcggtgaat acgttcccgg gccttgtaca 1380
caccgcccgt caagccatgg aagccggggg tgcctgaagt ccgtaaccgc gaggatcggc 1440
ctagggcaaa actggtaact ggggctaagt cgtaacaagg ta 1482

<210> SEQ ID NO 69
<211> LENGTH: 738
<212> TYPE: DNA
<213> ORGANISM: Unknown
<220> FEATURE:
<223> OTHER INFORMATION: Parabacteroides distasonis

<400> SEQUENCE: 69
cgaggggcag crcaggagtt agcaataccs ggtggcgacc ggcgcacggg tgagtaacgc 60
gtatgcaact trcctatcag agggggataa cccggcgaaa gtcggactaa taccgcatga 120
agcagggaty ccgcatgggr atatttgcta aagattcatc gctgatagat aggcatgcgt 180
tccattaggc agttggcggg gtaacrgccc accaaaccga cgatggatag gggttctgag 240
aggaaggtcc cccacattgg tactgagaca cggaccaaac tcctacggga ggcagcagtg 300
aggaatattg gtcaatggsc gwragsctga accagccaag tcgcgtgagg gatgaaggtt 360
ctatggatcg taaacctctt ttataaggga ataaagtgcg ggacgtgtcc yrttttgtat 420
gtaccttatg aataaggatc ggctaactcc gtgccagcag ccgcggtaat acggaggatc 480
cgagcgttat ccggatttat tgggtttaaa gggtgcgtag gcggcctttt aagtcagcgg 540
tgaaagtctg tggctcaacc atagaattgc cgttgaaact gggggggcttg agtatgtttg 600 aggcaggcgg aatgcgtggt gtagcggtga aatgcataga tatcacgcag aaccccgwtt 660
gcgaaggcag cctgccaagc cgtaactgac gcggatgcac gaaagcgtgg ggatcaaaca 720
ggattagata ccctggta 738

<210> SEQ ID NO 70
<211> LENGTH: 521
<212> TYPE: DNA
<213> ORGANISM: Unknown
<220> FEATURE:
<223> OTHER INFORMATION: Parabacteroides merdae

<400> SEQUENCE: 70
catgcaagtc gaggggcagc atgatttgta gcaatacaga ttgatggcga ccggcgcacg 60
ggtgagtaac gcgtatgcaa cttacctatc agagggggat agcccggcga aagtcggatt 120
aataccccat aaaacagggg tcccgcatgg gaatatttgt taaagattca tcgctgatag 180
ataggcatgc gttccattag gcagttggcg gggtaacggc ccaccaaacc gacgatggat 240
aggggttckg agaggaaggt cccccacatt ggtactgaga cacggaccaa actcctacgg 300
gaggcagcag tgaggaatat tggtcaatgg ccgagaggct gaaccagcca agtcgcgtga 360
aggaagaagg atctatggtt tgtaaacttc ttttataggg gaataaagtg gaggacgtgt 420

```
ccttttttgt atgtacccta tgaataagca tcggctaact ccgtgmsarc mgccgcggga    480

atacggaaga tgcagagcgt tatccggatw tattggggtt a                        521
```

<210> SEQ ID NO 71
<211> LENGTH: 1368
<212> TYPE: DNA
<213> ORGANISM: Unknown
<220> FEATURE:
<223> OTHER INFORMATION: Bacteroides xylanisolvens

<400> SEQUENCE: 71

```
catgcaagtc gaggggcagc attttagttt gcttgcaaac taaagatggc gaccggcgca     60

cgggtgagta acacgtatcc aacctgccga taactcgggg atagcctttc gaaagaaaga    120

ttaatatccg atagtatatt aaaaccgcat ggttttacta ttaaagaatt tcggttatcg    180

atggggatgc gttccattag tttgttggcg gggtaacggc ccaccaagac tacgatggat    240

aggggttctg agaggaaggt cccccacatt ggaactgaga cacggtccaa actcctacgg    300

gaggcagcag tgaggaatat tggtcaatgg acgagagtct gaaccagcca agtagcgtga    360

aggatgactg ccctatgggt tgtaaacttc ttttatatgg gaataaagta ttccacgtgt    420

gggattttgt atgtaccata tgaataagga tcggctaact ccgtgccagc agccgcggta    480

atacggagga tccgagcgtt atccggattt attgggttta aagggagcgt aggtggattg    540

ttaagtcagt tgtgaaagtt tgcggctcaa ccgtaaaatt gcagttgaaa ctggcagtct    600

tgagtacagt agaggtgggc ggaattcgtg gtgtagcggt gaaatgctta gatatcacga    660

agaactccga ttgcgaaggc agctcactag actgcaactg acactgatgc tcgaaagtgt    720

gggtatcaaa caggattaga taccctggta gtccacacag taaacgatga atactcgctg    780

tttgcgatat acagtaagcg gccaagcgaa agcattaagt attccacctg ggagtacgc    840

cggcaacggt gaaactcaaa ggaattgacg gggcccgca caagcggagg aacatgtggt    900

ttaattcgat gatacgcgag gaaccttacc cgggcttaaa ttgcatttga ataatctgga    960

aacaggttag ccgcaaggca aatgtgaagg tgctgcatgg ttgtcgtcag ctcgtgccgt   1020

gaggtgtcgg cttaagtgcc ataacgagcg caacccttat ctttagttac taacaggtta   1080

tgctgaggac tctagagaga ctgccgtcgt aagatgtgag gaaggtgggg atgacgtcaa   1140

atcagcacgg cccttacgtc cggggctaca cacgtgttac aatgggggt acagaaggca   1200

gctacctggc gacaggatgc taatcccaaa aacctctctc agttcggatc gaagtctgca   1260

acccgacttc gtgaagctgg attcgctagt aatcgcgcat cagccatggc gcggtgaata   1320

cgttcccggg ccttgtacac accgcccgtc aagccatgaa agccgggg                 1368
```

<210> SEQ ID NO 72
<211> LENGTH: 1399
<212> TYPE: DNA
<213> ORGANISM: Unknown
<220> FEATURE:
<223> OTHER INFORMATION: Blautia obeum

<400> SEQUENCE: 72

```
ggcgtgctta acacatgcaa gtcgaacggg aaacctttta ttgaagcttc ggcagattta     60

gctggtttct agtggcggac gggtgagtaa cgcgtgggta acctgcctta tacaggggga    120

taacaaccag aaatggttgc taataccgca taagcgcaca ggaccgcatg gtccggtgtg    180

aaaaactccg gtggtataag atggacccgc gttggattag ctagttggca gggtaacggc    240
```

```
ctaccaaggc gacgatccat agccggcctg agagggtgaa cggccacatt gggactgaga    300
cacggcccag actcctacgg gaggcagcag tggggaatat tgcacaatgg gggaaaccct    360
gatgcagcga cgccgcgtga aggaagaagt atctcggtat gtaaacttct atcagcaggg    420
aagatagtga cggtacctga ctaagaagcc ccggctaact acgtgccagc agccgcggta    480
atacgtaggg ggcaagcgtt atccggattt actgggtgta aagggagcgt agacggactg    540
gcaagtctga tgtgaaaggc gggggctcaa cccctggact gcattggaaa ctgttagtct    600
tgagtgccgg agaggtaagc ggaattccta gtgtagcggt gaaatgcgta gatattagga    660
ggaacaccag tggcgaaggc ggcttactgg acggtaactg acgttgaggc tcgaaagcgt    720
ggggagcaaa caggattaga taccctggta gtccacgccg taaacgatga atactaggtg    780
ttggggagca aagctcttcg gtgccgccgc aaacgcatta agtattccac ctggggagta    840
cgttcgcaag aatgaaactc aaaggaattg acggggaccc gcacaagcgg tggagcatgt    900
ggtttaattc gaagcaacgc gaagaacctt accaagtctt gacatccctc tgaccgttcc    960
ttaaccggaa ctttccttcg ggacagggga gacaggtggt gcatggttgt cgtcagctcg   1020
tgtcgtgaga tgttgggtta agtcccgcaa cgagcgcaac ccctatcccc agtagccagc   1080
agtccggctg ggcactctga ggagactgcc agggataacc tggaggaagg cggggatgac   1140
gtcaaatcat catgcccctt atgatttggg ctacacacgt gctacaatgg cgtaaacaaa   1200
gggaagcaag cctgcgaagg taagcaaatc ccaaaaataa cgtcccagtt cggactgcag   1260
tctgcaactc gactgcacga agctggaatc gctagtaatc gcggatcaga atgccgcggt   1320
gaatacgttc ccgggtcttg tacacaccgc ccgtcacacc atgggagtca gtaacgcccg   1380
aagtcagtga cctaactgc                                                1399

<210> SEQ ID NO 73
<211> LENGTH: 1485
<212> TYPE: DNA
<213> ORGANISM: Unknown
<220> FEATURE:
<223> OTHER INFORMATION: Alistipes putredinis

<400> SEQUENCE: 73

agagtttgat cctggctcag gatgaacgct agcggcaggc ttaacacatg caagtcgagg     60
ggcagcataa tggatagcaa tatctatggt ggcgaccggc gcacgggtgc gtaacgcgta    120
tgcaacctac ctttaacagg gggataacac tgagaaattg gtactaatac cccataatat    180
catagaaggc atcttttatg gttgaaaatt ccgatggtta gagatgggca tgcgttgtat    240
tagctagttg gtggggtaac ggctcaccaa ggcgacgata cataggggga ctgagaggtt    300
aaccccccac actggtactg agacacggac cagactccta cgggaggcag cagtgaggaa    360
tattggtcaa tggacgcaag tctgaaccag ccatgccgcg tgcaggatga cggctctatg    420
agttgtaaac tgcttttgta cgagggtaaa cgcagatacg tgtatctgtc tgaaagtatc    480
gtacgaataa ggatcggcta actccgtgcc agcagccgcg gtaatacgga ggattcaagc    540
gttatccgga tttattgggt ttaaagggtg cgtaggcggt ttgataagtt agaggtgaaa    600
tttcggggct caaccctgaa cgtgcctcta atactgttga gctagagagt agttgcggta    660
ggcggaatgt atggtgtagc ggtgaaatgc ttagagatca tacagaacac cgattgcgaa    720
ggcagcttac caaactatat ctgacgttga ggcacgaaag cgtggggagc aaacaggatt    780
agataccctg gtagtccacg cagtaaacga tgataactcg ttgtcggcga tacacagtcg    840
gtgactaagc gaaagcgata agttatccac ctggggagta cgttcgcaag aatgaaactc    900
```

```
aaaggaattg acgggggccc gcacaagcgg aggaacatgt ggtttaattc gatgatacgc    960

gaggaacctt acccgggctt gaaagttagc gacgattctt gaaagaggat ttcccttcgg   1020

ggcgcgaaac taggtgctgc atggttgtcg tcagctcgtg ccgtgaggtg tcgggttaag   1080

tcccataacg agcgcaaccc ctaccgttag ttgccatcag gtgaagctgg gcactctggc   1140

gggactgccg gtgtaagccg agaggaaggt ggggatgacg tcaaatcagc acggccctta   1200

cgtccggggc tacacacgtg ttacaatggt aggtacagag ggcagctacc cagcgatggg   1260

atgcgaatct cgaaagccta tctcagttcg gattggaggc tgaaacccgc ctccatgaag   1320

ttggattcgc tagtaatcgc gcatcagcca tggcgcggtg aatacgttcc cgggccttgt   1380

acacaccgcc cgtcaagcca tgggagccgg gggtgcctga agttcgtgac cgcaaggagc   1440

gacctagggc aaaactggtg actggggcta agtcgtaaca aggta                   1485


<210> SEQ ID NO 74
<211> LENGTH: 1464
<212> TYPE: DNA
<213> ORGANISM: Unknown
<220> FEATURE:
<223> OTHER INFORMATION: Collinsella aerofaciens

<400> SEQUENCE: 74

agagttcgat cctggctcag gatgaacgct ggcggcgcgc ctaacacatg caagtcgaac     60

ggcacctatc ttcggataga agcgagtggc gaacggctga gtaacacgtg gagaacctgc    120

cccctccccc gggatagccg cccgaaagga cgggtaatac cggatacccc ggggtgccgc    180

atggcacccc ggctaaagcc ccgacgggag gggatggctc cgcggcccat caggtagacg    240

gcggggtgac ggcccaccgt gccgacaacg ggtagccggg ttgagagacc gaccggccag    300

attgggactg agacacggcc cagactccta cgggaggcag cagtggggaa tcttgcgcaa    360

tggggggaac cctgacgcag cgacgccgcg tgcgggacgg aggccttcgg gtcgtaaacc    420

gctttcagca gggaagagtc aagactgtac ctgcagaaga agccccggct aactacgtgc    480

cagcagccgc ggtaatacgt agggggcgag cgttatccgg attcattggg cgtaaagcgc    540

gcgtaggcgg cccggcaggc cgggggtcga agcgggggc tcaacccccc gaagcccccg    600

gaacctccgc ggcttgggtc cggtagggga gggtggaaca cccggtgtag cggtggaatg    660

cgcagatatc gggtggaaca ccggtggcga aggcggccct ctgggccgag accgacgctg    720

aggcgcgaaa gctgggggag cgaacaggat tagataccct ggtagtccca gccgtaaacg    780

atggacgcta ggtgtggggg gacgatcccc ccgtgccgca gccaacgcat taagcgtccc    840

gcctggggag tacggccgca aggctaaaac tcaaaggaat tgacgggggc ccgcacaagc    900

agcggagcat gtggcttaat tcgaagcaac gcgaagaacc ttaccagggc ttgacatatg    960

ggtgaagcgg gggagacccc gtggccgaga ggagcccata caggtggtgc atggctgtcg   1020

tcagctcgtg tcgtgagatg ttgggttaag tcccgcaacg agcgcaaccc ccgccgcgtg   1080

ttgccatcgg gtgatgccgg gaacccacgc gggaccgccg ccgtcaaggc ggaggagggc   1140

ggggacgacg tcaagtcatc atgcccctta tgccctgggc tgcacacgtg ctacaatggc   1200

cggtacagag ggatgccacc ccgcgagggg gagcggatcc cggaaagccg gccccagttc   1260

ggattggggg ctgcaacccg cccccatgaa gtcggagttg ctagtaatcg cggatcagca   1320

tgccgcggtg aatgcgttcc cgggccttgt acacaccgcc cgtcacacca cccgagtcgt   1380

ctgcacccga agtcgccggc ccaaccgaga ggggggaggc gccgaaggtg tggagggtga   1440
```

gggggggtgaa gtcgtaacaa ggta 1464

<210> SEQ ID NO 75
<211> LENGTH: 1472
<212> TYPE: DNA
<213> ORGANISM: Unknown
<220> FEATURE:
<223> OTHER INFORMATION: Bacteroides faecis /Eubacterium hallii

<400> SEQUENCE: 75
ctcaggatga acgctagcta caggcttaac acatgcaagt cgaggggcag cattccagtt 60
tgcttgcaaa ctggagatgg cgaccggcgc acgggtgagt aacacgtatc caacctgccg 120
ataactcggg gatagccttt cgaaagaaag attaataccc gatggcataa tagaaccgca 180
tggtttgatt attaaagaat ttcggttatc gatggggatg cgttccatta ggcagttggt 240
ggggtaacgg cccaccaaac cttcgatgga taggggttct gagaggaagg tcccccacat 300
tggaactgag acacggtcca aactcctacg ggaggcagca gtgaggaata ttggtcaatg 360
gacgagagtc tgaaccagcc aagtagcgtg aaggatgact gccctatggg ttgtaaactt 420
cttttatatg ggaataaagt ggtccacgtg tggatttttg tatgtaccat atgaataagg 480
atcggctaac tccgtgccag cagccgcggt aatacggagg atccgagcgt tatccggatt 540
tattgggttt aaagggagcg taggtggaca gttaagtcag ttgtgaaagt ttgcggctca 600
accgtaaaat tgcagttgat actggctgtc ttgagtacag tagaggcggg cggaattcgt 660
ggtgtagcgg tgaaatgctt agatatcacg aagaactccg attgcgaagg cagctcactg 720
gactgcaact gacactgatg ctcgaaagtg tgggtatcaa acaggattag ataccctggt 780
agtccacaca gtaaacgatg aatactcgct gtttgcgata tacagtaagc ggccaagcga 840
aagcattaag tattccacct ggggagtacg ccggcaacgg tgaaactcaa aggaattgac 900
gggggcccgc acaagcggag gaacatgtgg tttaattcga tgatacgcga ggaaccttac 960
ccgggcttaa attgcatttg aatatattgg aaacagtata gtcgtaagac aaatgtgaag 1020
gtgctgcatg gttgtcgtca gctcgtgccg tgaggtgtcg gcttaagtgc cataacgagc 1080
gcaaccctta tctttagtta ctaacaggtc atgctgagga ctctggagag actgccgtcg 1140
taagatgtga ggaaggtggg gatgacgtca aatcagcacg gcccttacgt ccggggctac 1200
acacgtgtta caatgggggg tacagaaggc cgctacctgg tgacaggatg ctaatcccaa 1260
aagcctctct cagttcggat cgaagtctgc aacccgactt cgtgaagctg gattcgctag 1320
taatcgcgca tcagccatgg cgcggtgaat acgttcccgg gccttgtaca caccgcccgt 1380
caagccatga aagccggggg tacctgaagt acgtaaccgc aaggagcgtc ctagggtaaa 1440
actggtaatt ggggctaagt cgtaacaagg ta 1472

<210> SEQ ID NO 76
<211> LENGTH: 317
<212> TYPE: DNA
<213> ORGANISM: Unknown
<220> FEATURE:
<223> OTHER INFORMATION: Alistipes shahii

<400> SEQUENCE: 76
acataggggg wstgwkaggt twrccsccca cattsrtact gagmcatgaw cmaactctmt 60
acgggargsa gsagtgagga atattggtcr rtggacgcaa gtctgaacca gccatgccgs 120
gtgcrggaag acggctckat gagtkgkaaa ctgcttttgt acrarrgtaa acgctcttac 180
gtgtaagagc ctgaaagtat sgtacraatg aggatcggct aactccgtgc cagcagccgc 240
ggtaatacgg aggatccaag cgttatccgg atttattggg tttaaagggt gcgtaggcgg 300
gttgataaag ttagrgg 317

<210> SEQ ID NO 77
<211> LENGTH: 811
<212> TYPE: DNA
<213> ORGANISM: Unknown
<220> FEATURE:
<223> OTHER INFORMATION: Anaerostipes caccae

<400> SEQUENCE: 77
gcttacacat gcaagtcgaa cgaagcattt argattgaag ttttcggatg gatttcctat 60
atgactgagt ggcggacggg tgagtaacgc gtggggaacc tgccctatac agggggataa 120
cagctggaaa cggctgctaa taccgcataa gcgcacagaa tcgcatgatt cagtgtgaaa 180
agccctggca gtataggatg gtcccgcgtc tgattagctg gttggtgagg taacggctca 240
ccaaggcgac gatcagtagc cggcttgaga gagtgaacgg ccacattggg actgagacac 300
ggcccaaact cctacgggag gcagcagtgg ggaatattgc acaatggggg aaaccctgat 360
gcagcgacgc cgcgtgagtg aagaagtatt tcggtatgta aagctctatc agcagggaag 420
aaaacagacg gtacctgact aagaagcccc ggctaactac gtgccagcag ccgcggtaat 480
acgtaggggg caagcgttat ccggaattac tgggtgtaaa gggtgcgtag gtggcatggt 540
aagtcagaag tgaaagcccg gggcttaacc ccgggactgc ttttgaaact gtcatgctgg 600
agtgcaggag aggtaagcgg aattcctagt gtagcggtga aatgcgtaga tattaggagg 660
aacaccagtg gcgaaggcgg cttactggac tgtcactgac actgatgcac gaaagcgtgg 720
ggagcaaaca ggattagata ccctggtagt ccacgccgta aacgatgaat actaggtgtc 780
ggggccgtag aggcttcggt gccgcagcaa a 811

<210> SEQ ID NO 78
<211> LENGTH: 728
<212> TYPE: DNA
<213> ORGANISM: Phascolarctobacterium faecium

<400> SEQUENCE: 78
cggagaattt tcatttcggt agaattctta gtggcgaacg ggtgagtaac gcgtaggcaa 60
cctgcccttt agacggggac aacattccga aaggagtgct aataccggat gtgatcatcg 120
tgccgcatgg caggatgaag aaagatggcc tctacaagta agctatcgct aaaggatggg 180
cctgcgtctg attagctagt tggtagtgta acggactacc aaggcgatga tcagtagccg 240
gtctgagagg atgaacggcc acattgggac tgagacacgg cccaaactcc tacgggaggc 300
agcagtgggg aatcttccgc aatggacgaa agtctgacag agcaacgccg cgtgagtgat 360
gaaggatttc ggtctgtaaa gctctgttgt ttatgacgaa cgtgcagtgt gtgaacaatg 420
cattgcaatg acggtagtaa acgaggaagc cacggctaac tacgtgccag cagccgcggt 480
aatacgtagg tggcgagcgt tgtccggaat tattgggcgt aaagagcatg taggcggctt 540
aataagtcga gcgtgaaaaa tgcggggctc aaccccgtat ggcgctggaa actgttaggc 600
ttgagtgcag gagaggaaag gggaattccc agtgtagcgg tgaaatgcgt agatattggg 660
aggaacacca gtggcgaagg cgcctttctg gactgtgttt gacgctgaga tgcgaaagcc 720
agggtagc 728

<210> SEQ ID NO 79

<211> LENGTH: 707
<212> TYPE: DNA
<213> ORGANISM: Unknown
<220> FEATURE:
<223> OTHER INFORMATION: Agathobaculum butyriciproducens

<400> SEQUENCE: 79
tagtggcgga cgggtgagta acgcgtgagc aatctgcctt taagaggggg ataacagtcg 60
gaaacggctg ctaataccgc ataaagcatt gaattcgcat gttttcgatg ccaaaggagc 120
aatccgcttt tagatgagct cgcgtctgat tagctagttg gcggggtaac ggcccaccaa 180
ggcgacgatc agtagccgga ctgagaggtt gaacggccac attgggactg agacacggcc 240
cagactccta cgggaggcag cagtggggaa tattgcgcaa tgggggraac cctgacgcag 300
caacgccgcg tgattgaaga aggccttcgg gttgtaaaga tctttaatca gggacgaaam 360
atgacggtac ctgaagaata agctccggct aactacgtgc cagcagccgc ggtaatacgt 420
agggagcaag cgttatccgg atttactggg tgtaaagggc gcgcaggcgg gccggcaagt 480
tggaagtgaa atccgggggc ttaacccccg aactgctttc aaaactgctg gtcttgagtg 540
atggagaggc aggcggaatt ccgtgtgtag cggtgaaatg cgtagatata cggaggaaca 600
ccagtggcga aggcggcctg ctggacatta actgacgctg aggcgcgaaa gcgtggggag 660
caaacaggat tagataccct ggtagtccac gccgtaaacg atggata 707

<210> SEQ ID NO 80
<211> LENGTH: 1525
<212> TYPE: DNA
<213> ORGANISM: Bacteroides fragilis

<400> SEQUENCE: 80
atgaagagtt tgatcctggc tcaggatgaa cgctagctac aggcttaaca catgcaagtc 60
gaggggcatc aggaagaaag cttgctttct ttgctggcga ccggcgcacg ggtgagtaac 120
acgtatccaa cctgcccttt actcggggat agcctttcga aagaaagatt aatacccgat 180
ggcataatga ttccgcatgg tttcattatt aaaggattcc ggtaaaggat ggggatgcgt 240
tccattaggt tgttggtgag gtaacggctc accaagcctt cgatggatag gggttctgag 300
aggaaggtcc cccacattgg aactgagaca cggtccaaac tcctacggga ggcagcagtg 360
aggaatattg gtcaatgggc gctagcctga accagccaag tagcgtgaag gatgaaggct 420
ctatgggtcg taaacttctt ttatataaga ataaagtgca gtatgtatac tgttttgtat 480
gtattatatg aataaggatc ggctaactcc gtgccagcag ccgcggtaat acggaggatc 540
cgagcgttat ccggatttat tgggtttaaa gggagcgtag gtggactggt aagtcagttg 600
tgaaagtttg cggctcaacc gtaaaattgc agttgatact gtcagtcttg agtacagtag 660
aggtgggcgg aattcgtggt gtagcggtga aatgcttaga tatcacgaag aactccgatt 720
gcgaaggcag ctcactggac tgcaactgac actgatgctc gaaagtgtgg gtatcaaaca 780
ggattagata ccctggtagt ccacacagta aacgatgaat actcgctgtt tgcgatatac 840
agtaagcggc caagcgaaag cattaagtat tccacctggg gagtacgccg gcaacggtga 900
aactcaaagg aattgacggg ggcccgcaca agcggaggaa catgtggttt aattcgatga 960
tacgcgagga accttacccg ggcttaaatt gcagtggaat gatgtggaaa catgtcagtg 1020
agcaatcacc gctgtgaagg tgctgcatgg ttgtcgtcag ctcgtgccgt gaggtgtcgg 1080
cttaagtgcc ataacgagcg caacccttat ctttagttac taacaggtta tgctgaggac 1140
tctagagaga ctgccgtcgt aagatgtgag gaaggtgggg atgacgtcaa atcagcacgg 1200

```
cccttacgtc cggggctaca cacgtgttac aatggggggt acagaaggca gctagcgggt   1260

gaccgtatgc taatcccaaa agcctctctc agttcggatc gaagtctgca acccgacttc   1320

gtgaagctgg attcgctagt aatcgcgcat cagccacggc gcggtgaata cgttcccggg   1380

ccttgtacac accgcccgtc aagccatggg agccgggggt acctgaagta cgtaaccgca   1440

aggatcgtcc tagggtaaaa ctggtgactg gggctaagtc gtaacaaggt agccgtaccg   1500

gaaggtgcgg ctggaacacc tcctt                                         1525
```

<210> SEQ ID NO 81
<211> LENGTH: 1022
<212> TYPE: DNA
<213> ORGANISM: Fusobacterium mortiferum

<400> SEQUENCE: 81

```
tggctcagga tgaacgctga cagaatgctt aacacatgca agtctacttg atccttcggg     60

tgatggtggc ggacgggtga gtaacgcgta aagaacttgc cctgcagtct gggacaacat    120

ttggaaacga atgctaatac cggatattat gtatttctcg catgagtttt acatgaaagc    180

tatatgcgct gcaggagagc tttgcgtcct attagctagt tggtgaggta acggctcacc    240

aaggccatga taggtagccg gcctgagagg gtgaacggcc acaaggggac tgagacacgg    300

cccttactcc tacgggaggc agcagtgggg aatattggac aatggaccaa aagtctgatc    360

cagcaattct gtgtgcacga tgaagttttt cggaatgtaa agtgctttca gttgggacga    420

agtaagtgac ggtaccaaca gaagaagcga cggctaaata cgtgccagca gccgcggtaa    480

tacgtatgtc gcaagcgtta tccggattta ttgggcgtaa agcgcgtcta ggcggtttgg    540

taagtctgat gtgaaaatgc ggggctcaac tccgtattgc gttggaaact gctaaactag    600

agtactggag aggtgggcgg aactacaagt gtagaggtga aattcgtaga tatttgtagg    660

aatgccgatg gggaagccag cccactggac agatactgac gctaaagcgc gaaagcgtgg    720

gtagcaaaca ggattagata ccctggtagt ccacgccgta aacgatgatt actaggtgtt    780

gggggtcgaa cctcagcgcc caagctaacg cgataagtaa tccgcctggg gagtacgtac    840

gcaagtatga aactcaaagg aattgacggg gacccgcaca agcggtggag catgtggttt    900

aattcgacgc aacgcgagga accttaccag cgtttgacat cctaagaaat tagcagagat    960

gcttttgtgc cccttcgggg gaacttagtg acaggtggtg catggctgtc gtcagctcgt   1020

gt                                                                  1022
```

<210> SEQ ID NO 82
<211> LENGTH: 1490
<212> TYPE: DNA
<213> ORGANISM: Unknown
<220> FEATURE:
<223> OTHER INFORMATION: Paraclostridium benzoelyticum/ Clostridium bifermantans

<400> SEQUENCE: 82

```
agagtttgat cctggctcag gatgaacgct ggcggcgtgc ctaacacatg caagtcgagc     60

gatctcttcg gagagagcgg cggacgggtg agtaacgcgt gggtaacctg ccctgtacac    120

acggataaca taccgaaagg tatactaata cgggataaca tacgaaagtc gcatggcttt    180

tgtatcaaag ctccggcggt acaggatgga cccgcgtctg attagctagt tggtaaggta    240

atggcttacc aaggcaacga tcagtagccg acctgagagg gtgatcggcc acactggaac    300

tgagacacgg tccagactcc tacgggaggc agcagtgggg aatattgcac aatgggcgaa    360
```

agcctgatgc agcaacgccg cgtgagcgat gaaggccttc gggtcgtaaa gctctgtcct 420
caaggaagat aatgacggta cttgaggagg aagccccggc taactacgtg ccagcagccg 480
cggtaatacg taggggcta gcgttatccg gaattactgg gcgtaaaggg tgcgtaggtg 540 gtttttaag tcagaagtga aaggctacgg ctcaaccgta gtaagctttt gaaactagag 600
aacttgagtg caggagagga gagtagaatt cctagtgtag cggtgaaatg cgtagatatt 660
aggaggaata ccagtagcga aggcggctct ctggactgta actgacactg aggcacgaaa 720
gcgtggggag caaacaggat tagataccct ggtagtccac gccgtaaacg atgagtacta 780
ggtgtcgggg gttacccccc tcggtgccgc agctaacgca ttaagtactc cgcctgggaa 840
gtacgctcgc aagagtgaaa ctcaaaggaa ttgacgggga cccgcacaag tagcggagca 900
tgtggtttaa ttcgaagcaa cgcgaagaac cttacctaag cttgacatcc cactgacctc 960
tccctaatcg gagatttccc ttcggggaca gtggtgacag gtggtgcatg gttgtcgtca 1020
gctcgtgtcg tgagatgttg ggttaagtcc cgcaacgagc gcaacccttg cctttagttg 1080
ccagcattaa gttgggcact ctagagggac tgccgaggat aactcggagg aaggtgggga 1140
tgacgtcaaa tcatcatgcc ccttatgctt agggctacac acgtgctaca atgggtggta 1200
cagagggttg ccaagccgcg aggtggagct aatcccttaa agccattctc agttcggatt 1260
gtaggctgaa actcgcctac atgaagctgg agttactagt aatcgcagat cagaatgctg 1320
cggtgaatgc gttcccgggt cttgtacaca ccgcccgtca caccatggaa gttgggggcg 1380
cccgaagccg gttagctaac cttttaggaa gcggccgtcg aaggtgaaac caatgactgg 1440
ggtgaagtcg taacaaggta gccgtatcgg aaggtgcggc tggatcacct 1490

<210> SEQ ID NO 83
<211> LENGTH: 1538
<212> TYPE: DNA
<213> ORGANISM: Unknown
<220> FEATURE:
<223> OTHER INFORMATION: Escherichia fergusonii / Escherichia coli

<400> SEQUENCE: 83
ttgaagagtt tgatcatggc tcagattgaa cgctggcggc aggcctaaca catgcaagtc 60
gaacggtaac aggaagcagc ttgctgcttt gctgacgagt ggcggacggg tgagtaatgt 120
ctgggaaact gcctgatgga gggggataac tactggaaac ggtagctaat accgcataac 180
gtcgcaagac caaagagggg gaccttcggg cctcttgcca tcggatgtgc ccagatggga 240
ttagctagta ggtggggtaa cggctcacct aggcgacgat ccctagctgg tctgagagga 300
tgaccagcca cactggaact gagacacggt ccagactcct acgggaggca gcagtgggga 360
atattgcaca atgggcgcaa gcctgatgca gccatgccgc gtgtatgaag aaggccttcg 420
ggttgtaaag tactttcagc ggggaggaag ggagtaaagt taataccttt gctcattgac 480
gttacccgca gaagaagcac cggctaactc cgtgccagca gccgcggtaa tacggagggt 540
gcaagcgtta atcggaatta ctgggcgtaa agcgcacgca ggcggtttgt taagtcagat 600
gtgaaatccc cgggctcaac ctgggaactg catctgatac tggcaagctt gagtctcgta 660
gaggggggta gaattccagg tgtagcggtg aaatgcgtag agatctggag gaataccggt 720
ggcgaaggcg gccccctgga cgaagactga cgctcaggtg cgaaagcgtg gggagcaaac 780
aggattagat accctggtag tccacgccgt aaacgatgtc gacttggagg ttgtgccctt 840
gaggcgtggc ttccggagct aacgcgttaa gtcgaccgcc tggggagtac ggccgcaagg 900

-continued

```
ttaaaactca aatgaattga cgggggcccg cacaagcggt ggagcatgtg gtttaattcg    960

atgcaacgcg aagaacctta cctggtcttg acatccacgg aagttttcag agatgagaat   1020

gtgccttcgg gaaccgtgag acaggtgctg catggctgtc gtcagctcgt gttgtgaaat   1080

gttgggttaa gtcccgcaac gagcgcaacc cttatccttt gttgccagcg gtccggccgg   1140

gaactcaaag gagactgcca gtgataaact ggaggaaggt ggggatgacg tcaagtcatc   1200

atggccctta cgaccagggc tacacacgtg ctacaatggc gcatacaaag agaagcgacc   1260

tcgcgagagc aagcggacct cataaagtgc gtcgtagtcc ggattggagt ctgcaactcg   1320

actccatgaa gtcggaatcg ctagtaatcg tggatcagaa tgccacggtg aatacgttcc   1380

cgggccttgt acacaccgcc cgtcacacca tgggagtggg ttgcaaaaga agtaggtagc   1440

ttaaccttcg ggagggcgct taccactttg tgattcatga ctggggtgaa gtcgtaacaa   1500

ggtaaccgta ggggaacctg cggttggatc acctcctt                           1538
```

COMPOSITIONS AND METHODS FOR SUPPRESSING PATHOGENIC ORGANISMS

RELATED APPLICATIONS

This application is a national stage filing under 35 U.S.C. § 371 of international application number PCT/US2022/017043, filed Feb. 18, 2022, which was published under PCT Article 21 (2) in English and claims the benefit under 35 U.S.C. § 119 (e) of U.S. provisional application No. 63/151,003 filed Feb. 18, 2021, of each of which is herein incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Aug. 10, 2023, is named P074570026US01-SEQ-NTJ and is 157,195 bytes in size.

BACKGROUND

Multidrug resistant organisms (MDROs; "superbugs"), microorganisms that have developed resistance to one or more classes of antimicrobial agents, such as antibiotics, are emerging as serious global health threat. It is estimated that over 2 million people in the United States contract serious bacterial infections that are resistant to one or more antibiotics each year (CDC, Antibiotic Resistance Threats in the United States, 2013. Publication No. CS239559-B). Treatment options for subjects with MDROs are extremely limited; prevention of transmission is critical. The most important factor contributing to the generation and propagation of MDROs is the use and overuse/misuse of antibiotics and it is thought that the problem will increase in severity as further pathogenic organisms with antibiotic resistance arise (CDC, 2013; WHO 2017).

SUMMARY

In some aspects, the present disclosure provides compositions comprising two or more purified bacterial strains of species selected from the group consisting of a purified bacterial strain of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia A obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri.*

In some aspects, the present disclosure provides compositions comprising two or more purified bacterial strains, wherein the two or more purified bacterial strains comprise 16S rDNA sequences having at least 97% sequence identity with nucleic acid sequences selected from the group consisting of SEQ ID NOs: 1-47.

In some embodiments of the compositions provided herein, the composition comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, or at least 47 purified bacterial strains.

In some aspects, the present disclosure provides compositions comprising purified bacterial strains of species *Bacteroides faecis, Bacteroides vulgatus, Phascolartcobacterium faecium*, and *Clostridium citroniae*. In some aspects, the present disclosure provides compositions comprising purified bacterial strains comprising 16S rDNA sequences having at least 97% sequence identity to nucleic acid sequences of SEQ ID NOs: 10, 29, 30, and 36. In some embodiments of the compositions provided herein, the composition comprises bacterial strains that originate from more than one human donor. In some embodiments, any of the compositions described herein may further comprise taurine.

In some aspects, the present disclosure provides compositions comprising one or more purified bacterial strains belonging to the phylum Firmicutes or Bacteroidetes; one or more purified bacterial strains selected from the group consisting of an *Escherichia* species and a *Fusobacterium* species; and taurine. In some aspects, the present disclosure provides compositions comprising one or more purified bacterial strains belonging to the phylum Firmicutes; one or more purified bacterial strains of *Escherichia* species; and taurine. In some aspects, the present disclosure provides compositions comprising one or more purified bacterial strains belonging to the phylum Firmicutes; one or more purified bacterial strains of *Fusobacterium* species; and taurine. In some aspects, the present disclosure provides compositions comprising one or more purified bacterial strains belonging to the phylum Bacteroidetes; one or more purified bacterial strains of *Escherichia* species; and taurine. In some aspects, the present disclosure provides compositions comprising one or more purified bacterial strains belonging to the phylum Bacteroidetes; one or more purified bacterial strains of *Fusobacterium* species; and taurine.

In some aspects, the present disclosure provides compositions comprising a purified bacterial strain belonging to *Escherichia* species, a purified bacterial strain belonging to *Fusobacterium* species, and one or more purified bacterial strains of species selected from the group consisting of *Bifidobacterium pseudocatenulatum, Bifidobacterium adolescentis, Bifidobacterium longum, Clostridium citroniae, Clostridium clostridioforme, Clostridium bifermentans, Clostridium sordelli, Clostridium innocuum, Erysipelatoclostridium ramosum*, Erysipelotrichaceae bacterium 6_1_45, *Eubacterium hallii, Eubacterium rectale, Anaerostipes caccae, Blautia obeum, Blautia producta, Coprococcus comes, Dorea longicatena, Agathobaculum butyriciproducens*, and *Phascolarctobacterium faecis*; and taurine.

In some aspects, the present disclosure provides compositions comprising a purified bacterial strain belonging to *Escherichia* species, a purified bacterial strain belonging to

*Fusobacterium* species, and one or more purified bacterial strains of species selected from the group consisting of *Collinsella aerofaciens, Bifidobacterium longum, Bacteroides ovatus, Bacteroides vulgatus, Alistipes putredinis, Clostridium citroniae, Clostridium clostridioforme, Erysipelatoclostridium ramosum*, Erysipelotrichaceae bacterium 6_1_45, *Blautia obeum, Blautia producta, Dorea longicatena*, and *Phascolarctobacterium faecium*; and taurine.

In some aspects, the present disclosure provides compositions comprising a purified bacterial strain belonging to *Escherichia* species and one or more purified bacterial strains of species selected from the group consisting of *Bifidobacterium pseudocatenulatum, Bifidobacterium adolescentis, Bifidobacterium longum, Clostridium citroniae, Clostridium clostridioforme, Clostridium bifermentans, Clostridium sordelli, Clostridium innocuum, Erysipelatoclostridium ramosum*, Erysipelotrichaceae bacterium 6_1_45, *Eubacterium hallii, Eubacterium rectale, Anaerostipes caccae, Blautia obeum, Blautia producta, Coprococcus comes, Dorea longicatena, Agathobaculum butyriciproducens, and Phascolarctobacterium faecis*; and taurine.

In some aspects, the present disclosure provides compositions comprising purified bacterial strain belonging to *Fusobacterium* species and one or more purified bacterial strains of species selected from the group consisting of *Bifidobacterium pseudocatenulatum, Bifidobacterium adolescentis, Bifidobacterium longum, Clostridium citroniae, Clostridium clostridioforme, Clostridium bifermentans, Clostridium sordelli, Clostridium innocuum, Erysipelatoclostridium ramosum*, Erysipelotrichaceae bacterium 6_1_45, *Eubacterium* hallii, *Eubacterium rectale, Anaerostipes caccae, Blautia obeum, Blautia producta, Coprococcus comes, Dorea longicatena, Agathobaculum butyriciproducens*, and *Phascolarctobacterium faecis*; and taurine.

In some aspects, the present disclosure provides compositions comprising a purified bacterial strain belonging to *Escherichia* species, a purified bacterial strain belonging to *Fusobacterium* species, and one or more purified bacterial strains of species selected from the group consisting of *Bacteroides ovatus, Bacteroides thetaiotamicron, Bacteroides xyalinosolvens, Bacteroides caccae, Bacteroides cellulosilyticus, Bacteroides faecis, Bacteroides fragilis, Bacteroides uniformis, Bacteroides vulgatus, Odoribacter splanchnicus, Parabacteroides distasonis, Parabacteroides merdae, Alistipes putredinis*, and *Alistipes shahii*; and taurine.

In some aspects, the present disclosure provides compositions comprising a purified bacterial strain belonging to *Escherichia* species and one or more purified bacterial strains of species selected from the group consisting of *Collinsella aerofaciens, Bacteroides ovatus, Bacteroides thetaiotamicron, Bacteroides xyalinosolvens, Bacteroides caccae, Bacteroides cellulosilyticus, Bacteroides faecis, Bacteroides fragilis, Bacteroides uniformis, Bacteroides vulgatus, Odoribacter splanchnicus, Parabacteroides distasonis, Parabacteroides merdae, Alistipes putredinis*, and *Alistipes shahii*; and taurine.

In some aspects, the present disclosure provides compositions comprising a purified bacterial strain belonging to *Fusobacterium* species and one or more purified bacterial strains of species selected from the group consisting of *Collinsella aerofaciens, Bacteroides ovatus, Bacteroides thetaiotamicron, Bacteroides xyalinosolvens, Bacteroides caccae, Bacteroides cellulosilyticus, Bacteroides faecis, Bacteroides fragilis, Bacteroides uniformis, Bacteroides vulgatus, Odoribacter splanchnicus, Parabacteroides distasonis, Parabacteroides merdae, Alistipes putredinis*, and *Alistipes shahii*; and taurine.

In some aspects, the present disclosure provides compositions comprising *Clostridium bolteae, Anaerotruncus colihominis, Sellimonas intestinalis, Clostridium symbiosum, Blautia producta, Dorea longicatena*, Erysipelotrichaceae bacterium, *Flavinofractor plautii*, a purified bacterial strain belonging to *Escherichia* species, a purified bacterial strain belonging to *Fusobacterium* species; and taurine.

In some aspects, the present disclosure provides compositions comprising *Clostridium bolteae, Anaerotruncus colihominis, Sellimonas intestinalis, Clostridium symbiosum, Blautia producta, Dorea longicatena*, Erysipelotrichaceae bacterium, *Flavinofractor plautii*, a purified bacterial strain belonging to *Escherichia* species; and taurine.

In some aspects, the present disclosure provides compositions comprising *Clostridium bolteae, Anaerotruncus colihominis, Sellimonas intestinalis, Clostridium symbiosum, Blautia producta, Dorea longicatena*, Erysipelotrichaceae bacterium, *Flavinofractor plautii*, a purified bacterial strain belonging to *Fusobacterium* species; and taurine.

In some aspects, the present disclosure provides compositions comprising *Anaerotruncus colihominis, Sellimonas intestinalis, Clostridium symbiosum, Dorea longicatena*, Erysipelotrichaceae bacterium, *Flavinofractor plautii*, a purified bacterial strain belonging to *Escherichia* species, a purified bacterial strain belonging to *Fusobacterium* species; and taurine.

In some aspects, the present disclosure provides compositions comprising *Anaerotruncus colihominis, Sellimonas intestinalis, Clostridium symbiosum, Dorea longicatena*, Erysipelotrichaceae bacterium, *Flavinofractor plautii*, a purified bacterial strain belonging to *Escherichia* species; and taurine.

In some aspects, the present disclosure provides compositions comprising *Anaerotruncus colihominis, Sellimonas intestinalis, Clostridium symbiosum, Dorea longicatena*, Erysipelotrichaceae bacterium, *Flavinofractor plautii*, a purified bacterial strain belonging to *Fusobacterium* species; and taurine.

In some aspects, the present disclosure provides compositions comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (Lachnospiraceae bacterium 6_1_63FAA), *Clostridium* spp. (*Clostridium bolteae* ATCC BAA-613), cf. *Clostridium* sp. MLG055 (Erysipelotrichaceae bacterium 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (Lachnospiraceae bacterium 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (Lachnospiraceae bacterium 5_1_57FAA), Lachnospiraceae bacterium A4 (Lachnospiraceae bacterium 3_1_57FAA_CT1), *Clostridium* sp. 316002/08 (Clostriales bacterium 1_7_47FAA), Lachnospiraceae bacterium A4 (Lachnospiraceae bacterium 3_1_57FAA_CT1), a purified bacterial strain belonging to *Escherichia* species, a purified bacterial strain belonging to *Fusobacterium* species; and taurine.

In some aspects, the present disclosure provides compositions comprising *Clostridium saccharogumia* (*Clostridium ramosum* JCM 1298), *Flavonifractor plautii* (*Pseudofla-*

*vonifractor capillosus* ATCC 29799), *Clostridium hathewayi* (*Clostridium saccharolyticum* WM1), *Blautia coccoides* (Lachnospiraceae bacterium 6_1_63FAA), *Clostridium* spp. (*Clostridium bolteae* ATCC BAA-613), cf. *Clostridium* sp. MLG055 (Erysipelotrichaceae bacterium 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (Lachnospiraceae bacterium 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (Lachnospiraceae bacterium 5_1_57FAA), Lachnospiraceae bacterium A4 (Lachnospiraceae bacterium 3_1_57FAA_CT1), *Clostridium* sp. 316002/08 (Clostriales bacterium 1_7_47FAA), Lachnospiraceae bacterium A4 (Lachnospiraceae bacterium 3_1_57FAA_CT1), a purified bacterial strain belonging to *Escherichia* species; and taurine.

In some aspects, the present disclosure provides compositions comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (Lachnospiraceae bacterium 6_1_63FAA), *Clostridium* spp. (*Clostridium bolteae* ATCC BAA-613), cf. *Clostridium* sp. MLG055 (Erysipelotrichaceae bacterium 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (Lachnospiraceae bacterium 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (Lachnospiraceae bacterium 5_1_57FAA), Lachnospiraceae bacterium A4 (Lachnospiraceae bacterium 3_1_57FAA_CT1), *Clostridium* sp. 316002/08 (Clostriales 3_1_57FAA_CT1), a purified bacterial strain belonging to *Fusobacterium* species; and taurine.

In some aspects, the present disclosure provides compositions comprising *Clostridium bolteae, Anaerotruncus colihominis, Sellimonas intestinalis, Clostridium symbiosum, Blautia producta*, Erysipelotrichaceae bacterium, *Flavinofractor plautii*, a purified bacterial strain belonging to *Escherichia* species, a purified bacterial strain belonging to *Fusobacterium* species; and taurine.

In some aspects, the present disclosure provides compositions comprising *Clostridium bolteae, Anaerotruncus colihominis, Sellimonas intestinalis, Clostridium symbiosum, Blautia producta*, Erysipelotrichaceae bacterium, *Flavinofractor plautii*, a purified bacterial strain belonging to *Escherichia* species; and taurine.

In some aspects, the present disclosure provides compositions comprising *Clostridium bolteae, Anaerotruncus colihominis, Sellimonas intestinalis, Clostridium symbiosum, Blautia producta*, Erysipelotrichaceae bacterium, *Flavinofractor plautii*, a purified bacterial strain belonging to *Fusobacterium* species; and taurine.

In some aspects, the present disclosure provides compositions comprising *Collinsella aerofaciens, Bacteroides ovatus, Bacteroides thetaiotamicron, Bacteroides xyalinosolvens, Bacteroides caccae, Bacteroides cellulosilyticus, Bacteroides faecis, Bacteroides uniformis, Bacteroides vulgatus, Odoribacter splanchnicus, Parabacteroides distasonis, Parabacteroides merdae, Alistipes putredinis, Alistipes shahii, Bifidobacterium pseudocatenulatum, Bifidobacterium adolescentis, Bifidobacterium longum, Clostridium citroniae, Clostridium clostridioforme, Clostridium innocuum, Erysipelatoclostridium ramosum*, Erysipelotrichaceae bacterium 6_1_45, *Eubacterium* hallii, *Eubacterium rectale, Anaerostipes caccae, Blautia obeum, Blautia producta, Coprococcus comes, Dorea longicatena, Agathobaculum butyriciproducens, Phascolarctobacterium faecis*, a purified bacterial strain belonging to *Escherichia* species, a purified bacterial strain belonging to *Fusobacterium* species; and taurine.

In some aspects, the present disclosure provides compositions comprising *Collinsella aerofaciens, Bacteroides ovatus, Bacteroides thetaiotamicron, Bacteroides xyalinosolvens, Bacteroides cellulosilyticus, Bacteroides uniformis, Bacteroides vulgatus, Parabacteroides distasonis, Alistipes putredinis, Alistipes shahii, Bifidobacterium adolescentis, Bifidobacterium longum, Clostridium citroniae, Clostridium clostridioforme, Clostridium innocuum, Erysipelatoclostridium ramosum*, Erysipelotrichaceae bacterium 6_1_45, *Eubacterium rectale, Anaerostipes caccae, Blautia obeum, Blautia producta, Coprococcus comes, Dorea longicatena, Agathobaculum butyriciproducens, Phascolarctobacterium faecis*, a purified bacterial strain belonging to *Escherichia* species, a purified bacterial strain belonging to *Fusobacterium* species; and taurine.

In some aspects, the present disclosure provides compositions comprising *Bacteroides ovatus, Bacteroides thetaiotamicron, Bacteroides xyalinosolvens, Bacteroides caccae, Bacteroides cellulosilyticus, Bacteroides faecis, Bacteroides uniformis, Bacteroides vulgatus, Alistipes putredinis, Alistipes shahii, Clostridium citroniae, Clostridium clostridioforme, Clostridium innocuum, Erysipelatoclostridium ramosum*, Erysipelotrichaceae bacterium 6_1_45, *Eubacterium* hallii, *Eubacterium rectale, Blautia obeum, Blautia producta, Coprococcus comes, Dorea longicatena*, a purified bacterial strain belonging to *Escherichia* species, a purified bacterial strain belonging to *Fusobacterium* species; and taurine.

In some aspects, the present disclosure provides compositions comprising *Blautia producta, Bifidobacterium longum, Bifidobacterium adolescentis, Paeniclostridium sordellii, Bifidobacterium pseudocatenulatum, Erysipelatoclostridium ramosum, Escherichia coli, Clostridium clostridioforme, Paraclostridium bifermentans, Clostridium citroniae, Clostridium innocuum, Agathobaculum butyriciproducens, Clostridium innocuum, Dorea longicatena, Collinsella aerofaciens, Eubacterium hallii, Bacteroides faecis, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Blautia producta, Bifidobacterium longum, Bifidobacterium adolescentis, Paeniclostridium sordellii, Bifidobacterium pseudocatenulatum, Erysipelatoclostridium ramosum, Escherichia coli, Clostridium clostridioforme, Paraclostridium bifermentans, Clostridium citroniae, Anaerostipes caccae, Fusobacterium mortiferum, Clostridium clostridioforme, Blautia obeum, Clostridium innocuum, Agathobaculum butyriciproducens, Clostridium innocuum, Dorea longicatena, Collinsella aerofaciens, Eubacterium hallii, Bacteroides faecis, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Blautia producta, Bifidobacterium*

*longum, Bifidobacterium adolescentis, Paeniclostridium sordellii, Bifidobacterium pseudocatenulatum, Erysipelatoclostridium ramosum, Escherichia coli, Clostridium clostridioforme, Paraclostridium bifermentans, Clostridium citroniae, Anaerostipes caccae, Fusobacterium mortiferum, Blautia obeum, Clostridium innocuum, Agathobaculum butyriciproducens, Clostridium innocuum, Dorea longicatena, Collinsella aerofaciens, Eubacterium hallii, Bacteroides faecis, Odoribacter* sp., *Bacteroides fragilis, Bacteroides ovatus, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Blautia producta, Bifidobacterium longum, Bifidobacterium adolescentis, Paeniclostridium sordellii, Bifidobacterium pseudocatenulatum, Erysipelatoclostridium ramosum, Escherichia coli, Paraclostridium bifermentans, Clostridium citroniae, Anaerostipes caccae, Fusobacterium mortiferum, Blautia obeum, Clostridium innocuum, Agathobaculum butyriciproducens, Odoribacter* sp., *Bacteroides fragilis, Bacteroides ovatus, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Bacteroides cellulosilyticus, Bacteroides ovatus, Bacteroides thetaiotaomicron, Bacteroides uniformis, Bacteroides vulgatus, Bifidobacterium adolescentis, Bifidobacterium longum, Blautia producta, Clostridium citroniae, Clostridium clostridioforme, Clostridium innocuum, Clostridium innocuum, Coprococcus comes, Dorea longicatena, Erysipelatoclostridium ramosum, Eubacterium rectale, Parabacteroides distasonis, Bacteroides xylanisolvens, Blautia obeum, Alistipes putredinis, Collinsella aerofaciens, Eubacterium hallii, Anaerostipes caccae, Phascolarctobacterium faecium, Agathobaculum butyriciproducens, Fusobacterium mortiferum, Escherichia coli*; and taurine.

In some aspects, the present disclosure provides compositions comprising *Bacteroides caccae, Bacteroides cellulosilyticus, Bacteroides ovatus, Bacteroides thetaiotaomicron, Bacteroides uniformis, Bacteroides vulgatus, Bifidobacterium longum, Blautia producta, Clostridium clostridioforme, Clostridium innocuum, Coprococcus comes, Dorea longicatena, Erysipelatoclostridium ramosum, Clostridium citroniae, Odoribacter splanchnicus, Parabacteroides distasonis, Bacteroides xylanisolvens, Blautia obeum, Alistipes putredinis, Collinsella aerofaciens, Alistipes shahii, Anaerostipes caccae, Phascolarctobacterium faecium, Agathobaculum butyriciproducens, Bacteroides fragilis, Fusobacterium mortiferum, Escherichia coli*; and taurine.

In some aspects, the present disclosure provides compositions comprising *Bacteroides ovatus, Bacteroides vulgatus, Bifidobacterium adolescentis, Bifidobacterium longum, Bifidobacterium pseudocatenulatum, Blautia producta, Clostridium citroniae, Clostridium clostridioforme, Clostridium innocuum, Clostridium innocuum, Paeniclostridium sordellii, Coprococcus comes, Dorea longicatena, Erysipelatoclostridium ramosum, Eubacterium rectale, Odoribacter splanchnicus, Parabacteroides distasonis, Parabacteroides merdae, Bacteroides xylanisolvens, Blautia obeum, Alistipes putredinis, Collinsella aerofaciens, Eubacterium hallii, Alistipes shahii, Anaerostipes caccae, Phascolarctobacterium faecium, Agathobaculum butyriciproducens, Fusobacterium mortiferum, Paraclostridium bifermentans, Escherichia coli*; and taurine.

In some aspects, the present disclosure provides compositions comprising *Bacteroides ovatus, Bacteroides vulgatus, Bifidobacterium longum, Blautia producta, Clostridium citroniae, Clostridium clostridioforme, Clostridium innocuum, Coprococcus comes, Dorea longicatena, Erysipelatoclostridium ramosum, Odoribacter splanchnicus, Parabacteroides distasonis, Bacteroides xylanisolvens, Blautia obeum, Alistipes putredinis, Collinsella aerofaciens, Alistipes shahii, Anaerostipes caccae, Phascolarctobacterium faecium, Fusobacterium mortiferum, Escherichia coli*; and taurine.

In some aspects, the present disclosure provides compositions comprising *Bacteroides faecis, Bacteroides ovatus, Bacteroides vulgatus, Bifidobacterium adolescentis, Bifidobacterium longum, Blautia producta, Clostridium citroniae, Clostridium clostridioforme, Clostridium innocuum, Clostridium innocuum, Paeniclostridium sordellii, Dorea longicatena, Erysipelatoclostridium ramosum, Odoribacter splanchnicus, Blautia obeum, Alistipes putredinis, Collinsella aerofaciens, Eubacterium hallii, Anaerostipes caccae, Phascolarctobacterium faecium, Agathobaculum butyriciproducens, Bacteroides fragilis, Fusobacterium mortiferum, Paraclostridium bifermentans, Escherichia coli*; and taurine.

In some aspects, the present disclosure provides compositions comprising *Bacteroides faecis, Bacteroides ovatus, Bacteroides vulgatus, Bifidobacterium longum, Blautia producta, Clostridium citroniae, Clostridium clostridioforme, Clostridium innocuum, Dorea longicatena, Erysipelatoclostridium ramosum, Odoribacter splanchnicus, Alistipes putredinis, Collinsella aerofaciens, Blautia obeum, Anaerostipes caccae, Phascolarctobacterium faecium, Agathobaculum butyriciproducens, Fusobacterium mortiferum, Escherichia coli*; and taurine.

In some aspects, the present disclosure provides compositions comprising bacterial strains of species *Bacteroides vulgatus, Clostridium citroniae*, and *Phascolarctobacterium faecium*, and one or more purified bacterial strains of species selected from the group consisting of *Bacteroides faecis, Bacteroides ovatus, Bifidobacterium longum, Blautia producta, Clostridium clostridioforme, Clostridium innocuum, Dorea longicatena, Erysipelatoclostridium ramosum, Odoribacter splanchnicus, Alistipes putredinis, Collinsella aerofaciens, Blautia obeum, Anaerostipes caccae, Agathobaculum butyriciproducens, Fusobacterium mortiferum, Escherichia coli*; and taurine.

In some aspects, the present disclosure provides compositions comprising *Collinsella aerofaciens, Bifidobacterium longum, Bacteroides ovatus, Bacteroides faecis, Bacteroides vulgatus, Odoribacter splanchnicus, Alistipes putredinis, Clostridium citroniae, Clostridium clostridioforme, Erysipelatoclostridium ramosum*, Erysipelotrichaceae bacterium 6_1_45, *Anaerostipes caccae, Blautia obeum, Blautia producta, Dorea longicatena, Agathobaculum butyriciproducens, Phascolarctobacterium faecium, Escherichia coli, Fusobacterium mortiferum*; and taurine.

In some aspects, the present disclosure provides compositions comprising *Collinsella aerofaciens, Bifidobacterium longum, Bacteroides ovatus, Bacteroides vulgatus, Parabacteroides distasonis, Alistipes putredinis, Clostridium citroniae, Clostridium clostridioforme, Erysipelatoclostridium ramosum*, Erysipelotrichaceae bacterium 6_1_45, *Anaerostipes caccae, Blautia obeum, Blautia producta, Agathobaculum butyriciproducens, Phascolarctobacterium faecium, Escherichia coli, Fusobacterium mortiferum*; and taurine.

In some aspects, the present disclosure provides compositions comprising *Collinsella aerofaciens, Bifidobacterium longum, Bacteroides ovatus, Bacteroides vulgatus, Alistipes putredinis, Clostridium citroniae, Clostridium clostridioforme, Erysipelatoclostridium ramosum*, Erysipelotrichaceae bacterium 6_1_45, *Blautia obeum, Blautia producta, Dorea longicatena, Phascolarctobacterium faecium, Escherichia coli, Fusobacterium mortiferum*; and taurine.

In some aspects, the present disclosure provides compositions comprising purified bacterial strains of species *Bacteroides faecis, Bacteroides vulgatus, Phascolartcobacterium faecium*, and *Clostridium citroniae*; and taurine. In some aspects, the present disclosure provides compositions comprising purified bacterial strains comprising 16S rDNA sequences having at least 97% sequence identity to the nucleic acid sequences of SEQ ID NOs: 10, 29, 30, and 36; and taurine.

In some embodiments, any of the compositions described herein may further comprise one or more bacterial strain selected from the group consisting of *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*.

In some embodiments, the composition further comprises taurine. In some embodiments, the composition comprises between about 40 mg to about 3000 mg taurine. In some embodiments, the composition comprises between about 100 mg to about 2000 mg taurine. In some embodiments, the composition comprises between about 500 mg to about 1500 mg taurine.

In some embodiments, the composition is effective in suppressing the replication, survival, and/or colonization of one or more pathogenic organisms. In some embodiments, the composition is effective in treating an infection by a pathogenic organism in a subject. In some embodiments, the pathogenic organism is susceptible to antibiotics. In some embodiments, the pathogenic organism is resistant to one or more antibiotics. In some embodiments, the pathogenic organism is a multi-drug resistant organism.

In some embodiments, the multi-drug resistant organism is Carbapenem Resistant Enterobacteriaceae (CRE) or Extended spectrum beta-lactamase (ESBL)-producing Enterobacteriaceae. In some embodiments, the Carbapenem Resistant Enterobacteriaceae (CRE) is carbapenem-resistant *Klebsiella pneumoniae*. In some embodiments, the carbapenem-resistant *Klebsiella pneumoniae* is carbapenem-resistant *Klebsiella pneumoniae* ATCC 700721. In some embodiments, the ESBL-producing Enterobacteriaceae is ESBL-producing *K. pneumoniae* or EBSL-producing *E. coli*. In some embodiments, the ESBL-producing Enterobacteriaceae is ESBL-producing *K. pneumoniae* subsp. *pneumoniae* (ATCC 700721), ESBL-producing *E. coli* ATCC BAA 2777, adherent/invasive *E. coli* (AIEC), Shiga toxin-producing *E. coli* (STEC), Verocytotoxin-producing *E. coli* (VTEC), enterohemorrhagic *E. coli* (EHEC), enteropathogenic *E. coli* (EPEC), enteroaggregative *E. coli* (EAEC), enteroinvasive *E. coli* (EIEC), or diffusely adherent *E. coli* (DAEC).

In some embodiments, the bacterial strains are lyophilized. In some embodiments, the bacterial strains are spray-dried. In some embodiments, one or more of the bacterial strains are in spore form. In some embodiments, each of the bacterial strains is in spore form. In some embodiments, one or more of the bacterial strains are in vegetative form. In some embodiments, each of the bacterial strains is in vegetative form. In some embodiments, the composition further comprises one or more enteric polymers.

In some embodiments, the pharmaceutical composition comprises between $1\times10^6$ and $1\times10^{10}$ colony forming units (CFUs) per bacterial strain. In some embodiments, each bacterial strain is present in the composition in the same CFU quantities (e.g., each strain is present at $1\times10^8$ CFU).

In some aspects, the present disclosure provides pharmaceutical compositions comprising any of the compositions described herein and a pharmaceutically acceptable excipient.

In some embodiments, the pharmaceutical composition is formulated for oral delivery. In some embodiments, the pharmaceutical composition is formulated for delivery to the intestine. In some embodiments, the pharmaceutical composition is formulated for delivery to the colon. In some embodiments, the pharmaceutical composition is administered as one dose. In some embodiments, the pharmaceutical composition is administered as multiple doses. In some embodiments, each dose comprises the administration of multiple capsules.

In some aspects, the present disclosure provides a food product comprising any of the compositions comprising bacterial strains provided herein, and a nutrient.

In some aspects, the present disclosure provides a method of suppressing infection by a pathogenic organism in a subject, comprising administering to the subject a therapeutically effective amount of any of the compositions comprising bacterial strains, pharmaceutical compositions, or food products described herein.

In some aspects, the present disclosure provides a method of reducing or preventing colonization by a pathogenic organism in a subject, comprising administering to the subject a therapeutically effective amount of any of the compositions comprising bacterial strains, pharmaceutical compositions, or food products described herein.

In some aspects, the present disclosure provides a method of treating infection by a pathogenic organism in a subject, comprising administering to the subject a therapeutically effective amount of any of the compositions comprising bacterial strains, pharmaceutical compositions, or food products described herein.

In some embodiments of the methods provided herein, the pathogenic organism is a multi-drug resistant organism. In some embodiments, the pathogenic organism is *Klebsiella pneumoniae*. In some embodiments, the *Klebsiella pneumoniae* is multi-drug resistant. In some embodiments, the multi-drug resistant *Klebsiella pneumoniae* is carbapenem-resistant *Klebsiella pneumoniae*.

In some embodiments, the pathogenic organism is Extended spectrum beta-lactamase (ESBL)-producing Enterobacteriaceae. In some embodiments, the ESBL producing Enterobacteriaceae is *Escherichia coli* (*E. coli*). In some embodiments, the *E. coli* is adherent/invasive *E. coli* (AIEC), Shiga toxin-producing *E. coli* (STEC), Verocytotoxin-producing *E. coli* (VTEC), enterohemorrhagic *E. coli* (EHEC), enteropathogenic *E. coli* (EPEC), enteroaggregative *E. coli* (EAEC), enteroinvasive *E. coli* (EIEC), or diffusely adherent *E. coli* (DAEC).

In some embodiments, the subject is human. In some embodiments, the composition is administered to the subject by oral administration. In some embodiments, the composition is administered to the subject by rectal administration. In some embodiments, the administering suppresses the replication, survival, and/or colonization of the pathogenic organism. In some embodiments, the administration of the composition is not preceded by administration of vancomycin. In some embodiments, further comprising administering an antibiotic to the subject prior to administration of the composition. In some embodiments, the antibiotic is vancomycin.

In some embodiments, the method further comprises administering a composition comprising taurine to the subject. In some embodiments, the composition comprising taurine is administered to the subject prior to or after administration of any of the compositions or food products described herein containing a purified bacterial mixture. In some embodiments, the subject is administered between about 40 mg to about 3000 mg taurine per day. In some embodiments, the subject is administered between about 100 mg to about 2000 mg taurine per day. In some embodiments, the subject is administered between about 500 mg to about 1500 mg taurine per day.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIG. 3 is a table showing the phylum, family, and species names of the bacterial strains present in a composition of 47 bacterial strains, referred to herein as "47-mix."

FIG. 5A shows extended spectrum beta-lactamase (ESBL) producing Enterobacteriaceae colonization (colony forming units, "CFU") levels in mice at 7, 10, and 14 days post-treatment ("days post Tx"). FIG. 5B shows CRE colonization (colony forming units, "CFU") levels in mice at 7, 10, and 14 days post-treatment ("days post Tx"). For each time point, data are shown from left to right from mice treated with control (PBS), a composition of 47 strains (47-mix), a stool fraction from a second human donor (Donor 2 "SFL"), or a bacterial composition obtained by introducing fecal matter from a first human donor into a germ-free mouse and obtaining stool from the mouse to prepare a fecal matter transplant (Donor 1-inoculated mouse FMT). The dashed line represents the limit of detection.

DETAILED DESCRIPTION

Figure 1:
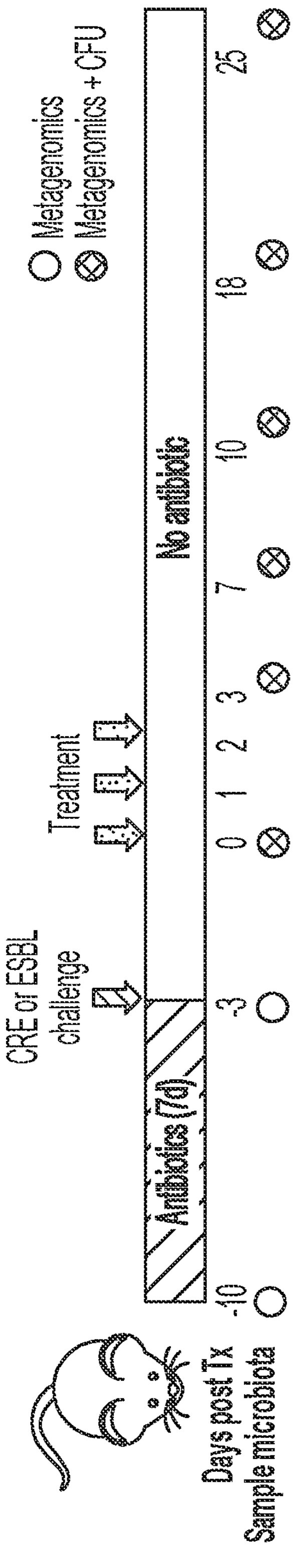
FIG. 1 presents a timeline of an exemplary mouse model of carbapenem-resistant Enterobacteriaceae ("CRE") or extended spectrum beta-lactamase-producing Enterobacteriaceae ("ESBL") colonization experiment.

Suppressing or preventing undesired bacteria in a subject or suppressing or preventing colonization of bacteria in a particular region of the body can be challenging. Bacterial colonization may induce immune responses (local or systemic) in the subject, which may lead to serious disease. In particular, for multi-drug resistant organisms, or organisms that have acquired antibiotic resistance, elimination with many conventional therapeutics, such as antibiotics, may not be possible due to resistance or tolerance to the therapeutic. Additionally, it has been recently appreciated that intestinal colonization by bacteria of the oral microbiome may influence the immune environment of the intestine, such as induce Th1-dominated immune responses and lead to chronic inflammation and inflammatory conditions (see, e.g., Atarashi et al. Science (2017) 358 (359-365)). Normal bacterial colonization of different regions of the body, such as the oral cavity, may provide a reservoir of bacteria that can migrate and colonize other regions, such as the intestines.

Development of a live biotherapeutic product that is effective in promoting intestinal decolonization against multiple pathogens (e.g., both carbapenem-resistant Enterobacteriaceae and extended spectrum beta-lactamase-producing Enterobacteriaceae) has been challenging. Provided herein are compositions and methods for reducing/suppressing and/or preventing colonization by pathogenic organisms, such as multi-drug resistant organisms, for example carbapenem resistant Enterobacteriaceae (CRE) and extended spectrum beta-lactamase (ESBL)-producing Enterobacteriaceae. Provided herein are compositions and methods for suppressing infection by pathogenic organisms. Provided herein are compositions and methods for treating infection by a pathogenic organism. Also provided herein are compositions and methods for inducing regulatory T cell (Treg) production in response to pathogenic organisms. Provided herein are compositions and methods for inducing production of short chain fatty acids (SCFAs) in response to pathogenic organisms. Also provided herein are compositions comprising purified bacterial mixture and taurine, which may further aid in the colonization of the microbiota by beneficial bacterial strains and/or reduction in colonization (resistance) to pathogens.

In some embodiments, the one or more of the bacterial strains of the compositions provided herein colonize or recolonize the intestinal tract or parts of the intestinal tract (e.g., the colon or the cecum) of the subject. Such colonization or recolonization may also be referred to as grafting. In some embodiments, the one or more of the bacterial strains of the compositions recolonize the intestinal tract (e.g., the colon or the cecum) of the subject, for example after another organism or population of organisms has been partially or completely removed (e.g., by antibiotic treatment). In some embodiments, one or more of the bacterial strains of the compositions recolonize the intestinal tract (e.g., the colon or the cecum) after one or more pathogenic organisms or other organism (e.g., bacteria that induce an immune response) has been removed. In some embodiments, the recolonization of the intestinal tract or parts thereof by the bacterial strains of the compositions described herein prevents or suppresses colonization by undesired organisms (e.g., pathogenic organisms, multi-drug resistant organisms, oral microbiome bacteria, bacteria that induce immune responses, pathobionts, bacteria that reduce Treg production, bacteria that reduce SCFA production).

In some embodiments, the one or more of the bacterial strains of the compositions can "outgrow" a pathogen or undesired bacteria, such as a pathogenic organism, for example carbapenem resistant Enterobacteriaceae (CRE) and/or extended spectrum beta-lactamase (ESBL)-producing Enterobacteriaceae. Thus, in some embodiments, if a pathogen or undesired bacteria (e.g., pathogenic organisms, multi-drug resistant organism, for example carbapenem resistanct Enterobacteriaceae (CRE) and extended spectrum beta-lactamase (ESBL)-producing Enterobacteriaceae) and one or more bacteria of compositions provided herein are both present in the intestinal tract (e.g., the colon or the cecum), the one or more bacteria of compositions provided herein grow faster (e.g., have a shorter doubling time) than the pathogen, thereby preventing the pathogen from accumulating in the intestinal tract (e.g., the colon or the cecum). In some embodiments, the one or more bacteria of compositions provided herein grow faster than the pathogen in an otherwise intact or complete microbiome. In some embodiments, the one or more bacteria of compositions provided herein grow faster than the pathogen in a depleted microbiome (e.g., following antibiotic treatment). In some embodiments, the faster growth results because the one or more bacteria of the compositions provided herein are better at grafting in the intestinal tract (e.g., the colon or the cecum). In some embodiments, the faster growth results because the one or more bacteria of the compositions provided herein are better at metabolizing nutrients present in the intestinal tract (e.g., the colon or the cecum). In some embodiments, the compositions of bacterial strains provided herein prevent or inhibit replication of the pathogen. In some embodiments, the compositions of bacterial strains provided herein induce death of (kill) the pathogen. In some embodiments, the bacterial strains of the compositions provided herein can treat pathogenic infections, because of the synergy between the bacterial strains.

In some embodiments, the bacterial compositions described herein prevent recolonization by a pathogen or undesired bacteria (e.g., pathogenic organisms, multi-drug resistant organisms, for example carbapenem resistant Enterobacteriaceae (CRE) and extended spectrum beta-lactamase (ESBL)-producing Enterobacteriaceae). For example, in some embodiments, the pathogen or undesired bacteria have been reduced or eliminated from the subject, for example, using a first therapeutic agent (such as an antibiotic), and the bacterial compositions described herein are administered to prevent recolonization of the subject. In some embodiments, the bacterial compositions described herein reduce or eliminate a pathogen or undesired bacteria from the subject and prevent recolonization of the subject.

In some embodiments, the combination of bacterial strains of the compositions provided herein is superior in the use of nutrients when compared to the pathogen or undesired bacteria, thereby suppressing the growth of the pathogen or undesired bacteria. In some embodiments, the combination of bacterial strains of the compositions provided herein is superior in grafting when compared to the pathogen or undesired bacteria, thereby suppressing the growth of the pathogen or undesired bacteria. In some embodiments, the combination of bacterial strains of the compositions provided herein is superior in the use of nutrients and in grafting when compared to the pathogen or undesired bacteria, thereby suppressing the growth of the pathogen or undesired bacteria. In some embodiments, the combination of bacterial strains of the compositions provided herein inhibits the growth, survival, and/or colonization of the pathogen or undesired bacteria.

In some embodiments, the combination of bacterial strains of the compositions provided herein has antagonizing or inhibitory activity towards the pathogen or undesired bacteria, thereby inhibiting the growth, survival, and/or colonization of the pathogen or undesired bacteria. In some embodiments, at least one bacterial strain of the compositions provided herein has antagonizing or inhibitory activity towards the pathogen or undesired bacteria, thereby inhibiting the growth, survival, and/or colonization of the pathogen or undesired bacteria.

In some embodiments, the bacterial strains of the compositions provide a synergistic effect in colonizing specific niches in the intestinal tract (e.g., the colon or the cecum). In some embodiments, the synergistic effect is provided by the capacity of the combination to metabolize specific nutrients. In some embodiments, the synergistic effect is provided by the capacity of the combination to provide specific metabolites to the environment.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated, and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments, the bacteria of the compositions provided herein are anaerobic bacteria. In some embodiments, the bacteria of the compositions provided herein are obligate anaerobic bacteria.

In general, bacterial strains may be classified phylogenetically with other closely related strains and species based on their 16S rRNA (or 16S rDNA) nucleic acid sequence. Methods for determining the identity of specific bacterial species based on their 16S rRNA (or 16S rDNA) nucleic acid sequence are well known in the art (See, e.g., Jumpstart Consortium Human Microbiome Project Data Generation Working, G. PLOS One (2012) 7, e39315).

It should be appreciated that any of the compositions described herein may contain multiple strains of a particular bacterial species. For example, in some embodiments, the composition may comprise two strains of the species *Absiella innocuum.*

The disclosure encompasses compositions comprising bacterial strains having close sequence identity or homology to and/or fall within the species of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Clostridium bifermentans, Paeniclostridium sordellii, Clostridium sordellii, Absiella innocuum, Absiella innocuum, Erysipelatoclostridium ramosum, Clostridium_M citroniae, Clostridium citroniae, Clostridium_M clostridioforme, Clostridium clostridioforme, Eubacterium_E hallii, Eubacterium hallii, Agatho-*

*bacter rectale, Eubacterium rectale, Blautia producta, Blautia_A obeum, Blautia obeum Dorea longicatena, Coprococcus_B comes, Coprococcus comes, Anaerostipes caccae, Agathobaculum* sp, *Agathobaculum buryriciproducens, Phascolarctobacterium faecium, Escherichia coli, Escherichia* sp. 3_2_53FAA, *Fusobacterium_A* sp, *Fusobacterium* sp, *Fusobacterium mortiferum, Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri.*

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47 or more bacterial strains (e.g., purified bacterial strains).

It should be appreciated that the terms "bacteria" and "bacterial strains" as used herein are interchangeable. The compositions described herein containing multiple purified bacterial strains may also be referred to as "live bacterial products."

Figure 4:
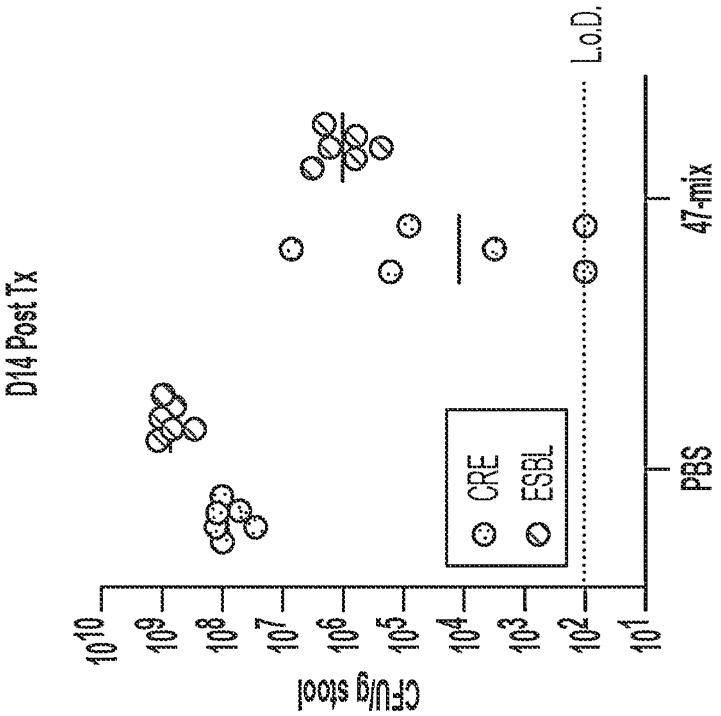
FIG. 4 shows carbapenem-resistant *Klebsiella pneumoniae* (CRE) or extended spectrum beta-lactamase (ESBL) producing Enterobacteriaceae colonization (colony forming units, "CFU") levels in mice at 14 days post-treatment ("D14 post Tx"). Mice were treated with control (PBS) or a composition of 47 bacterial strains. For each treatment, data points in the left column represent CRE colonization, and data points in the right column represent ESBL colonization, L.o.D. (dashed line) represents the limit of detection.

In one aspect, the disclosure provides a live bacterial product referred to as "47-mix" (see, FIGS. 3-5). As shown in FIG. 3 and Table 1, the composition referred to as the 47-mix contains 47 bacterial strains related to the following species: *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_A obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions comprise two or more (e.g., 2, 3, 4, 5, or more) purified bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides* thetaiotaomicron, *Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_A obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions consist of two or more (e.g., 2, 3, 4, 5, or more) bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides* thetaiotaomicron, *Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri.*

In some embodiments, the compositions consist essentially of two or more (e.g., 2, 3, 4, 5, or more) bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides* thetaiotaomicron, *Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions comprise bacterial strains of species *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacte-*

*roides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia* A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions consist of bacterial strains of species *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia* A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions consist essentially of bacterial strains of species *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine. In some embodiments, consisting essentially of, as used herein, refers to compositions that do not include any additional therapeutically active bacterial strains.

In some embodiments, the compositions comprise 38 bacterial strains, which may be referred to as a "38-mix." In some embodiments, the compositions comprise 38 bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions consist of 38 bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions consist essentially of 38 bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium fae-*

*cium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions comprise 33 bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium* A sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions consist of 33 bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some embodiments, the compositions consist essentially of 33 bacterial strains of species selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri*. In some embodiments, the composition further comprises taurine.

In some aspects, the present disclosure provides compositions comprising one or more purified bacterial strains belonging to the phylum Firmicutes or Bacteroidetes; one or more purified bacterial strains selected from the group consisting of an *Escherichia* species and a *Fusobacterium* species; and taurine. In some aspects, the present disclosure provides compositions comprising one or more purified bacterial strains belonging to the phylum Firmicutes; one or more purified bacterial strains of *Escherichia* species; and taurine. In some aspects, the present disclosure provides compositions comprising one or more purified bacterial strains belonging to the phylum Firmicutes; one or more purified bacterial strains of *Fusobacterium* species; and taurine.

The Firmicutes phylum, also referred to as the phylum Bacillota, is a phylum of Gram-positive bacteria, many of which are spore-forming. Classes within the Firmicutes phylum include the obligate anaerobe class Clostridia, and Bacilli, which may be obligate or facultative anaerobes. In some embodiments of compositions comprising a purified bacterial strain belonging to the phylum Firmicutes, the bacterial strain belongs to a class selected from the group consisting of Bacilli, Clostridia, and Negativicutes. In some embodiments, the composition comprises two or more bacterial strains belonging to the phylum Firmicutes, and each of the bacterial strains independently belongs to a class selected from the group consisting of Bacilli, Clostridia, and Negativicutes.

Families within the Firmicutes phylum include Peptostreptococcaceae, Erysipelatotrichiaceae, Lachnospiraceae, Ruminococcaceae, Acidaminococcaceae, and Clostridiaceae. In some embodiments of compositions comprising a purified bacterial strain belonging to the phylum Firmicutes, the bacterial strain belongs to a family selected from the group consisting of Peptostreptococcaceae, Erysipelatotrichiaceae, Lachnospiraceae, Ruminococcaceae, Acidaminococcaceae, and Clostridiaceae. In some embodiments, the composition comprises two or more bacterial strains belonging to the phylum Firmicutes, and the two or more bacterial strains independently belong to a family independently selected from the group consisting of Peptostreptococcaceae, Erysipelatotrichiaceae, Lachnospiraceae, Ruminococcaceae, Acidaminococcaceae, and Clostridiaceae. In some embodiments, each of the bacterial strains belonging to the phylum Firmicultes independently belongs to a family selected from the group consisting of Peptostreptococcaceae, Erysipelatotrichiaceae, Lachnospiraceae, Ruminococcaceae, Acidaminococcaceae, and Clostridiaceae.

The Bacteroidetes phylum, also referred to as the Bacteroidota phylum, is a phylum of Gram-negative, non-spore-forming bacteria, which may be aerobic or anaerobic. Classes within the Bacteroidetes phylum include Bacteroidia, Chitinophagia, Cytophagia, Flavobacteria, Saprospiria, and Sphingobacteriia. In some embodiments of compositions comprising a purified bacterial strain belonging to the phylum Bacteroidetes, the bacterial strain belongs to the class Bacteroidia. In some embodiments, the composition comprises two or more bacterial strains belonging to the phylum Bacteroidetes, and two or more of the bacterial strains belong to the class Bacteroidia. In some embodiments, each of the bacterial strains of the composition belonging to the phylum Bacteroidetes belongs to the class Bacteroidia.

Families within the Bacteroidetes phylum include Bacteroidaceae, Marinifilaceae, Tannerellaceae, Rikenellaceae, Porphyromonadaceae, Odorbacteraceae, and Prevotellaceae. In some embodments of compositions comprising a purified bacterial strain belonging to the phylum Bacteroidetes, the bacterial strain belongs to a family selected from the group consisting of Bacteroidaceae, Marinifilaceae, Tannerellaceae, Rikenellaceae, Porphyromonadaceae, Odorbacteraceae, and Prevotellaceae. In some embodiments, the composition comprises two or more bacterial strains belonging to the phylum Bacteroidetes, and the two or more bacterial strains belongs to a family independently selected from the group consisting of Bacteroidaceae, Marinifilaceae, Tannerellaceae, Rikenellaceae, Porphyromonadaceae, Odorbacteraceae, and Prevotellaceae.

In some aspects, the present disclosure provides compositions comprising one or more purified bacterial strains belonging to the phylum Bacteroidetes; one or more purified bacterial strains of *Escherichia* species; and taurine. In some aspects, the present disclosure provides compositions comprising one or more purified bacterial strains belonging to the phylum Bacteroidetes; one or more purified bacterial strains of *Fusobacterium* species; and taurine.

In some aspects, the present disclosure provides compositions comprising a purified bacterial strain belonging to *Escherichia* species, a purified bacterial strain belonging to *Fusobacterium* species, and one or more purified bacterial strains of species selected from the group consisting of *Bifidobacterium pseudocatenulatum, Bifidobacterium adolescentis, Bifidobacterium longum, Clostridium citroniae, Clostridium clostridioforme, Clostridium bifermentans, Clostridium sordelli, Clostridium innocuum, Erysipelatoclostridium ramosum*, Erysipelotrichaceae bacterium 6_1_45, *Eubacterium* hallii, *Eubacterium rectale, Anaerostipes caccae, Blautia obeum, Blautia producta, Coprococcus comes, Dorea longicatena, Agathobaculum butyriciproducens*, and *Phascolarctobacterium faecis*; and taurine.

In some aspects, the present disclosure provides compositions comprising a purified bacterial strain belonging to *Escherichia* species, a purified bacterial strain belonging to *Fusobacterium* species, and one or more purified bacterial strains of species selected from the group consisting of *Collinsella aerofaciens, Bifidobacterium longum, Bacteroides ovatus, Bacteroides vulgatus, Alistipes putredinis, Clostridium citroniae, Clostridium clostridioforme, Erysipelatoclostridium ramosum*, Erysipelotrichaceae bacterium 6_1_45, *Blautia obeum, Blautia producta, Dorea longicatena*, and *Phascolarctobacterium faecium*; and taurine.

In some aspects, the present disclosure provides compositions comprising a purified bacterial strain belonging to *Escherichia* species and one or more purified bacterial strains of species selected from the group consisting of *Bifidobacterium pseudocatenulatum, Bifidobacterium adolescentis, Bifidobacterium longum, Clostridium citroniae, Clostridium clostridioforme, Clostridium bifermentans, Clostridium sordelli, Clostridium innocuum, Erysipelatoclostridium ramosum*, Erysipelotrichaceae bacterium 6_1_45, *Eubacterium* hallii, *Eubacterium rectale, Anaerostipes caccae, Blautia obeum, Blautia producta, Coprococcus comes, Dorea longicatena, Agathobaculum butyriciproducens*, and *Phascolarctobacterium faecis*; and taurine.

In some aspects, the present disclosure provides compositions comprising a purified bacterial strain belonging to *Fusobacterium* species and one or more purified bacterial strains of species selected from the group consisting of *Bifidobacterium pseudocatenulatum, Bifidobacterium adolescentis, Bifidobacterium longum, Clostridium citroniae, Clostridium clostridioforme, Clostridium bifermentans, Clostridium sordelli, Clostridium innocuum, Erysipelatoclostridium ramosum*, Erysipelotrichaceae bacterium 6_1_45, *Eubacterium* hallii, *Eubacterium rectale, Anaerostipes caccae, Blautia obeum, Blautia producta, Coprococcus comes, Dorea longicatena, Agathobaculum butyriciproducens*, and *Phascolarctobacterium faecis*; and taurine.

In some aspects, the present disclosure provides compositions comprising a purified bacterial strain belonging to *Escherichia* species, a purified bacterial strain belonging to *Fusobacterium* species, and one or more purified bacterial strains of species selected from the group consisting of *Bacteroides ovatus, Bacteroides thetaiotamicron, Bacteroides xyalinosolvens, Bacteroides caccae, Bacteroides cellulosilyticus, Bacteroides faecis, Bacteroides fragilis, Bacteroides uniformis, Bacteroides vulgatus, Odoribacter splanchnicus, Parabacteroides distasonis, Parabacteroides merdae, Alistipes putredinis*, and *Alistipes shahii*; and taurine.

In some aspects, the present disclosure provides compositions comprising a purified bacterial strain belonging to *Escherichia* species and one or more purified bacterial strains of species selected from the group consisting of *Collinsella aerofaciens, Bacteroides ovatus, Bacteroides thetaiotamicron, Bacteroides xyalinosolvens, Bacteroides caccae, Bacteroides cellulosilyticus, Bacteroides faecis, Bacteroides fragilis, Bacteroides uniformis, Bacteroides vulgatus, Odoribacter splanchnicus, Parabacteroides distasonis, Parabacteroides merdae, Alistipes putredinis*, and *Alistipes shahii*; and taurine.

In some aspects, the present disclosure provides compositions comprising a purified bacterial strain belonging to *Fusobacterium* species and one or more purified bacterial strains of species selected from the group consisting of *Collinsella aerofaciens, Bacteroides ovatus, Bacteroides thetaiotamicron, Bacteroides xyalinosolvens, Bacteroides caccae, Bacteroides cellulosilyticus, Bacteroides faecis, Bacteroides fragilis, Bacteroides uniformis, Bacteroides vulgatus, Odoribacter splanchnicus, Parabacteroides distasonis, Parabacteroides merdae, Alistipes putredinis*, and *Alistipes shahii*; and taurine.

In some aspects, the present disclosure provides compositions comprising *Clostridium bolteae, Anaerotruncus colihominis, Sellimonas intestinalis, Clostridium symbiosum, Blautia producta, Dorea longicatena*, Erysipelotrichaceae bacterium, *Flavinofractor plautii*, a purified bacterial strain belonging to *Escherichia* species, a purified bacterial strain belonging to *Fusobacterium* species; and taurine.

In some aspects, the present disclosure provides compositions comprising *Clostridium bolteae, Anaerotruncus colihominis, Sellimonas intestinalis, Clostridium symbiosum, Blautia producta, Dorea longicatena*, Erysipelotrichaceae bacterium, *Flavinofractor plautii*, a purified bacterial strain belonging to *Escherichia* species; and taurine.

In some aspects, the present disclosure provides compositions comprising *Clostridium bolteae, Anaerotruncus colihominis, Sellimonas intestinalis, Clostridium symbiosum, Blautia producta, Dorea longicatena*, Erysipelotrichaceae bacterium, *Flavinofractor plautii*, a purified bacterial strain belonging to *Fusobacterium* species; and taurine.

In some aspects, the present disclosure provides compositions comprising *Anaerotruncus colihominis, Sellimonas intestinalis, Clostridium symbiosum, Dorea longicatena*, Erysipelotrichaceae bacterium, *Flavinofractor plautii*, a purified bacterial strain belonging to *Escherichia* species, a purified bacterial strain belonging to *Fusobacterium* species; and taurine.

In some aspects, the present disclosure provides compositions comprising *Anaerotruncus colihominis, Sellimonas intestinalis, Clostridium symbiosum, Dorea longicatena*, Erysipelotrichaceae bacterium, *Flavinofractor plautii*, a purified bacterial strain belonging to *Escherichia* species; and taurine.

In some aspects, the present disclosure provides compositions comprising *Anaerotruncus colihominis, Sellimonas intestinalis, Clostridium symbiosum, Dorea longicatena*, Erysipelotrichaceae bacterium, *Flavinofractor plautii*, a purified bacterial strain belonging to *Fusobacterium* species; and taurine.

In some aspects, the present disclosure provides compositions comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (Lachnospiraceae bacterium 6_1_63FAA), *Clostridium* spp. (*Clostridium bolteae* ATCC BAA-613), cf. *Clostridium* sp. MLG055 (Erysipelotrichaceae bacterium 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (Lachnospiraceae bacterium 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (Lachnospiraceae bacterium 5_1_57FAA), Lachnospiraceae bacterium A4 (Lachnospiraceae bacterium 3_1_57FAA_CT1), *Clostridium* sp. 316002/08 (Clostriales bacterium 1_7_47FAA), Lachnospiraceae bacterium A4 (Lachnospiraceae bacterium 3_1_57FAA_CT1), a purified bacterial strain belonging to *Escherichia* species, a purified bacterial strain belonging to *Fusobacterium* species; and taurine.

In some aspects, the present disclosure provides compositions comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (Lachnospiraceae bacterium 6_1_63FAA), *Clostridium* spp. (*Clostridium bolteae* ATCC BAA-613), cf. *Clostridium* sp. MLG055 (Erysipelotrichaceae bacterium 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (Lachnospiraceae bacterium 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (Lachnospiraceae bacterium 5_1_57FAA), Lachnospiraceae bacterium A4 (Lachnospiraceae bacterium 3_1_57FAA_CT1), *Clostridium* sp. 316002/08 (Clostriales bacterium 1_7_47FAA), Lachnospiraceae bacterium A4 (Lachnospiraceae bacterium 3_1_57FAA_CT1), a purified bacterial strain belonging to *Escherichia* species; and taurine.

In some aspects, the present disclosure provides compositions comprising *Clostridium saccharogumia* (*Clostridium ramosum* JCM 1298), *Flavonifractor plautii* (*Pseudoflavonifractor capillosus* ATCC 29799), *Clostridium hathewayi* (*Clostridium saccharolyticum* WM1), *Blautia coccoides* (Lachnospiraceae bacterium 6_1_63FAA), *Clostridium* spp. (*Clostridium bolteae* ATCC BAA-613), cf. *Clostridium* sp. MLG055 (Erysipelotrichaceae bacterium 2_2_44A), *Clostridium indolis* (*Anaerostipes caccae* DSM 14662), *Anaerotruncus colihominis* (*Anaerotruncus colihominis* DSM 17241), *Ruminococcus* sp. ID8 (Lachnospiraceae bacterium 2_1_46FAA), *Clostridium lavalense* (*Clostridium asparagiforme* DSM 15981), *Clostridium symbiosum* (*Clostridium symbiosum* WAL-14163), *Clostridium ramosum, Eubacterium contortum* (*Clostridium* sp. D5), *Clostridium scindens* (Lachnospiraceae bacterium 5_1_57FAA), Lachnospiraceae bacterium A4 (Lachnospiraceae bacterium 3_1_57FAA_CT1), *Clostridium* sp. 316002/08 (Clostriales bacterium 1_7_47FAA), Lachnospiraceae bacterium A4 (Lachnospiraceae bacterium 3_1_57FAA_CT1), a purified bacterial strain belonging to *Fusobacterium* species; and taurine.

In some aspects, the present disclosure provides compositions comprising *Clostridium bolteae, Anaerotruncus colihominis, Sellimonas intestinalis, Clostridium symbiosum, Blautia producta*, Erysipelotrichaceae bacterium, *Flavinofractor plautii*, a purified bacterial strain belonging to *Escherichia* species, a purified bacterial strain belonging to *Fusobacterium* species; and taurine.

In some aspects, the present disclosure provides compositions comprising *Clostridium bolteae, Anaerotruncus colihominis, Sellimonas intestinalis, Clostridium symbiosum, Blautia producta*, Erysipelotrichaceae bacterium, *Flavinofractor plautii*, a purified bacterial strain belonging to *Escherichia* species; and taurine.

In some aspects, the present disclosure provides compositions comprising *Clostridium bolteae, Anaerotruncus colihominis, Sellimonas intestinalis, Clostridium symbiosum, Blautia producta*, Erysipelotrichaceae bacterium, *Flavinofractor plautii*, a purified bacterial strain belonging to *Fusobacterium* species; and taurine.

In some aspects, the present disclosure provides compositions comprising *Collinsella aerofaciens, Bacteroides ovatus, Bacteroides thetaiotamicron, Bacteroides xyalinosolvens, Bacteroides caccae, Bacteroides cellulosilyticus, Bacteroides faecis, Bacteroides uniformis, Bacteroides vulgatus, Odoribacter splanchnicus, Parabacteroides distasonis, Parabacteroides merdae, Alistipes putredinis, Alistipes shahii, Bifidobacterium pseudocatenulatum, Bifidobacterium adolescentis, Bifidobacterium longum, Clostridium citroniae, Clostridium clostridioforme, Clostridium innocuum, Erysipelatoclostridium ramosum*, Erysipelotrichaceae bacterium 6_1_45, *Eubacterium* hallii, *Eubacterium rectale, Anaerostipes caccae, Blautia obeum, Blautia producta, Coprococcus comes, Dorea longicatena, Agathobaculum butyriciproducens, Phascolarctobacterium faecis*, a purified bacterial strain belonging to *Escherichia* species, a purified bacterial strain belonging to *Fusobacterium* species; and taurine.

In some aspects, the present disclosure provides compositions comprising *Collinsella aerofaciens, Bacteroides ovatus, Bacteroides thetaiotamicron, Bacteroides xyalinosolvens, Bacteroides cellulosilyticus, Bacteroides uniformis, Bacteroides vulgatus, Parabacteroides distasonis, Alistipes putredinis, Alistipes shahii, Bifidobacterium adolescentis, Bifidobacterium longum, Clostridium citroniae, Clostridium clostridioforme, Clostridium innocuum, Erysipelatoclo-*

*stridium ramosum*, Erysipelotrichaceae bacterium 6_1_45, *Eubacterium rectale, Anaerostipes caccae, Blautia obeum, Blautia producta, Coprococcus comes, Dorea longicatena, Agathobaculum butyriciproducens, Phascolarctobacterium faecis*, a purified bacterial strain belonging to *Escherichia* species, a purified bacterial strain belonging to *Fusobacterium* species; and taurine.

In some aspects, the present disclosure provides compositions comprising *Bacteroides ovatus, Bacteroides thetaiotamicron, Bacteroides xyalinosolvens, Bacteroides caccae, Bacteroides cellulosilyticus, Bacteroides faecis, Bacteroides uniformis, Bacteroides vulgatus, Alistipes putredinis, Alistipes shahii, Clostridium citroniae, Clostridium clostridioforme, Clostridium innocuum, Erysipelatoclostridium ramosum*, Erysipelotrichaceae bacterium 6_1_45, *Eubacterium* hallii, *Eubacterium rectale, Blautia obeum, Blautia producta, Coprococcus comes, Dorea longicatena*, a purified bacterial strain belonging to *Escherichia* species, a purified bacterial strain belonging to *Fusobacterium* species; and taurine.

In some aspects, the present disclosure provides compositions comprising *Blautia producta, Bifidobacterium longum, Bifidobacterium adolescentis, Paeniclostridium sordellii, Bifidobacterium pseudocatenulatum, Erysipelatoclostridium ramosum, Escherichia coli, Clostridium clostridioforme, Paraclostridium bifermentans, Clostridium citroniae, Clostridium innocuum, Agathobaculum butyriciproducens, Clostridium innocuum, Dorea longicatena, Collinsella aerofaciens, Eubacterium hallii, Bacteroides faecis, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Blautia producta, Bifidobacterium longum, Bifidobacterium adolescentis, Paeniclostridium sordellii, Bifidobacterium pseudocatenulatum, Erysipelatoclostridium ramosum, Escherichia coli, Clostridium clostridioforme, Paraclostridium bifermentans, Clostridium citroniae, Anaerostipes caccae, Fusobacterium mortiferum, Clostridium clostridioforme, Blautia obeum, Clostridium innocuum, Agathobaculum butyriciproducens, Clostridium innocuum, Dorea longicatena, Collinsella aerofaciens, Eubacterium hallii, Bacteroides faecis, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Blautia producta, Bifidobacterium longum, Bifidobacterium adolescentis, Paeniclostridium sordellii, Bifidobacterium pseudocatenulatum, Erysipelatoclostridium ramosum, Escherichia coli, Clostridium clostridioforme, Paraclostridium bifermentans, Clostridium citroniae, Anaerostipes caccae, Fusobacterium mortiferum, Blautia obeum, Clostridium innocuum, Agathobaculum butyriciproducens, Clostridium innocuum, Dorea longicatena, Collinsella aerofaciens, Eubacterium hallii, Bacteroides faecis, Odoribacter* sp., *Bacteroides fragilis, Bacteroides ovatus, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Blautia producta, Bifidobacterium longum, Bifidobacterium adolescentis, Paeniclostridium sordellii, Bifidobacterium pseudocatenulatum, Erysipelatoclostridium ramosum, Escherichia coli, Paraclostridium bifermentans, Clostridium citroniae, Anaerostipes caccae, Fusobacterium mortiferum, Blautia obeum, Clostridium innocuum, Agathobaculum butyriciproducens, Odoribacter* sp., *Bacteroides fragilis, Bacteroides ovatus, Clostridium bolteae, Anaerotruncus colihominis, Drancourtella massiliensis, Clostridium symbiosum, Blautia producta, Dorea longicatena*, Erysipelotrichaceae bacterium, *Flavonifractor plautii*; and taurine.

In some aspects, the present disclosure provides compositions comprising *Bacteroides cellulosilyticus, Bacteroides ovatus, Bacteroides thetaiotaomicron, Bacteroides uniformis, Bacteroides vulgatus, Bifidobacterium adolescentis, Bifidobacterium longum, Blautia producta, Clostridium citroniae, Clostridium clostridioforme, Clostridium innocuum, Clostridium innocuum, Coprococcus comes, Dorea longicatena, Erysipelatoclostridium ramosum, Eubacterium rectale, Parabacteroides distasonis, Bacteroides xylanisolvens, Blautia obeum, Alistipes putredinis, Collinsella aerofaciens, Eubacterium hallii, Anaerostipes caccae, Phascolarctobacterium faecium, Agathobaculum butyriciproducens, Fusobacterium mortiferum, Escherichia coli*; and taurine.

In some aspects, the present disclosure provides compositions comprising *Bacteroides caccae, Bacteroides cellulosilyticus, Bacteroides ovatus, Bacteroides thetaiotaomicron, Bacteroides uniformis, Bacteroides vulgatus, Bifidobacterium longum, Blautia producta, Clostridium clostridioforme, Clostridium innocuum, Coprococcus comes, Dorea longicatena, Erysipelatoclostridium ramosum, Clostridium citroniae, Odoribacter splanchnicus, Parabacteroides distasonis, Bacteroides xylanisolvens, Blautia obeum, Alistipes putredinis, Collinsella aerofaciens, Alistipes shahii, Anaerostipes caccae, Phascolarctobacterium faecium, Agathobaculum butyriciproducens, Bacteroides fragilis, Fusobacterium mortiferum, Escherichia coli*; and taurine.

In some aspects, the present disclosure provides compositions comprising *Bacteroides ovatus, Bacteroides vulgatus, Bifidobacterium adolescentis, Bifidobacterium longum, Bifidobacterium pseudocatenulatum, Blautia producta, Clostridium citroniae, Clostridium clostridioforme, Clostridium innocuum, Clostridium innocuum, Paeniclostridium sordellii, Coprococcus comes, Dorea longicatena, Erysipelatoclostridium ramosum, Eubacterium rectale, Odoribacter splanchnicus, Parabacteroides distasonis, Parabacteroides merdae, Bacteroides xylanisolvens, Blautia obeum, Alistipes putredinis, Collinsella aerofaciens, Eubacterium hallii, Alistipes shahii, Anaerostipes caccae, Phascolarctobacterium faecium, Agathobaculum butyriciproducens, Fusobacterium mortiferum, Paraclostridium bifermentans, Escherichia coli*; and taurine.

In some aspects, the present disclosure provides compositions comprising *Bacteroides ovatus, Bacteroides vulgatus, Bifidobacterium longum, Blautia producta, Clostridium citroniae, Clostridium clostridioforme, Clostridium innocuum, Coprococcus comes, Dorea longicatena, Erysipelatoclostridium ramosum, Odoribacter splanchnicus, Parabacteroides distasonis, Bacteroides xylanisolvens, Blautia obeum, Alistipes putredinis, Collinsella aerofaciens, Alistipes shahii, Anaerostipes caccae, Phascolarctobacterium faecium, Fusobacterium mortiferum, Escherichia coli*; and taurine.

In some aspects, the present disclosure provides compositions comprising *Bacteroides faecis, Bacteroides ovatus, Bacteroides vulgatus, Bifidobacterium adolescentis, Bifidobacterium longum, Blautia producta, Clostridium citroniae, Clostridium clostridioforme, Clostridium innocuum,*

*Clostridium innocuum, Paeniclostridium sordellii, Dorea longicatena, Erysipelatoclostridium ramosum, Odoribacter splanchnicus, Blautia obeum, Alistipes putredinis, Collinsella aerofaciens, Eubacterium hallii, Anaerostipes caccae, Phascolarctobacterium faecium, Agathobaculum butyriciproducens, Bacteroides fragilis, Fusobacterium mortiferum, Paraclostridium bifermentans, Escherichia coli*; and taurine.

In some aspects, the present disclosure provides compositions comprising *Bacteroides faecis, Bacteroides ovatus, Bacteroides vulgatus, Bifidobacterium longum, Blautia producta, Clostridium citroniae, Clostridium clostridioforme, Clostridium innocuum, Dorea longicatena, Erysipelatoclostridium ramosum, Odoribacter splanchnicus, Alistipes putredinis, Collinsella aerofaciens, Blautia obeum, Anaerostipes caccae, Phascolarctobacterium faecium, Agathobaculum butyriciproducens, Fusobacterium mortiferum, Escherichia coli*; and taurine.

In some aspects, the present disclosure provides compositions comprising bacterial strains of species *Bacteroides vulgatus, Clostridium citroniae*, and *Phascolarctobacterium faecium*, and one or more purified bacterial strains of species selected from the group consisting of *Bacteroides faecis, Bacteroides ovatus, Bifidobacterium longum, Blautia producta, Clostridium clostridioforme, Clostridium innocuum, Dorea longicatena, Erysipelatoclostridium ramosum, Odoribacter splanchnicus, Alistipes putredinis*, Collinsella aerofaciens, *Blautia obeum, Anaerostipes caccae, Agathobaculum butyriciproducens, Fusobacterium mortiferum, Escherichia coli*; and taurine.

In some aspects, the present disclosure provides compositions comprising *Collinsella aerofaciens, Bifidobacterium longum, Bacteroides ovatus, Bacteroides faecis, Bacteroides vulgatus, Odoribacter splanchnicus, Alistipes putredinis, Clostridium citroniae, Clostridium clostridioforme, Erysipelatoclostridium ramosum*, Erysipelotrichaceae bacterium 6_1_45, *Anaerostipes caccae, Blautia obeum, Blautia producta, Dorea longicatena, Agathobaculum butyriciproducens, Phascolarctobacterium faecium, Escherichia coli, Fusobacterium mortiferum*; and taurine.

In some aspects, the present disclosure provides compositions comprising *Collinsella aerofaciens, Bifidobacterium longum, Bacteroides ovatus, Bacteroides vulgatus, Parabacteroides distasonis, Alistipes putredinis, Clostridium citroniae, Clostridium clostridioforme, Erysipelatoclostridium ramosum*, Erysipelotrichaceae bacterium 6_1_45, *Anaerostipes caccae, Blautia obeum, Blautia producta, Agathobaculum butyriciproducens, Phascolarctobacterium faecium, Escherichia coli, Fusobacterium mortiferum*; and taurine.

In some aspects, the present disclosure provides compositions comprising *Collinsella aerofaciens, Bifidobacterium longum, Bacteroides ovatus, Bacteroides vulgatus, Alistipes putredinis, Clostridium citroniae, Clostridium clostridioforme, Erysipelatoclostridium ramosum*, Erysipelotrichaceae bacterium 6_1_45, *Blautia obeum, Blautia producta, Dorea longicatena, Phascolarctobacterium faecium, Escherichia coli, Fusobacterium mortiferum*; and taurine.

In some aspects, the present disclosure provides compositions comprising a purified bacterial mixture comprising bacterial strains of the species *Bacteroides faecis, Bacteroides vulgatus, Phascolartcobacterium faecium*, and *Clostridium citroniae*. In some aspects, the disclosure provides compositions comprising a purified bacterial mixture consisting of bacterial strains of the species *Bacteroides faecis, Bacteroides vulgatus, Phascolartcobacterium faecium*, and *Clostridium citroniae*. In some aspects, the present disclosure provides compositions comprising bacterial strains of the species *Bacteroides faecis, Bacteroides vulgatus, Phascolartcobacterium faecium*, and *Clostridium citroniae*; and taurine. In some aspects, the disclosure provides a composition comprising taurine and a purified bacterial mixture consisting of bacterial strains of the species *Bacteroides faecis, Bacteroides vulgatus, Phascolartcobacterium faecium*, and *Clostridium citroniae*. In some embodiments, a bacterial strain of *Bacteroides faecis* comprises a 16S rDNA sequence comprising at least 97% sequence identity to the nucleic acid sequence of SEQ ID NO: 30. In some embodiments, a bacterial strain of *Bacteroides vulgatus* comprises a 16S rDNA sequence comprising at least 97% sequence identity to the nucleic acid sequence of SEQ ID NO: 10. In some embodiments, a bacterial strain of *Phascolartcobacterium faecium* comprises a 16S rDNA sequence comprising at least 97% sequence identity to the nucleic acid sequence of SEQ ID NO: 36. In some embodiments, a bacterial strain of *Clostridium citroniae* comprises a 16S rDNA sequence comprising at least 97% sequence identity to the nucleic acid sequence of SEQ ID NO: 29.

In some aspects, the present disclosure provides compositions comprising purified bacterial strains comprising 16S rDNA sequences having at least 97% sequence identity to nucleic acid sequences of SEQ ID NOs: 10, 29, 30, and 36. In some aspects, the present disclosure provides compositions comprising purified bacterial strains comprising 16S rDNA sequences having at least 97% sequence identity to nucleic acid sequences of SEQ ID NOS: 10, 29, 30, and 36; and taurine. In some aspects, the present disclosure provides compositions comprising a purified bacterial mixture consisting of bacterial strains comprising 16S rDNA sequences having at least 97% sequence identity to the nucleic acid sequences of SEQ ID NOs: 10, 29, 30, and 36. In some aspects, the present disclosure provides compositions comprising taurine and a purified bacterial mixture consisting of bacterial strains comprising 16S rDNA sequences having at least 97% sequence identity to the nucleic acid sequences of SEQ ID NOs: 10, 29, 30, and 36.

In some embodiments, any of the compositions described herein further comprises one or more bacterial strain selected from the group consisting of *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri.*

As will be appreciated by one of skill in the art, any one or more bacterial strain identified as having pathogen-antagonizing activity may be included in any of the compositions described herein.

Aspects of the disclosure relate to bacterial strains with 16S rDNA sequences that have sequence identity to a nucleic acid sequence of any one of the sequences of the bacterial strains or species described herein. The terms "identical," or percent "identity," in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% sequence identity) over a specified region of a nucleic acid or amino acid sequence or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% sequence identity relative to any of the strains or bacterial species described herein over a specified region or over the entire sequence. It would be appreciated by one of skill in the art that the term "sequence identity" or "percent sequence identity," in the context of two or more nucleic acid sequences or amino acid sequences, refers to a measure of similarity between two or more sequences or portion(s) thereof.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. (1970) 48:443, by the search for similarity method of Pearson and Lipman. Proc. Natl. Acad. Sci. USA 85:2444, 1988, by computerized implementations of these algorithms (GAP, BESTFIT, FASTA, and TFASTA in the Wisconsin Genetics Software Package, Genetics Computer Group. Madison. WI), or by manual alignment and visual inspection (sec. e.g., Brent et al., *Current Protocols in Molecular Biology*, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res.* 25:3389-3402, 1977; and Altschul et al., *J. Mol. Biol.* 215:403-410, 1990, respectively.

In one aspect, the bacterial composition comprises two or more (e.g., 2, 3, 4, 5 or more) purified bacterial strains comprising 16S rDNA sequences having at least 97% (e.g., 97%, 98%, 99.%, 99.1%, 99.2%, 99.3%, 99.4%, 99.5%, 99.6%, 99.7%, 99.8%, 99.9%, or 100%) sequence identity with the nucleic acid sequence selected from SEQ ID NOs: 1-83. In one aspect, the bacterial composition consists of two or more (e.g., 2, 3, 4, 5 or more) purified bacterial strains comprising 16S rDNA sequences having at least 97% (e.g., 97%, 98%, 99,%, 99.1%. 99.2%, 99.3%, 99.4%, 99.5%, 99.6%, 99.7%, 99.8%, 99.9%, or 100%) sequence identity with the nucleic acid sequence selected from SEQ ID NOs: 1-83. In one aspect, the bacterial composition consists essentially of two or more (e.g., 2, 3, 4, 5 or more) purified bacterial strains comprising 16S rDNA sequences having at least 97% (e.g., 97%, 98%, 99,%, 99.1%, 99.2%, 99.3%, 99.4%, 99.5%, 99.6%, 99.7%, 99.8%, 99.9%, or 100%) sequence identity with the nucleic acid sequence selected from SEQ ID NOs: 1-83.

In one aspect, the bacterial composition comprises two or more (e.g., 2, 3, 4, 5 or more) purified bacterial strains comprising 16S rDNA sequences having at least 97% (e.g., 97%, 98%, 99,%, 99.1%, 99.2%, 99.3%, 99.4%, 99.5%, 99.6%, 99.7%, 99.8%, 99.9%, or 100%) sequence identity with the nucleic acid sequence selected from SEQ ID NOs: 1-47. In one aspect, the bacterial composition consists of two or more (e.g., 2, 3, 4, 5 or more) purified bacterial strains comprising 16S rDNA sequences having at least 97% (e.g., 97%, 98%, 99,%. 99.1%, 99.2%, 99.3%, 99.4%, 99.5%, 99.6%, 99.7%, 99.8%, 99.9%, or 100%) sequence identity with the nucleic acid sequence selected from SEQ ID NOs: 1-47. In one aspect, the bacterial composition consists essentially of two or more (e.g., 2, 3, 4, 5 or more) purified bacterial strains comprising 16S rDNA sequences having at least 97% (e.g., 97%, 98%, 99,%, 99.1%, 99.2%, 99.3%, 99.4%, 99.5%, 99.6%, 99.7%, 99.8%, 99.9%, or 100%) sequence identity with the nucleic acid sequence selected from SEQ ID NOs: 1-47.

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, or more bacterial strains (e.g., purified bacterial strains).

In some embodiments, the bacterial composition comprises purified bacterial strains comprising 16S rDNA sequences having at least 97% (e.g., 97%, 98%, 99,%, 99.1%, 99.2%. 99.3%. 99.4%, 99.5%, 99.6%, 99.7%, 99.8%, 99.9%, or 100%) sequence identity with the nucleic acid sequences provided by SEQ ID NOs: 1-47. In some embodiments, the bacterial composition consists of purified bacterial strains comprising 16S rDNA sequences having at least 97% (e.g., 97%, 98%, 99,%, 99.1%, 99.2%, 99.3%, 99.4%, 99.5%, 99.6%, 99.7%, 99.8%, 99.9%, or 100%) sequence identity with the nucleic acid sequences of SEQ ID NOS: 1-47. In some embodiments, the bacterial composition consists essentially of purified bacterial strains comprising 16S rDNA sequences having at least 97% (e.g., 97%, 98%, 99,%. 99.1%, 99.2%, 99.3%, 99.4%, 99.5%, 99.6%, 99.7%, 99.8%, 99.9%, or 100%) sequence identity with the nucleic acid sequence of SEQ ID NOs: 1-47.

In some embodiments, the bacterial composition comprises 38 purified bacterial strains comprising 16S rDNA sequences having at least 97% (e.g., 97%, 98%, 99,%, 99.1%, 99.2%, 99.3%, 99.4%, 99.5%, 99.6%, 99.7%, 99.8%, 99.9%, or 100%) sequence identity with any of the nucleic acid sequences provided by SEQ ID NOs: 1-47. In some embodiments, the bacterial composition consists of 38 purified bacterial strains comprising 16S rDNA sequences having at least 97% (e.g., 97%, 98%, 99,%, 99.1%, 99.2%, 99.3%. 99.4%, 99.5%, 99.6%, 99.7%, 99.8%, 99.9%, or 100%) sequence identity with any of the nucleic acid sequences of SEQ ID NOs: 1-47. In some embodiments, the bacterial composition consists essentially of 38 purified bacterial strains comprising 16S rDNA sequences having at least 97% (e.g., 97%, 98%, 99,%, 99.1%, 99.2%, 99.3%, 99.4%, 99.5%, 99.6%. 99.7%, 99.8%, 99.9%, or 100%) sequence identity with any of the nucleic acid sequence of SEQ ID NOs: 1-47.

In some embodiments, the bacterial composition comprises 33 purified bacterial strains comprising 16S rDNA sequences having at least 97% (e.g., 97%, 98%, 99,%, 99.1%, 99.2%, 99.3%, 99.4%, 99.5%, 99.6%, 99.7%, 99.8%, 99.9%, or 100%) sequence identity with any of the nucleic acid sequences provided by SEQ ID NOs: 1-47. In some embodiments, the bacterial composition consists of 33 purified bacterial strains comprising 16S rDNA sequences having at least 97% (e.g., 97%, 98%, 99,%, 99.1%, 99.2%, 99.3%, 99.4%, 99.5%, 99.6%, 99.7%, 99.8%, 99.9%, or 100%) sequence identity with any of the nucleic acid sequences of SEQ ID NOs: 1-47. In some embodiments, the bacterial composition consists essentially of 33 purified bacterial strains comprising 16S rDNA sequences having at least 97% (e.g., 97%, 98%, 99,%, 99.1%, 99.2%, 99.3%, 99.4%, 99.5%, 99.6%. 99.7%, 99.8%, 99.9%, or 100%) sequence identity with any of the nucleic acid sequence of SEQ ID NOs: 1-47.

Provided herein are bacterial strains and combinations of bacterial strains that are homologous or have a high percent of homology with bacterial strains comprising 16S rDNA sequences selected from SEQ ID NO: 1-83. It should be appreciated that the bacterial strains described herein have a 16S rDNA sequence selected from SEQ ID NO: 1-83 may also be homologous to other strains based on their whole genome sequence, or subset of their whole genome sequence.

In one aspect, the compositions comprise a fraction of a fecal sample. In some embodiments, the compositions comprise a non-spore forming fraction of a fecal sample. In some embodiments, the compositions comprise a spore forming fraction of a fecal sample.

In some embodiments, the compositions described herein comprise spore forming and non-spore forming bacterial strains. In some embodiments, the compositions described herein comprise spore forming bacterial strains. In some embodiments, the compositions described herein comprise only spore forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore form may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form. As discussed above, spore forming bacteria can also be in vegetative form. In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) is present in the composition in vegetative form. In some embodiments, at least one bacterial strain that is considered able to form spores is present in the composition both in spore form and in vegetative form.

In some embodiments, the compositions comprise bacterial strains that are spore forming bacterial strains. In some embodiments, the compositions comprise bacterial strains that are non-spore forming bacterial strains. In some embodiments, the compositions comprise bacterial strains that are spore forming bacterial strains and bacterial strains that are non-spore forming bacterial strains. In some embodiments, the compositions comprise a mixture of bacterial strains wherein at least 10% of the bacterial strains are spore forming bacterial strains, at least 20% of the bacterial strains are spore forming bacterial strains, at least 30% of the bacterial strains are spore forming bacterial strains, at least 40% of the bacterial strains are spore forming bacterial strains, at least 50% of the bacterial strains are spore forming bacterial strains, at least 60% of the bacterial strains are spore forming bacterial strains, at least 70% of the bacterial strains are spore forming bacterial strains, at least 80% of the bacterial strains are spore forming bacterial strains, at least 90% of the bacterial strains are spore forming bacterial strains bacteria or up to 100% of the bacterial strains are spore forming bacterial strains. Whether a bacterial strain is a spore forming strain can be determined for instance by evaluating the genome of the bacterial strain for the presence of sporulation genes. However, it should be appreciated that not all bacteria that are predicted to encode spore forming genes can be made to sporulate. In addition, whether a bacterial strain is a spore forming strain can be determined by exposing the bacterial strain to stress conditions, e.g., heat or exposure to chemicals (e.g., ethanol or chloroform), that are known to induce sporulation.

It should be appreciated that spore forming bacteria can be in spore form or in vegetative form. In some embodiments of the compositions provided herein, the spore forming bacteria are in spore form. In some embodiments, the spore forming bacteria are in vegetative form. In some embodiments, the spore forming bacteria are both present in spore form and in vegetative form. In some embodiments, compositions comprise spore forming bacteria and at least 10% of the spore forming bacteria are in spore format, at least 20% of the spore forming bacteria are in spore format, at least 30% of the spore forming bacteria are in spore format, at least 40% of the spore forming bacteria are in spore format, at least 50% of the spore forming bacteria are in spore format, at least 60% of the spore forming bacteria are in spore format, at least 70% of the spore forming bacteria are in spore format, at least 80% of the spore forming bacteria are in spore format, at least 90% of the spore forming bacteria are in spore format, or up to 100% of the spore forming bacteria are in spore format.

It is envisioned that the bacterial strains of the compositions provided herein are alive and will be alive when they reach the target area (e.g., the intestines). Bacterial spores are considered to be alive in this regard. In some embodiments, bacteria that are administered as spores may germinate in the target area (e.g., the intestines). It should further be appreciated that not all of the bacteria are alive, and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

Methods of inducing sporulation of spore-forming bacterial strains are well-known in the art (see, e.g., Paredes-Sabja et al., *Trends Microbiol.* (2011) 19(2):85-94). Generally, bacterial strains that are spore-formers can be made to go into spore form by stressing the bacterial strains. Non-limiting examples of stresses that can induce sporulation are an increase in temperature, change in the nutrients available and/or exposure to chemicals (e.g., ethanol or chloroform). It should be noted that bacteria that are non-spore formers, for instance because they are missing sporulation genes, cannot be made to sporulate by stress. To prepare compositions in which all the bacterial strains are in the spore form, the composition or bacterial cultures used to prepare the composition may be subjected to treatment to kill any bacteria not in spore form (e.g., in vegetative form), for example by exposing the composition to heat and chemically breaking down the non-spore bacteria. The bacteria in spore format can subsequently be separated from the non-spore bacteria for instance by filtration.

The amount of spores can be quantified using techniques known in the art. These techniques include phase contrast microscopy for enumerating spores using a hemocytometer. In addition, the viability of spores can be determined by plating the spores and growing the spores. For instance, spores can be plated in appropriate media and incubated in the anaerobic chamber for a period of time (e.g., 48-96 hrs.). Viability can subsequently be determined by quantifying the colony forming units which correspond to spores that germinated. For instance, spores can be plated on TCCFA plates (taurocholate, cycloserine, cefoxintin, fructose agar plates), in which taurocholate helps the spores to germinate. In addition, spores can be quantified using the dipicolinic assay (DPA assay). DPA is an agent that allows for spore selection and is a clear indicator of endospores. When complexed with terbium, bright green luminescence is observed.

In some embodiments, the compositions comprise bacterial strains that are non-spore forming bacterial strains. In some embodiments, the compositions comprise bacterial strains that are spore forming bacterial strains and bacterial strains that are non-spore forming bacterial strains. In some embodiments, the compositions comprise a mixture of bacterial strains wherein at least 10% of the bacterial strains are non-spore forming bacterial strains, at least 20% of the bacterial strains are non-spore forming bacterial strains, at least 30% of the bacterial strains are non-spore forming bacterial strains, at least 40% of the bacterial strains are non-spore forming bacterial strains, at least 50% of the bacterial strains are non-spore forming bacterial strains, at least 60% of the bacterial strains are non-spore forming bacterial strains, at least 70% of the bacterial strains are non-spore forming bacterial strains, at least 80% of the bacterial strains are non-spore forming bacterial strains, at least 90% of the bacterial strains are non-spore forming bacterial strains, or up to 100% non-spore forming bacterial strains.

In any of the compositions provided herein, the bacterial strains may be purified. In any of the compositions provided herein, the bacterial strains may be isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals.

As used herein, the term "isolated" refers to a bacterium or bacterial strain that has been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected.

As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In some embodiments, the bacterial strains of the compositions provided herein are obligate anaerobes. In some embodiments, the bacterial strains of the compositions provided.

Aspects of the present disclosure are related to methods for suppressing undesired bacteria. As used herein, the term "suppressing" refers to any form of inhibiting undesired bacteria. In some embodiments, the methods described herein reduce/inhibit or prevent the colonization, replication, proliferation, and/or survival of the undesired bacteria (e.g., pathogenic organisms, multi-drug resistant organisms, for example carbapenem resistanct Enterobacteriaceae (CRE) and extended spectrum beta-lactamase (ESBL)-producing Enterobacteriaceae). In some embodiments, the methods described herein directly or indirectly induce death of the undesired bacteria (e.g., pathogenic organism, multi-drug resistant organisms, for example carbapenem resistanct Enterobacteriaceae (CRE) and extended spectrum beta-lactamase (ESBL)-producing Enterobacteriaceae).

Aspects of the present disclosure are related to methods for suppressing infection by a pathogenic organism in a subject. Aspects of the present disclosure are related to methods for reducing or preventing colonization by a pathogenic organism (e.g., bacterium, virus, fungus, or parasite) in a subject. Aspects of the present disclosure are related to methods for treating infection with a pathogenic organism. In some embodiments, the pathogenic organism is not multi-drug resistant. In some embodiments, the pathogenic organism resistant to one or more drugs (e.g., antibacterial, anti-viral, anti-fungal agent). In some embodiments, the pathogenic organism is multi-drug resistant. The methods described herein involve administering to a subject a therapeutically effective amount of any of the compositions described herein. As used herein, a "subject," "individual," and "patient" are used interchangeably, and refer to a vertebrate, preferably a mammal such as a human. Mammals include, but are not limited to, human primates, non-human primates or murine, bovine, equine, canine or feline species. In some embodiments, the subject is a human.

In some embodiments, any of the compositions described herein are effective in suppressing the replication, survival, and/or colonization of one or more pathogenic organism. In some instances, the pathogenic organism is susceptible to antibiotics, while in other instances, the pathogenic organism is resistant to antibiotics. In some embodiments, the pathogenic organism is a multi-drug resistant organism, which are described elsewhere herein. In some embodiments, the pathogenic organism is an oral microbiome bacterium. It should be noted that oral microbiome bacteria are not necessarily pathogenic, but may become so when located elsewhere, such as in the gastrointestinal tract. The amount of suppression of replication, survival, and/or colonization of the one or more pathogenic organism can be measured or identified using standard assays known in the art, some of which are further described and exemplified herein.

In some embodiments, administration of the compositions described herein reduces/inhibits or prevents the colonization, re-colonization, replication, proliferation, and/or survival of pathogenic organism, such as multi-drug resistant organisms. In some embodiments, administration of the compositions described herein allows for colonization of the gastrointestinal tract of the subject by the bacterial strain(s) of the compositions thereby preventing colonization by multi-drug resistant organisms.

In some embodiments, the pathogenic organism is a pathobiont, i.e., a potentially pathogenic organism which, under normal circumstances, lives as a symbiont.

In some embodiments, the subject is a carrier of a multi-drug resistant organism and is suffering from the effects of the infection. In some embodiments the subject is an asymptomatic carrier of a multi-drug resistant organism. In some embodiments, the subject has experienced recurrent or chronic colonization with a multi-drug resistant organism. In some embodiments, the subject is suffering from a first occurrence of a particular multi-drug resistant organism. In some embodiments, the subject is at risk of colonization with a multi-drug resistant organism, such as prior antibiotic use. In some embodiments, the subject has a risk factor associated with colonization with a multidrug resistant organism. In some embodiments, the subject has had a previous infection or colonization with a multi-drug resistant organism. In some embodiments, the subject has been treated with antibiotics which resulted in the recurrence of the multi-drug resistant organism.

In some embodiments, the subject is to undergo a procedure that puts the subject at a higher risk of colonization and the compositions are administered prophylactically. In some embodiments, the subject has a disease or disorder associated with use of a proton pump inhibitor, which may increase the likelihood of an oral bacterium migrating to the intestine. In some embodiments, the compositions provided herein are administered to a subject to lower the risk of becoming colonized with a multidrug resistant organism. In some embodiments, the bacterial compositions provided herein administered to a subject that is receiving a proton pump inhibitor.

Individuals may be at risk of acquiring a multi-drug resistant organism if they have recently received antimicrobials, are in an immunosuppressed state (e.g., on chemotherapy, have a malignancy, undergoing or received a transplant), have a chronic disease or inflammatory condition (such as diabetes, renal disease, etc.), are older, are undergoing hemodialysis, surgery or other invasive procedures, have indwelling device(s), and/or are living in a long-term care facility or are hospitalized. In some embodiments, the subject is colonized with a multi-drug resistant organism. Skin and mucosal colonization are common (Cassone et al., *Curr Geriatr Rep*. (2015) 4(1): 87-89), but multi-drug resistant organisms may also colonize the gastrointestinal (GI) tract and oral cavity, causing inflammation (Atarashi et al., *Science* (2017) 358, 359-365). Colonization can lead to significant infections, such as in the skin, lungs, urinary tract, or bloodstream, which may result in serious complications, including death (CDC, 2013). In some instances, multi-drug resistant organisms may be ingested, leading to consequences throughout the digestive system. In some embodiments, a multi-drug resistant organism may colonize the oral cavity.

In some embodiments, the multi-drug resistant organism is Vancomycin Resistant Enterococci (VRE), Carbapenem Resistant Enterobacteriaceae (CRE), *Neisseria gonorrheae*, Multidrug Resistant *Acinetobacter, Campylobacter*, Extended spectrum beta-lactamase (ESBL) producing Enterobacteriaceae, ESBL-producing *Escherichia coli*, Multidrug Resistant *Pseudomonas aeruginosa, Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, or Clindamycin resistant Group B *Streptococcus*. In some embodiments, the multi-drug resistant organism is Vancomycin Resistant Enterococci (VRE). In some embodiments, the multi-drug resistant organism is Carbapenem Resistant Enterobacteriaceae (CRE).

In some embodiments, the compositions described herein are effective in reducing or preventing colonization by more than one multi-drug resistant organism. In some embodiments, the compositions described herein are effective in treating infection of more than one multi-drug resistant organism. For example, in some embodiments, the compositions described herein are effective in reducing or preventing, or treating infection, with a carbapenem resistant Enterobacteriaceae (CRE) and Extended spectrum beta-lactamase (ESBL) producing Enterobacteriaceae, Enterobacteriaceae is a broad family of bacteria that includes a number of bacterial pathogens. Bacteria belonging to the Enterobacteriaceae family are characterized as being Gram negative and are frequently found in the gut flora of the intestinal tract of humans and mammals but may also be found in water and soil. Non-limiting examples of bacterial genera belonging to the Enterobacteriaceae family include *Alishewanella, Buttiauxella, Grimontella, Pectobacterium, Salmonella, Yokenella, Alterococcus, Cedecea, Hafnia, Phlomobacter, Samsonia, Aquamonas, Citrobacter, Klebsiella, Photorhabdus, Serratia, Aranicola, Cronobacter, Kluyvera, Poodoomaamaana, Shigella, Arsenophonus, Dickeya, Leclercia, Plesiomonas, Sodalis, Azotivirga, Edwardsiella, Leminorella, Pragia, Tatumella, Blochmannia, Enterobacter, Moellerella, Proteus, Trabulsiella, Brenneria, Erwinia, Morganella, Providencia, Wigglesworthia, Buchnera, Escherichia, Obesumbacterium Rahnella, Xenorhabdus, Budvicia, Ewingella, Pantoea, Raoultella*, and *Yersinia*.

In some embodiments, the compositions described herein are effective in reducing or preventing, or treating infection, with a carbapenem resistant Enterobacteriaceae (CRE). As used herein, the terms "carbapenem resistant Enterobacteriaceae" or "CRE" refer to a bacterial strain or species that belongs to the Enterobacteriaceae family and has developed resistance to carbapenem antibiotics. In some embodiments, the CRE is also resistant to additional antibiotics in addition to carbapenem antibiotics.

In some embodiments, the Carbapenem Resistant Enterobacteriaceae is carbapenem-resistant *Klebsiella pneumoniae*. Examples of CRE *Klebsiella pneumoniae* is *Klebsiella pneumoniae* strain ATCC 700721.

In some embodiments, the compositions described herein are effective in reducing or preventing, or treating infection, with an extended spectrum beta-lactamase (ESBL) producing Enterobacteriaceae. As used herein, the terms "extended spectrum beta-lactamase Enterobacteriaceae" or "ESBL-Enterobacteriaceae" refer to a bacterial strain or species that belongs to the Enterobacteriaceae family and produce or are capable of producing beta-lactamase enzymes that breakdown or inactivate antibiotics. In some embodiments, the ESBL Enterobacteriaceae is resistant to one or more antibiotics (e.g., beta-lactam antibiotics).

In some embodiments, the ESBL Enterobacteriaceae is also resistant to additional antibiotics in addition to beta-lactam antibiotics.

In some embodiments, the ESBL-producing Enterobacteriaceae is ESBL-producing *K. pneumoniae* or ESBL-producing *E. coli*. In some embodiments, the ESBL-producing Enterobacteriaceae is ESBL-producing *K. pneumoniae* subsp. *pneumoniae* (ATCC 700721), ESBL-producing *E. coli* ATCC BAA 2777 adherent/invasive *E. coli* (AIEC), Shiga toxin-producing *E. coli* (STEC), Verocytotoxin-producing *E. coli* (VTEC), enterohemorrhagic *E. coli* (EHEC), enteropathogenic *E. coli* (EPEC), enteroaggregative *E. coli* (EAEC), enteroinvasive *E. coli* (EIEC), or diffusely adherent *E. coli* (DAEC).

In some embodiments, the CRE or ESBL-producing Enterobacteriaceae is *Citrobacter freundii, Citrobacter koseri, Enterobacter cloacae, Enterobacter aerogenes, Enterobacter sakasakii, Escherichia coli, Escherichia albertii, Proteus mirabilis, Proteus vulgaris, Salmonella enterica, Serratia marcescens, Shigella dysenterii, Shigella flexneri, Shigella sonnei, Shigella boydii, Yersinia pestis, Yersinia enterocolitica*, or *Yersinia pseudotuberculosis.*

Aspects of the present disclosure are related to methods for suppressing pathogenic organisms in a subject. In some embodiments, the pathogenic organism is susceptible to antibiotics (e.g., not a multi-drug resistant organism). Pathogenic organisms are organisms that are capable of causing disease in a subject and may be viruses, bacteria, fungi, protozoa, and worms. Non-limiting examples of pathogenic organisms of the present disclosure include *Salmonella, Shigella, Staphylococcus, Streptococcus, Enterococcus, Enterobacteriaceae, Neisseria gonorrheae, Acinetobacter, Campylobacter, Clostridium, Listeria, Escherichia, Pseudomonas aeruginosa, Salmonella, Shigella, Staphylococcus aureus, Streptococcus pneumoniae*, Tuberculosis, Group A *Streptococcus*, or Group B *Streptococcus, Toxoplasma, Cyclospora, Giardia, Cryptosporidium*, and *Trichinella.*

In some embodiments, pathogenic organisms in the subject are resistant to treatment with a drug. In some embodiments, pathogenic organisms in the subject are resistant to treatment with multiple drugs (e.g., multi-drug resistant). Drugs that may be used to treat pathogenic organisms of the present disclosure may include antibiotics, antivirals, antifungals, and antiparasitics.

In some embodiments, a pathogenic organism that is susceptible to a drug may acquire resistance to one or more drugs. In some embodiments, a pathogenic organism that is susceptible to antibiotics may acquire resistance to one or more antibiotics. In some embodiments, a pathogenic organism is resistant to one or more drugs (e.g., antibiotics) and may acquire resistance to one or more drugs (e.g., antibiotics). In some embodiments, the pathogenic organism is resistant to one or more drugs (e.g., antibiotics) and may become a multi-drug resistant organism by acquiring resistance to more than one drugs (e.g., antibiotics).

In general, there are multiple means by which an organism may acquire drug resistance. In some embodiments, the organism may acquire drug resistance by acquiring mutations in its genome that promote survival of the organism in the presence of at least one drug. In some embodiments, the organism acquires DNA from an organism that is resistant to one or more drugs (e.g., antibiotics), thereby becoming resistant to the drug (e.g., antibiotic). In some embodiments, the organism acquires a plasmid, such as a plasmid containing one or more drug (e.g., antibiotic) resistance genes, from an organism that is resistant to one or more drugs (e.g., antibiotics), thereby becoming resistant to the drug (e.g., antibiotic).

In some embodiments, administration of the compositions described herein reduces/inhibits or prevents intestinal colonization with oral microbiome bacteria. In some embodiments, administration of the compositions described herein reduces/inhibits or prevents the colonization, replication, proliferation, and/or survival of oral microbiome bacteria in the intestinal tract of the subject. In some embodiments, administration of the compositions described herein allows for colonization of the gastrointestinal tract of the subject by the bacterial strain(s) of the compositions thereby preventing colonization by oral microbiome bacteria.

In some embodiments, the subject is a carrier of an oral bacterium and is suffering from the effects of the infection. In some embodiments the subject is an asymptomatic carrier of an oral bacterium. In some embodiments, the subject has experienced recurrent or chronic colonization with an oral bacterium. In some embodiments, the subject is at risk of colonization with an oral bacterium. In some embodiments, the subject has a risk factor associated with colonization with an oral bacterium. In some embodiments, the subject is taking a proton pump inhibitor. In some embodiments, the subject has had a previous infection or colonization with an oral bacterium.

In some embodiments, the subject is to undergo a procedure that puts the subject at a higher risk of colonization and the compositions are administered prophylactically. In some embodiments, the compositions provided herein are administered to a subject to lower the risk of becoming colonized with an oral bacterium.

Over 700 bacterial species or phylotypes have been found in the oral cavity; however, over 50% have not yet been cultivated. A number of phyla have been identified in the oral microbiome Actinobacteria, *Arachnia*, Bacteroidetes, *Bifidobacterium*, Chlamydiae, Chloroflexi, *Eubacterium, Euryarchaeota, Fusobacterium*, Firmicutes, Fusobacteria, *Lactobacillus, Leptotrichia, Peptococcus, Peptostreptococcus, Propionibacterium*, Proteobacteria, *Selenomonas*, Spirochaetes, SRI, Synergistetes, Tenericutes, *Treponema*, TM7, and *Veillonella* (Dewhirst et al., J. Bacteriology (2010) 192(19): 5002-5010). Examples of oral microbiome bacteria include, without limitation, *Streptococcus sanguis, Streptococcus salivarius, Streptococcus mitis, Streptococcus mutans, Treponema denticola, Eikenella corrodens, Streptococcus gordonii, Streptococcus oralis, Acinomyces maeslundii*, and *Bacteroides melaningenicus*. A list of example species found in the human oral cavity can be found on the Human Oral Microbiome Database (homd.org). In some embodiments, the oral microbiome bacteria may be pathogenic. In some embodiments, the oral microbiome bacteria may be pathogenic if the bacteria gain access to another site of the body. In some embodiments, the oral microbiome bacteria are not pathogenic.

In some embodiments, administration of the compositions described herein reduces/inhibits or prevents intestinal colonization with oral microbiome bacteria. In some embodiments, the oral microbiome bacteria are *Fusobacterium nucleatum* (See e.g., Yoneda et al. *J Gastrointest Dig Syst* (2016) 6:2). In some embodiments, the oral microbiome bacteria are *Campylobacter concisus* (See e.g., Yoneda et al. *J Gastrointest Dig Syst* (2016) 6:2). In some embodiments, the oral microbiome bacteria are *Streptococcus mutans* (See e.g., Yoneda et al. J Gastrointest Dig Syst (2016) 6:2). Additional oral microbiome bacteria are described in Table S1A of Atarashi et al. (Atarashi et al., *Science* (2017) 358, 359-365), such as *Rothia mucilaginosa, Neisseria subflava, Granulicatella para-adiacens, Streptococcus salivarius, Streptococcus mitis, Fusobacterium* sp. 1_1_41FAA, *Streptococcus oralis, Streptococcus salivarius, Neisseria subflava, Prevotella scopos, Veillonella parvula, Streptococcus* sp. M143, *Haemophilus parainfluenzae, Prevotella* sp. CD3_34, *Neisseria macacae, Prevotella histicola, Prevotella pallens, Streptococcus infantis, Streptococcus parasanguinis, Porphyromonas* CW034, *Streptococcus* sp. oral strain T1-E5, Gemella sp. 933-88, *Veillonella parvula*, and *Prevotella* sp. C561.

In some embodiments, intestinal colonization with an oral microbiome bacterium induces a Th1 immune response in the subject. Examples of oral microbiome bacteria that may induce Th1 immune responses have been isolated, showing significant similarity (>96.3%) to the following species: *Mogibacterium* sp. CM96, *Peptostreptococcus stomatis, Bifidobacterium* sp. Group III-3, *Slackia exigua, Veillonella denticariosi, Atopobium parvulum, Veillonella* sp. 2011_oral_VSA_A3, *Campylobacter concisus, Actinomyces odontolyticus, Solobacterium moorei, Enterococcus faecium, Bifidobacterium dentium, Veillonella parvela, Fusobacterium* sp. 3_1_33, *Klebsiella aeromobilis*, and *Klebsiella pneumoniae* (see, e.g., Atarashi et al., *Science* (2017) 358: 359-365, Schirmer et al., *Cell Host and Microbe* (2018) 24: 600-610).

In some embodiments, the bacterium that induces a Th1 immune response (e.g., IBD) in a subject is a pathobiont. "Pathobiont" refers to a potentially pathological (disease-causing) organism which, under normal circumstances, lives as a symbiont. Examples of pathobionts include a bacterium that is associated with chronic inflammatory conditions (e.g., IBD). Non-limiting examples of pathobionts include *Shigella* spp., *Campylobacter* spp., *Cryptosporidium* spp., *Salmonella* spp., *Escherichia coli* strains (e.g., Enteropathogenic *E. coli*, Enteroaggregative *E. coli*, Enterotoxigenic *E. coli*), *Veillonella dispar, Aggregatibacter segnis, Campylobacter*, Lachnospiraceae, *Veillonella parvula, Haemophilus parainfluenzae, Megasphaera, Escherichia coli, Enterobacteriaceae* spp., *Enterococcus* spp., *Fusobacterium* spp., *Gemella* spp., *Veillonella* spp., *Pasteurella* spp., *Neisseria* spp., *Haemophilus* spp., *Campylobacter* spp., and *Bifidobacterium* spp.

In some embodiments, the methods may involve determining whether an oral bacterium is present in the subject. In some embodiments, the methods may involve determining whether an oral bacterium colonizes the oral cavity of the subject. In some embodiments, a subject may be at risk of intestinal colonization if the oral bacterium is present in the oral cavity of the subject. In some embodiments, the methods involve administering the combinations described herein to the subject, if an oral bacterium is detected in the oral cavity of the subject.

In some embodiments, the methods may involve determining whether an oral bacterium is present in the intestine of the subject. In some embodiments, the methods involve administering the combinations described herein to the subject, if an oral bacterium is detected in the intestine of the subject.

In some embodiments, the methods are for treating a disease or disorder associated with bacterial colonization in a subject. In some embodiments, the methods are for treating a disease or disorder associated with an immune response induced by bacteria in a subject. In some embodiments, the methods are for treating a disease or disorder associated with an undesired immune response induced by bacteria in a subject.

In some embodiments, the methods may involve determining whether the subject is colonized with bacteria. In some embodiments, the methods may involve determining whether the subject has or is experiencing an immune response induced by bacterial colonization. In some embodiments, a subject may be at risk of an immune response induced by bacterial colonization if the subject is colonized by the bacteria. In some embodiments, the methods involve administering the combinations described herein to the subject, if the subject is determined to be colonized by the bacteria. In some embodiments, the methods involve administering the combinations described herein to the subject, if the subject is determined to be experiencing or have experienced an immune response induced by bacterial colonization.

In some embodiments, the immune response induced by bacterial colonization is a Th1 immune response. As will be evident to one of skill in the art, Th1 immune responses are mediated the Th1 population of CD4+ cells. Th1 cells produce IFN-γ and other pro-inflammatory factors. The differentiation of CD4+ cells to Th1 cells is promoted by the presence of IL-2 and/or IL-12 and activation of the transcription factors STAT4 and T-bet. In some embodiments, the immune responses induced by bacterial colonization are Th1 pro-inflammatory responses. Any direct or indirect measure of Th1 immune response, such as the amount of IFN-γ or the number of Th1 cells, may be used to assess the level or extent of the immune response in a sample from a subject.

In some embodiments, the compositions provided herein are administered to a subject if the subject has an autoimmune disease. Examples of autoimmune diseases include, without limitation, inflammatory bowel disease (IBD), ulcerative colitis, Crohn's disease, sprue, autoimmune arthritis, rheumatoid arthritis, graft versus host disease, Type I diabetes, multiple sclerosis, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, sarcoidosis, atherosclerosis, disseminated intravascular coagulation, Kawasaki's disease, Grave's disease, nephrotic syndrome, chronic fatigue syndrome, Wegener's granulomatosis, Henoch- Schoenlejn purpurea, microscopic vasculitis of the kidneys, chronic active hepatitis, uveitis, cachexia, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, yersinia and salmonella associated arthropathy, spondyloarhopathy, atheromatous disease/arteriosclerosis, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic cosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, cosinophilic esophagitis, hypereosinophilic syndrome, eosinophilic gastroenteritis cutaneous lupus erythematosus, eosinophilic esophagitis, hypereosinophilic syndrome, and cosinophilic gastroenteritis, and diarrhea. In some embodiments, the autoimmune disease is inflammatory bowel disease (IBD). In some embodiments, the autoimmune disease is ulcerative colitis. In some embodiments, the autoimmune disease is Crohn's disease.

In some embodiments, the compositions provided herein are administered to a subject if the subject has non-alcoholic steatohepatitis (NASH), primary sclerosing cholangitis (PSC), non-alcoholic fatty liver disease (NAFLD), gastroesophageal reflux disease (GERD), or alcoholism.

In some embodiments, the compositions provided herein are administered to a subject if an immune response associated with bacterial colonization has been detected in the subject. In some embodiments, the methods involve determining whether the subject has an immune response induced by or associated with colonization with an undesired organism.

In some embodiments, the compositions provided herein are administered to a subject if the subject has a dysbiosis (e.g., has as microbiome associated with a disease state). In some embodiments, treatment with the compositions provided herein results in the change in the microbiome of the subject. In some embodiments, treatment with the compositions provided herein removes the dysbiosis in the subject resulting in a healthy microbiome. In some embodiments, treatment with the compositions provided herein removes the dysbiosis in the subject resulting in microbiome refractory or less susceptible to infection by a pathogen.

In some embodiments, the compositions and methods described herein are for the treatment and/or prevention of sepsis. In some embodiments, the compositions provided herein are administered to a subject if the subject has or is at risk for sepsis. In some embodiments, the compositions and methods described herein are for the treatment and/or prevention of sepsis in critically ill subjects, such as patients in an intensive care unit (ICU, also referred to as an intensive therapy unit or intensive treatment unit (ITU) or critical care unit (CCU)). In some embodiments, the compositions provided herein are administered to a subject if the subject is a critically ill subject and has or is at risk for sepsis. As will be evident to one of ordinary skill in the art, sepsis is a systemic inflammatory response that is typically due to infection with bacterium, fungus, virus, or protozoa. The severity of sepsis can range from mild (sepsis) to severe sepsis or even septic shock. Subjects of advanced age (e.g., over 65 years old), young age (e.g., under 1 year old), and/or having a compromised immune systems, including due to cancer, diabetes, burns, trauma, or other disease or disorder resulting in a critical illness, may be at increased risk of developing sepsis.

In some embodiments, the compositions and methods described herein are for the treatment and/or prevention of infection in critically ill subjects, such as patients in an intensive care unit (ICU). In some embodiments, the compositions provided herein are administered to a subject if the subject is a critically ill subject. In some embodiments, the subject may be a patient in an intensive care unit. In some embodiments, any of the compositions described herein may be administered to a subject to treat and/or prevent a bacterial infection, fungal infection, viral infection, or protozoan infection in a critically ill subject.

In some embodiments, the compositions and methods described herein are for the treatment and/or prevention of infection following a surgical procedure involving the gastrointestinal tract (i.e., gastrointestinal surgery). In some embodiments, the compositions and methods described herein are administered to a subject if the subject has undergone a surgical procedure involving the gastrointestinal tract. In some embodiments, the compositions and methods described herein are administered to a subject if the subject will be undergoing a surgical procedure involving the gastrointestinal tract (e.g., administered prior to the surgical procedure). In some embodiments, the subject has a disease or disorder associated with the gastrointestinal tract. In some embodiments, any of the compositions described herein may be administered to a subject to treat and/or prevent a bacterial infection, fungal infection, viral infection, or protozoan infection.

In some embodiments, the compositions and methods described herein are for the treatment and/or prevention of infection in subjects having cirrhosis (i.e., a cirrhosis patient). In some embodiments, the compositions and methods described herein are administered to a subject if the subject has or is at risk of cirrhosis. As will be evident to one of ordinary skill in the art, cirrhosis, also referred to as liver cirrhosis or hepatic cirrhosis, is a condition associated with liver dysfunction, predominantly due to long-term damage of the liver tissue and cells thereof. Cirrhosis may be caused by any of a variety of factors, for example, hepatitis (e.g., viral infection with Hepatitis B or Hepatitis C, autoimmune hepatitis), and excessive alcohol consumption. In some embodiments, any of the compositions described herein may be administered to a subject to treat and/or prevent a bacterial infection, fungal infection, viral infection, or protozoan infection in a cirrhosis patient.

In some embodiments, the compositions and methods described herein are for the treatment and/or prevention of infection in subjects who received a bone marrow transplant (i.e., bone marrow transplant patients). In some embodiments, the compositions and methods described herein are administered to a subject if the subject has undergone or will undergo a bone marrow transplant. In some embodiments, any of the compositions described herein may be administered to a subject to treat and/or prevent a bacterial infection, fungal infection, viral infection, or protozoan infection in a bone marrow transplant patient.

Any of the compositions described herein may be administered to a subject in a therapeutically effective amount or a dose of a therapeutically effective amount to treat or prevent a disease or disorder, for example associated with colonization with bacteria or an immune response associated with colonization with bacteria. The terms "treat" and "treatment" refer to reducing or alleviating one or more of the symptoms associated with colonization with bacteria or an immune response associated with colonization with bacteria. In some embodiments, any of the compositions described herein may be administered to a subject to prevent a disease or disorder. In some embodiments, any of the compositions described herein may be administered to a subject to prevent a Th1 related disease or disorder. In some embodiments, any of the compositions described herein may be administered to a subject to prevent IBD. The terms "prevent" and "prevention" encompass prophylactic administration and may reduce the incidence or likelihood of colonization with bacteria or an immune response associated with colonization with bacteria. For instance, in some embodiments, administration of the compositions provided herein result in a healthy microbiome that is refractory to pathogenic infection, thereby preventing the pathogenic infection or re-colonization with the pathogenic organism.

As used herein, a "therapeutically effective amount" may be used interchangeably with the term "effective amount." A therapeutically effective amount or an effective amount of composition, such as a pharmaceutical composition, is any amount that results in a desired response or outcome in a subject, such as those described herein, including but not limited to reducing or preventing colonization with bacteria or an immune response associated with colonization with bacteria.

It should be appreciated that the term effective amount may be expressed as the number of bacteria or bacterial spores to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to enhance survival of the subject, reduce or prevent bacterial colonization of the subject, and/or reduce or inhibit toxin production by the pathogenic infection. In some embodiments, colonization may be assessed by detecting and/or quantifying the bacteria in a sample from the subject, such as a fecal sample. In some embodiments, the therapeutically effective amount is an amount sufficient to reduce the colonization bacteria (e.g., pathogenic organisms, multi-drug resistant organisms, for example carbapenem resistant *Enterobacteriaceae* or extended spectrum beta-lactamase producing *Enterobacteriaceae*) in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the bacterial burden in a subject that has not received any of the compositions described herein, or as compared to a fecal sample from the same subject that was collected prior to administration of any of the compositions.

In some embodiments, the compositions provided herein reduce an immune response associated with bacterial colonization or induced by bacterial colonization. In some embodiments, the therapeutically effective amount is an amount sufficient to reduce an immune response associated with bacterial colonization or induced by bacterial colonization by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the immune response associated with bacterial colonization or induced by bacterial colonization prior to administration of any of the compositions.

In some embodiments, the therapeutically effective amount is an amount sufficient to recolonize or repopulate the gastrointestinal tract of the subject with non-pathogenic bacteria. In some embodiments, the therapeutically effective amount is an amount sufficient to graft one or more of the bacterial strains of the composition in the gastrointestinal tract of the subject. In some embodiments, a fecal sample is obtained from the subject to assess the bacterial burden of undesired bacteria (e.g., pathogenic organisms, multi-drug resistant organisms, for example carbapenem resistant *Enterobacteriaceae* or extended spectrum beta-lactamase producing *Enterobacteriaceae*) and/or evaluate the efficacy of administration of the bacterial compositions described herein. In some embodiments, the microbiota of the subject (e.g., the identity and abundance of strains and/or species of the microbiota) may be assessed to determine a disease state of the subject and/or assess progress of the treatment. In some embodiments, the microbiota of the subject having a pathogenic infection is compared to the microbiota of a healthy subject, such as a subject that is not experiencing or has not experienced the pathogenic infection. In some embodiments, the microbiota of the subject having a pathogenic infection is compared to the microbiota of the same subject from a fecal sample obtained from the subject prior to the pathogenic infection.

In some embodiments, administration of the compositions provided herein results in a healthy microbiome that reduces or prevents colonization of the subject by any undesired organism. In some embodiments, administration of the compositions provided herein results in a healthy microbiome that reduces or prevents intestinal colonization of the subject by any undesired organism (e.g., pathogenic organisms, multi-drug resistant organisms, for example carbapenem resistant *Enterobacteriaceae* or extended spectrum beta-lactamase producing *Enterobacteriaceae*). In some embodiments, administration of the compositions provided herein results in a healthy microbiome that reduces an immune response associated with bacterial colonization, such as colonization with undesired bacteria. In some embodiments, administration of the compositions provided herein results in a healthy microbiome that reduces a Th1 immune response in the subject.

Any of the compositions described herein may be administered in combination with one or more additional compositions that can suppress a Th1 response and/or induces the accumulation and/or proliferation of regulatory T cells, and/or Th17 cells. In some embodiments, any of the compositions described herein may be administered in combination with a composition that induces the proliferation and/or accumulation of regulatory T cells ("Treg").

In some embodiments, any of the compositions described herein may be administered in combination with a Treg inducing composition of bacterial strains, described for instance in Atarashi et al., Nature (2013) 500: 232-236. In some embodiments, the Treg inducing composition comprises at least 5, at least 10, at least 11, at least 12, at least 13, at least 14, at least 15, at least 16, or at least 17 of the following species: *Clostridium* saccharogumia, *Flavonifractor plautii, Clostridium* hathewayi, *Blautia* coccoides, *Clostridium bolteae* ATCC BAA-613, cf. *Clostridium* sp. MLG055, *Clostridium indolis, Anaerotruncus colihominis, Ruminococcus* sp. ID8, *Clostridium asparagiforme* DSM 15981, *Clostridium* symbiosum, *Clostridium ramosum, Eubacterium contortum*, Lachnospiraceae bacterium 5_1_57FAA, Lachnospiraceae bacterium 3_1_57FAA_CT1, Clostridiales bacterium 1_7_47FAA, and Lachnospiraceae bacterium A4. It should be appreciated that subsets of the bacterial compositions described above can also induce Treg cells. Examples of subsets bacteria that induce Treg cells are found for instance in Atarashi et al., *Nature* (2013) 500: 232-236 and corresponding Supplemental Information. In some embodiments, any of the compositions described herein may be administered in combination with any of the bacterial compositions as described in PCT Publication WO 2016/209806.

In some embodiments, any of the compositions described herein may be administered in combination with any of the bacterial compositions described in PCT Publication WO 2019/094837, which is incorporated herein by reference in its entirety. In some embodiments, any of the compositions described herein may be administered in combination with any of the bacterial compositions described in PCT Publication WO 2019/118515, which is incorporated herein by reference in its entirety. In some embodiments, any of the compositions described herein are administered in combination with a composition of 36 bacterial strains (e.g., the 36-mix, shown in FIG. 2).

As used herein, the phrase "induces proliferation and/or accumulation of regulatory T cells" refers to an effect of inducing the differentiation of immature T cells into regulatory T cells, which differentiation leads to the proliferation and/or the accumulation of regulatory T cells. Further, the meaning of "induces proliferation and/or accumulation of regulatory T cells" includes in vivo effects, in vitro effects, and/or ex vivo effects. In some embodiments, the proliferation and/or accumulation of regulatory T cells may be assessed by detecting and/or quantifying the number of cells that express markers of regulatory T cells (e.g., Foxp3 and CD4), for example by flow cytometry. In some embodiments, the proliferation and/or accumulation of regulatory T cells may be assessed by determining the activity of the regulatory T cells, such as the production of cytokines (e.g., IL-10).

In some embodiments, any of the compositions described herein may be administered in combination with a composition that induces the accumulation and/or proliferation of Th17 cells, see e.g., compositions disclosed in PCT Publication WO 2015/156419, which is incorporated herein by reference in its entirety.

In some embodiments, suppressing live bacterial product also repopulates the microbiota of the subject.

In some embodiments, administration of the compositions described herein results in an increase in the proliferation and/or accumulation of regulatory T cells (e.g., total Tregs or pathogenic organism-specific Tregs) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or pathogenic organism-specific Tregs) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the quantity of regulatory T cells in another subject (e.g., a reference subject) who did not receive the compositions.

In some embodiments, administration of the compositions described herein results in an increase the proliferation and/or accumulation of regulatory T cells (e.g., total Tregs or pathogenic organism-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or pathogenic organism-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the quantity of regulatory T cells in another subject (e.g., a reference subject) who did not receive the compositions.

The induction of Treg cells and corresponding decolonization of pathogenic organisms are intricately related. In some embodiments, administration of the compositions described herein results in an increase the proliferation and/or accumulation of regulatory T cells (e.g., total Tregs or pathogenic organism-specific Tregs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of regulatory T cells in the subject (or particular site in the subject) prior to administration of the compositions. In some embodiments, administration of the compositions described herein results in an increase the proliferation and/or accumulation of regulatory T cells (e.g., total Tregs or pathogenic organism-specific Tregs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of regulatory T cells in another subject (e.g., a reference subject) who did not receive the compositions.

In some embodiments, administration of the compositions described herein results in an increase in activity of regulatory T cells (e.g., total Tregs or pathogenic organism-specific Tregs) at a particular site (e.g., the gastrointestinal tract) in the subject. In some embodiments, administration of the compositions described herein results in an increase in activity of regulatory T cells (e.g., total Tregs or pathogenic organism-specific Tregs) by at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the activity of regulatory T cells in the subject (or particular site in the subject) prior to administration of the compositions. In some embodiments, administration of the compositions described herein results in an increase in activity of regulatory T cells (e.g., total Tregs or pathogenic organism-specific Tregs) by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, $10^4$-fold, $10^5$-fold or more, as compared to the activity of regulatory T cells in another subject (e.g., a reference subject) who did not receive the compositions.

In some embodiments, administration of the compositions described herein results in an increase in the activity of regulatory T cells (e.g., total Tregs or pathogenic organism-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the activity of regulatory T cells in the subject (or particular site in the subject) prior to administration of the compositions. In some embodiments, administration of the compositions described herein results in an increase in the activity of regulatory T cells (e.g., total Tregs or pathogenic organism-specific Tregs) by at least 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 125%, 150% or more, as compared to the activity of regulatory T cells in another subject (e.g., a reference subject) who did not receive the compositions.

The abundance of regulatory T cells (e.g., total Tregs or pathogenic organism-specific Tregs) can be assessed by any method known in the art, for example by detecting a cellular marker indicative of regulatory T cells (e.g., FoxP3), assessing a direct or indirect activity of regulatory T cells, and/or by measuring the production of one or more cytokines produced by regulatory T cells (e.g., IL-10).

Some aspects compositions and methods described herein increase production of short chain fatty acids (e.g., in the gastrointestinal tract of the subject). In some embodiments, the methods involve administering to a subject one or more compositions containing bacterial strains that produce short chain fatty acids. SCFAs are abundant in healthy subjects (e.g., subjects not having a pathogenic organism infection) and decreased in subjects having pathogenic organism infections (e.g., *Clostridium difficile* infections and rCDIs). Fecal matter transplant (FMT) have been shown to increase SCFA following rCDI (Seckatz, et al., *Anaerobe* (2018) 53: 64-73.

SCFA produced in the gastrointestinal tract are thought to function as signaling molecules between the gut microbiota and the host organism, with the SCFA playing a in local, intermediary and peripheral metabolism of the host. Sec, e.g., Morrison, et al. Gut Microbes (2016) 7(3): 189-200. In some embodiments, a damaged gut mucosal barrier can be repaired by providing SCFA.

Examples of SCFA include, without limitation, formic acid, acetic acid, butyric acid, isobutyric acid, valeric acid, or isovaleric acid. In some embodiments, the SCFA is butyric acid (butyrate).

The production of SCFAs and corresponding decolonization of pathogenic organisms are intricately related. In some embodiments, administration of the compositions described herein results in an increase in the production and/or accumulation of SCFAs (e.g., total SCFAs or pathogenic organism-specific SCFAs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of SCFAs in the subject (or particular site in the subject) prior to administration of the compositions. In some embodiments, administration of the compositions described herein results in an increase in the production and/or accumulation of SCFAs (e.g., total SCFAs or pathogenic organism-specific SCFAs) by between 1% and 20%, 2% and 19%, 3% and 17%, 4% and 16%, 4% and 15%, 5% and 15%, 6% and 14%, 7% and 13%, 8% and 12%, 5% and 10%, 5% and 15%, 10% and 15%, or 8% and 15% as compared to the quantity of SCFAs in another subject (e.g., a reference subject) who did not receive the compositions.

In some embodiments, the compositions and methods described herein result in an increase in the amount of SCFAs produced in the gastrointestinal tract of the subject. In some embodiments, the SCFAs are increased by 10-fold to 500-fold following administration of the composition as described herein. In some embodiments, SCFAs are increased by 20-fold to 250-fold following administration of the compositions described herein. In some embodiments, SCFAs are increased by 100-fold to 500-fold following administration of the compositions described herein. In some embodiments, SCFAs are increased by at least 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, or 500-fold following administration of the compositions described herein.

In some embodiments, SCFAs comprise butyrate. In some embodiments, the level of butyrate (e.g., in the gastrointestinal tract of the subject) is increased by 10-fold to 500-fold following administration of the compositions described herein. In some embodiments, the level of butyrate is increased by 20-fold to 250-fold following administration of compositions described herein. In some embodiments, the level of butyrate is increased by 100-fold to 500-fold following administration of the compositions described herein. In some embodiments, the level of butyrate is increased by at least 2-fold, 5-fold 10-fold, 20-fold, 30-fold, 40-fold, 50-fold, 60-fold, 70-fold, 80-fold, 90-fold, 100-fold, 200-fold, 300-fold, 400-fold, or 500-fold following administration of the compositions described herein.

In some embodiments, SCFAs comprise propionate. In some embodiments, the level of propionate (e.g., in the gastrointestinal tract of the subject) is increased by 10-fold to 500-fold following administration of the compositions described herein. In some embodiments, the level of propionate is increased by 20-fold to 250-fold following administration of compositions described herein. In some embodiments, the level of propionate is increased by 100-fold to 500-fold following administration of the compositions described herein. In some embodiments, the level of propionate is increased by at least 2-fold, 5-fold 10-fold, 20-fold, 30-fold, 40-fold, 50-fold, 60-fold, 70-fold, 80-fold, 90-fold, 100-fold, 200-fold, 300-fold, 400-fold, or 500-fold following administration of the compositions described herein.

In some embodiments, SCFAs comprise acetate. In some embodiments, the level of acetate (e.g., in the gastrointestinal tract of the subject) is increased by 10-fold to 500-fold following administration of the compositions described herein. In some embodiments, the level of acetate is increased by 20-fold to 250-fold following administration of compositions described herein. In some embodiments, the level of acetate is increased by 100-fold to 500-fold following administration of the compositions described herein. In some embodiments, the level of acetate is increased by at least 2-fold, 5-fold 10-fold, 20-fold, 30-fold, 40-fold, 50-fold, 60-fold, 70-fold, 80-fold, 90-fold, 100-fold, 200-fold, 300-fold, 400-fold, or 500-fold following administration of the compositions described herein.

In some embodiments, SCFAs comprise formate. In some embodiments, the level of acetate (e.g., in the gastrointestinal tract of the subject) is increased by 10-fold to 500-fold following administration of the compositions described herein. In some embodiments, the level of formate is increased by 20-fold to 250-fold following administration of compositions described herein. In some embodiments, the level of formate is increased by 100-fold to 500-fold following administration of the compositions described herein. In some embodiments, the level of formate is increased by at least 2-fold, 5-fold 10-fold, 20-fold, 30-fold, 40-fold, 50-fold, 60-fold, 70-fold, 80-fold, 90-fold, 100-fold, 200-fold, 300-fold, 400-fold, or 500-fold following administration of the compositions described herein.

In some embodiments, the subject is infected with a pathogenic organism. In some embodiments, the subject has a *Clostridium difficile* infection (CDI). In some embodiments, the CDI is recurrent (rCDI). rCDI is CDI that occurs more than once in the same subject and is associated with reduced short chain fatty acids (SCFAs), increased primary bile acids, and decreased secondary bile acids in the gut microbiota of the subject.

Bile acids are steroid acids that allow the digestion of dietary fats and oils by acting as surfactants that turn the fats and oils into micelles. Bile acids also act as hormones utilizing the farnesoid X receptor and GBPAR1. Primary bile acids are synthesized in the liver from cholesterol and a conjugated with either taurine or glycine prior to secretion. When the primary bile acids are secreted into the lumen of the intestine, bacteria partially dehydroxylate and remove the glycine or taurine groups, forming secondary bile acids.

Non-limiting examples of primary bile acids are cholic acid (CA), chenodeoxycholic acid (CDCA), glycocholic acid (GCA), glycochenodeoxycholic acid (GCDCA), glycodeoxycholic acid (GDCA), taurocholic acid (TCA), and turochenodeoxycholic acid (TCDCA). Non-limiting examples of secondary bile acids are deoxycholic acid (DCA), lithocholic acid (LCA), ursodeoxycholic acid (UDCA), taurodeoxycholic acid (TDCA), taurolithocholic acid (TLCA), and tauroursodeoxycholic acid (TUDCA).

Pathogenic organism infection, including *Clostridium difficile* infection and rCDI, are associated with increased primary bile acids and reduced secondary bile acids. The primary bile acids are reduced, and the secondary bile acids are increased following fecal matter transplant (FMT) (Seckatz, et al., Anaerobe (2018) 53: 64-73). In some embodiments, administration of the bacterial strains or a pharmaceutical composition as described herein reduces primary bile acids and/or increases secondary bile acids.

In some embodiments, the levels of primary bile acids are reduced by 10-fold to 100,000-fold following administration of the bacterial strains or the pharmaceutical composition. In some embodiments, the levels of primary bile acids are reduced by 10-fold to 1,000-fold following administration of the bacterial strains or the pharmaceutical composition. In some embodiments, the levels of primary bile acids are reduced 20-fold to 10,000-fold following administration of the bacterial strains or the pharmaceutical composition. In some embodiments, the levels of primary bile acids are reduced by 10-fold, 100-fold, 200-fold, 300-fold, 400-fold, 500-fold, 600-fold, 700-fold, 800-fold, 900-fold, 1,000-fold, 10,000-fold, 20,000-fold, 30,000-fold, 40,000-fold, 50,000-fold, 60,000-fold, 70,000-fold, 80,000-fold, 90,000-fold, or 100,000-fold following administration of the bacterial strains or the pharmaceutical composition.

In some embodiments, the levels of secondary bile salts are increased by 10-fold to 10,000-fold following administration of the bacterial strains or the pharmaceutical composition. In some embodiments, the levels of secondary bile acids are increased by 10-fold to 1,000-fold following administration of the bacterial strains or the pharmaceutical composition. In some embodiments, the levels of secondary bile acids are increased by 20-fold to 100-fold following administration of the bacterial strains or the pharmaceutical composition. In some embodiments, the levels of secondary bile acids are increased by 10-fold, 20-fold, 50-fold, 100-fold, 200-fold, 300-fold, 400-fold, 500-fold, 600-fold, 700-fold, 800-fold, 900-fold, 1,000-fold, 2,000-fold, 3,000-fold, 4,000-fold, 5,000-fold, 6,000-fold, 7,000-fold, 8,000-fold, 9,000-fold, or 1,000-fold following administration of the bacterial strains or the pharmaceutical composition.

In general, short chain fatty acids (SCFAs) are fatty acids containing six or less carbon atoms. SCFAs are produced when dietary fiber is fermented in the intestine. Non-limiting examples of SCFAs include hexanoate, pentanoate, butyrate, propionate, acetate, and formate. SCFAs are primarily absorbed in the portal vein following lipid digestion, and can affect the production of lipids, energy, and vitamins. Further, SCFAs play a critical role in maintaining intestinal epithelial cell membrane integrity for preventing pathogenic organism (e.g., *Clostridium difficile*) infection.

In one aspect, the disclosure provides methods comprising administration of multiple doses of the pharmaceutical compositions. In some embodiments, the disclosure provides methods comprising administration of antibiotic (e.g., vancomycin) followed by multiple doses of the pharmaceutical compositions. In some embodiments, administration of multiple doses of the pharmaceutical compositions described herein provides enhanced colonization (engraftment) of one or more bacterial strains of the pharmaceutical compositions as compared to administration of a single dose of the pharmaceutical composition. In some embodiments, administration of multiple doses of the pharmaceutical compositions described herein provides enhanced recovery of one or more bacterial strains of the pharmaceutical compositions as compared to administration of a single dose of the pharmaceutical composition. In some embodiments, administration of multiple doses of the pharmaceutical compositions described herein provides increased abundance of one or more bacterial strains of the pharmaceutical compositions as compared to administration of a single dose of the pharmaceutical composition. In some embodiments, administration of multiple doses of the pharmaceutical compositions described herein provides an increase in the number of subjects that were colonized with of all of bacterial strains of the pharmaceutical compositions as compared to administration of a single dose of the pharmaceutical composition. In some embodiments, administration of multiple doses of the pharmaceutical compositions described herein provides durable colonization (e.g., up to 6 months) of one or more bacterial strains of the pharmaceutical compositions as compared to administration of a single dose of the pharmaceutical composition. In some embodiments, administration of multiple doses of the pharmaceutical compositions described herein provides durable colonization (e.g., up to 6 months) of all of the bacterial strains of the pharmaceutical compositions as compared to administration of a single dose of the pharmaceutical composition. It should further be appreciated that administration of multiple dose my results in a combination of the results described. Thus, for example, in some embodiments, administration of multiple doses of the pharmaceutical compositions described herein provides enhanced colonization (engraftment) and increased rate of recovery of one or more bacterial strains of the pharmaceutical compositions as compared to administration of a single dose of the pharmaceutical composition.

In some embodiments, administration of multiple doses of the pharmaceutical compositions described herein provides enhanced colonization (engraftment) of one or more bacterial strains of the pharmaceutical compositions as compared to administration of a single dose of the pharmaceutical composition. Administration of multiple doses of the pharmaceutical composition may result in enhanced colonization (engraftment) and an increased abundance of each of the bacterial strains of the pharmaceutical composition. In some embodiments, administration of a single dose of the pharmaceutical composition results in the same or a similar level of engraftment (e.g., total bacteria) as administration of multiple doses of the pharmaceutical composition, however the engraftment may be dominated by one bacterial strain or only a subset of the bacterial strains of the pharmaceutical compositions.

Any of the methods described herein may involve administering an antibiotic to the subject prior to administration of the pharmaceutical compositions described herein. In some embodiments, the antibiotic is vancomycin, fidaxomycin or ridinilazole. Non-limiting examples of antibiotics that may be used in any of the methods provided herein include cephalosporin antibiotics cephalexin, cefuroxime, cefadroxil, cefazolin, cephalothin, cefaclor, cefamandole, cefoxitin, cefprozil, ceftobiprole, clindamycin, ceftriaxone, cefotaxime, cefazolin, cefoperazone, cefuroxime, cefmetazole, fluoroquinolone, ciprofloxacin, Levaquin, floxin, tequin, avelox, norflox, tetracycline, minocycline, oxytetracycline, doxycycline, amoxicillin, ampicillin, penicillin V, dicloxacillin, benzylpenicillin, carbenicillin, vancomycin, and methicillin, ertapenem, doripenem, imipenem/cilastatin, meropenem, clavulanate, tazobactam, piperacillin, ceftriaxone, cefotaxime, cefazolin, fluoroquinolone, imipenem, meropenem, metronidazole, fidaxomyxin, or ridinilazole.

In some embodiments, any of the methods described herein may further comprise administering vancomycin to the subject prior to administration of the pharmaceutical compositions described herein. In some embodiments, the method does not comprise administering an antibiotic to the subject prior to administration of the pharmaceutical compositions described herein. In some embodiments, the method does not comprise administering vancomycin to the subject prior to administration of the pharmaceutical compositions described herein. Vancomycin administration has been found to alter the composition of human gut microbiota. See, e.g., Reijnders et al. *Cell Metabolism* (2016) 24(1): 63-72. Without wishing to be bound by any particular theory, it is thought that administration of vancomycin may aid engraftment of the bacterial strain(s) of the pharmaceutical compositions described herein, for example by removing other microbes present in the gastrointestinal tract.

In some embodiments, the antibiotic (e.g., vancomycin) is administered to the subject once, as a single dose. In some embodiments, the antibiotic (e.g., vancomycin) is administered to the subject in multiple doses. In some embodiments, the antibiotic (e.g., vancomycin) is administered to the subject in at least 2, 3, 4, 5, 6, 7, 8, 9, 10, 11, 12, 13, 14, 15 or more doses. The multiple doses of the antibiotic (e.g., vancomycin) may be administered to the subject at regular intervals prior to administering any of the pharmaceutical compositions described herein. In some embodiments, each of the multiple doses of the antibiotic (e.g., vancomycin) are administered on consecutive days (e.g., first dose on day 1, second dose of day 2, third dose on day 3, etc.). In some embodiments, the antibiotic (e.g., vancomycin) is administered to the subject for 2, 3, 4, 5, 6, 7, 8, 9, 10, 11, 12, 13, 14, 15 or more consecutive days. In some embodiments, the antibiotic (e.g., vancomycin) is administered to the subject each day for three consecutive days. In some embodiments, the antibiotic (e.g., vancomycin) administered to the subject each day for five consecutive days. In some embodiments, the antibiotic (e.g., vancomycin) administered to the subject each day for seven consecutive days. In some embodiments, the antibiotic (e.g., vancomycin) administered to the subject for one day. In any of the embodiments described herein, a subject may be administered one or more doses of a first antibiotic followed by one or more doses of a second antibiotic.

In some embodiments, a single dose, or the first dose in a treatment regimen of multiple doses, is administered, the same day as the administration of the final dose of the antibiotic (e.g., vancomycin). In some embodiments, a single dose, or the first dose in a treatment regimen of multiple doses, is administered, the day after administration of the final dose of the antibiotic (e.g., vancomycin). In some embodiments, a single dose, or the first dose in a treatment regimen of multiple doses, is administered, two days after administration of the final dose of the antibiotic (e.g., vancomycin). In some embodiments, the methods provided herein allow for a wash out day between the final dose of the antibiotic (e.g., vancomycin) and the first dose of the pharmaceutical composition. In some embodiments, a single dose, or the first dose in a treatment regimen of multiple doses, is administered, three days, four days, five days, six days, ten days or more, after administration of the final dose of the antibiotic (e.g., vancomycin). In some embodiments, the methods provided herein allow for multiple wash out days between the final dose of the antibiotic (e.g., vancomycin) and the first dose of the pharmaceutical composition.

Each dose of the antibiotic (e.g., vancomycin) may be the same amount of the antibiotic or may be a different amount of the antibiotic. In some embodiments, the antibiotic (e.g., vancomycin) is administered in an amount sufficient to allow for colonization of one or more of the bacterial strains of the pharmaceutical compositions described herein. In some embodiments, the subject is administered between about 50 mg and 1 g, 100 mg and 750 mg, 100 mg and 500 mg. 200 mg and 750 mg. 200 mg and 500 mg, 300 mg and 750 mg, 300 mg and 500 mg, 100 mg and 400 mg, 100 mg and 300 mg, 100 mg and 200 mg, 200 mg and 400 mg. 200 mg and 300 mg, or 450 mg to 550 mg of the antibiotic per day. As will be appreciated by one of skill in the art, the total amount of vancomycin administered to the subject per day may be administered in a single dose or between multiple doses, which in sum results in the total amount of the antibiotic per day.

In some example, the subject is administered about 500 mg vancomycin per day prior to administration of any of the pharmaceutical compositions described herein. In some embodiments, 500 mg of vancomycin per day is administered in a single dose (e.g., 500 mg). In some embodiments, 500 mg of vancomycin per day is administered in multiple doses (e.g., 2, 3, 4, 5 or more), which in sum results in 500 mg vancomycin per day. In some embodiments, 500 mg vancomycin is administered in 4 doses of 125 mg vancomycin per day. In some embodiments, 500 mg of vancomycin is administered to the subject for one day. In some embodiments, 500 mg of vancomycin is administered to the subject per day for two days. In some embodiments, 500 mg vancomycin is administered to the subject per day for three days. In some embodiments, 500 mg vancomycin is administered to the subject per day for four days. In some embodiments, 500 mg vancomycin is administered to the subject per day for five days. In some embodiments, 500 mg vancomycin is administered to the subject per day for six days. In some embodiments, 500 mg vancomycin is administered to the subject per day for seven days. In some embodiments, 500 mg vancomycin is administered to the subject per day for eight days. In some embodiments, 500 mg vancomycin is administered to the subject per day for nine days. In some embodiments, 500 mg vancomycin is administered to the subject per day for ten days.

In some embodiments, the subject is administered about 250 mg vancomycin per day prior to administration of any of the pharmaceutical compositions described herein. In some embodiments, 250 mg vancomycin per day is administered in a single dose (e.g., 250 mg). In some embodiments, 250 mg vancomycin per day is administered in multiple doses (e.g., 2, 3, 4, 5 or more), which in sum results in 250 mg vancomycin per day. In some embodiments, 250 mg vancomycin is administered in 2 doses of 125 mg vancomycin per day. In some embodiments, 250 mg vancomycin is administered to the subject for one day. In some embodiments, 250 mg vancomycin is administered to the subject per day for two days. In some embodiments, 250 mg vancomycin is administered to the subject per day for three days. In some embodiments, 250 mg vancomycin is administered to the subject per day for four days. In some embodiments, 250 mg vancomycin is administered to the subject per day for five days. In some embodiments, 250 mg vancomycin is administered to the subject per day for six days. In some embodiments, 250 mg vancomycin is administered to the subject per day for seven days. In some embodiments, 250 mg vancomycin is administered to the subject per day for eight days. In some embodiments, 250 mg vancomycin is administered to the subject per day for nine days. In some embodiments, 250 mg vancomycin is administered to the subject per day for ten days.

In some embodiments, the subject is administered about 125 mg vancomycin per day prior to administration of any of the pharmaceutical compositions described herein. In some embodiments, the 125 mg vancomycin per day is administered in a single dose (e.g., 125 mg). In some embodiments, the 125 mg vancomycin per day is administered in multiple doses (e.g., 2, 3, 4, 5 or more), which in sum results in 125 mg vancomycin per day. In some embodiments, 125 mg vancomycin is administered to the subject for one day. In some embodiments, 125 mg vancomycin is administered to the subject per day for two days. In some embodiments, 125 mg vancomycin is administered to the subject per day for three days. In some embodiments, 125 mg vancomycin is administered to the subject per day for four days. In some embodiments, 125 mg vancomycin is administered to the subject per day for five days. In some embodiments, 125 mg vancomycin is administered to the subject per day for six days. In some embodiments, 125 mg vancomycin is administered to the subject per day for seven days. In some embodiments, 125 mg vancomycin is administered to the subject per day for eight days. In some embodiments, 125 mg vancomycin is administered to the subject per day for nine days. In some embodiments, 125 mg vancomycin is administered to the subject per day for ten days.

In some embodiments, the disclosure provides methods comprising administering one or more antibiotics to the subject and subsequently administering any of the bacterial compositions to the subject once, twice, 3 times, 4 times, 5 times, 6 times, 7 times, 8 times, 9 times, or at least 10 times, or more. In some embodiments, the disclosure provides methods comprising administering one or more antibiotics to the subject and subsequently administering any of the bacterial compositions described herein to the subject in multiple doses at a regular interval, such as every 2 weeks, every month, every 2 months, every 3 months, every 4 months, every 5 months, every 6 months, or more. In some embodiments, one dose of any of the compositions described herein is administered and a second dose of the composition is administered the following day (e.g., consecutive day). In some embodiments, one dose of any of the compositions described herein is administered and each of the additional doses of the composition are administered on consecutive days (e.g., first dose on day 1, second dose of day 2, third dose on day 3, etc.).

In one aspect, the disclosure provides methods comprising administering one or more antibiotics to the subject and subsequently administering any of the bacterial compositions as multiple daily doses of the pharmaceutical compositions. In some embodiments, the pharmaceutical compositions are administered on a daily basis for 2 days, 3 days, 4, days, 5, days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months or more.

In some embodiments, the antibiotic (e.g., vancomycin) is administered according to a pulse tapered regime. See e.g., Sirbu et al., *Clinical Infectious Diseases* (2017) 65: 1396-1399.

In some embodiments, the antibiotic (e.g., vancomycin) is administered to the subject at least 1, 2, 3, 4, 5, 6, 7 days or more prior to administration of the pharmaceutical compositions described herein. In some embodiments, administration of antibiotic (e.g., vancomycin) is terminated at least one day (e.g., 1, 2, 3, 4, 5, or more) prior to administration of any of the pharmaceutical compositions described herein.

In some embodiments, additional antibiotics are administered in combination with the vancomycin regimes provided herein.

It should be appreciated, in some embodiments, that any of the vancomycin doses or administration regimens may be combined with any of the pharmaceutical composition doses or administration regimens provided herein.

In one aspect the disclosure provides methods comprising the administration of an antibiotic (e.g., vancomycin) followed by the administration of a pharmaceutical composition provided herein, wherein the administration of an antibiotic (e.g., vancomycin) is followed by the administration of a single dose or multiple doses of the pharmaceutical composition. In some embodiments, administration of an antibiotic (e.g., vancomycin) followed by the administration of a single dose or multiple doses of the pharmaceutical composition results in an increase in the abundance of bacterial strains of the pharmaceutical compositions in the microbiome of the subject (engraftment) compared to the administration of a pharmaceutical composition without the administration of the antibiotic. In some embodiments, administration of an antibiotic (e.g., vancomycin) followed by the administration of a single dose or multiple doses of the pharmaceutical composition results in an increase in the duration of the colonization of bacterial strains of the pharmaceutical composition in the microbiome of the subject (e.g., up to 6 months) compared to the administration of a pharmaceutical composition without the administration of the antibiotic.

In some embodiments, administration of an antibiotic (e.g., vancomycin) followed by the administration of a single dose or multiple doses of the pharmaceutical composition results in an increase in the rate of engraftment of the initial amount of the bacterial strains of the pharmaceutical composition in the microbiome of the subject by between ten- to one hundred-fold (e.g., within the first 48 hours) compared to the administration of a pharmaceutical composition without the administration of the antibiotic.

In some embodiments, administration of an antibiotic (e.g., vancomycin) followed by the administration of a single dose or multiple doses of the pharmaceutical composition results in a greater number (amount) of subjects having all of the bacterial strains of the pharmaceutical composition present in their microbiome as compared to compared to the administration of a pharmaceutical composition without the administration of the antibiotic.

In some embodiments, administration of an antibiotic (e.g., vancomycin) followed by the administration of multiple doses of the pharmaceutical composition results in an increase in the abundance of bacterial strains of the pharmaceutical composition in the microbiome of the subject (engraftment) compared to the administration of a single dose of the pharmaceutical composition. In some embodiments, the disclosure provides methods comprising the administration of a pharmaceutical composition provided herein, wherein the administration of multiple doses of the pharmaceutical composition increases the abundance of bacterial strains in the microbiota of the subject (engraftment) of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in an increase in the rate of engraftment of the initial amount of the bacterial strains of the pharmaceutical composition in the microbiome of the subject as compared to the administration of a single dose of the pharmaceutical composition. In some embodiments, the disclosure provides methods comprising the administration of a pharmaceutical composition provided herein, wherein the administration of multiple doses of the pharmaceutical composition increases the rate of engraftment of the initial amount of the bacterial strains of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in a higher abundance of the bacterial strains of the pharmaceutical composition in the microbiome of the subject as compared to the administration of a single dose of the pharmaceutical composition. In some embodiments, the disclosure provides methods comprising the administration of a pharmaceutical composition provided herein, wherein the administration of multiple doses of the pharmaceutical composition results in higher abundance of the bacterial strains of the pharmaceutical composition in the microbiome of the subject compared to the administration of a single dose of the pharmaceutical composition.

In some embodiments, administration of an antibiotic (e.g., vancomycin) followed by the administration of multiple doses of the pharmaceutical composition results in a greater number (amount) of subjects having all of the bacterial strains of the pharmaceutical composition present in their microbiome as compared to the administration of a single dose of the pharmaceutical composition. In some embodiments, the disclosure provides methods comprising the administration of a pharmaceutical composition provided herein, wherein the administration of multiple doses of the pharmaceutical results in a greater number (amount) of subject having all of the bacterial strains of the pharmaceutical composition in their microbiome as compared to the administration of a single dose of the pharmaceutical composition.

In some embodiments, administration of an antibiotic (e.g., vancomycin) followed by the administration of multiple doses of the pharmaceutical composition results in an accelerated recovery of the microbiome (e.g., increase in bacterial species of Bacteroidetes and/or Firmicutes, and/or decrease in Proteobacteria) as compared to the administration of a single dose of the pharmaceutical composition. In some embodiments, the disclosure provides methods comprising the administration of a pharmaceutical composition provided herein, wherein the administration of multiple doses of the pharmaceutical results in an accelerated recovery of the microbiome (e.g., increase in bacterial species of Bacteroidetes and/or Firmicutes, and/or decrease in Proteobacteria) as compared the administration of a single dose of the pharmaceutical composition.

In some embodiments, administration of an antibiotic (e.g., vancomycin) followed by the administration of a single dose or multiple doses of the pharmaceutical composition results in an accelerated recovery of the microbiome (e.g., increase in bacterial species of Bacteroidetes and/or Firmicutes, and/or decrease in Proteobacteria) as compared to the administration of an antibiotic (e.g., vancomycin) without the administration of a pharmaceutical composition.

In some embodiments, any of the methods described herein may further comprise administering a composition comprising taurine to the subject. In some embodiments, the composition comprising taurine is administered concomitantly with any of the pharmaceutical compositions comprising a purified bacterial mixture described herein. In some embodiments, the composition comprising taurine is administered prior to administration of any of the pharmaceutical compositions comprising a purified bacterial mixture described herein. In some embodiments, the composition comprising taurine is administered after administration of any of the pharmaceutical compositions comprising a purified bacterial mixture described herein. In some embodiments, the composition comprising taurine is administered prior to and after administration of any of the pharmaceutical compositions comprising a purified bacterial mixture described herein.

Taurine, also referred to as 2-aminoethanesulfonic acid, is an organic compound that is widely distributed in animal tissues and is a major constituent of bile and can be found conjugated to bile acids. Taurine may account for up to 0.1% of total human body weight and can be found in the large intestine, among other locations. The precise function of taurine in the physiological processes is not known, but without wishing to be bound by any particular theory, it is thought that taurine may help support muscle maintenance.

Taurine occurs naturally in fish and meat, and consumption in humans generally varies between 40 and 400 mg per day. However, in recent years, energy drinks for human consumption have included taurine. One example energy drink, marketed under the trademark Red Bull®, contains approximately 1000 mg of taurine per can (serving). High consumption of taurine is generally considered to be safe with no adverse effects noted from up to 3000 mg taurine per day.

Taurine administration has been found to alter the composition of mouse gut microbiota. It has recently been reported that infection may induce host taurine production and the expansion of taurine utilizers. Upon release of bile acids from the gallbladder into the gut, bacteria present in the gut may cleave taurine from bile acids, making the taurine available for use as an energy source. Bacteria, for example of the class Deltaproteobacteria, such as *Biophila wadsworthia*, utilize taurine in anaerobic respiration, and the expansion of Deltaproteobacteria following taurine administration is thought to aid in inhibiting intestinal colonization by *Klebsiella pneumoniae* and *Citrobacter rodentium*, a mouse model of pathogenic *E. coli*. Sec, e.g., Stacy et al. *Cell.* 2021 184(3):615-627.

As a result, gut microbiota from previously infected hosts were found to display enhanced resistance to infection. The microbiota from previously infected hosts has been associated with altered bile acid metabolism leading to the expansion of taxa that utilize the sulfonic acid, taurine. Indeed, it was reported that supplying exogenous taurine alone was sufficient to induce this alteration in microbiota function and enhance resistance. Mechanistically, taurine potentiates the microbiota's production of sulfide, an inhibitor of cellular respiration, which is key to host invasion by numerous pathogens. Sec, e.g., Stacy et al. *Cell.* 2021 184(3):615-627.

Without wishing to be bound by any particular theory, it is thought that administration of taurine may promote replication and/or aid engraftment of the bacterial strain(s) of the pharmaceutical compositions described herein, for example by serving as an energy source for bacteria present in the gastrointestinal tract or pharmaceutical composition.

In some embodiments, compositions comprising at least two of the strains selected from the group consisting of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Erysipelatoclostridium ramosum, Clostridium_M citroniae, Clostridium_M clostridioforme, Eubacterium_E hallii, Agathobacter rectale, Blautia producta, Blautia_*A *obeum, Dorea longicatena, Coprococcus_B comes, Anaerostipes caccae, Agathobaculum* sp, *Phascolarctobacterium faecium, Escherichia coli, Fusobacterium_A* sp, *Barnesiella intestinihominis, Blautia luti, Blautia faecis, Blautia wexlerae, Ruminococcus faecis, Clostridium bolteae, Butyricimonas synergistica, Bilophila wadsworthia, Akkermansia muciniphila, Parasuterella excrementinihominis*, and *Prevotella copri* in combination with taurine may be effective at inhibiting infection and/or reducing/preventing colonization with a pathogen that is more than additive of either taurine alone or the bacterial compositions alone.

As described herein, any of the bacterial compositions may further comprise taurine. In such embodiments, the bacterial strain and taurine are administered to the subject at the same time. In some embodiments, taurine is administered to the subject in a separate composition, such as a pharmaceutical composition or food product, including beverage product.

In some embodiments, the composition comprises between about 40 mg to about 3000 mg taurine. In some embodiments, the composition comprises between about 100 mg to about 2000 mg taurine. In some embodiments, the composition comprises between about 500 mg to about 1500 mg taurine.

In some embodiments, the compositions comprising bacterial strains also comprise taurine. In some embodiments, the composition comprises about 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, 1800 mg, 1900 mg, 2000 mg. 2100 mg, 2200 mg, 2300 mg, 2400 mg, 2500 mg, 2600 mg, 2700 mg, 2800 mg, 2900 mg, or 3000 mg taurine.

In some embodiments, the subject is administered between about 40 mg to about 3000 mg of taurine per day. In some embodiments, the subject is administered between about 100 mg to about 2000 mg taurine per day. In some embodiments, the subject is administered between about 500 mg to about 1500 mg taurine per day. Any of the daily amounts of taurine may be administered to the subject as a single dosage or as multiple dosages across the day.

In some embodiments, a composition comprising taurine is administered to the subject once, as a single dose. In some embodiments, the composition comprising taurine is administered to the subject in multiple doses. In some embodiments, the composition comprising taurine is administered to the subject in at least 2, 3, 4, 5, 6, 7, 8, 9, 10, 11, 12, 13, 14, 15 or more doses.

One or more doses of a composition comprising taurine may be administered to the subject prior to administering any of the pharmaceutical compositions containing purified bacterial strains described herein. In some embodiments, a composition comprising taurine is administered in multiple doses, such as on consecutive days (e.g., first dose on day 1, second dose of day 2, third dose on day 3, etc.) prior to administering any of the pharmaceutical compositions containing purified bacterial strains described herein. In some embodiments, a composition comprising taurine is administered to the subject for 2, 3, 4, 5, 6, 7, 8, 9, 10, 11, 12, 13, 14, 15, or more consecutive days prior to administering any of the pharmaceutical compositions containing purified bacterial strains described herein. In some embodiments, a composition comprising taurine is administered to the subject each day for three consecutive days prior to administering any of the pharmaceutical compositions containing purified bacterial strains described herein. In some embodiments, the composition comprising taurine is administered to the subject each day for five consecutive days prior to administering any of the pharmaceutical compositions containing purified bacterial strains described herein. In some embodiments, a composition comprising taurine is administered to the subject each day for seven consecutive days prior to administering any of the pharmaceutical compositions containing purified bacterial strains described herein. In some embodiments, a composition comprising taurine is administered to the subject for one day prior to administering any of the pharmaceutical compositions containing purified bacterial strains described herein.

One or more doses of a composition comprising taurine may be administered to the subject after administering any of the pharmaceutical compositions containing purified bacterial strains described herein. In some embodiments, a composition comprising taurine is administered in multiple doses, such as on consecutive days (e.g., first dose on day 1, second dose of day 2, third dose on day 3, etc.) after administering any of the pharmaceutical compositions containing purified bacterial strains described herein. In some embodiments, a composition comprising taurine is administered to the subject for 2, 3, 4, 5, 6, 7, 8, 9, 10, 11, 12, 13, 14, 15, or more consecutive days after administering any of the pharmaceutical compositions containing purified bacterial strains described herein. In some embodiments, a composition comprising taurine is administered to the subject each day for three consecutive days after administering any of the pharmaceutical compositions containing purified bacterial strains described herein. In some embodiments, the composition comprising taurine is administered to the subject each day for five consecutive days after administering any of the pharmaceutical compositions containing purified bacterial strains described herein. In some embodiments, a composition comprising taurine is administered to the subject each day for seven consecutive days after administering any of the pharmaceutical compositions containing purified bacterial strains described herein. In some embodiments, a composition comprising taurine is administered to the subject for one day after administering any of the pharmaceutical compositions containing purified bacterial strains described herein.

In some embodiments, a composition comprising taurine is administered the same day as the administration of any of the pharmaceutical compositions containing purified bacterial strains described herein. In some embodiments, a composition comprising taurine is administered at the same time (simultaneously) or substantially at the same time as the administration of any of the pharmaceutical compositions containing purified bacterial strains described herein. In some embodiments, a composition comprising taurine is administered within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours of the administration of any of the pharmaceutical compositions containing purified bacterial strains described herein.

The composition comprising taurine may in any form for human administration, such as a food product/beverage, capsule, pill, tablet, or liquid composition.

In some embodiments, the methods described herein may involve subjecting the subject to a bowel lavage (bowel irrigation, whole bowel irrigation, gastrointestinal lavage, gastric lavage) prior to administration of the compositions described herein. In some embodiments, a bowel lavage may remove or aid in removing microbiota from the gastrointestinal tract of the subject, creating a niche for the bacterial strains of the compositions described herein. In some embodiments, the bowel lavage may be an oral bowel lavage or a rectal bowel lavage.

Methods of performing a bowel lavage are known in the art, and generally involve the rapid administration of large volumes of a solution, such as polyethylene glycol or a balanced electrolyte solution. A rectal bowel lavage can involve the administration of a solution or a suppository containing the pharmaceutical composition. A bowel lavage may be performed under doctor supervision, hospitalization, or at home.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. Sec, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

In some embodiments, one or more of the bacterial strains of the compositions, including pharmaceutical compositions and food products, has been spray-dried. In some embodiments, a subset of the bacterial strains is spray-dried. The process of spray-drying refers to production of dry powder from a liquid comprising bacterial compositions (Sec, e.g., Ledet, et al., Spray Draying of Pharmaceuticals in "*Lyophilized Biologics and Vaccines*" pages 273-294, Springer). In general, the process involves rapidly drying the bacterial compositions with a hot gas. A bacterial strain may be combined with a pharmaceutical excipient prior to combining it with the other bacterial strains or multiple spray-dried bacterial strains may be combined while in spray-dried form and the mixture of bacterial strains, once combined, may be subsequently combined with a pharmaceutical excipient.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions disclosed herein can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like. In some embodiments, the pharmaceutical compositions can be used by injection, such as by intravenous, intramuscular, subcutaneous, or intradermal administration.

Aspects of the present disclosure relate to administration of compositions comprising taurine. In some embodiments, a composition comprising any of the purified bacterial strains described herein may further comprise taurine. In such embodiments, administration of the composition results in administration to the subject of both the purified bacterial strains and taurine. In some embodiments, a composition comprising any of the purified bacterial strains described herein does not contain taurine. In some embodiments, a composition that is not the composition comprising the purified bacterial strains comprises taurine. In some embodiments, the methods involve administering to a subject a composition comprising purified bacterial strains and administering to the subject a second composition comprising taurine.

In some embodiments, the compositions comprising bacterial strains are formulated for delivery to the intestines (e.g., the small intestine and/or the colon). In some embodiments, the compositions comprising bacterial strains are formulated with an enteric coating that increases the survival of the bacteria through the harsh environment in the stomach. The enteric coating is one which resists the action of gastric juices in the stomach so that the bacteria of the composition therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, *AAPS PharmSciTech* (2016) 17(1): 56-67).

The compositions comprising bacterial strains may also be formulated for rectal delivery to the intestine (e.g., the colon). Thus, in some embodiments, compositions comprising bacterial strains may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., *Int J Pharm* (2015) 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect) . In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions disclosed herein can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect is achieved. In general, effective doses of the compositions, for the prophylactic or therapeutic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times. In some embodiments, any of the compositions described herein are administered the subject in multiple doses at a regular interval, such as every 2 weeks, every month, every 2 months, every 3 months, every 4 months, every 5 months, every 6 months, or more.

The compositions, including the pharmaceutical compositions disclosed herein, include compositions that contain selected bacterial strains. The amount of bacteria, including the amount of bacteria cells of each of the bacterial strains, in the compositions, including pharmaceutical compositions, may be expressed in weight, number of bacteria and/or CFUs (colony forming units). In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacterial strains per dosage amount. In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacterial cells per dosage amount. It should further be appreciated that bacteria of each of the bacterial strains may be present in different amounts. Thus, for instance, as a non-limiting example, composition may include $10^3$ of bacteria A, $10^4$ of bacteria B and $10^6$ of bacteria C. In some embodiments, compositions, including pharmaceutical composition, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more bacterial cells or CFUs of each of the bacterial strains per dosage amount. In some embodiments, compositions, including pharmaceutical compositions, comprise about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more bacterial cells or CFUs in total for all of the bacterial strains combined per dosage amount. As discussed above, bacteria of each of the bacterial strains may be present in different amounts. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria (bacterial cells or CFU) of each of the bacterial strains in the composition per dosage amount. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria (bacterial cells or CFU) in total for all of the bacterial strains combined per dosage amount.

In some embodiments, the dosage amount is one administration device (e.g., one table, pill or capsule). In some embodiments, the dosage amount is the amount administered at one time, which may be in the form of more than one administration device (e.g., more than one table, pill or capsule). In some embodiment, the dosage amount is the amount that is administered in a particular period (e.g., one day or one week).

As described herein, any of the pharmaceutical compositions described herein may be administered once, as a single dose. In some embodiments, the pharmaceutical compositions described herein are administered in multiple doses. In some embodiments, each dose is administered in the form of one or more capsules. In some embodiments, each dose comprises administration of multiple capsules. In some embodiments, each dose is administered in the form of 1, 2, 3, 4, 5, 6, 7, 8, 9, 10, 11, 12, 13, 14, 15, or more capsules.

In some embodiments, each capsule contains between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ bacterial cells or CFU of each of the bacterial strains per capsule.

In some embodiments, each capsule contains between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacterial cells or CFU per capsule. In some embodiments, each capsule contains between $10^7$ and $10^9$, between $10^7$ and $10^8$, or between $10^8$ and $10^9$ total bacteria. In some embodiments, each capsule contains about $1.0 \times 10^7$, $2.0 \times 10^7$, $3.0 \times 10^7$, $4.0 \times 10^7$, $5.0 \times 10^7$, $6.0 \times 10^7$, $7.0 \times 10^7$, $8.0 \times 10^7$, $9.0 \times 10^7$, $1.0 \times 10^8$, $2.0 \times 10^8$, $3.0 \times 10^8$, $4.0 \times 10^8$, $5.0 \times 10^8$, $6.0 \times 10^8$, $7.0 \times 10^8$, $8.0 \times 10^8$, $9.0 \times 10^8$, $1.0 \times 10^9$, $1.1 \times 10^9$, $1.2 \times 10^9$, $1.3 \times 10^9$, $1.4 \times 10^9$, $1.5 \times 10^9$, $1.6 \times 10^9$, $1.7 \times 10^9$, $1.8 \times 10^9$, $1.9 \times 10^9$, $2.0 \times 10^9$, $2.1 \times 10^9$, $2.2 \times 10^9$, $2.3 \times 10^9$, $2.4 \times 10^9$, $2.5 \times 10^9$, $2.6 \times 10^9$, $2.7 \times 10^9$, $2.8 \times 10^9$, $2.9 \times 10^9$, $3.0 \times 10^9$, $3.1 \times 10^9$, $3.2 \times 10^9$, $3.3 \times 10^9$, $3.4 \times 10^9$, $3.5 \times 10^9$, $3.6 \times 10^9$, $3.7 \times 10^9$, $3.8 \times 10^9$, $3.9 \times 10^9$, $4.0 \times 10^9$, $4.1 \times 10^9$, $4.2 \times 10^9$, $4.3 \times 10^9$, $4.4 \times 10^9$, $4.5 \times 10^9$, $4.6 \times 10^9$, $4.7 \times 10^9$, $4.8 \times 10^9$, $4.9 \times 10^9$, $5.0 \times 10^9$ total bacterial cells or CFU.

In some embodiments, each capsule contains between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ bacterial cells or CFU of each bacterial strain per capsule.

In some embodiments, the pharmaceutical compositions contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ bacterial cells or CFUs of each of the bacterial strains per dosage amount. In some embodiments, the pharmaceutical compositions contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacterial cells or CFUs per dosage amount.

In some embodiments, the compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacteria or colony forming units per milliliter.

In some embodiments, the compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ bacterial cells or colony forming units of bacteria. In some embodiments, the compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ bacterial cells or colony forming units of bacteria per milliliter.

In some embodiments, a composition that includes more than one bacterial strain may contain each bacterial strain in the same quantities, in terms of bacterial cells or CFUs. For example, a composition of the invention comprising *Collinsella aerofaciens* and *Bifidobacterium longum* may comprise $1\times10^8$ CFU of *Collinsella aerofaciens* and $1\times10^8$ CFU of *Bifidobacterium longum* per milliliter or may comprise $1\times10^8$ *Collinsella aerofaciens* cells and $1\times10^8$ *Bifidobacterium longum* cells per milliliter.

In some embodiments, the pharmaceutical composition comprises at least $1.6\times10^9$ total CFUs. In some embodiments, the pharmaceutical composition comprises at least $1.6\times10^9$ total CFUs and is administered as a single dose. In some embodiments, the pharmaceutical composition comprises at least $1.6\times10^9$ total CFUs and is administered as multiple (e.g., 2, 3, 4, 5, or more) doses. In some embodiments, the pharmaceutical composition comprises at least $1.6\times10^9$ total CFUs and is administered as two, three, four, five, six, seven, eight, nine, ten, eleven, twelve, thirteen, fourteen, fifteen or more doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $4.0\times10^9$ total CFUs. In some embodiments, the pharmaceutical composition comprises at least $4.0\times10^9$ total CFUs and is administered as a single dose. In some embodiments, the pharmaceutical composition comprises at least $4.0\times10^9$ total CFUs and is administered as multiple (e.g., 2, 3, 4, 5, or more) doses. In some embodiments, the pharmaceutical composition comprises at least $4.0\times10^{10}$ total CFUs and is administered as two, three, four, five, six, seven, eight, nine, ten, eleven, twelve, thirteen, fourteen, fifteen or more doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $8.0\times10^9$ total CFUs. In some embodiments, the pharmaceutical composition comprises at least $8.0\times10^9$ total CFUs and is administered as a single dose. In some embodiments, the pharmaceutical composition comprises at least $8.0\times10^9$ total CFUs and is administered as multiple (e.g., 2, 3, 4, 5, or more) doses. In some embodiments, the pharmaceutical composition comprises at least $8.0\times10^9$ total CFUs and is administered as two, three, four, five, six, seven, eight, nine, ten, eleven, twelve, thirteen, fourteen, fifteen or more doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $2.8\times10^{10}$ total CFUs. In some embodiments, the pharmaceutical composition comprises at least $2.8\times10^{10}$ total CFUs and is administered as a single dose. In some embodiments, the pharmaceutical composition comprises at least $2.8\times10^{10}$ total CFUs and is administered as multiple (e.g., 2, 3, 4, 5, or more) doses. In some embodiments, the pharmaceutical composition comprises at least $2.8\times10^{10}$ total CFUs and is administered as two, three, four, five, six, seven, eight, nine, ten, eleven, twelve, thirteen, fourteen, fifteen or more doses. In some embodiments, the pharmaceutical composition comprises at least $2.8\times10^{10}$ total CFUs and is administered as seven doses. In some embodiments, each of the multiple doses are administered at regular intervals. In some embodiments, each of the multiple doses are on consecutive days (e.g., first dose on day 1, second dose of day 2, third dose on day 3, etc.).

In some embodiments, the pharmaceutical composition comprises at least $4.0\times10^{10}$ total CFUs. In some embodiments, the pharmaceutical composition comprises at least $4.0\times10^{10}$ total CFUs and is administered as a single dose. In some embodiments, the pharmaceutical composition comprises at least $4.0\times10^{10}$ total CFUs and is administered as multiple (e.g., 2, 3, 4, 5, or more) doses. In some embodiments, the pharmaceutical composition comprises at least $4.0\times10^{10}$ total CFUs and is administered as two, three, four, five, six, seven, eight, nine, ten, eleven, twelve, thirteen, fourteen, fifteen or more doses. In some embodiments, the pharmaceutical composition comprises at least $4.0\times10^{10}$ total CFUs and is administered as five doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least $4.0\times10^{10}$ total CFUs and is administered as five doses, each of which are administered on five consecutive days.

In some embodiments, the pharmaceutical composition comprises at least $5.6\times10^{10}$ total CFUs. In some embodiments, the pharmaceutical composition comprises at least $5.6\times10^{10}$ total CFUs and is administered as a single dose. In some embodiments, the pharmaceutical composition comprises at least $5.6\times10^{10}$ total CFUs and is administered as multiple (e.g., 2, 3, 4, 5, or more) doses. In some embodiments, the pharmaceutical composition comprises at least $5.6\times10^{10}$ total CFUs and is administered as two, three, four, five, six, seven, eight, nine, ten, eleven, twelve, thirteen, fourteen, fifteen or more doses. In some embodiments, the pharmaceutical composition comprises at least $5.6\times10^{10}$ total CFUs and is administered as fourteen doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least $5.6\times10^{10}$ total CFUs and is administered as fourteen doses, each of which are administered on fourteen consecutive days.

In some embodiments, the pharmaceutical composition comprises at least $1.1\times10^{11}$ total CFUs. In some embodiments, the pharmaceutical composition comprises at least $1.1\times10^{11}$ total CFUs and is administered as a single dose. In some embodiments, the pharmaceutical composition comprises at least $1.1\times10^{11}$ total CFUs and is administered as multiple (e.g., 2, 3, 4, 5, or more) doses. In some embodiments, the pharmaceutical composition comprises at least $1.1\times10^{11}$ total CFUs and is administered as two, three, four, five, six, seven, eight, nine, ten, eleven, twelve, thirteen, fourteen, fifteen or more doses. In some embodiments, the pharmaceutical composition comprises at least $1.1\times10^{11}$ total CFUs and is administered as fourteen doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least $1.1\times10^{11}$ total CFUs and is administered as fourteen doses, each of which are administered on fourteen consecutive days.

In some embodiments, the pharmaceutical composition comprises at least $2.1\times10^{10}$ total CFUs. In some embodiments, the pharmaceutical composition comprises at least $2.1\times10^{10}$ total CFUs and is administered as a single dose. In some embodiments, the pharmaceutical composition comprises at least $2.1\times10^{10}$ total CFUs and is administered as multiple (e.g., 2, 3, 4, 5, or more) doses. In some embodiments, the pharmaceutical composition comprises at least $2.1\times10^{10}$ total CFUs and is administered as two, three, four, five, six, seven, eight, nine, ten, eleven, twelve, thirteen, fourteen, fifteen or more doses. In some embodiments, the pharmaceutical composition comprises at least $2.1\times10^{10}$ total CFUs and is administered as five doses. In some embodiments, each of the multiple doses are administered at regular intervals. In some embodiments, each of the multiple doses are on consecutive days (e.g., first dose on day 1, second dose of day 2, third dose on day 3, etc.). In some embodiments, the pharmaceutical composition comprises at least $2.1\times10^{10}$ total CFUs and is administered as five doses, each of which are administered on five consecutive days.

As described herein, any of the pharmaceutical compositions described herein may be administered to a subject in one dose or in multiple doses (e.g., initial administration), which may be followed by one or more additional doses of any of the pharmaceutical compositions described herein. In some embodiments, any of pharmaceutical composition described herein may be administered to a subject in one dose or in multiple doses in an initial administration, followed by one or more additional doses of a pharmaceutical composition comprising the same one or more bacterial strains as the pharmaceutical composition of the initial administration. In some embodiments, any of pharmaceutical composition described herein may be administered to a subject in one dose or in multiple doses in an initial administration, followed by one or more additional doses of a pharmaceutical composition comprising more total bacteria (colony-forming units) relative to the initial administration of the pharmaceutical composition. In some embodiments, any of pharmaceutical composition described herein may be administered to a subject in one dose or in multiple doses in an initial administration, followed by one or more additional doses of a pharmaceutical composition comprising fewer total bacteria (colony-forming units) relative to the initial administration of the pharmaceutical composition. In some embodiments, the initial administration includes at least 1, 2, 3, 4, 5, 6, 7, 8, 9, 10, 11, 12, 13, 14, 15 or more doses of any of the pharmaceutical compositions described herein. In some embodiments, the additional administration includes at least 1, 2, 3, 4, 5, 6, 7, 8, 9, 10, 11, 12, 13, 14, 15 or more doses of any of the pharmaceutical compositions described herein. In some embodiments, the initial administration comprises two doses of any of the pharmaceutical composition and the additional administration comprises three doses of any of the pharmaceutical compositions described herein.

In some embodiments, any of pharmaceutical composition described herein may be administered to a subject in one dose or in multiple doses in an initial administration, followed by one or more additional doses of a pharmaceutical composition comprising fewer total bacteria (colony-forming units) relative to the initial administration of the pharmaceutical composition. In such embodiments, the dose(s) of the initial administration may be referred to as a "high dose" and the dose(s) of the additional administration may be referred to as a "low dose. In some embodiments, the high dose is at least 1.1-fold, 1.2-fold, 1.3-fold, 1.4-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold or more higher than the low dose. In some embodiments, the high dose is $8.0\times10^9$ CFUs. In some embodiments, the low dose is $1.6\times10^9$ CFUs. In some embodiments, the initial administration comprises multiple doses (e.g., 2, 3, 4, 5 or more) of $8.0\times10^9$ CFUs and the additional administration comprises multiple doses (e.g., 2, 3, 4, 5 or more) of $1.6\times10^9$ CFUs. In some embodiments, the low dose is $1.6\times10^9$ CFUs. In some embodiments, the initial administration comprises two doses of $8.0\times10^9$ CFUs and the additional administration comprises three doses of $1.6\times10^9$ CFUs.

In some embodiments, the one or more additional administrations is performed on the day following the initial administration (e.g., consecutive days). In some embodiments, the one or more additional administrations is performed at least 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks or longer following the initial administration. In some embodiments, the one or more additional administrations is performed at least 6 weeks after the initial administration. In some embodiments, the one or more additional administrations is performed at least 12 weeks after the initial administration.

In some embodiments, the compositions, including pharmaceutical compositions, contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^{9}$ and $10^{11}$, between $10^{10}$ and $10^{11}$, between 10 and $10^{10}$, between $10^{2}$ and $10^{10}$, between $10^{3}$ and $10^{10}$, between $10^{4}$ and $10^{10}$, between $10^{5}$ and $10^{10}$, between $10^{6}$ and $10^{10}$, between $10^{7}$ and $10^{10}$, between $10^{8}$ and $10^{10}$, between $10^{9}$ and $10^{10}$, between 10 and $10^{9}$, between $10^{2}$ and $10^{9}$, between $10^{3}$ and $10^{9}$, between $10^{4}$ and $10^{9}$, between $10^{5}$ and $10^{9}$, between $10^{6}$ and $10^{9}$, between $10^{7}$ and $10^{9}$, between $10^{8}$ and $10^{9}$, between 10 and $10^{8}$, between $10^{2}$ and $10^{8}$, between $10^{3}$ and $10^{8}$, between $10^{4}$ and $10^{8}$, between $10^{5}$ and $10^{8}$, between $10^{6}$ and $10^{8}$, between $10^{7}$ and $10^{8}$, between 10 and $10^{7}$, between $10^{2}$ and $10^{7}$, between $10^{3}$ and $10^{7}$, between $10^{4}$ and $10^{7}$, between $10^{5}$ and $10^{7}$, between $10^{6}$ and $10^{7}$, between 10 and $10^{6}$, between $10^{2}$ and $10^{6}$, between $10^{3}$ and $10^{6}$, between $10^{4}$ and $10^{6}$, between $10^{5}$ and $10^{6}$, between 10 and $10^{5}$, between $10^{2}$ and $10^{5}$, between $10^{3}$ and $10^{5}$, between $10^{4}$ and $10^{5}$, between 10 and $10^{4}$, between $10^{2}$ and $10^{4}$, between $10^{3}$ and $10^{4}$, between 10 and $10^{3}$, between $10^{2}$ and $10^{3}$, or between 10 and $10^{2}$ bacterial cells or CFUs of each of the bacterial strains per dosage amount. In some embodiments, the compositions, including pharmaceutical compositions contain between 10 and $10^{13}$, between $10^{2}$ and $10^{13}$, between $10^{3}$ and $10^{13}$, between $10^{4}$ and $10^{13}$, between $10^{5}$ and $10^{13}$, between $10^{6}$ and $10^{13}$, between $10^{7}$ and $10^{13}$, between $10^{8}$ and $10^{13}$, between $10^{9}$ and $10^{13}$, between $10^{10}$ and $10^{13}$, between $10^{11}$ and $10^{13}$, between $10^{12}$ and $10^{13}$, between 10 and $10^{12}$, between $10^{2}$ and $10^{12}$, between $10^{3}$ and $10^{12}$, between $10^{4}$ and $10^{12}$, between $10^{5}$ and $10^{12}$, between $10^{6}$ and $10^{12}$, between $10^{7}$ and $10^{12}$, between $10^{8}$ and $10^{12}$, between $10^{9}$ and $10^{12}$, between $10^{10}$ and $10^{12}$, between $10^{11}$ and $10^{12}$, between 10 and $10^{11}$, between $10^{2}$ and $10^{11}$, between $10^{3}$ and $10^{13}$, between $10^{4}$ and $10^{13}$, between $10^{5}$ and $10^{13}$, between $10^{6}$ and $10^{13}$, between $10^{7}$ and $10^{11}$, between $10^{8}$ and $10^{11}$, between $10^{9}$ and $10^{11}$, between $10^{10}$ and $10^{11}$, between 10 and $10^{10}$, between $10^{2}$ and $10^{10}$, between $10^{3}$ and $10^{10}$, between $10^{4}$ and $10^{10}$, between $10^{5}$ and $10^{10}$, between $10^{6}$ and $10^{10}$, between $10^{7}$ and $10^{10}$, between $10^{8}$ and $10^{10}$, between $10^{9}$ and $10^{10}$, between 10 and $10^{9}$, between $10^{2}$ and $10^{9}$, between $10^{3}$ and $10^{9}$, between $10^{4}$ and $10^{9}$, between $10^{5}$ and $10^{9}$, between $10^{6}$ and $10^{9}$, between $10^{7}$ and $10^{9}$, between $10^{8}$ and $10^{9}$, between 10 and $10^{8}$, between $10^{2}$ and $10^{8}$, between $10^{3}$ and $10^{8}$, between $10^{4}$ and $10^{8}$, between $10^{5}$ and $10^{8}$, between $10^{6}$ and $10^{8}$, between $10^{7}$ and $10^{8}$, between 10 and $10^{7}$, between $10^{2}$ and $10^{7}$, between $10^{3}$ and $10^{7}$, between $10^{4}$ and $10^{7}$, between $10^{5}$ and $10^{7}$, between $10^{6}$ and $10^{7}$, between 10 and $10^{6}$, between $10^{2}$ and $10^{6}$, between $10^{3}$ and $10^{6}$, between $10^{4}$ and $10^{6}$, between $10^{5}$ and $10^{6}$, between 10 and $10^{5}$, between $10^{2}$ and $10^{5}$, between $10^{3}$ and $10^{5}$, between $10^{4}$ and $10^{5}$, between 10 and $10^{4}$, between $10^{2}$ and $10^{4}$, between $10^{3}$ and $10^{4}$, between 10 and $10^{3}$, between $10^{2}$ and $10^{3}$, or between 10 and $10^{2}$ total bacterial cells or CFUs per dosage amount.

In some embodiments, the compositions, including pharmaceutical compositions, contain between $10^{-7}$ and $10^{-1}$, between $10^{-6}$ and $10^{-1}$, between $10^{5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{5}$, or between $10^{-7}$ and $10^{6}$ grams of bacteria of each of the bacterial strains in the composition per dosage amount. In some embodiments, the compositions, including pharmaceutical compositions, disclosed herein contain between $10^{-7}$ and $10^{-1}$, between $10^{-6}$ and $10^{-1}$, between $10^{5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{6}$ and $10^{-3}$, between $10^{-5}$ and $10^{-3}$, between $10^{-4}$ and $10^{-3}$, between $10^{-7}$ and $10^{-4}$, between $10^{6}$ and $10^{4}$, between $10^{-5}$ and $10^{4}$, between $10^{-7}$ and $10^{5}$, between $10^{-6}$ and $10^{5}$, or between $10^{-7}$ and $10^{-6}$ grams of all of the bacteria combined (total) per dosage amount.

Aspects of the present disclosure also provide food products comprising any of the compositions described herein and a nutrient. Also with the scope of the present disclosure are food products comprising any of the bacterial strains described herein and a nutrient. In some embodiments, the food product may further comprise taurine. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed.

Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a readyto-eat product, a nutritional formula, such as a nutritional supplementary formulation, a food or beverage additive.

TABLE 1

Examples of bacterial species of the bacterial strains disclosed herein

| 47-mix (Closely related species based on 16S sequence) | Additional closely related species | SEQ ID NO: | Strain |
|---|---|---|---|
| *Collinsella aerofaciens*_F | *Collinsella aerofaciens* | 1 | 1 |
| *Bacteroides xylanisolvens* | | 2 | 2 |
| *Alistipes putredinis* | | 3 | 3 |
| *Alistipes shahii* | | 4 | 4 |
| *Eubacterium*_E *hallii* | *Eubacterium hallii* | 5 | 5 |
| *Blautia*_A *obeum* | *Blautia obeum* | 6 | 6 |
| *Odoribacter splanchnicus* | | 7 | 7 |
| *Bacteroides cellulosilyticus* | | 8 | 8 |
| *Bacteroides uniformis* | | 9 | 9 |
| *Bacteroides*_B *vulgatus* | *Bacteroides vulgatus* | 10 | 10 |
| *Bacteroides fragilis* | | 11 | 11 |
| *Bacteroides caccae* | | 12 | 12 |
| *Paeniclostridium sordellii* | *Clostridium sordellii* | 13 | 13 |
| *Blautia producta* | | 14 | 14 |
| *Absiella innocuum* | *Erysipelotrichaceae bacterium* | 15 | 15 |
| *Clostridium*_M *clostridioforme* | *Clostridium clostridioforme* | 16 | 16 |
| *Paraclostridium massiliensis* | *Clostridium bifermentans* | 17 | 17 |
| *Dorea longicatena B* | *Dorea longicatena* | 18 | 18 |
| *Bacteroides thetaiotaomicron* | | 19 | 19 |
| *Parabacteroides distasonis* | | 20 | 20 |
| *Escherichia coli* | | 21 | 21 |
| *Bifidobacterium longum* | | 22 | 22 |
| *Absiella innocuum* | *Clostridium innoccum* | 23 | 23 |
| *Fusobacterium*_A sp | *Fusobacterium mortiferum* | 24 | 24 |
| *Parabacteroides merdae* | | 25 | 25 |

TABLE 1-continued

Examples of bacterial species of the bacterial strains disclosed herein

| 47-mix (Closely related species based on 16S sequence) | Additional closely related species | SEQ ID NO: | Strain |
|---|---|---|---|
| *Coprococcus*_B *comes* | *Coprococcus comes* | 26 | 26 |
| *Agathobacter rectale* | *Eubacterium rectale* | 27 | 27 |
| *Erysipelatoclostridium ramosum* | | 28 | 28 |
| *Clostridium*_*M citroniae* | *Clostridium citroniae* | 29 | 29 |
| *Bacteroides faecis* | | 30 | 30 |
| *Bacteroides ovatus* | | 31 | 31 |
| *Bifidobacterium pseudocatenulatum* | | 32 | 32 |
| *Bacteroides caccae* | | 33 | 33 |
| *Bifidobacterium adolescentis* | | 34 | 34 |
| *Agathobaculum* sp MUR_P3C8a | *Agathobaculum* sp, *Agathobaculum butyriciproducens* | 35 | 35 |
| *Phascolarctobacterium faecium* MUR_P6E9 | *Phascolarctobacterium faecium* | 36 | 36 |
| *Akkermansia muciniphila* | | 37 | 37 |
| *Barnesiella intestinihominis* | | 38 | 38 |
| *Bilophila wadsworthia* | | 39 | 39 |
| *Blautia faecis* | | 40 | 40 |
| *Blautia wexlerae* | | 41 | 41 |
| *Blautia luti* | | 42 | 42 |
| *Butyricimonas synergistica* | | 43 | 43 |
| *Clostridium bolteae* | | 44 | 44 |
| *Parasutterella excrementihominis* | | 45 | 45 |
| *Prevotella copri* | | 46 | 46 |
| *Ruminococcus faecis* | | 47 | 47 |

SEQUENCES

SEQ ID NO: 1 *Collinsella aerofaciens*_F Strain 1
AGAGTTCGATCCTGGCTCAGGATGAACGCTGGCGGCGCGCCTAACACATGCAAGT
CGAACGGCACCCCTCTCCGGAGGGAAGCGAGTGGCGAACGGCTGAGTAACACGTG
GAGAACCTGCCCCCTCCCCCGGGATAGCCGCCCGAAAGGACGGGTAATACCGGAT
ACCCCGGGGTGCCGCATGGCACCCCGGCTAAAGCCCCGACGGGAGGGGATGGCT
CCGCGGCCCATCAGGTAGACGGCGGGGTGACGGCCCACCGTGCCGACAACGGGT
AGCCGGGTTGAGAGACCGACCGGCCAGATTGGGACTGAGACACGGCCCAGACTCC
TACGGGAGGCAGCAGTGGGGAATCTTGCGCAATGGGGGGAACCCTGACGCAGCGA
CGCCGCGTGCGGGACGGAGGCCTTCGGGTCGTAAACCGCTTTCAGCAGGGAAGAG
TCAAGACTGTACCTGCAGAAGAAGCCCCGGCTAACTACGTGCCAGCAGCCGCGGT
AATACGTAGGGGGCGAGCGTTATCCGGATTCATTGGGCGTAAAGCGCGCGTAGGC
GGCCCGGCAGGCCGGGGGTCGAAGCGGGGGGCTCAACCCCCCGAAGCCCCCGGA
ACCTCCGCGGCTTGGGTCCGGTAGGGGAGGGTGGAACACCCGGTGTAGCGGTGG
AATGCGCAGATATCGGGTGGAACACCGGTGGCGAAGGCGGCCCTCTGGGCCGAGA
CCGACGCTGAGGCGCGAAAGCTGGGGGAGCGAACAGGATTAGATACCCTGGTAGT
CCCAGCCGTAAACGATGGACGCTAGGTGTGGGGGGACGATCCCCCCGTGCCGCAG
CCAACGCATTAAGCGTCCCGCCTGGGGAGTACGGCCGCAAGGCTAAAACTCAAAG
GAATTGACGGGGGCCCGCACAAGCAGCGGAGCATGTGGCTTAATTCGAAGCAACG
CGAAGAACCTTACCAGGGCTTGACATATGGGTGAAGCGGGGGAGACCCCGTGGCC
GAGAGGAGCCCATACAGGTGGTGCATGGCTGTCGTCAGCTCGTGTCGTGAGATGTT
GGGTTAAGTCCCGCAACGAGCGCAACCCCCGCCGCGTGTTGCCATCGGGTGATGC
CGGGAACCCACGCGGGACCGCCGCCGTCAAGGCGGAGGAGGGGGGGGACGACGT
CAAGTCATCATGCCCCTTATGCCCTGGGCTGCACACGTGCTACAATGGCCGGTACA
GAGGGATGCCACCCCGCGAGGGGGAGCGGATCCCGGAAAGCCGGCCCCAGTTCG
GATTGGGGGCTGCAACCCGCCCCCATGAAGTCGGAGTTGCTAGTAATCGCGGATC
AGCATGCCGCGGTGAATGCGTTCCCGGGCCTTGTACACACCGCCCGTCACACCAC
CCGAGTCGTCTGCACCCGAAGTCGCCGGCCCAACCGAGAGGGGGGAGGCGCCGA
AGGTGTGGAGGGTGAGGGGGGTGAAGTCGTAACAAGGTA SEQ ID NO: 2 *Bacteroides xylanisolvens* Strain 2
AGAGTTTGATCCTGGCTCAGGATGAACGCTAGCTACAGGCTTAACACATGCAAGTC
GAGGGGCAGCATTTTAGTTTGCTTGCAAACTAAAGATGGCGACCGGCGCACGGGTG
AGTAACACGTATCCAACCTGCCGATAACTCGGGGATAGCCTTTCGAAAGAAAGATTA
ATATCCGATAGTATATTAAAACCGCATGGTTTTACTATTAAAGAATTTCGGTTATCGA
TGGGGATGCGTTCCATTAGTTTGTTGGCGGGGTAACGGCCCACCAAGACTACGATG
GATAGGGGTTCTGAGAGGAAGGTCCCCCACATTGGAACTGAGACACGGTCCAAACT
CCTACGGGAGGCAGCAGTGAGGAATATTGGTCAATGGACGAGAGTCTGAACCAGC -continued

| SEQUENCES |
| --- |
| CAAGTAGCGTGAAGGATGACTGCCCTATGGGTTGTAAACTTCTTTTATATGGGAATA<br>AAGTATTCCACGTGTGGGATTTTGTATGTACCATATGAATAAGGATCGGCTAACTCC<br>GTGCCAGCAGCCGCGGTAATACGGAGGATCCGAGCGTTATCCGGATTTATTGGGTT<br>TAAAGGGAGCGTAGGTGGATTGTTAAGTCAGTTGTGAAAGTTTGCGGCTCAACCGT<br>AAAATTGCAGTTGAAACTGGCAGTCTTGAGTACAGTAGAGGTGGGCGGAATTCGTG<br>GTGTAGCGGTGAAATGCTTAGATATCACGAAGAACTCCGATTGCGAAGGCAGCTCA<br>CTAGACTGCAACTGACACTGATGCTCGAAAGTGTGGGTATCAAACAGGATTAGATA<br>CCCTGGTAGTCCACACAGTAAACGATGAATACTCGCTGTTTGCGATATACAGTAAGC<br>GGCCAAGCGAAAGCATTAAGTATTCCACCTGGGGAGTACGCCGGCAACGGTGAAA<br>CTCAAAGGAATTGACGGGGGCCCGCACAAGCGGAGGAACATGTGGTTTAATTCGAT<br>GATACGCGAGGAACCTTACCCGGGCTTAAATTGCATTTGAATAATCTGGAAACAGGT<br>TAGCCGCAAGGCAAATGTGAAGGTGCTGCATGGTTGTCGTCAGCTCGTGCCGTGAG<br>GTGTCGGCTTAAGTGCCATAACGAGCGCAACCCTTATCTTTAGTTACTAACAGGTTA<br>TGCTGAGGACTCTAGAGAGACTGCCGTCGTAAGATGTGAGGAAGGTGGGGATGAC<br>GTCAAATCAGCACGGCCCTTACGTCCGGGGCTACACACGTGTTACAATGGGGGGTA<br>CAGAAGGCAGCTACCTGGCGACAGGATGCTAATCCCAAAAACCTCTCTCAGTTCGG<br>ATCGAAGTCTGCAACCCGACTTCGTGAAGCTGGATTCGCTAGTAATCGCGCATCAG<br>CCATGGCGCGGTGAATACGTTCCCGGGCCTTGTACACACCGCCCGTCAAGCCATG<br>AAAGCCGGGGGTACCTGAAGTACGTAACCGCAAGGAGCGTCCTAGGGTAAAACTG<br>GTAATTGGGGCTAAGTCGTAACAAGGTAGCCGTACCGGAAGGTGCGGCTGGAACA<br>CCT |
| SEQ ID NO: 3 *Alistipes putredinis* Strain 3<br>AGAGTTTGATCCTGGCTCAGGATGAACGCTAGCGGCAGGCTTAACACATGCAAGTC<br>GAGGGGCAGCATAATGGATAGCAATATCTATGGTGGCGACCGGCGCACGGGTGCG<br>TAACGCGTATGCAACCTACCTTTAACAGGGGGATAACACTGAGAAATTGGTACTAAT<br>ACCCCATAATATCATAGAAGGCATCTTTTATGGTTGAAAATTCCGATGGTTAGAGAT<br>GGGCATGCGTTGTATTAGCTAGTTGGTGGGGTAACGGCTCACCAAGGCGACGATAC<br>ATAGGGGGACTGAGAGGTTAACCCCCCACACTGGTACTGAGACACGGACCAGACT<br>CCTACGGGAGGCAGCAGTGAGGAATATTGGTCAATGGACGCAAGTCTGAACCAGC<br>CATGCCGCGTGCAGGATGACGGCTCTATGAGTTGTAAACTGCTTTTGTACGAGGGT<br>AAACGCAGATACGTGTATCTGTCTGAAAGTATCGTACGAATAAGGATCGGCTAACTC<br>CGTGCCAGCAGCCGCGGTAATACGGAGGATTCAAGCGTTATCCGGATTTATTGGGT<br>TTAAAGGGTGCGTAGGCGGTTTGATAAGTTAGAGGTGAAATTTCGGGGCTCAACCC<br>TGAACGTGCCTCTAATACTGTTGAGCTAGAGAGTAGTTGCGGTAGGCGGAATGTAT<br>GGTGTAGCGGTGAAATGCTTAGAGATCATACAGAACACCGATTGCGAAGGCAGCTT<br>ACCAAACTATATCTGACGTTGAGGCACGAAAGCGTGGGGAGCAAACAGGATTAGAT<br>ACCCTGGTAGTCCACGCAGTAAACGATGATAACTCGTTGTCGGCGATACACAGTCG<br>GTGACTAAGCGAAAGCGATAAGTTATCCACCTGGGGAGTACGTTCGCAAGAATGAA<br>ACTCAAAGGAATTGACGGGGGCCCGCACAAGCGGAGGAACATGTGGTTTAATTCGA<br>TGATACGCGAGGAACCTTACCCGGGCTTGAAAGTTAGCGACGATTCTTGAAAGAGG<br>ATTTCCCTTCGGGGCGCGAAACTAGGTGCTGCATGGTTGTCGTCAGCTCGTGCCGT<br>GAGGTGTCGGGTTAAGTCCCATAACGAGCGCAACCCCTACCGTTAGTTGCCATCAG<br>GTGAAGCTGGGCACTCTGGGGGGACTGCCGGTGTAAGCCGAGAGGAAGGTGGGG<br>ATGACGTCAAATCAGCACGGCCCTTACGTCCGGGGCTACACACGTGTTACAATGGT<br>AGGTACAGAGGGCAGCTACCCAGCGATGGGATGCGAATCTCGAAAGCCTATCTCAG<br>TTCGGATTGGAGGCTGAAACCCGCCTCCATGAAGTTGGATTCGCTAGTAATCGCGC<br>ATCAGCCATGGCGCGGTGAATACGTTCCCGGGCCTTGTACACACCGCCCGTCAAG<br>CCATGGGAGCCGGGGGTGCCTGAAGTTCGTGACCGCAAGGAGCGACCTAGGGCAA<br>AACTGGTGACTGGGGCTAAGTCGTAACAAGGTA |
| SEQ ID NO: 4 *Alistipes shahii* Strain 4<br>AGAGTTTGATCCTGGCTCAGGATGAACGCTAGCGGCAGGCCTAACACATGCAAGTC<br>GAGGGGCAGCACGGTGTAGCAATACACTGGTGGCGACCGGCGCACGGGTGCGTAA<br>CGCGTATGCAACCTACCCATAACAGGGGGATAACACTGAGAAATTGGTACTAATAC<br>CCCATAACATCAGGACCGGCATCGGTTCTGGTTGAAAACTCCGGTGGTTATGGATG<br>GGCATGCGTTGTATTAGCTGGTTGGTGAGGTAACGGCTCACCAAGGCAACGATACA<br>TAGGGGGACTGAGAGGTTAACCCCCCACATTGGTACTGAGACACGGACCAAACTCC<br>TACGGGAGGCAGCAGTGAGGAATATTGGTCAATGGACGCAAGTCTGAACCAGCCAT<br>GCCGCGTGCAGGAAGACGGCTCTATGAGTTGTAAACTGCTTTTGTACGAGAGTAAA<br>CGCTCTTACGTGTAAGAGCCTGAAAGTATCGTACGAATAAGGATCGGCTAACTCCG<br>TGCCAGCAGCCGCGGTAATACGGAGGATCCAAGCGTTATCCGGATTTATTGGGTTT<br>AAAGGGTGCGTAGGCGGTTTGATAAGTTAGAGGTGAAATACCGGTGCTTAACACCG<br>GAACTGCCTCTAATACTGTTGAACTAGAGAGTAGTTGCGGTAGGCGGAATGTATGG<br>TGTAGCGGTGAAATGCTTAGAGATCATACAGAACACCGATTGCGAAGGCAGCTTAC<br>CAAACTATATCTGACGTTGAGGCACGAAAGCGTGGGGAGCAAACAGGATTAGATAC<br>CCTGGTAGTCCACGCAGTAAACGATGATAACTCGCTGTCGGCGATACACAGTCGGC<br>GGCTAAGCGAAAGCGATAAGTTATCCACCTGGGGAGTACGTTCGCAAGAATGAAAC<br>TCAAAGGAATTGACGGGGGCCCGCACAAGCGGAGGAACATGTGGTTTAATTCGATG<br>ATACGCGAGGAACCTTACCCGGGCTTGAAAGTTACTGACGATTCTGGAAACAGGAT<br>TTCCCTTCGGGGCAGGAAACTAGGTGCTGCATGGTTGTCGTCAGCTCGTGCCGTGA<br>GGTGTCGGGTTAAGTCCCATAACGAGCGCAACCCCTACCGTTAGTTGCCATCAGGT<br>CAAGCTGGGCACTCTGGGGGGACTGCCGGTGTAAGCCGAGAGGAAGGTGGGGATG<br>ACGTCAAATCAGCACGGCCCTTACGTCCGGGGCTACACACGTGTTACAATGGTAGG<br>TACAGAGGGCAGCTACCCAGTGATGGGATGCGAATCTCGAAAGCCTATCTCAGTTC<br>GGATCGGAGGCTGAAACCCGCCTCCGTGAAGTTGGATTCGCTAGTAATCGCGCATC<br>AGCCATGGCGCGGTGAATACGTTCCCGGGCCTTGTACACACCGCCCGTCAAGCCA |

-continued

| SEQUENCES |
| --- |

TGGAAGCTGGGGGTGCCTGAAGTTCGTGACCGCAAGGAGCGACCTAGGGCAAAAC
CGGTGACTGGGGCTAAGTCGTAACAAGGTAGCCGTACCGGAAGGTGCGGCTGGAA
CACCT

SEQ ID NO: 5 *Eubacterium_E hallii* Strain 5
CTCAGGATGAACGCTAGCTACAGGCTTAACACATGCAAGTCGAGGGGCAGCATTCC
AGTTTGCTTGCAAACTGGAGATGGCGACCGGCGCACGGGTGAGTAACACGTATCCA
ACCTGCCGATAACTCGGGGATAGCCTTTCGAAAGAAAGATTAATACCCGATGGCAT
AATAGAACCGCATGGTTTGATTATTAAAGAATTTCGGTTATCGATGGGGATGCGTTC
CATTAGGCAGTTGGTGGGGTAACGGCCCACCAAACCTTCGATGGATAGGGGTTCTG
AGAGGAAGGTCCCCCACATTGGAACTGAGACACGGTCCAAACTCCTACGGGAGGC
AGCAGTGAGGAATATTGGTCAATGGACGAGAGTCTGAACCAGCCAAGTAGCGTGAA
GGATGACTGCCCTATGGGTTGTAAACTTCTTTTATATGGGAATAAAGTGGTCCACGT
GTGGATTTTTGTATGTACCATATGAATAAGGATCGGCTAACTCCGTGCCAGCAGCCG
CGGTAATACGGAGGATCCGAGCGTTATCCGGATTTATTGGGTTTAAAGGGAGCGTA
GGTGGACAGTTAAGTCAGTTGTGAAAGTTTGCGGCTCAACCGTAAAATTGCAGTTG
ATACTGGCTGTCTTGAGTACAGTAGAGGGGGGGGGAATTCGTGGTGTAGCGGTGAA
ATGCTTAGATATCACGAAGAACTCCGATTGCGAAGGCAGCTCACTGGACTGCAACT
GACACTGATGCTCGAAAGTGTGGGTATCAAACAGGATTAGATACCCTGGTAGTCCA
CACAGTAAACGATGAATACTCGCTGTTTGCGATATACAGTAAGCGGCCAAGCGAAA
GCATTAAGTATTCCACCTGGGGAGTACGCCGGCAACGGTGAAACTCAAAGGAATTG
ACGGGGGCCCGCACAAGCGGAGGAACATGTGGTTTAATTCGATGATACGCGAGGA
ACCTTACCCGGGCTTAAATTGCATTTGAATATATTGGAAACAGTATAGTCGTAAGAC
AAATGTGAAGGTGCTGCATGGTTGTCGTCAGCTCGTGCCGTGAGGTGTCGGCTTAA
GTGCCATAACGAGCGCAACCCTTATCTTTAGTTACTAACAGGTCATGCTGAGGACTC
TGGAGAGACTGCCGTCGTAAGATGTGAGGAAGGTGGGGATGACGTCAAATCAGCA
CGGCCCTTACGTCCGGGGCTACACACGTGTTACAATGGGGGGTACAGAAGGCCGC
TACCTGGTGACAGGATGCTAATCCCAAAAGCCTCTCTCAGTTCGGATCGAAGTCTG
CAACCCGACTTCGTGAAGCTGGATTCGCTAGTAATCGCGCATCAGCCATGGCGCGG
TGAATACGTTCCCGGGCCTTGTACACACCGCCCGTCAAGCCATGAAAGCCGGGGG
TACCTGAAGTACGTAACCGCAAGGAGCGTCCTAGGGTAAAACTGGTAATTGGGGCT
AAGTCGTAACAAGGTA SEQ ID NO: 6 *Blautia_A obeum* Strain 6
AGAGTTTGATCCTGGCTCAGGATGAACGCTGGGGGCGTGCTTAACACATGCAAGTC
GAACGGGAAACCTTTTATTGAAGCTTCGGCAGATTTAGCTGGTTTCTAGTGGCGGA
CGGGTGAGTAACGCGTGGGTAACCTGCCTTATACAGGGGGATAACAACCAGAAATG
GTTGCTAATACCGCATAAGCGCACAGGACCGCATGGTCCGGTGTGAAAAACTCCGG
TGGTATAAGATGGACCCGCGTTGGATTAGCTAGTTGGCAGGGTAACGGCCTACCAA
GGCGACGATCCATAGCCGGCCTGAGAGGGTGAACGGCCACATTGGGACTGAGACA
CGGCCCAGACTCCTACGGGAGGCAGCAGTGGGGAATATTGCACAATGGGGGAAAC
CCTGATGCAGCGACGCCGCGTGAAGGAAGAAGTATCTCGGTATGTAAACTTCTATC
AGCAGGGAAGATAGTGACGGTACCTGACTAAGAAGCCCCGGCTAACTACGTGCCA
GCAGCCGCGGTAATACGTAGGGGGCAAGCGTTATCCGGATTTACTGGGTGTAAAG
GGAGCGTAGACGGACTGGCAAGTCTGATGTGAAAGGCGGGGGCTCAACCCCTGGA
CTGCATTGGAAACTGTTAGTCTTGAGTGCCGGAGAGGTAAGCGGAATTCCTAGTGT
AGCGGTGAAATGCGTAGATATTAGGAGGAACACCAGTGGCGAAGGCGGCTTACTG
GACGGTAACTGACGTTGAGGCTCGAAAGCGTGGGGAGCAAACAGGATTAGATACC
CTGGTAGTCCACGCCGTAAACGATGAATACTAGGTGTTGGGGAGCAAAGCTCTTCG
GTGCCGCCGCAAACGCATTAAGTATTCCACCTGGGGAGTACGTTCGCAAGAATGAA
ACTCAAAGGAATTGACGGGGACCCGCACAAGCGGTGGAGCATGTGGTTTAATTCGA
AGCAACGCGAAGAACCTTACCAAGTCTTGACATCCCTCTGACCGTTCCTTAACCGG
AACTTTCCTTCGGGACAGGGGAGACAGGTGGTGCATGGTTGTCGTCAGCTCGTGTC
GTGAGATGTTGGGTTAAGTCCCGCAACGAGCGCAACCCCTATCCCCAGTAGCCAGC
AGTCCGGCTGGGCACTCTGAGGAGACTGCCAGGGATAACCTGGAGGAAGGCGGGG
ATGACGTCAAATCATCATGCCCCTTATGATTTGGGCTACACACGTGCTACAATGGCG
TAAACAAAGGGAAGCA-
AGCCTGCGAAGGTAAGCAAATCCCAAAAATAACGTCCCAGTTCGGACTGCAGTCTG
CAACTCGACTGCACGAAGCTGGAATCGCTAGTAATCGCGGATCAGAATGCCGCGGT
GAATACGTTCCCGGGTCTTGTACACACCGCCCGTCACACCATGGGAGTCAGTAACG
CCCGAAGTCAGTGACCTAACTGCAAAGAAGGAGCTGCCGAAGGGGGGACCGATGA
CTGGGGTGAAGTCGTAACAAGGTA SEQ ID NO: 7 *Odoribacter splanchnicus* Strain 7
AGAGTTTGATCCTGGCTCAGGATGAACGCTAGCGACAGGCTTAACACATGCAAGTC
GAGGGGCATCATGAGGTAGCAATACCTTGATGGCGACCGGCGCACGGGTGAGTAA
CGCGTATGCAACCTGCCTGATACCGGGGTATAGCCCATGGAAACGTGGATTAACAC
CCCATAGTACTTTTATCCTGCATGGGATGTGAGTTAAATGTTTAAGGTATCGGATGG
GCATGCGTCCTATTAGTTAGTTGGGGGGGTAACAGCCCACCAAGACGATGATAGGT
AGGGGTTCTGAGAGGAAGGTCCCCCACATTGGAACTGAGACACGGTCCAAACTCCT
ACGGGAGGCAGCAGTGAGGAATATTGGTCAATGGACGAGAGTCTGAACCAGCCAA
GTCGCGTGAGGGAAGACTGCCCTATGGGTTGTAAACCTCTTTTATAAGGGAAGAAT
AAGTTCTACGTGTAGAATGATGCCTGTACCTTATGAATAAGCATCGGCTAACTCCGT
GCCAGCAGCCGCGGTAATACGGAGGATGCGAGCGTTATCCGGATTTATTGGGTTTA
AAGGGTGCGTAGGCGGTTTATTAAGTTAGTGGTTAAATATTTGAGCTAAACTCAATT
GTGCCATTAATACTGGTAAACTGGAGTACAGACGAGGTAGGCGGAATAAGTTAAGT
AGCGGTGAAATGCATAGATATAACTTAGAACTCCGATAGCGAAGGCAGCTTACCAG -continued

| SEQUENCES |
|---|
| ACTGTAACTGACGCTGATGCACGAGAGCGTGGGTAGCGAACAGGATTAGATACCCT<br>GGTAGTCCACGCCGTAAACGATGCTCACTGGTTCTGTGCGATATATTGTACGGGAT<br>TAAGCGAAAGTATTAAGTGAGCCACCTGGGGAGTACGTCGGCAACGATGAAACTCA<br>AAGGAATTGACGGGGGCCCGCACAAGCGGAGGAACATGTGGTTTAATTCGATGATA<br>CGCGAGGAACCTTACCTGGGTTTAAATGGGAAATGTCGTATTTGGAAACAGATATTC<br>TCTTCGGAGCGTTTTTCAAGGTGCTGCATGGTTGTCGTCAGCTCGTGCCGTGAGGT<br>GTCGGGTTAAGTCCCATAACGAGCGCAACCCTTACCGTTAGTTGCTAGCATGTAAT<br>GATGAGCACTCTAACGGGACTGCCACCGTAAGGTGAGAGGAAGGCGGGGATGACG<br>TCAAATCAGCACGGCCCTTACACCCAGGGCTACACACGTGTTACAATGGCCGGTAC<br>AGAGGGCCGCTACCAGGTGACTGGATGCCAATCTCAAAAGCCGGTCGTAGTTCGG<br>ATTGGAGTCTGTAACCCGACTCCATGAAGTTGGATTCGCTAGTAATCGCGCATCAG<br>CCATGGCGCGGTGAATACGTTCCCGGGCCTTGTACACACCGCCCGTCAAGCCATG<br>GAAGCCGGGGGTGCCTGAAGTCCGTAACCGCGAGGATCGGCCTAGGGCAAAACTG<br>GTAACTGGGGCTAAGTCGTAACAAGGTAGCCGTACCGGAAGGTGCGGCTGGAACA<br>CCT |
| SEQ ID NO: 8 *Bacteroides cellulosilyticus* Strain 8<br>AGAGTTTGATCCTGGCTCAGGATGAACGCTAGCTACAGGCTTAACACATGCAAGTC<br>GAGGGGCAGCATGACCTAGCAATAGGTTGATGGCGACCGGCGCACGGGTGAGTAA<br>CACGTATCCAACCTACCGGTTATTCCGGGATAGCCTTTCGAAAGAAAGATTAATACC<br>GGATAGTATAACGAGAAGGCATCTTTTTGTTATTAAAGAATTTCGATAACCGATGGG<br>GATGCGTTCCATTAGTTTGTTGGCGGGGTAACGGCCCACCAAGACATCGATGGATA<br>GGGGTTCTGAGAGGAAGGTCCCCCACATTGGAACTGAGACACGGTCCAAACTCCTA<br>CGGGAGGCAGCAGTGAGGAATATTGGTCAATGGACGAGAGTCTGAACCAGCCAAG<br>TAGCGTGAAGGATGACTGCCCTATGGGTTGTAAACTTCTTTTATATGGGAATAAAGT<br>GAGCCACGTGTGGCTTTTTGTATGTACCATACGAATAAGGATCGGCTAACTCCGTG<br>CCAGCAGCCGCGGTAATACGGAGGATCCGAGCGTTATCCGGATTTATTGGGTTTAA<br>AGGGAGCGTAGGCGGACTATTAAGTCAGCTGTGAAAGTTTGCGGCTCAACCGTAAA<br>ATTGCAGTTGATACTGGTCGTCTTGAGTGCAGTAGAGGTAGGCGGAATTCGTGGTG<br>TAGCGGTGAAATGCTTAGATATCACGAAGAACTCCGATTGCGAAGGCAGCTTACTG<br>GACTGTAACTGACGCTGATGCTCGAAAGTGTGGGTATCAAACAGGATTAGATACCC<br>TGGTAGTCCACACAGTAAACGATGAATACTCGCTGTTTGCGATATACGGCAAGCGG<br>CCAAGCGAAAGCATTAAGTATTCCACCTGGGGAGTACGCCGGCAACGGTGAAACTC<br>AAAGGAATTGACGGGGGCCCGCACAAGCGGAGGAACATGTGGTTTAATTCGATGAT<br>ACGCGAGGAACCTTACCCGGGCTTAAATTGCAAATGAATATAGTGGAAACATTATAG<br>CCGCAAGGCATTTGTGAAGGTGCTGCATGGTTGTCGTCAGCTCGTGCCGTGAGGTG<br>TCGGCTTAAGTGCCATAACGAGCGCAACCCTTATCTTTAGTTACTAACAGGTCATGC<br>TGAGGACTCTAGAGAGACTGCCGTCGTAAGATGTGAGGAAGGTGGGGATGACGTC<br>AAATCAGCACGGCCCTTACGTCCGGGGCTACACACGTGTTACAATGGGGGGTACAG<br>AAGGCAGCTACACAGCGATGTGATGCTAATCCCAAAAGCCTCTCTCAGTTCGGATT<br>GGAGTCTGCAACCCGACTCCATGAAGCTGGATTCGCTAGTAATCGCGCATCAGCCA<br>CGGCGCGGTGAATACGTTCCCGGGCCTTGTACACACCGCCCGTCAAGCCATGAAA<br>GCCGGGGGTACCTGAAGTCCGTAACCGTAAGGAGCGGCCTAGGGTAAAACTGGTA<br>ATTGGGGCTAAGTCGTA |
| SEQ ID NO: 9 *Bacteroides uniformis* Strain 9<br>CTGGCTCAGGATGAACGCTAGCTACAGGCTTAACACATGCAAGTCGAGGGGCAGCA<br>TGAACTTAGCTTGCTAAGTTTGATGGCGACCGGCGCACGGGTGAGTAACACGTATC<br>CAACCTGCCGATGACTCGGGGATAGCCTTTCGAAAGAAAGATTAATACCCGATGGC<br>ATAGTTCTTCCGCATGGTAGAACTATTAAAGAATTTCGGTCATCGATGGGGATGCGT<br>TCCATTAGGTTGTTGGCGGGGTAACGGCCCACCAAGCCTTCGATGGATAGGGGTTC<br>TGAGAGGAAGGTCCCCCACATTGGAACTGAGACACGGTCCAAACTCCTACGGGAG<br>GCAGCAGTGAGGAATATTGGTCAATGGACGAGAGTCTGAACCAGCCAAGTAGCGTG<br>AAGGATGACTGCCCTATGGGTTGTAAACTTCTTTTATACGGGAATAAAGTGAGGCAC<br>GTGTGCCTTTTTGTATGTACCGTATGAATAAGGATCGGCTAACTCCGTGCCAGCAGC<br>CGCGGTAATACGGAGGATCCGAGCGTTATCCGGATTTATTGGGTTTAAAGGGAGCG<br>TAGGCGGACGCTTAAGTCAGTTGTGAAAGTTTGCGGCTCAACCGTAAAATTGCAGT<br>TGATACTGGGTGTCTTGAGTACAGTAGAGGCAGGCGGAATTCGTGGTGTAGCGGTG<br>AAATGCTTAGATATCACGAAGAACTCCGATTGCGAAGGCAGCTTGCTGGACTGTAA<br>CTGACGCTGATGCTCGAAAGTGTGGGTATCAAACAGGATTAGATACCCTGGTAGTC<br>CACACAGTAAACGATGAATACTCGCTGTTTGCGATATACAGTAAGCGGCCAAGCGA<br>AAGCGTTAAGTATTCCACCTGGGGAGTACGCCGGCAACGGTGAAACTCAAAGGAAT<br>TGACGGGGGCCCGCACAAGCGGAGGAACATGTGGTTTAATTCGATGATACGCGAG<br>GAACCTTACCCGGGCTTGAATTGCAACTGAATGATGTGGAGACATGTCAGCCGCAA<br>GGCAGTTGTGAAGGTGCTGCATGGTTGTCGTCAGCTCGTGCCGTGAGGTGTCGGC<br>TTAAGTGCCATAACGAGCGCAACCCTTATCGATAGTTACCATCAGGTTATGCTGGG<br>GACTCTGTCGAGACTGCCGTCGTAAGATGTGAGGAAGGTGGGGATGACGTCAAATC<br>AGCACGGCCCTTACGTCCGGGGCTACACACGTGTTACAATGGGGGGTACAGAAGG<br>CAGCTACACGGCGACGTGATGCTAATCCCTAAAGCCTCTCTCAGTTCGGATTGGAG<br>TCTGCAACCCGACTCCATGAAGCTGGATTCGCTAGTAATCGCGCATCAGCCACGGC<br>GCGGTGAATACGTTCCCGGGCCTTGTACACACCGCCCGTCAAGCCATGAAAGCCG<br>GGGGTACCTGAAGTGCGTAACCGCGAGGAGCGCCCTAGGGTAAAACTGGTGATTG<br>GGGCTAAGTCGTAACAAGGTA |
| SEQ ID NO: 10 *Bacteroides_B vulgatus* Strain 10<br>ATGAAGAGTTTGATCCTGGCTCAGGATGAACGCTAGCTACAGGCTTAACACATGCA<br>AGTCGAGGGGCAGCATGGTCTTAGCTTGCTAAGGCCGATGGCGACCGGCGCACGG |

-continued

| SEQUENCES |
| --- |

GTGAGTAACACGTATCCAACCTGCCGTCTACTCTTGGACAGCCTTCTGAAAGGAAG
ATTAATACAAGATGGCATCATGAGTCCGCATGTTCACATGATTAAAGGTATTCCGGT
AGACGATGGGGATGCGTTCCATTAGATAGTAGGCGGGGTAACGGCCCACCTAGTCT
TCGATGGATAGGGGTTCTGAGAGGAAGGTCCCCCACATTGGAACTGAGACACGGTC
CAAACTCCTACGGGAGGCAGCAGTGAGGAATATTGGTCAATGGGCGAGAGCCTGA
ACCAGCCAAGTAGCGTGAAGGATGACTGCCCTATGGGTTGTAAACTTCTTTTATAAA
GGAATAAAGTCGGGTATGGATACCCGTTTGCATGTACTTTATGAATAAGGATCGGCT
AACTCCGTGCCAGCAGCCGCGGTAATACGGAGGATCCGAGCGTTATCCGGATTTAT
TGGGTTTAAAGGGAGCGTAGATGGATGTTTAAGTCAGTTGTGAAAGTTTGCGGCTC
AACCGTAAAATTGCAGTTGATACTGGATATCTTGAGTGCAGTTGAGGCAGGCGGAA
TTCGTGGTGTAGCGGTGAAATGCTTAGATATCACGAAGAACTCCGATTGCGAAGGC
AGCCTGCTAAGCTGCAACTGACATTGAGGCTCGAAAGTGTGGGTATCAAACAGGAT
TAGATACCCTGGTAGTCCACACGGTAAACGATGAATACTCGCTGTTTGCGATATACA
GCAAGCGGCCAAGCGAAAGCGTTAAGTATTCCACCTGGGGAGTACGCCGGCAACG
GTGAAACTCAAAGGAATTGACGGGGGCCCGCACAAGCGGAGGAACATGTGGTTTAA
TTCGATGATACGCGAGGAACCTTACCCGGGCTTAAATTGCAGATGAATTACGGTGA
AAGCCGTAAGCCGCAAGGCATCTGTGAAGGTGCTGCATGGTTGTCGTCAGCTCGTG
CCGTGAGGTGTCGGCTTAAGTGCCATAACGAGCGCAACCCTTGTTGTCAGTTACTA
ACAGGTTCCGCTGAGGACTCTGACAAGACTGCCATCGTAAGATGTGAGGAAGGTGG
GGATGACGTCAAATCAGCACGGCCCTTACGTCCGGGGCTACACACGTGTTACAATG
GGGGGTACAGAGGGCCGCTACCACGCGAGTGGATGCCAATCCCAAAAACCTCTCT
CAGTTCGGACTGGAGTCTGCAACCCGACTCCACGAAGCTGGATTCGCTAGTAATCG
CGCATCAGCCACGGCGCGGTGAATACGTTCCCGGGCCTTGTACACACCGCCCGTC
AAGCCATGGGAGCCGGGGGTACCTGAAGTGCGTAACCGCGAGGAGCGCCCTAGG
GTAAAACTGGTGACTGGGGCTAAGTCGTAACAAGGTAGCCGTACCGGAAG

SEQ ID NO: 11 *Bacteroides fragilis* Strain 11
ATGAAGAGTTTGATCCTGGCTCAGGATGAACGCTAGCTACAGGCTTAACACATGCA
AGTCGAGGGGCATCAGGAAGAAAGCTTGCTTTCTTTGCTGGCGACCGGCGCACGG
GTGAGTAACACGTATCCAACCTGCCCTTTACTCGGGGATAGCCTTTCGAAAGAAAG
ATTAATACCCGATGGCATAATGATTCCGCATGGTTTCATTATTAAAGGATTCCGGTA
AAGGATGGGGATGCGTTCCATTAGGTTGTTGGTGAGGTAACGGCTCACCAAGCCTT
CGATGGATAGGGGTTCTGAGAGGAAGGTCCCCCACATTGGAACTGAGACACGGTC
CAAACTCCTACGGGAGGCAGCAGTGAGGAATATTGGTCAATGGGCGCTAGCCTGAA
CCAGCCAAGTAGCGTGAAGGATGAAGGCTCTATGGGTCGTAAACTTCTTTTATATAA
GAATAAAGTGCAGTATGTATACTGTTTTGTATGTATTATATGAATAAGGATCGGCTAA
CTCCGTGCCAGCAGCCGCGGTAATACGGAGGATCCGAGCGTTATCCGGATTTATTG
GGTTTAAAGGGAGCGTAGGTGGACTGGTAAGTCAGTTGTGAAAGTTTGCGGCTCAA
CCGTAAAATTGCAGTTGATACTGTCAGTCTTGAGTACAGTAGAGGTGGGCGGAATT
CGTGGTGTAGCGGTGAAATGCTTAGATATCACGAAGAACTCCGATTGCGAAGGCAG
CTCACTGGACTGCAACTGACACTGATGCTCGAAAGTGTGGGTATCAAACAGGATTA
GATACCCTGGTAGTCCACACAGTAAACGATGAATACTCGCTGTTTGCGATATACAGT
AAGCGGCCAAGCGAAAGCATTAAGTATTCCACCTGGGGAGTACGCCGGCAACGGT
GAAACTCAAAGGAATTGACGGGGGCCCGCACAAGCGGAGGAACATGTGGTTTAATT
CGATGATACGCGAGGAACCTTACCCGGGCTTAAATTGCAGTGGAATGATGTGGAAA
CATGTCAGTGAGCAATCACCGCTGTGAAGGTGCTGCATGGTTGTCGTCAGCTCGTG
CCGTGAGGTGTCGGCTTAAGTGCCATAACGAGCGCAACCCTTATCTTTAGTTACTAA
CAGGTTATGCTGAGGACTCTAGAGAGACTGCCGTCGTAAGATGTGAGGAAGGTGG
GGATGACGTCAAATCAGCACGGCCCTTACGTCCGGGGCTACACACGTGTTACAATG
GGGGGTACAGAAGGCAGCTAGCGGGTGACCGTATGCTAATCCCAAAAGCCTCTCTC
AGTTCGGATCGAAGTCTGCAACCCGACTTCGTGAAGCTGGATTCGCTAGTAATCGC
GCATCAGCCACGGCGCGGTGAATACGTTCCCGGGCCTTGTACACACCGCCCGTCA
AGCCATGGGAGCCGGGGGTACCTGAAGTACGTAACCGCAAGGATCGTCCTAGGGT
AAAACTGGTGACTGGGGCTAAGTCGTAACAAGGTAGCCGTACCGGAAGGTGCGGC
TGGAACACCTCCTT SEQ ID NO: 12 *Bacteroides caccae* Strain 12
TGGCTCAGGATGAACGCTAGCTACAGGCTTAACACATGCAAGTCGAGGGGCATCAG
TTTGGTTTGCTTGCAAACCAAAGCTGGCGACCGGCGCACGGGTGAGTAACACGTAT
CCAACCTGCCTCATACTCGGGGATAGCCTTTCGAAAGAAAGATTAATATCCGATAGC
ATATATTTCCCGCATGGGTTTTATATTAAAGAAATTCGGTATGAGATGGGGATGCGT
TCCATTAGTTTGTTGGGGGGGTAACGGCCCACCAAGACTACGATGGATAGGGGTTC
TGAGAGGAAGGTCCCCCACATTGGAACTGAGACACGGTCCAAACTCCTACGGGAG
GCAGCAGTGAGGAATATTGGTCAATGGACGCGAGTCTGAACCAGCCAAGTAGCGTG
AAGGATGACTGCCCTATGGGTTGTAAACTTCTTTTATATGGGAATAAAGTTGTCCAC
GTGTGGATTTTTGTATGTACCATATGAATAAGGATCGGCTAACTCCGTGCCAGCAGC
CGCGGTAATACGGAGGATCCGAGCGTTATCCGGATTTATTGGGTTTAAAGGGAGCG
TAGGCGGATTGTTAAGTCAGTTGTGAAAGTTTGCGGCTCAACCGTAAAATTGCAGTT
GATACTGGCAGTCTTGAGTGCAGTAGAGGTGGGCGGAATTCGTGGTGTAGCGGTG
AAATGCTTAGATATCACGAAGAACTCCGATTGCGAAGGCAGCTCACTGGAGTGTAA
CTGACGCTGATGCTCGAAAGTGTGGGTATCAAACAGGATTAGATACCCTGGTAGTC
CACACAGTAAACGATGAATACTCGCTGTTTGCGATATACAGTAAGCGGCCAAGCGA
AAGCATTAAGTATTCCACCTGGGGAGTACGCCGGCAACGGTGAAACTCAAAGGAAT
TGACGGGGGCCCGCACAAGCGGAGGAACATGTGGTTTAATTCGATGATACGCGAG
GAACCTTACCCGGGCTTAAATTGCAAATGAATTATGGGGAAACCCATAGGCCGCAA
GGCATTTGTGAAGGTGCTGCATGGTTGTCGTCAGCTCGTGCCGTGAGGTGTCGGCT
TAAGTGCCATAACGAGCGCAACCCTTATCTTCAGTTACTAACAGGTCATGCTGAGGA -continued

| SEQUENCES |
| --- |

CTCTGGAGAGACTGCCGTCGTAAGATGTGAGGAAGGTGGGGATGACGTCAAATCA
GCACGGCCCTTACGTCCGGGGCTACACACGTGTTACAATGGGGGGTACAGAAGGC
CGCTACCTGGTGACAGGATGCCAATCCCAAAAACCTCTCTCAGTTCGGATCGAAGT
CTGCAACCCGACTTCGTGAAGCTGGATTCGCTAGTAATCGCGCATCAGCCATGGCG
CGGTGAATACGTTCCCGGGCCTTGTACACACCGCCCGTCAAGCCATGAAAGCCGG
GGGTACCTGAAGTACGTAACCGCAAGGAGCGTCCTAGGGTAAAACTGGTAATTGGG
GCTAAGTCGTAACAAGGTA

SEQ ID NO: 13 *Paeniclostridium sordellii* Strain 13
GTTTGATCCTGGCTCAGGATGAACGCTGGCGGCGTGCCTAACACATGCAAGTCGAG
CGAACCCTTCGGGGTGAGCGGCGGACGGGTGAGTAACGCGTGGGTAACCTGCCCT
GTACACACGGATAACATACCGAAAGGTATGCTAATACGGGATAATATATGAGAGTCG
CATGGCTTTTGTATCAAAGCTCTGGCGGTACAGGATGGACCCGCGTCTGATTAGCT
AGTTGGTAAGGTAACGGCTTACCAAGGCAACGATCAGTAGCCGACCTGAGAGGGTG
ATCGGCCACATTGGAACTGAGACACGGTCCAAACTCCTACGGGAGGCAGCAGTGG
GGAATATTGCACAATGGGCGAAAGCCTGATGCAGCAACGCCGCGTGAGCGATGAA
GGCCTTCGGGTCGTAAAGCTCTGTCCTCAAGGAAGATAATGACGGTACTTGAGGAG
GAAGCCCCGGCTAACTACGTGCCAGCAGCCGCGGTAATACGTAGGGGGCTAGCGT
TATCCGGAATTACTGGGCGTAAAGGGTGCGTAGGCGGTCTTTCAAGCCAGAAGTGA
AAGGCTACGGCTCAACCGTAGTAAGCTTTTGGAACTGTAGGACTTGAGTGCAGGAG
AGGAGAGTGGAATTCCTAGTGTAGCGGTGAAATGCGTAGATATTAGGAGGAACACC
AGTAGCGAAGGCGGCTCTCTGGACTGTAACTGACGCTGAGGCACGAAAGCGTGGG
GAGCAAACAGGATTAGATACCCTGGTAGTCCACGCCGTAAACGATGAGTACTAGGT
GTCGGGGGTTACCCCCCTCGGTGCCGCAGCTAACGCATTAAGTACTCCGCCTGGG
AAGTACGCTCGCAAGAGTGAAACTCAAAGGAATTGACGGGGACCCGCACAAGTAGC
GGAGCATGTGGTTTAATTCGAAGCAACGCGAAGAACCTTACCTAAGCTTGACATCC
CACTGACCTCTCCCTAATCGGAGATTTCCCTTCGGGGACAGTGGTGACAGGTGGTG
CATGGTTGTCGTCAGCTCGTGTCGTGAGATGTTGGGTTAAGTCCCGCAACGAGCGC
AACCCTTGCCTTTAGTTGCCAGCATTAAGTTGGGCACTCTAGAGGGACTGCCGAGG
ATAACTCGGAGGAAGGTGGGGATGACGTCAAATCATCATGCCCCTTATGCTTAGGG
CTACACACGTGCTACAATGGGTGGTACAGAGGGTTGCCAAGCCGTGAGGTGGAGC
TAATCCCTTAAAGCCATTCTCAGTTCGGATTGTAGGCTGAAACTCGCCTACATGAAG
CTGGAGTTACTAGTAATCGCAGATCAGAATGCTGCGGTGAATGCGTTCCCGGGTCT
TGTACACACCGCCCGTCACACCATGGGAGTTGGGGGCGCCCGAAGCCGGTTAGCT
AACCTTTTAGGAAGCGGCCGTCGAAGGTGAAACCAATGACTGGGGTGAAGTCGTAA
CAAGGTAGCCGTATCGGAAGGTGCGGCTGGATCACCTCCTTT SEQ ID NO: 14 *Blautia producta* Strain 14
AGAGTTTGATCCTGGCTCAGGATGAACGCTGGCGGCGTGCTTAACACATGCAAGTC
GAGCGAAGCACTAAGACAGATTTCTTCGGATTGAAGTCTTTGTGACTGAGCGGCGG
ACGGGTGAGTAACGCGTGGGTAACCTGCCTCATACAGGGGGATAACAGTTAGAAAT
GACTGCTAATACCGCATAAGCGCACAGGACCGCATGGTCTGGTGTGAAAAACTCCG
GTGGTATGAGATGGACCCGCGTCTGATTAGCTAGTTGGAGGGGTAACGGCCCACC
AAGGCGACGATCAGTAGCCGGCCTGAGAGGGTGAACGGCCACATTGGGACTGAGA
CACGGCCCAGACTCCTACGGGAGGCAGCAGTGGGGAATATTGCACAATGGGGGAA
ACCCTGATGCAGCGACGCCGCGTGAAGGAAGAAGTATCTCGGTATGTAAACTTCTA
TCAGCAGGGAAGAAAATGACGGTACCTGACTAAGAAGCCCCGGCTAACTACGTGCC
AGCAGCCGCGGTAATACGTAGGGGGCAAGCGTTATCCGGATTTACTGGGTGTAAAG
GGAGCGTAGACGGAAGAGCAAGTCTGATGTGAAAGGCTGGGGCTTAACCCCAGGA
CTGCATTGGAAACTGTTGTTCTAGAGTGCCGGAGAGGTAAGCGGAATTCCTAGTGT
AGCGGTGAAATGCGTAGATATTAGGAGGAACACCAGTGGCGAAGGCGGCTTACTG
GACGGTAACTGACGTTGAGGCTCGAAAGCGTGGGGAGCAAACAGGATTAGATACC
CTGGTAGTCCACGCCGTAAACGATGAATACTAGGTGTCGGGTGGCAAAGCCATTCG
GTGCCGCAGCAAACGCAATAAGTATTCCACCTGGGGAGTACGTTCGCAAGAATGAA
ACTCAAAGGAATTGACGGGGACCCGCACAAGCGGTGGAGCATGTGGTTTAATTCGA
AGCAACGCGAAGAACCTTACCAAGTCTTGACATCCCTCTGACCGTCCCGTAACGGG
GGCTTCCCTTCGGGGCAGAGGAGACAGGTGGTGCATGGTTGTCGTCAGCTCGTGT
CGTGAGATGTTGGGTTAAGTCCCGCAACGAGCGCAACCCTTATCCTTAGTAGCCAG
CACATGATGGTGGGCACTCTAGGGAGACTGCCGGGGATAACCCGGAGGAAGGCGG
GGACGACGTCAAATCATCATGCCCCTTATGATTTGGGCTACACACGTGCTACAATG
GCGTAAACAAAGGGAAGCGAGACAGCGATGTTGAGCGAATCCCAAAAATAACGTCC
CAGTTCGGACTGCAGTCTGCAACTCGACTGCACGAAGCTGGAATCGCTAGTAATCG
CGGATCAGAATGCCGCGGTGAATACGTTCCCGGGTCTTGTACACACCGCCCGTCAC
ACCATGGGAGTCAGTAACGCCCGAAGTCAGTGACCTAACCGAAAGGAAGGAGCTG
CCGAAGGGGGGACCGATAACTGGGGTGAAGTCGTAACAAGGTA SEQ ID NO: 15 *Absiella innocuum* Strain 15
ATGGAGAGTTTGATCCTGGCTCAGGATGAACGCTGGCGGCATGCCTAATACATGCA
AGTCGAACGAAGT-
TTCGAGGAAGCTTGCTTCCAAAGAGACTTAGTGGCGAACGGGTGAGTAACACGTAG
GTAACCTGCCCATGTGTCCGGGATAACTGCTGGAAACGGTAGCTAAAACCGGATAG
GTATACAGAGCGCATGCTCAGTATATTAAAGCGCCCATCAAGGCGTGAACATGGAT
GGACCTGCGGCGCATTAGCTAGTTGGTGAGGTAACGGCCCACCAAGGCGATGATG
CGTAGCCGGCCTGAGAGGGTAAACGGCCACATTGGGACTGAGACACGGCCCAAAC
TCCTACGGGAGGCAGCAGTAGGGAATTTTCGTCAATGGGGGAAACCCTGAACGAG
CAATGCCGCGTGAGTGAAGAAGGTCTTCGGATCGTAAAGCTCTGTTGTAAGTGAAG
AACGGCTCATAGAGGAAATGCTATGGGAGTGACGGTAGCTTACCAGAAAGCCACGG -continued

| SEQUENCES |
| --- |

CTAACTACGTGCCAGCAGCCGCGGTAATACGTAGGTGGCAAGCGTTATCCGGAATC
ATTGGGCGTAAAGGGTGCGTAGGTGGCGTACTAAGTCTGTAGTAAAAGGCAATGGC
TCAACCATTGTAAGCTATGGAAACTGGTATGCTGGAGTGCAGAAGAGGGCGATGGA
ATTCCATGTGTAGCGGTAAAATGCGTAGATATATGGAGGAACACCAGTGGCGAAGG
CGGTCGCCTGGTCTGTAACTGACACTGAGGCACGAAAGCGTGGGGAGCAAATAGG
ATTAGATACCCTAGTAGTCCACGCCGTAAACGATGAGAACTAAGTGTTGGAGGAATT
CAGTGCTGCAGTTAACGCAATAAGTTCTCCGCCTGGGGAGTATGCACGCAAGTGTG
AAACTCAAAGGAATTGACGGGGCCCGCACAAGCGGTGGAGTATGTGGTTTAATTC
GAAGCAACGCGAAGAACCTTACCAGGCCTTGACATGGAAACAAATACCCTAGAGAT
AGGGGGATAATTATGGATCACACAGGTGGTGCATGGTTGTCGTCAGCTCGTGTCGT
GAGATGTTGGGTTAAGTCCCGCAACGAGCGCAACCCTTGTCGCATGTTACCAGCAT
CAAGTTGGGGACTCATGCGAGACTGCCGGTGACAAACCGGAGGAAGGTGGGGATG
ACGTCAAATCATCATGCCCCTTATGGCCTGGGCTACACACGTACTACAATGGCGAC
CACAAAGAGCAGCGACACAGTGATGTGAAGCGAATCTCATAAAGGTCGTCTCAGTT
CGGATTGAAGTCTGCAACTCGACTTCATGAAGTCGGAATCGCTAGTAATCGCAGAT
CAGCATGCTGCGGTGAATACGTTCTCGGGCCTTGTACACACCGCCCGTCAAACCAT
GGGAGTCAGTAATACCCGAAGCCGGTGGCATAACCGTAAGGAGTGAGCCGTCGAA
GGTAGGACCGA

SEQ ID NO: 16 *Clostridium_M clostridioforme* Strain 16
AGAGTTTGATCCTGGCTCAGGATGAACGCTGGCGGCGTGCCTAACACATGCAAGTC
GAACGAAGCAATTAAGATGAAGTTTTCGGATGGAATCTTGATTGACTGAGTGGCGG
ACGGGTGAGTAACGCGTGGATAACCTGCCTCACACTGGGGGATAACAGTTAGAAAT
GACTGCTAATACCGCATAAGCGCACAGTGCCGCATGGCAGTGTGTGAAAAACTCCG
GTGGTGTGAGATGGATCCGCGTCTGATTAGCCAGTTGGCGGGGTAACGGCCCACC
AAAGCGACGATCAGTAGCCGACCTGAGAGGGTGACCGGCCACATTGGGACTGAGA
CACGGCCCAAACTCCTACGGGAGGCAGCAGTGGGGAATATTGCACAATGGGCGAA
AGCCTGATGCAGCGACGCCGCGTGAGTGAAGAAGTATTTCGGTATGTAAAGCTCTA
TCAGCAGGGAAGAAAATGACGGTACCTGACTAAGAAGCCCCGGCTAACTACGTGCC
AGCAGCCGCGGTAATACGTAGGGGGCAAGCGTTATCCGGATTTACTGGGTGTAAAG
GGAGCGTAGACGGCGAAGCAAGTCTGAAGTGAAAACCCGGGGCTCAACCCTGGGA
CTGCTTTGGAAACTGTTTTGCTAGAGTGTCGGAGAGGTAAGTGGAATTCCTAGTGTA
GCGGTGAAATGCGTAGATATTAGGAGGAACACCAGTGGCGAAGGCGGCTTACTGG
ACGATAACTGACGTTGAGGCTCGAAAGCGTGGGGAGCAAACAGGATTAGATACCCT
GGTAGTCCACGCCGTAAACGATGAATGCTAGGTGTTGGGGGGCAAAGCCCTTCGG
TGCCGCCGCAAACGCAGTAAGCATTCCACCTGGGGAGTACGTTCGCAAGAATGAAA
CTCAAAGGAATTGACGGGGACCCGCACAAGCGGTGGAGCATGTGGTTTAATTCGAA
GCAACGCGAAGAACCTTACCAAGTCTTGACATCCCCCTGACGGGCCGGTAACGCG
GCCTTTCCTTCGGGACAGGGGAGACAGGTGGTGCATGGTTGTCGTCAGCTCGTGT
CGTGAGATGTTGGGTTAAGTCCCGCAACGAGCGCAACCCTTATCCTTAGTAGCCAG
CAGGTAGAGCCGGGCACTCTAGGGAGACTGCCAGGGATAACCTGGAGGAAGGTGG
GGATGACGTCAAATCATCATGCCCCTTATGATTTGGGCTACACACGTGCTACAATGG
CGTAAACAAAGGGAAGCGAGACAGTGATGTGGAGCAAATCCCAAAAATAACGTCCC
AGTTCGGACTGTAGTCTGCAACCCGACTACACGAAGCTGGAATCGCTAGTAATCGC
GAATCAGAATGTCGCGGTGAATACGTTCCCGGGTCTTGTACACACCGCCCGTCACA
CCATGGGAGTCAGCAACGCCCGAAGTCAGTGACCCAAC-CGAAAG-
GAGGGAGCTGCCGAAGGGGGGGCAGGTAACTGGGGTGAAGTCGTAACAAGGTAGC
CGTA SEQ ID NO: 17 *Paraclostridium massiliensis* Strain 17
AGAGTTTGATCCTGGCTCAGGATGAACGCTGGCGGCGTGCCTAACACATGCAAGTC
GAGCGATCTCTTCGGAGAGAGCGGCGGACGGGTGAGTAACGCGTGGGTAACCTGC
CCTGTACACACGGATAACATACCGAAAGGTATACTAATACGGGATAACATACGAAAG
TCGCATGGCTTTTGTATCAAAGCTCCGGCGGTACAGGATGGACCCGCGTCTGATTA
GCTAGTTGGTAAGGTAATGGCTTACCAAGGCAACGATCAGTAGCCGACCTGAGAGG
GTGATCGGCCACACTGGAACTGAGACACGGTCCAGACTCCTACGGGAGGCAGCAG
TGGGGAATATTGCACAATGGGCGAAAGCCTGATGCAGCAACGCCGCGTGAGCGAT
GAAGGCCTTCGGGTCGTAAAGCTCTGTCCTCAAGGAAGATAATGACGGTACTTGAG
GAGGAAGCCCCGGCTAACTACGTGCCAGCAGCCGCGGTAATACGTAGGGGGCTAG
CGTTATCCGGAATTACTGGGCGTAAAGGGTGCGTAGGTGGTTTTTTAAGTCAGAAG
TGAAAGGCTACGGCTCAACCGTAGTAAGCTTTTGAAACTAGAGAACTTGAGTGCAG
GAGAGGAGAGTAGAATTCCTAGTGTAGCGGTGAAATGCGTAGATATTAGGAGGAAT
ACCAGTAGCGAAGGCGGCTCTCTGGACTGTAACTGACACTGAGGCACGAAAGCGT
GGGGAGCAAACAGGATTAGATACCCTGGTAGTCCACGCCGTAAACGATGAGTACTA
GGTGTCGGGGGTTACCCCCCTCGGTGCCGCAGCTAACGCATTAAGTACTCCGCCT
GGGAAGTACGCTCGCAAGAGTGAAACTCAAAGGAATTGACGGGGACCCGCACAAG
TAGCGGAGCATGTGGTTTAATTCGAAGCAACGCGAAGAACCTTACCTAAGCTTGAC
ATCCCACTGACCTCTCCCTAATCGGAGATTTCCCTTCGGGGACAGTGGTGACAGGT
GGTGCATGGTTGTCGTCAGCTCGTGTCGTGAGATGTTGGGTTAAGTCCCGCAACGA
GCGCAACCCTTGCCTTTAGTTGCCAGCATTAAGTTGGGCACTCTAGAGGGACTGCC
GAGGATAACTCGGAGGAAGGTGGGGATGACGTCAAATCATCATGCCCCTTATGCTT
AGGGCTACACACGTGCTACAATGGGTGGTACAGAGGGTTGCCAAGCCGCGAGGTG
GAGCTAATCCCTTAAAGCCATTCTCAGTTCGGATTGTAGGCTGAAACTCGCCTACAT
GAAGCTGGAGTTACTAGTAATCGCAGATCAGAATGCTGCGGTGAATGCGTTCCCGG
GTCTTGTACACACCGCCCGTCACACCATGGAAGTTGGGGGCGCCCGAAGCCGGTT
AGCTAACCTTTTAGGAAGCGGCCGTCGAAGGTGAAACCAATGACTGGGGTGAAGTC
GTAACAAGGTAGCCGTATCGGAAGGTGCGGCTGGATCACCT -continued

| SEQUENCES |
|---|

SEQ ID NO: 18 *Dorea longicatena* B Strain 18
AGAGTTTGATCCTGGCTCAGGATGAACGCTGGCGGCGTGCTTAACACATGCAAGTC
GAGCGAAGCACTTAAGTCTGA-TTCTTCGGA-
TGAAGACTTTTGTGACTGAGCGGCGGACGGGTGAGTAACGCGTGGGTAACCTGCC
TCATACAGGGGGATAACAGTTAGAAATGACTGCTAATACCGCATAAGACCACGGTA
CCGCATGGTACAGTGGTAAAAACTCCGGTGGTATGAGATGGACCCGCGTCTGATTA
GGTAGTTGGTGGGGTAACGGCCTACCAAGCCGACGATCAGTAGCCGACCTGAGAG
GGTGACCGGCCACATTGGGACTGAGACACGGCCCAGACTCCTACGGGAGGCAGCA
GTGGGGAATATTGCACAATGGAGGAAACTCTGATGCAGCGACGCCGCGTGAAGGA
TGAAGTATTTCGGTATGTAAACTTCTATCAGCAGGGAAGAAAATGACGGTACCTGAC
TAAGAAGCCCCGGCTAACTACGTGCCAGCAGCCGCGGTAATACGTAGGGGGCAAG
CGTTATCCGGATTTACTGGGTGTAAAGGGAGCGTAGACGGCACGGCAAGCCAGAT
GTGAAAGCCCGGGGCTCAACCCCGGGACTGCATTTGGAACTGCTG-
AGCTAGAGTGTCGGAGAGGCAAGTGGAATTCCTAGTGTAGCGGTGAAATGCGTAGA
TATTAGGAGGAACACCAGTGGCGAAGGCGGCTTGCTGGACGATGACTGACGTTGA
GGCTCGAAAGCGTGGGGAGCAAACAGGATTAGATACCCTGGTAGTCCACGCCGTA
AACGATGACTGCTAGGTGTCGGGTGGCAAAGCCATTCGGTGCCGCAGCTAACGCA
ATAAGCAGTCCACCTGGGGAGTACGTTCGCAAGAATGAAACTCAAAGGAATTGACG
GGGACCCGCACAAGCGGTGGAGCATGTGGTTTAATTCGAAGCAACGCGAAGAACC
TTACCTGATCTTGACATCCCGATGACCG-
CTTCGTAATGGAAGCTTTTCTTCGGAACATCGGTGACAGGTGGTGCATGGTTGTCG
TCAGCTCGTGTCGTGAGATGTTGGGTTAAGTCCCGCAACGAGCGCAACCCCTATCT
TCAGTAGCCAGCAGGTTAAGCTGGGCACTCTGGAGAGACTGCCAGGGATAACCTG
GAGGAAGGTGGGGATGACGTCAAATCATCATGCCCCTTATGACCAGGGCTACACAC
GTGCTACAATGGCGTAAACAAAGAGAAGCGA-
ACTCGCGAGGGTAAGCAAATCTCAAAAATAACGTCTCAGTTCGGATTGTAGTCTGCA
ACTCGACTACATGAAGCTGGAATCGCTAGTAATCGCAGATCAGAATGCTGCGGTGA
ATACGTTCCCGGGTCTTGTACACACCGCCCGTCACACCATGGGAGTCAGTAACGCC
CGAAGTCAGTGACCCAACCGTAAGGAGGGAGCTGCCGAAGGTGGGACCGATAACT
GGGGTGAAGTCGTAACAAGGTAGCCGTATCGGAAGGTGCGGCTGGATCACCTCCT
T SEQ ID NO: 19 *Bacteroides thetaiotaomicron* Strain 19
ATGAAGAGTTTGATCCTGGCTCAGGATGAACGCTAGCTACAGGCTTAACACATGCA
AGTCGAGGGGCAGCATTTCAGTTTGCTTGCAAACTGGAGATGGCGACCGGCGCAC
GGGTGAGTAACACGTATCCAACCTGCCGATAACTCGGGGATAGCCTTTCGAAAGAA
AGATTAATACCCGATGGCATAAT-
AGAACCGCATGGTTTTTTTATTAAAGAATTTCGGTTATCGATGGGGATGCGTTCCAT
TAGGCAGTTGGTGAGGTAACGGCTCACCAAACCTTCGATGGATAGGGGTTCTGAGA
GGAAGGTCCCCCACATTGGAACTGAGACACGGTCCAAACTCCTACGGGAGGCAGC
AGTGAGGAATATTGGTCAATGGACG-
AGAGTCTGAACCAGCCAAGTAGCGTGAAGGATGACTGCCCTATGGGTTGTAAACTT
CTTTTATATGGGAATAAAGTTTTCCACGTGTGGAATTTTGTATGTACCATATGAATAA
GGATCGGCTAACTCCGTGCCAGCAGCCGCGGTAATACGGAGGATCCGAGCGTTAT
CCGGATTTATTGGGTTTAAAGGGAGCGTAGGTGGACAGTTAAGTCAGTTGTGAAAG
TTTGCGGCTCAACCGTAAAATTGCAGTTGATACTGGCTGTCTTGAGTACAGTAGAGG
TGGGCGGAATTCGTGGTGTAGCGGTGAAATGCTTAGATATCACGAAGAACTCCGAT
TGCGAAGGCAGCTCACTGGACTGCAACTGACACTGATGCTCGAAAGTGTGGGTATC
AAACAGGATTAGATACCCTGGTAGTCCACACAGTAAACGATGAATACTCGCTGTTTG
CGATATACAGTAAGCGGCCAAGCGAAAGCATTAAGTATTCCACCTGGGGAGTACGC
CGGCAAC-
GGTGAAACTCAAAGGAATTGACGGGGGCCCGCACAAGCGGAGGAACATGTGGTTT
AATTCGATGATACGCGAGGAACCTTACCCGGGCTTAAATTGCATTTGAATATATTGG
AAACAGTATAGTCGTAAGACAAATGTGAAGGTGCTGCATGGTTGTCGTCAGCTCGT
GCCGTGAGGTGTCGGCTTAAGTGCCATAACGAGCGCAACCCTTATCTTTAGTTACTA
ACAGGTCATGCTGAGGACTCTAGAGAGACTGCCGTCGTAAGATGTGAGGAAGGTG
GGGATGACGTCAAATCAGCACGGCCCTTACGTCCGGGGCTACACACGTGTTACAAT
GGGGGGTACAGAAGGCAGCTACCTGGTGACAGGATGCTAATCCCAAAAGCCTCTCT
CAGTTCGGATCGAAGTCTGCAACCCGACTTCGTGAAGCTGGATTCGCTAGTAATCG
CGCATCAGCCATGGCGCGGTGAATACGTTCCCGGGCCTTGTACACACCGCCCGTC
AAGCCATGAAAGCCGGGGGTACCTGAAGTACGTAACCGCAAGGAGCGTCCTAGGG
TAAAACTGGTAATTGGGGC SEQ ID NO: 20 Parabacteroides distasonis Strain 20
CGAAGAGTTTGATCCTGGCTCAGGATGAACGCTAGCGACAGGCTTAACACATGCAA
GTCGAGGGGCAGCACAG-GTAGCAATAC-
CGGGTGGCGACCGGCGCACGGGTGAGTAACGCGTATGCAACTTGCCTATCAGAGG
GGGATAACCCGGCGAAAGTCGGACTAATACCGCATGAAGCAGGGATCCCGCATGG
GAATATTTGCTAAAGATTCATCGCTGATAGATAGGCATGCGTTCCATTAGGCAGTTG
GCGGGGTAACAGCCCACCAAACCGACGATGGATAGGGGTTCTGAGAGGAAGGTCC
CCCACATTGGTACTGAGACACGGACCAAACTCCTACGGGAGGCAGCAGTGAGGAAT
ATTGGTCAATGGCCGAGAGGCTGAACCAGCCAAGTCGCGTGAGGGATGAAGGTTC
TATGGATCGTAAACCTCTTTTATAAGGGAATAAAGTGCGGGACGTGTCCCGTTTTGT
ATGTACCTTATGAATAAGGATCGGCTAACTCCGTGCCAGCAGCCGCGGTAATACGG
AGGATCCGAGCGTTATCCGGATTTATTGGGTTTAAAGGGTGCGTAGGCGGCCTTTT
AAGTCAGCGGTGAAAGTCTGTGGCTCAACCATAGAATTGCCGTTGAAACTGGGGGG -continued

| SEQUENCES |
| --- |

CTTGAGTATGTTTGAGGCAGGCGGAATGCGTGGTGTAGCGGTGAAATGCATAGATA
TCACGCAGAACCCCGATTGCGAAGGCAGCCTGCCAAGCCATGACTGACGCTGATG
CACGAAAGCGTGGGGATCAAACAGGATTAGATACCCTGGTAGTCCACGCAGTAAAC
GATGATCACTAGCTGTTTGCGATACACTGTAAGCGGCACAGCGAAAGCGTTAAGTG
ATCCACCTGGGGAGTACGCCGGCAACGGTGAAACTCAAAGGAATTGACGGGGGCC
CGCACAAGCGGAGGAACATGTGGTTTAATTCGATGATACGCGAGGAACCTTACCCG
GGTTTGAACGCATTCGGACCGAGGTGGAAACACCTTTTCTAGCAATAGCCGTTTGC
GAGGTGCTGCATGGTTGTCGTCAGCTCGTGCCGTGAGGTGTCGGCTTAAGTGCCAT
AACGAGCGCAACCCTTGCCACTAGTTACTAACAGGTAAAGCTGAGGACTCTGGTGG
GACTGCCAGCGTAAGCTGCGAGGAAGGCGGGGATGACGTCAAATCAGCACGGCCC
TTACATCCGGGGCGACACACGTGTTACAATGGCGTGGACAAAGGGAAGCCACCTG
GCGACAGGGAGCGAATCCCCAAACCACGTCTCAGTTCGGATCGGAGTCTGCAACC
CGACTCCGTGAAGCTGGATTCGCTAGTAATCGCGCATCAGCCATGGCGCGGTGAAT
ACGTTCCCGGGCCTTGTACACACCGCCCGTCAAGCCATGGGAGCCGGGGGTACCT
GAAGTCCGTAACCGCGAGGATCGGCCTAGGGTAAAACTGGTGACTGGGGCTAAGT
CGTAACAAG

SEQ ID NO: 21 *Escherichia coli* Strain 21
TTGAAGAGTTTGATCATGGCTCAGATTGAACGCTGGCGGCAGGCCTAACACATGCA
AGTCGAACGGTAACAGGAAGCAGCTTGCTGCTTTGCTGACGAGTGGCGGACGGGT
GAGTAATGTCTGGGAAACTGCCTGATGGAGGGGGATAACTACTGGAAACGGTAGCT
AATACCGCATAACGTCGCAAGACCAAAGAGGGGGACCTTCGGGCCTCTTGCCATCG
GATGTGCCCAGATGGGATTAGCTAGTAGGTGGGGTAACGGCTCACCTAGGCGACG
ATCCCTAGCTGGTCTGAGAGGATGACCAGCCACACTGGAACTGAGACACGGTCCAG
ACTCCTACGGGAGGCAGCAGTGGGGAATATTGCACAATGGGCGCAAGCCTGATGC
AGCCATGCCGCGTGTATGAAGAAGGCCTTCGGGTTGTAAAGTACTTTCAGCGGGGA
GGAAGGGAGTAAAGTTAATACCTTTGCTCATTGACGTTACCCGCAGAAGAAGCACC
GGCTAACTCCGTGCCAGCAGCCGCGGTAATACGGAGGGTGCAAGCGTTAATCGGA
ATTACTGGGCGTAAAGCGCACGCAGGCGGTTTGTTAAGTCAGATGTGAAATCCCCG
GGCTCAACCTGGGAACTGCATCTGATACTGGCAAGCTTGAGTCTCGTAGAGGGGG
GTAGAATTCCAGGTGTAGCGGTGAAATGCGTAGAGATCTGGAGGAATACCGGTGGC
GAAGGCGGCCCCCTGGACGAAGACTGACGCTCAGGTGCGAAAGCGTGGGGAGCAA
ACAGGATTAGATACCCTGGTAGTCCACGCCGTAAACGATGTCGACTTGGAGGTTGT
GCCCTTGAGGCGTGGCTTCCGGAGCTAACGCGTTAAGTCGACCGCCTGGGGAGTA
CGGCCGCAAGGTTAAAACTCAAATGAATTGACGGGGGCCCGCACAAGCGGTGGAG
CATGTGGTTTAATTCGATGCAACGCGAAGAACCTTACCTGGTCTTGACATCCACGGA
AGTTTTCAGAGATGAGAATGTGCCTTCGGGAACCGTGAGACAGGTGCTGCATGGCT
GTCGTCAGCTCGTGTTGTGAAATGTTGGGTTAAGTCCCGCAACGAGCGCAACCCTT
ATCCTTTGTTGCCAGCGGTCCGGCCGGGAACTCAAAGGAGACTGCCAGTGATAAAC
TGGAGGAAGGTGGGGATGACGTCAAGTCATCATGGCCCTTACGACCAGGGCTACA
CACGTGCTACAATGGCGCATACAAAGAGAAGCGACCTCGCGAGAGCAAGCGGACC
TCATAAAGTGCGTCGTAGTCCGGATTGGAGTCTGCAACTCGACTCCATGAAGTCGG
AATCGCTAGTAATCGTGGATCAGAATGCCACGGTGAATACGTTCCCGGGCCTTGTA
CACACCGCCCGTCACACCATGGGAGTGGGTTGCAAAAGAAGTAGGTAGCTTAACCT
TCGGGAGGGCGCTTACCACTTTGTGATTCATGACTGGGGTGAAGTCGTAACAAGGT
AACCGTAGGGGAACCTGCGGTTGGATCACCTCCTT SEQ ID NO: 22 *Bifidobacterium longum* Strain 22
TGGCTCAGGATGAACGCTGGCGGCGTGCTTAACACATGCAAGTCGAACGGGATCC
ATCAGGCTTTGCTTGGTGGTGAGAGTGGCGAACGGGTGAGTAATGCGTGACCGAC
CTGCCCCATACACCGGAATAGCTCCTGGAAACGGGTGGTAATGCCGGATGCTCCAG
TTGATCGCATGGTCTTCTGGGAAAGCTTTCGCGGTATGGGATGGGGTCGCGTCCTA
TCAGCTTGACGGCGGGGTAACGGCCCACCGTGGCTTCGACGGGTAGCCGGCCTGA
GAGGGCGACCGGCCACATTGGGACTGAGATACGGCCCAGACTCCTACGGGAGGCA
GCAGTGGGGAATATTGCACAATGGGCGCAAGCCTGATGCAGCGACGCCGCGTGAG
GGATGGAGGCCTTCGGGTTGTAAACCTCTTTTATCGGGGAGCAAGCGAGAGTGAGT
TTACCCGTTGAATAAGCACCGGCTAACTACGTGCCAGCAGCCGCGGTAATACGTAG
GGTGCAAGCGTTATCCGGAATTATTGGGCGTAAAGGGCTCGTAGGCGGTTCGTCGC
GTCCGGTGTGAAAGTCCATCGCTTAACGGTGGATCCGCGCCGGGTACGGGGGGC
TTGAGTGCGGTAGGGGAGACTGGAATTCCCGGTGTAACGGTGGAATGTGTAGATAT
CGGGAAGAACACCAATGGCGAAGGCAGGTCTCTGGGCCGTTACTGACGCTGAGGA
GCGAAAGCGTGGGGAGCGAACAGGATTAGATACCCTGGTAGTCCACGCCGTAAAC
GGTGGATGCTGGATGTGGGGCCCGTTCCACGGGTTCCGTGTCGGAGCTAACGCGT
TAAGCATCCCGCCTGGGGAGTACGGCCGCAAGGCTAAAACTCAAAGAAATTGACGG
GGGCCCGCACAAGCGGCGGAGCATGCGGATTAATTCGATGCAACGCGAAGAACCT
TACCTGGGCTTGACATGTTCCCGACGGTCGTAGAGATACGGCTTCCCTTCGGGGCG
GGTTCACAGGTGGTGCATGGTCGTCGTCAGCTCGTGTCGTGAGATGTTGGGTTAAG
TCCCGCAACGAGCGCAACCCTCGCCCCGTGTTGCCAGCGGATTATGCCGGGAACT
CACGGGGGACCGCCGGGGTTAACTCGGAGGAAGGTGGGGATGACGTCAGATCATC
ATGCCCCTTACGTCCAGGGCTTCACGCATGCTACAATGGCCGGTACAACGGGATGC
GACGCGGCGACGCGGAGCGGATCCCTGAAAACCGGTCTCAGTTCGGATCGCAGTC
TGCAACTCGACTGCGTGAAGGCGGAGTCGCTAGTAATCGCGAATCAGCAACGTCGC
GGTGAATGCGTTCCCGGGCCTTGTACACACCGCCCGTCAAGTCATGAAAGTGGGCA
GCACCCGAAGCCGGTGGCCTAACCCCTTGTGGGATGGAGCCGTCTAAGGTGAGGC
TCGTGATTGGGACTAAGTCGTAACAAGGTAGCCGTACCGGAAGGTGCGGCTGGATC
ACCTCCTT -continued

| SEQUENCES |
| --- |

SEQ ID NO: 23 *Absiella innocuum* Strain 23
ATGGAGAGTTTGATCCTGGCTCAGGATGAACGCTGGCGGCATGCCTAATACATGCA
AGTCGAACGAAGT-
TTCGAGGAAGCTTGCTTCCAAAGAGACTTAGTGGCGAACGGGTGAGTAACACGTAG
GTAACCTGCCCATGTGTCCGGGATAACTGCTGGAAACGGTAGCTAAAACCGGATAG
GTATACAGAGCGCATGCTCAGTATATTAAAGCGCCCATCAAGGCGTGAACATGGAT
GGACCTGCGGCGCATTAGCTAGTTGGTGAGGTAACGGCCCACCAAGGCGATGATG
CGTAGCCGGCCTGAGAGGGTAAACGGCCACATTGGGACTGAGACACGGCCCAAAC
TCCTACGGGAGGCAGCAGTAGGGAATTTTCGTCAATGGGGGAAACCCTGAACGAG
CAATGCCGCGTGAGTGAAGAAGGTCTTCGGATCGTAAAGCTCTGTTGTAAGTGAAG
AACGGCTCATAGAGGAAATGCTATGGGAGTGACGGTAGCTTACCAGAAAGCCACGG
CTAACTACGTGCCAGCAGCCGCGGTAATACGTAGGTGGCAAGCGTTATCCGGAATC
ATTGGGCGTAAAGGGTGCGTAGGTGGCGTACTAAGTCTGTAGTAAAAGGCAATGGC
TCAACCATTGTAAGCTATGGAAACTGGTATGCTGGAGTGCAGAAGAGGGCGATGGA
ATTCCATGTGTAGCGGTAAAATGCGTAGATATATGGAGGAACACCAGTGGCGAAGG
CGGTCGCCTGGTCTGTAACTGACACTGAGGCACGAAAGCGTGGGGAGCAAATAGG
ATTAGATACCCTAGTAGTCCACGCCGTAAACGATGAGAACTAAGTGTTGGAGGAATT
CAGTGCTGCAGTTAACGCAATAAGTTCTCCGCCTGGGGAGTATGCACGCAAGTGTG
AAACTCAAAGGAATTGACGGGGGCCCGCACAAGCGGTGGAGTATGTGGTTTAATTC
GAAGCAACGCGAAGAACCTTACCAGGCCTTGACATGGAAACAAATACCCTAGAGAT
AGGGGGATAATTATGGATCACACAGGTGGTGCATGGTTGTCGTCAGCTCGTGTCGT
GAGATGTTGGGTTAAGTCCCGCAACGAGCGCAACCCTTGTCGCATGTTACCAGCAT
CAAGTTGGGGACTCATGCGAGACTGCCGGTGACAAACCGGAGGAAGGTGGGGATG
ACGTCAAATCATCATGCCCCTTATGGCCTGGGCTACACACGTACTACAATGGCGGC
CACAAAGAGCAGCGACACAGTGATGTGAAGCGAATCTCATAAAGGTCGTCTCAGTT
CGGATTGAAGTCTGCAACTCGACTTCATGAAGTCGGAATCGCTAGTAATCGCAGAT
CAGCATGCTGCGGTGAATACGTTCTCGGGCCTTGTACACACCGCCCGTCAAACCAT
GGGAGTCAGTAATACCCGAAGCCGGTGGCATAACCGTAAGGAGTGAGCCGTCGAA
GGTAGGACCGA SEQ ID NO: 24 *Fusobacterium_A* sp Strain 24
AGAGTTTGATCCTGGCTCAGGATGAACGCTGACAGAATGCTTAACACATGCAAGTC
TA-
CTTGATCCTTCGGGTGATGGTGGGGACGGGTGAGTAACGCGTAAAGAACTTGCCC
TGCAGTCTGGGACAACATTTGGAAACGAATGCTAATACCGGATATTATGT-
ATTTCTCGCATGAGTTTTACATGAAAGCTATATGCGCTGCAGGAGAGCTTTGCGTCC
TATTAGCTAGTTGGTGAGGTAACGGCTCACCAAGGCCATGATAGGTAGCCGGCCTG
AGAGGGTGAACGGCCACAAGGGGACTGAGACACGGCCCTTACTCCTACGGGAGGC
AGCAGTGGGGAATATTGGACAATGGACCAAAAGTCTGATCCAGCAATTCTGTGTGC
ACGATGAAGTTTTTCGGAATGTAAAGTGCTTTCAGTTGGGACGAAGTAAGTGACGGT
ACCAACAGAAGAAGCGACGGCTAAATACGTGCCAGCAGCCGCGGTAATACGTATGT
CGCAAGCGTTATCCGGATTTATTGGGCGTAAAGCGCGTC-
TAGGCGGTTTGGTAAGTCTGATGTGAAAATGCGGGGCTCAACTCCGTATTGCGTTG
GAAACTG-
CTAAACTAGAGTACTGGAGAGGTGGGGGGAACTACAAGTGTAGAGGTGAAATTCGT
AGATATTTGTAGGAATGCCGATGGGGAAGCCAGCCCACTGGACAGATACTGACGCT
AAAGCGCGAAAGCGTGGGTAGCAAACAGGATTAGATAC-----
CCTGGTAGTCCACGCCGTAAACGATGATTACTAGGTGTTGGGGGTCGAACCTCAGC
GCCCAAGCTAACGCGATAAGTAATCCGCCTGGGGAGTACGTACGCAAGTATGAAAC
TCAAAGGAATTGACGGGGACCCGCACAAGCGGTGGAGCATGTGGTTTAATTCGACG
CAACGCGAGGAACCTTACCAGCGTTTGACATCCTAAGAAATTAGCAGAGATGCTTTT
GTGCCCCTTCGGGGGAACTTAGTGACAGGTGGTGCATGGCTGTCGTCAGCTCGTG
TCGTGAGATGTTGGGTTAAGTCCCGCAACGAGCGCAACCCCTTTCGTATGTTGCCA
TCATTAAGTTGGGCACTCATGCGATACTGCCTGCGATGAGCAGGAGGAAGGTGGG
GATGACGTCAAGTCATCATGCCCCTTATACGCTGGGCTACACACGTGCTACAATGG
GTAGTACAGAGAGTCGCAAACCTGCGAGGGGGAGCTAATCTCAGAAAACTATTCTC
AGTTCGGATTGTACTCTGCAACTCGAGTACATGAAGTTGGAATCGCTAGTAATCGCA
AATCAGCTATGTTGCGGTGAATACGTTCTCGGGTCTTGTACACACCGCCCGTCACA
CCACGAGAGTTGGTTGCACCTGAAGTAGCAGGCCTAACCGCAAGGAGGGATGCTC
CGAGGGTGTGATTAGCGATTGGGGTGAAGTCGTAACAAGGTATCCGTACGGGAAC
GTGCGGATGGATCACCTCCTT SEQ ID NO: 25 *Parabacteroides merdae* Strain 25
AGAGTTTGATCCTGGCTCAGGATGAACGCTAGCGACAGGCTTAACACATGCAAGTC
GAGGGGCAGCATGATTTGTAGCAATACAGATTGATGGCGACCGGCGCACGGGTGA
GTAACGCGTATGCAACTTACCTATCAGAGGGGGATAGCCCGGCGAAAGTCGGATTA
ATACCCCATAAAACAGGGGTCCCGCATGGGAATATTTGTTAAAGATTCATCGCTGAT
AGATAGGCATGCGTTCCATTAGGCAGTTGGGGGGTAACGGCCCACCAAACCGAC
GATGGATAGGGGTTCTGAGAGGAAGGTCCCCCACATTGGTACTGAGACACGGACC
AAACTCCTACGGGAGGCAGCAGTGAGGAATATTGGTCAATGGCCGAGAGGCTGAA
CCAGCCAAGTCGCGTGAAGGAAGAAGGATCTATGGTTTGTAAACTTCTTTTATAGGG
GAATAAAGTGGAGGACGTGTCCTTTTTTGTATGTACCCTATGAATAAGCATCGGCTA
ACTCCGTGCCAGCAGCCGCGGTAATACGGAGGATGCGAGCGTTATCCGGATTTATT
GGGTTTAAAGGGTGCGTAGGTGGTGATTTAAGTCAGCGGTGAAAGTTTGTGGCTCA
ACCATAAAATTGCCGTTGAAACTGGGTTACTTGAGTGTGTTTGAGGTAGGCGGAAT
GCGTGGTGTAGCGGTGAAATGCATAGATATCACGCAGAACTCCGATTGCGAAGGCA
GCTTACTAAACCATAACTGACACTGAAGCACGAAAGCGTGGGGATCAAACAGGATT -continued

| SEQUENCES |
| --- |

AGATACCCTGGTAGTCCACGCAGTAAACGATGATTACTAGGAGTTTGCGATACAATG
TAAGCTCTACAGCGAAAGCGTTAAGTAATCCACCTGGGGAGTACGCCGGCAACGGT
GAAACTCAAAGGAATTGACGGGGGCCCGCACAAGCGGAGGAACATGTGGTTTAATT
CGATGATACGCGAGGAACCTTACCCGGGTTTGAACGTAGTCTGACCGGAGTGGAAA
CACTCTTTCTAGCAATAGCAGATTACGAGGTGCTGCATGGTTGTCGTCAGCTCGTG
CCGTGAGGTGTCGGCTTAAGTGCCATAACGAGCGCAACCCTTATCACTAGTTACTA
ACAGGTGAAGCTGAGGACTCTGGTGAGACTGCCAGCGTAAGCTGTGAGGAAGGTG
GGGATGACGTCAAATCAGCACGGCCCTTACATCCGGGGCGACACACGTGTTACAAT
GGCATGGACAAAGGGCAGCTACCTGGTGACAGGATGCTAATCTCCAAACCATGTCT
CAGTTCGGATCGGAGTCTGCAACTCGACTCCGTGAAGCTGGATTCGCTAGTAATCG
CGCATCAGCCATGGCGCGGTGAATACGTTCCCGGGCCTTGTACACACCGCCCGTC
AAGCCATGGGAGCCGGGGGTACCTGAAGTCCGTAACCGCAAGGATCGGCCTAGGG
TAAAACTGGTGACTGGGGCTAAGTCGTAACAAGGTA

SEQ ID NO: 26 *Coprococcus_B* comes Strain 26
GAGAGTTTGATCCTGGCTCAGGATGAACGCTGGC-GG-
CGTGCTTAACACATGCAAGTCGAACGAAGCACTTACCTTTGA-TTCTTCGGA-
TGAAGGTTTTTG-
TGACTGAGTGGGGGACGGGTGAGTAACGCGTGGGTAACCTGCCTCATACAGGGGG
ATAACAGTTAGAAATGACTGCTAATACCGCATAAGACCACAGAGCTGCATGGCTCA
GTGGGAAAAACTCCGGTGGTATGAGATGGACCCGCGTCTGATTAGGTAGTTGGTGG
GGTAACGGCCTACCAAGCCAACGATCAGTAGCCGACCTGAGAGGGTGACCGGCCA
CATTGGGACTGAGACACGGCCCAAACTCCTACGGGAGGCAGCAGTGGGGAATATT
GCACAATGGGGGAAACCCTGATGCAGCGACGCCGCGTGAGCGAAGAAGTATTTCG
GTATGTAAAGCTCTATCAGCAGGGAAGAAAATGACGGTACCTGACTAAGAAGCACC
GGCTAAATACGTGCCAGCAGCCGCGGTAATACGTATGGTGCAAGCGTTATCCGGAT
TTACTGGGTGTAAAGGGAGCGTAGACGGCTGTGTAAGTCTGAAGTGAAAGCCCGG
GGCTCAACCCCGGGACTGCTTTGGAAACTATGCAGCTAGAGTGTCGGAGAGGTAAG
TGGAATTCCCAGTGTAGCGGTGAAATGCGTAGATATTGGGAGGAACACCAGTGGCG
AAGGCGGCTTACTGGACGATGACTGACGTTGAGGCTCGAAAGCGTGGGGAGCAAA
CAGGATTAGATACCCTGGTAGTCCACGCCGTAAACGATGACTACTAGGTGTCGGGG
AGCAGAGCTCTTCGGTGCCGCAGCAAACGCAATAAGTAGTCCACCTGGGGAGTAC
GTTCGCAAGAATGAAACTCAAAGGAATTGACGGGGACCCGCACAAGCGGTGGAGC
ATGTGGTTTAATTCGAAGCAACGCGAAGAACCTTACCTGCTCTTGACATCCCGGTGA
CCGG-
CATGTAATGATGCCTTTTCTTCGGAACACCGGTGACAGGTGGTGCATGGTTGTCGT
CAGCTCGTGTCGTGAGATGTTGGGTTAAGTCCCGCAACGAGCGCAACCCTTATCTT
CAGTAGCCAGCAATTCGGATGGGCACTCTGGAGAGACTGCCAGGGATAACCTGGA
GGAAGGTGGGGATGACGTCAAATCATCATGCCCCTTATGAGCAGGGCTACACACGT
GCTACAATGACGTAAACAAAGGGAAGCGAGCCTGCGAGGGTAAGCAAATCTCAAAA
ATAACGTCTCAGTTCGGATTGTAGTCTGCAACTCGACTACATGAAGCTGGAATCGCT
AGTAATCGCGAATCAGCATGTCGCGGTGAATACGTTCCCGGGTCTTGTACACACCG
CCCGTCACACCATGGGAGTTGGTAACGCCCGAAGTCAGTGACCCAACCGTAAGGA
GGGAGCTGCCGAAGGTGGGACCGATAACTGGGGTGAAGTCGTAACAAGGTAGCCG
TATCGGAAGGTGCGGCTGGATCACCTCC SEQ ID NO: 27 *Agathobacter rectale* Strain 27
AGAGTTTGATCCTGGCTCAGGATGAACGCTGGCGGCGTGCTTAACACATGCAAGTC
GAACGAAGCACTTTATTTGATTTCCTTCGGGACTGATTATTTTGTGACTGAGTGGCG
GACGGGTGAGTAACGCGTGGGTAACCTGCCTTGTACAGGGGGATAACAGTTGGAA
ACGGCTGCTAATACCGCATAAGCGCACGGCATCGCATGATGCAGTGTGAAAAACTC
CGGTGGTATAAGATGGACCCGCGTTGGATTAGCTAGTTGGTGAGGTAACGGCCCAC
CAAGGCGACGATCCATAGCCGACCTGAGAGGGTGACCGGCCACATTGGGACTGAG
ACACGGCCCAAACTCCTACGGGAGGCAGCAGTGGGGAATATTGCACAATGGGCGA
AAGCCTGATGCAGCGACGCCGCGTGAGCGAAGAAGTATTTCGGTATGTAAAGCTCT
ATCAGCAGGGAAGATAATGACGGTACCTGACTAAGAAGCACCGGCTAAATACGTGC
CAGCAGCCGCGGTAATACGTATGGTGCAAGCGTTATCCGGATTTACTGGGTGTAAA
GGGAGCGCAGGCGGTGCGGCAAGTCTGATGTGAAAGCCCGGGGCTCAACCCCGG
TACTGCATTGGAAACTGTCGTACTAGAGTGTCGGAGGGGTAAGCGGAATTCCTAGT
GTAGCGGTGAAATGCGTAGATATTAGGAGGAACACCAGTGGCGAAGGCGGCTTACT
GGACGATAACTGACGCTGAGGCTCGAAAGCGTGGGGAGCAAACAGGATTAGATAC
CCTGGTAGTCCACGCCGTAAACGATGAATACTAGGTGTTGGGAAGCATTGCTTCTC
GGTGCCGTCGCAAACGCAGTAAGTATTCCACCTGGGGAGTACGTTCGCAAGAATGA
AACTCAAAGGAATTGACGGGGACCCGCACAAGCGGTGGAGCATGTGGTTTAATTCG
AAGCAACGCGAAGAACCTTACCAAGTCTTGACATCCTTCTGACCGGTACTTAACCGT
ACCTTCTCTTCGGAGCAGGAGTGACAGGTGGTGCATGGTTGTCGTCAGCTCGTGTC
GTGAGATGTTGGGTTAAGTCCCGCAACGAGCGCAACCCTTATCTTTAGTAGCCAGC
GGTTCGGCCGGGCACTCTAGAGAGACTGCCAGGGATAACCTGGAGGAAGGCGGGG
ATGACGTCAAATCATCATGCCCCTTATGACTTGGGCTACACACGTGCTACAATGGC
GTAAACAAAGGGAAGCAAAGCTGTGAAGCCGAGCAAATCTCAAAAATAACGTCTCA
GTTCGGACTGTAGTCTGCAACCCGACTACACGAAGCTGGAATCGCTAGTAATCGCA
GATCAGAATGCTGCGGTGAATACGTTCCCGGGTCTTGTACACACCGCCCGTCACAC
CATGGGAGTTGGGAATGCCCGAAGCCAGTGACCTAACCGAAAGGAAGGAGCTGTC
GAAGGCAGGCTCGATAACTGGGGTGAAGTCGTAACAAGGTAGCCGTATCGGAAGG
TGCGGCTGGATCACCT -continued

| SEQUENCES |
| --- |

SEQ ID NO: 28 *Erysipelatoclostridium ramosum* Strain 28
GAGAGTTTGATCCTGGCTCAGGATGAACGCTGGCGGCGTGCCTAATACATGCAAGT
CGAACGCGAGCACTTGTGCTCGAGTGGCGAACGGGTGAGTAATACATAAGTAACCT
GCCCTAGACAGGGGGATAACTATTGGAAAC-
GATAGCTAAGACCGCATAGGTACGGACACTGCATGGTGACCGTATTAAAAGTGCCT
CAAAGCACTGGTAGAGGATGGACTTATGGCGCATTAGCTGGTTGGCGGGGTAACG
GCCCACCAAGGCGACGATGCGTAGCCGACCTGAGAGGGTGACCGGCCACACTGGG
ACTGAGACACGGCCCAGACTCCTACGGGAGGCAGCAGTAGGGAATTTTCGGCAAT
GGGGGAAACCCTGACCGAGCAACGCCGCGTGAAGGAAGAAGGTTTTCGGATTGTA
AACTTCTGTTATAAAGGAAGAACGGGGGCTACAGGAAATGGTAGCCGAGTGACGGT
ACTTTA--
TTAGAAAGCCACGGCTAACTACGTGCCAGCAGCCGCGGTAATACGTAGGTGGCAAG
CGTTATCCGGAATTATTGGGCGTAAAGAGGGAGCAGGGGGCAGCAAGGGTCTGTG
GTGAAAGCCTGAAGCTTAACTTCAGTAAGCCATAGAAACCAGGCAGCTAGAGTGCA
GGAGAGGATCGTGGAATTCCATGTGTAGCGGTGAAATGCGTAGATATATGGAGGAA
CACCAGTGGCGAAGGCGACGATCTGGCCTGCAACTGACGCTCAGTCCCGAAAGCG
TGGGGAGCAAATAGGATTAGATACCCTAGTAGTCCACGCCGTAAACGATGAGTACT
AAGTGTTGGATGTCAAAGTTCAGTGCTGCAGTTAACGCAATAAGTACTCCGCCTGA
GTAGTACGTTCGCAAGAATGAAACTCAAAGGAATTGACGGGGGCCCGCACAAGCG
GTGGAGCATGTGGTTTAATTCGAAGCAACGCGAAGAACCTTACCAGGTCTTGACAT
ACTCATAAAGGCTCCAGAGATGGAGAGATAGCTATATGAGATACAGGTGGTGCATG
GTTGTCGTCAGCTCGTGTCGTGAGATGTTGGGTTAAGTCCCGCAACGAGCGCAACC
CTTATCGTTAGTTACCATCATTAAGTTGGGGACTCTAGCGAGACTGCCAGTGACAAG
CTGGAGGAAGGCGGGGATGACGTCAAATCATCATG-CCCTTATGACCTGGGCT--
ACACGTGCTACAATGGATGGTGCAGAGAGAGGCGAGCCGCG-
GGCGAAACAAAAGCCCATAAAA-CCATT-
TCAGTTCCGGATTGTAGTCTGCAACTCGACTTTATTACATGAGAGTTGGAATCGCTA
GTAATCGCGAATCAGCATGTCGCGGTTTGAATACGTTCTCGGGCCTT-
ACCGCCCGTCACACCAA-AGGATTGATAACAC--G--GC-GGTGG-
CTAACCGCAAGGAAAG-
GCTGTCTAAGGTGGGATTGATGATTGGGGTAAAGTCGTAACGAAGGTATCCCTACG
GGAACGTGGGGATGGATCACCTCC SEQ ID NO: 29 *Clostridium_M citroniae* Strain 29
AGAGTTTGATCCTGGCTCAGGATGAACGCTGGCGGCGTGCCTAACACATGCAAGTC
GAACGAAGCAATTAGAAAGAAGTTTTCGGATGGATTTCTGATTGACTGAGTGGCGG
ACGGGTGAGTAACGCGTGGATAACCTGCCTCACACTGGGGGATAACAGTTAGAAAT
GGCTGCTAATACCGCATAAGCGCACAGTACCGCATGGTACGGTGTGAAAAACTCCG
GTGGTGTGAGATGGATCCGCGTCTGATTAGTTAGTTGGCGGGGTAACGGCCCACCA
AGACAGCGATCAGTAGCCGACCTGAGAGGGTGACCGGCCACATTGGGACTGAGAC
ACGGCCCAAACTCCTACGGGAGGCAGCAGTGGGGAATATTGCACAATGGGCGAAA
GCCTGATGCAGCGACGCCGCGTGAGTGAAGAAGTATTTCGGTATGTAAAGCTCTAT
CAGCAGGGAAGAAACTGACGGTACCTGACTAAGAAGCCCCGGCTAACTACGTGCCA
GCAGCCGCGGTAATACGTAGGGGGCAAGCGTTATCCGGATTTACTGGGTGTAAAG
GGAGCGTAGACGGCGAAGCAAGTCTGGAGTGAAAACCCAGGGCTCAACCCTGGGA
CTGCTTTGGAAACTGTTTTGCTAGAGTGTCGGAGAGGTAAGTGGAATTCCTAGTGTA
GCGGTGAAATGCGTAGATATTAGGAGGAACACCAGTGGCGAAGGCGGCTTACTGG
ACGATAACTGACGTTGAGGCTCGAAAGCGTGGGGAGCAAACAGGATTAGATACCCT
GGTAGTCCACGCCGTAAACGATGAATGCTAGGTGTTGGGGGGCAAAGCCCTTCGG
TGCCGTCGCAAACGCAATAAGCATTCCACCTGGGGAGTACGTTCGCAAGAATGAAA
CTCAAAGGAATTGACGGGGACCCGCACAAGCGGTGGAGCATGTGGTTTAATTCGAA
GCAACGCGAAGAACCTTACCAAGTCTTGACATCCCCCTGACCGGTCAGTAAAGTGA
CCTTTCCTTCGGGACAGGGGAGACAGGTGGTGCATGGTTGTCGTCAGCTCGTGTC
GTGAGATGTTGGGTTAAGTCCCGCAACGAGCGCAACCCTTATCCTTAGTAGCCAGC
AGGTAAAGCTGGGCACTCTAGGGAGACTGCCAGGGATAACCTGGAGGAAGGTGGG
GATGACGTCAAATCATCATGCCCCTTATGATTTGGGCTACACACGTGCTACAATGGC
GTAAACAAAGGGAAGCGACCCTGCGAAGGCAAGCAAATCCCAAAAATAACGTCCCA
GTTCGGACTGTAGTCTGCAACCCGACTACACGAAGCTGGAATCGCTAGTAATCGCG
AATCAGAATGTCGCGGTGAATACGTTCCCGGGTCTTGTACACACCGCCCGTCACAC
CATGGGAGTCAGCAACGCCCGAAGTCAGTGACCCAAC-CGAAAG-
GAGGGAGCTGCCGAAGGCGGGGCAGGTAACTGGGGTGAAGTCGTAACAAGGTAGC
CGTA SEQ ID NO: 30 *Bacteroides faecis* Strain 30
ATGAAGAGTTTGATCCTGGCTCAGGATGAACGCTAGCTACAGGCTTAACACATGCA
AGTCGAGGGGCATCAGGAAGAAAGCTTGCTTTCTTTGCTGGCGACCGGCGCACGG
GTGAGTAACACGTATCCAACCTGCCCTTTACTCGGGGATAGCCTTTCGAAAGAAAG
ATTAATACCCGATGGCATAATGATTCCGCATGGTTTCATTATTAAAGGATTCCGGTA
AAGGATGGGGATGCGTTCCATTAGGTTGTTGGTGAGGTAACGGCTCACCAAGCCTT
CGATGGATAGGGGTTCTGAGAGGAAGGTCCCCCACATTGGAACTGAGACACGGTC
CAAACTCCTACGGGAGGCAGCAGTGAGGAATATTGGTCAATGGGCGATAGCCTGAA
CCAGCCAAGTAGCGTGAAGGATGACTGCCCTATGGGTTGTAAACTTCTTTTATAAAG
GAATAAAGTCGGGTATGCATACCCGTTTGCATGTACTTTATGAATAAGGATCGGCTA
ACTCCGTGCCAGCAGCCGCGGTAATACGGAGGATCCGAGCGTTATCCGGATTTATT
GGGTTTAAAGGGAGCGTAGGTGGA-
TGTTTAAGTCAGTTGTGAAAGTTTGCGGCTCAACCGTAAAATTGCAGTTGATACTGG
CTGTCTTGAGTGCAGTTGAGGCAGGCGGAATTCGTGGTGTAGCGGTGAAATGCTTA -continued

| SEQUENCES |
| --- |

GATATCACGAAGAACTCCGATTGCGAAGGCAGCCTGCTAAGCTGCAACTGACATTG
AGGCTCGAAAGTGTGGGTATCAAACAGGATTAGATACCCTGGTAGTCCACACGGTA
AACGATGAATACTCGCTGTTTGCGATATACGGCAAGCGGCCAAGCGAAAGCGTTAA
GTATTCCACCTGGGGAGTACGCCGGCAACGGTGAAACTCAAAGGAATTGACGGGG
GCCCGCACAAGCGGAGGAACATGTGGTTTAATTCGATGATACGCGAGGAACCTTAC
CCGGGCTTAAATTGCAGTGGAATGATGTGGAAACATGTCAGTGAGCAATCACCGCT
GTGAAGGTGCTGCATGGTTGTCGTCAGCTCGTGCCGTGAGGTGTCGGCTTAAGTGC
CATAACGAGCGCAACCCTTATCTTTAGTTACTAACAGGTGATGCTGAGGACTCTGGA
GAGACTGCCATCGTAAGATGTGAGGAAGGTGGGGATGACGTCAAATCAGCACGGC
CCTTACGTCCGGGGCTACACACGTGTTACAATGGGAGGTACAGAAGGCAGCTACCC
GGCGACGGGATGCCAATCCCCAAAACCTCTCTCAGT

SEQ ID NO: 31 *Bacteroides ovatus* Strain 31
ATGAAGAGTTTGATCCTGGCTCAGGATGAACGCTAGCTACAGGCTTAACACATGCA
AGTCGAGGGGCAGCATGGTCTTAGCTTGCTAAGGCTGATGGCGACCGGCGCACGG
GTGAGTAACACGTATCCAACCTGCCGTCTACTCTTGGCCAGCCTTCTGAAAGGAAG
ATTAATCCAGGATGGGATCATGAGTTCACATGTCCGCATGATTAAAGGTATTTTCCG
GTAGACGATGGGGATGCGTTCCATTAGATAGTTGGCGGGGTAACGGCCCACCAAAC
CGACGATGGATAGGGGTTCTGAGAGGAAGGTCCCCCACATTGGTACTGAGACACG
GACCAAACTCCTACGGGAGGCAGCAGTGAGGAATATTGGTCAATGGGCGAGAGCC
TGAACCAGCCAAGTAGCGTGAAGGATGACTGCCCTATGGGTTGTAAACTTCTTTTAT
AAGGGAATAAAGTCGGGTATGCATACCCGTTTGCATGTACTTTATGAATAAGGATCG
GCTAACTCCGTGCCAGCAGCCGCGGTAATACGGAGGATCCGAGCGTTATCCGGATT
TATTGGGTTTAAAGGGAGCGTAGGTGGACGTTTAAGTCAGTTGTGAAAGTTTGCGG
CTCAACCGTAAAATTGCAGTTGATACTGGATGTCTTGAGTGCAGTTGAGGCAGGCG
GAATTCGTGGTGTAGCGGTGAAATGCTTAGATATCACGAAGAACTCCGATTGCGAA
GGCAGCCTGCTAAGCTGCAACTGACATTGAGGCTCGAAAGTGTGGGTATCAAACAG
GATTAGATACCCTGGTAGTCCACACGGTAAACGATGAATACTCGCTGTTTGCGATAT
ACGGCAAGCGGCCAAGCGAAAGCGTTAAGTATTCCACCTGGGGAGTACGCCGGCA
ACGGTGAAACTCAAAGGAATTGACGGGGGCCCGCACAAGCGGAGGAACATGTGGT
TTAATTCGATGATACGCGAGGAACCTTACCCGGGCTTAAATTGCAGACGAATTACGA
GGAAACTTGTAAGCCGCAAGGCGTCTGTGAAGGTGCTGCATGGTTGTCGTCAGCTC
GTGCCGTGAGGTGTCGGCTTAAGTGCCATAACGAGCGCAACCCTTATCTTTAGTTA
CTAACAGGTTATGCTGAGGACTCTAGAG-
AGACTGCCATCGTAAGATGTGAGGAAGGTGGGGATGACGTCAAATCAGCACGGCC
CTTACGTCCGGGGCTACACACGTGTTACAATGGGGGGTACAGAGGGCCGCTACCA
CGCGAGTGGATGCCAATCCCTAAAACCCCTCTCAGTTCGGACTGGAGTCTGCAACC
CGACTCCACGAAGCTGGATTCGCTAGTAATCGCGCATCAGCCACGGCGCGGTGAAT
ACGTTCCCGGGCCTTGTACACACCGCCCGTCAAGCCATGGGAGCCGGGGGTACCT
GAAGTGCGTAACCGCGAGGATCGCCCTAGGGTAAAACTGGTGACTGGGGCTAAGT
CGTAACAAGGTAGCCGTACCGGAAG SEQ ID NO: 32 *Bifidobacterium pseudocatenulatum* Strain 32
TTCGATTCTGGCTCAGGATGAACGCTGGCGGCGTGCTTAACACATGCAAGTCGAAC
GGGATCCATCAGGCTTTGCTTGGTGGTGAGAGTGGCGAACGGGTGAGTAATGCGT
GACCGACCTGCCCCATACACCGGAATAGCTCCTGGAAACGGGTGGTAATGCCGGA
TGCTCCGACTCCTCGCATGGGGTGTCGGGAAAGATTTCATCGGTATGGGATGGGGT
CGCGTCCTATCAGGTAGTCGGGGGGGTAACGGCCCACCGAGCCTACGACGGGTAG
CCGGCCTGAGAGGGCGACCGGCCACATTGGGACTGAGATACGGCCCAGACTCCTA
CGGGAGGCAGCAGTGGGGAATATTGCACAATGGGCGCAAGCCTGATGCAGCGACG
CCGCGTGCGGGATGACGGCCTTCGGGTTGTAAACCGCTTTTGATCGGGAGCAAGC
CTTCGGGTGAGTGTACCTTTCGAATAAGCACCGGCTAACTACGTGCCAGCAGCCGC
GGTAATACGTAGGGTGCAAGCGTTATCCGGAATTATTGGGCGTAAAGGGCTCGTAG
GCGGTTCGTCGCGTCCGGTGTGAAAGTCCATCGCTTAACGGTGGATCTGCGCCGG
GTACGGGGGGGCTGGAGTGCGGTAGGGGAGACTGGAATTCCCGGTGTAACGGTGG
AATGTGTAGATATCGGGAAGAACACCAATGGCGAAGGCAGGTCTCTGGGCCGTTAC
TGACGCTGAGGAGCGAAAGCGTGGGGAGCGAACAGGATTAGATACCCTGGTAGTC
CACGCCGTAAACGGTGGATGCTGGATGTGGGGCCCGTTCCACGGGTTCCGTGTCG
GAGCTAACGCGTTAAGCATCCCGCCTGGGGAGTACGGCCGCAAGGCTAAAACTCA
AAGAAATTGACGGGGGCCCGCACAAGCGGCGGAGCATGCGGATTAATTCGATGCA
ACGCGAAGAACCTTACCTGGGCTTGACATGTTCCCGACAGCCGTAGAGATATGGCC
TCCCTTCGGGGGGGGTTCACAGGTGGTGCATGGTCGTCGTCAGCTCGTGTCGTGA
GATGTTGGGTTAAGTCCCGCAACGAGCGCAACCCTCGCCCTGTGTTGCCAGCACGT
CATGGTGGGAACTCACGGGGGACCGCCGGGGTCAACTCGGAGGAAGGTGGGGAT
GACGTCAGATCATCATGCCCCTTACGTCCAGGGCTTCACGCATGCTACAATGGCCG
GTACAACGGGATGCGACACGGCGACGTGGAGCGGATCCCTGAAAACCGGTCTCAG
TTCGGATTGGAGTCTGCAACCCGACTCCATGAAGGGGGGAGTCGCTAGTAATCGCGG
ATCAGCAACGCCGCGGTGAATGCGTTCCCGGGCCTTGTACACACCGCCCGTCAAG
TCATGAAAGTGGGTAGCACCCGAAGCCGGTGGCCTAACCCTTTGTGGATGGAGCC
GTCTAAGGTGAGACTCGTGATTGGGACTAAGTCGTAACAAGGTAGCCGTACCGGAA
GGTGCGGCTGGATCACC SEQ ID NO: 33 *Anaerostipes caccae* Strain 33
GCTTAACACATG-
CAAGTCGAACGAAGCATTTAGGATTGAAGTTTTCGGATGGATTTCCTATATGACTGA
GTGGCGGACGGGTGAGTAACGCGTGGGGAACCTGCCCTATACAGGGGGATAACAG
CTGGAAACGGCTGCTAATACCGCATAAGCGCACAGAATCGCATGATTCAGTGTGAA -continued

| SEQUENCES |
|---|
| AAGCCCTGGCAGTATAGGATGGTCCCGCGTCTGATTAGCTGGTTGGTGAGGTAACG<br>GCTCACCAAGGCGACGATCAGTAGCCGGCTTGAGAGAGTGAACGGCCACATTGGG<br>ACTGAGACACGGCCCAAACTCCTACGGGAGGCAGCAGTGGGGAATATTGCACAAT<br>GGGGG-<br>AAACCCTGATGCAGCGACGCCGCGTGAGTGAAGAAGTATTTCGGTATGTAAAGCTC<br>TATCAGCAGGGAAGAAAACAGACGGTACCTGACTAAGAAGCCCCGGCTAACTACGT<br>GCCAGCAGCCGCGGTAATACGTAGGGGGCAAGCGTTATCCGGAATTACTGGGTGT<br>AAAGGGTGCGTAGGTGGCATGGTAAGTCAGAAGTGAAAGCCCGGGGCTTAACCCC<br>GGGACTGCTTTTGAAACTGTCATGCTGGAGTGCAGGAGAGGTAAGCGGAATTCCTA<br>GTGTAGCGGTGAAATGCGTAGATATTAGGAGGAACACCAGTGGCGAAGGCGGCTTA<br>CTGGACTGTCACTGACACTGATGCACGAAAGCGTGGGGAGCAAACAGGATTAGATA<br>CCCTGGTAGTCCACGCCGTAAACGATGAATACTAGGTGTCGGGGCCGTAGAGGCTT<br>CGGTGCCGCAGCAAACGCAGTAAGTATTCCACCTGGGGAGTACGTTCGCAAGAATG<br>AAACTCAAAGGAATTGACGGGGACCCGCACAAGCGGTGGAGCATGTGGTTTAATTC<br>GAAGCAACGCGAAGAACCTTACCTGGTCTTGACATCCCAATGACCGAACCTTAACC<br>GGTTTTTTCTTTCGAGACATTGGAGACAGGTGGTGCATGGTTGTCGTCAGCTCGTGT<br>CGTGAGATGTTGGGTTAAGTCCCGCAACGAGCGCAACCCCTATCTTTAGTAGCCAG<br>CATTTAAGGTGGGCACTCTAGAGAGACTGCCAGGGATAACCTGGAGGAAGGTGGG<br>GACGACGTCAAATCATCATGCCCCTTATGGCCAGGGCTACACACGTGCTACAATGG<br>CGTAAACAAAGGGAAGCGAAGTCGTGAGGCGAAGCAAATCCCAGAAATAACGTCTC<br>AGTTCGGATTGTAGTCTGCAACTCGACTACATGAAGCTGGAATCGCTAGTAATCGTG<br>AATCAGAATGTCACGGTGAATACGTTCCCGGGTCTTGTACACACCGCCCGTCACAC<br>CATGGGAGTCAGTAACGCCCGAAGTCAGTGACCCAACCGCAAGGAGGGAGCTGCC<br>GAAGGTGGGACCGATAACTGGGGTGAAGTCGTAACAAGG |
| SEQ ID NO: 34 *Bifidobacterium adolescentis* Strain 34<br>TGTGGAGGGTTCGATTCTGGCTCAGGATGAACGCTGGCGGCGTGCTTAACACATGC<br>AAGTCGAACGGGATC-CCAGGAGCTTGCTCCTGG-<br>GTGAGAGTGGCGAACGGGTGAGTAATGCGTGACCGACCTGCCCCATACACCGGAA<br>TAGCTCCTGGAAACGGGTGGTAATGCCGGATGCTCCAGTTGGATGCATGTCCTTCT<br>GGGAAAGATTC-<br>ATCGGTATGGGATGGGGTCGCGTCCTATCAGCTTGATGGGGGGGTAACGGCCCAC<br>CATGGCTTCGACGGGTAGCCGGCCTGAGAGGGCGACCGGCCACATTGGGACTGAG<br>ATACGGCCCAGACTCCTACGGGAGGCAGCAGTGGGGAATATTGCACAATGGGCGC<br>AAGCCTGATGCAGCGACGCCGCGTGCGGGATGACGGCCTTCGGGTTGTAAACCGC<br>TTTTGACTGGGAGCAAGCCCTTCGGGGTGAGTGTACCTTTCGAATAAGCACCGGCT<br>AACTACGTGCCAGCAGCCGCGGTAATACGTAGGGTGCAAGCGTTATCCGGAATTAT<br>TGGGCGTAAAGGGCTCGTAGGCGGTTCGTCGCGTCCGGTGTGAAAGTCCATCGCT<br>TAACGGTGGATCCGCGCCGGGTACGGGGGGCTTGAGTGCGGTAGGGGAGACTG<br>GAATTCCCGGTGTAACGGTGGAATGTGTAGATATCGGGAAGAACACCAATGGCGAA<br>GGCAGGTCTCTGGGCCGTCACTGACGCTGAGGAGCGAAAGCGTGGGGAGCGAACA<br>GGATTAGATACCCTGGTAGTCCACGCCGTAAACGGTGGATGCTGGATGTGGGGAC<br>CATTCCACGGTCTCCGTGTCGGAGCCAACGCGTTAAGCATCCCGCCTGGGGAGTA<br>CGGCCGCAAGGCTAAAACTCAAAGAAATTGACGGGGGCCCGCACAAGCGGCGGAG<br>CATGCGGATTAATTCGATGCAACGCGAAGAACCTTACCTGGGCTTGACATGTTCCC<br>GACAGCCCCAGAGATGGGGCCTCCCTTCGGGGGGGGTTCACAGGTGGTGCATGGT<br>CGTCGTCAGCTCGTGTCGTGAGATGTTGGGTTAAGTCCCGCAACGAGCGCAACCCT<br>CGCCCTGTGTTGCCAGCACGTCGTGGTGGGAACTCACGGGGGACCGCCGGGGTCA<br>ACTCGGAGGAAGGTGGGGATGACGTCAGATCATCATGCCCCTTACGTCCAGGGCTT<br>CACGCATGCTACAATGGCCGGTACAACGGGATGCGACACT-<br>GTGAGGTGGAGCGGATCCCTTAAAACCGGTCTCAGTTCGGATTGGAGTCTGCAACC<br>CGACTCCATGAAGGGGAGTCGCTAGTAATCGCGGATCAGCAACGCCGCGGTGAA<br>TGCGTTCCCGGGCCTTGTACACACCGCCCGTCAAGTCATGAAAGTGGGTAGCACCC<br>GAAGCCGGTGGCCCAACCTTTTTGGGGGAGCCGTCTAAGGTGAGACTCGTGATT<br>GGGACTAAGTCGTAACAAGGTAGCCGTACCGGAAGGTGCGGCTGGATCACCTCCTT<br>T |
| SEQ ID NO: 35 *Agathobaculum* sp MUR_P3C8a Strain 35<br>AGTTTGATCCTGGCTCAGGATGAACGCTGGCGGCGTGCCTAACACATGCAAGTCGA<br>ACGGGGTTATTTTGGAAAATCCTTCGGGATTGGAATTCTT--<br>AACCTAGTGGCGGACGGGTGAGTAACGCGTGAGCAATCTGCCTTTAAGAGGGGGA<br>TAACAGTCGGAAACGGCTGCTAATACCGCATAAAGCATTGAATTCGCATGTTTTCGA<br>TGCCAAAGGAGCAATCCGCTTTTAGATGAGCTCGCGTCTGATTAGCTAGTTGGCGG<br>GGTAACGGCCCACCAAGGCGACGATCAGTAGCCGGACTGAGAGGTTGAACGGCCA<br>CATTGGGACTGA-GACACGGCCCAGACTCCTA-<br>CGGGAGGCAGCAGTGGGGAATATTGCGCAATGGGGGGAACCCTGACGCAGCAACG<br>CCGCGTGATTGAAGAAGGCCTTCGGGTTGTAAAGATCTTTAATCAGGGACGAAAC--<br>ATGACGGTACCTGAAGAATAAGCTCCGGCTAACTACGTGCCAGCAGCCGCGGTAAT<br>ACGTAGGGAGCAAGCGTTATCCGGATTTACTGGGTGTAAAGGGCGCGCAGGGGGG<br>CCGGCAAGTTGGAAGTGAAATCCGGGGGCTTAACCCCCGAACTGCTTTCAAAACTG<br>CTGGTCTTGAGTGATGGAGAGGCAGGCGGAATTCCGTGTGTAGCGGTGAAATGCG<br>TAGATATACGGAGGAACACCAGTGGCGAAGGCGGCCTGCTGGACATTAACTGACG<br>CTGAGGCGCGAAAGCGTGGGGAGCAAACAGGATTAGATACCCTGGTAGTCCACGC<br>CGTAAACGATGGATACTAGGTGTGGGAGGTATTGACCCCTTCCGTGCCGCAGTTAA<br>CACAATAAGTATCCCACCTGGGGAGTACGGCCGCAAGGTTGAAACTCAAAGGAATT<br>GACGGGGGCCCGCACAAGCAGTGGAGTATGTGGTTTAATTCGAAGCAACGCG-<br>AAGAACCTTACCAGGCCTTGACATCCCGATGACCGGTCTAGAGATAGACCTTCTCTT |

-continued

| SEQUENCES |
| --- |
| CGGAGCATCGGAGACAGGTGGTGCATGGTTGTCGTCAGCTCGTGTCGTGAGATGTT GGGTTAAGTCCCGCAACGAGCGCAACCCTTAC- GGTTAGTTGATACGCAAGATCACTCTAGCCGGACTGCCGTTGACAAAACGGAGGAA GGTGGGGACGACGTCAAATCATCATGCCCCTTATGGCCTGGGCTACACACGTACTA CAATGGCAGTCATACAGAGGGAAGCAAAATCGCGAGGTGGAGCAAATCCCTAAAAG CTGTCCCAGTTCAGATTGCAGGCTGCAACCCGCCTGCATGAAGTCGGAATTGCTAG TAATCGCGGATCAGCATGCCGCGGTGAATACGTTCCCGGGCCTTGTACACACCGCC CGTCACACCATGAGAGCCGTCAATACCCGAAGTCCGTAGCCTAACCGTAAGGAGGG CGCGGCCGAAGGTAGGGGTGGTAATTAGGGTGAAGTCGT |
| SEQ ID NO: 36 *Phascolarctobacterium faecium* MUR_P6E9 Strain 36 ATCCTGGCTCAGGACGAACGCTGGCGGCGTGCCTAACACATGCAAGTCGAACGGA GAATTTTATTTCGGTAGAATTCTTAGTGGCGAAGGGGTGAGTAACGCGTAGGCAAC CTGCCCTTTAGACGGGGACAACATTCCGAAAGGAGTGCTAATACCGGATGTGATCA TCGTGCCGCATGGCAGGATGAAGAAAGATGGCCTCTACAAGTAAGCTATCGCTAAA GGATGGGCCTGCGTCTGATTAGCTAGTTGGTAGTGTAACGGACTACCAAGGCGATG ATCAGTAGCCGGTCTGAGAGGATGAACGGCCACATTGGGACTGAGACACGGCCCA AACTCCTACGGGAGGCAGCAGTGGGGAATCTTCCGCAATGGACGAAAGTCTGACG GAGCAACGCCGCGTGAGTGATGAAGGATTTCGGTCTGTAAAGCTCTGTTGTTTATG ACGAACGTGCAGTGTGTGAACAATGCATTGCAATGACGGTAGTAAACGAGGAAGCC ACGGCTAACTACGTGCCAGCAGCCGCGGTAATACGTAGGTGGCGAGCGTTGTCCG GAATTATTGGGCGTAAAGAGCATGTAGGCGGCTTAATAAGTCGAGCGTGAAAATGC GGGGCTCAACCCCGTATGGCGCTGGAAACTGTTAGGCTTGAGTGCAGGAGAGGAA AGGGGAATTCCCAGTGTAGCGGTGAAATGCGTAGATATTGGGAGGAACACCAGTGG CGAAGGCGCCTTTCTGGACTGTGTCTGACGCTGAGATGCGAAAGCCAGGGTAGCG AACGGGATTAGATACCCCGGTAGTCCTGGCCGTAAACGATGGGTACTAGGTGTAGG AGGTATCGACCCCTTCTGTGCCGGAGTTAACGCAATAAGTACCCCGCCTGGGGAGT ACGGCCGCAAGGTTGAAACTCAAAGGAATTGACGGGGGCCCGCACAAGCGGTGGA GTATGTGGTTTAATTCGACGCAACGCGAAGAACCTTACCAAGGCTTGACATTGATTG AACGCTCTAGAGATAGAGCTTTCCCTTCGGGGACAAGAAAACAGGTGGTGCATGGC TGTCGTCAGCTCGTGTCGTGAGATGTTGGGTTAAGTCCCGCAACGAGCGCAACCCC TATCCTATGTTACCAGCAAGTAAAGTTGGGGACTCATGGGAGACTGCCAGGGACAA CCTGGAGGAAGGCGGGGATGACGTCAAGTCATCATGCCCCTTATGTCTTGGGCTAC ACACGTACTACAATGGTCGGAAACAGAGGGAAGCGAAGCCGCGAGGCAGAGCAAA CCCCAGAAACCCGATCTCAGTTCGGATCGCAGGCTGCAACCCGCCTGCGTGAAGT CGGAATCGCTAGTAATCGCAGGTCAGCATACTGCGGTGAATACGTTCCCGGGCCTT GTACACACCGCCCGTCACACCACGAAAGTTGGTAACACCCGAAGCCGGTGAGGTAA CCTATAAGGAGCCAGCCGTCTAAGGTGGGGCCGATGATTGGGGTGAAGTCGTAAC AAGGTAGC |
| SEQ ID NO: 37 *Akkermansia muciniphila* Strain 37 AGAGTTTGATTCTGGCTCAGAACGAACGCTGGGGGCGTGGATAAGACATGCAAGTC GAACGAGAGAATTGCTAGCTTGCTAATAATTCTCTAGTGGCGCACGGGTGAGTAAC ACGTGAGTAACCTGCCCCCAAGAGTGGGATAGCCCCGGGAAACTGGGATTAATACC GCATAAAATCGCAAGATTAAAGCAGCAATGCGCTTGGGGATGGGCTCGCGTCCTAT TAGTTAGTTGGTGAGGTAACGGCTCACCAAGGCGATGACGGGTAGCCGGTCTGAG AGGATGTCCGGCCACACTGGAACTGAGACACGGTCCAGACACCTACGGGTGGCAG CAGTCGAGAATCATTCACAATGGGGGAAACCCTGATGGTGCGACGCCGCGTGGGG GAATGAAGGTCTTCGGATTGTAAACCCCTGTCATGTGGGAGCAAATTAAAAAGATAG TACCACAAGAGGAAGAGACGGCTAACTCTGTGCCAGCAGCCGCGGTAATACAGAG GTCTCAAGCGTTGTTCGGAATCACTGGGCGTAAAGCGTGCGTAGGCGGTTTCGTAA GTCGTGTGTGAAAGGCGGGGGCTCAACCCCCGGACTGCACATGATACTGCGAGAC TAGAGTAATGGAGGGGGAACCGGAATTCTCGGTGTAGCAGTGAAATGCGTAGATAT CGAGAGGAACACTCGTGGCGAAGGGGGGTTCCTGGACATTAACTGACGCTGAGGC ACGAAGGCCAGGGGAGCGAAAGGGATTAGATACCCCTGTAGTCCTGGCAGTAAAC GGTGCACGCTTGGTGTGCGGGGAATCGACCCCCTGCGTGCCGGAGCTAACGCGTT AAGCGTGCCGCCTGGGGAGTACGGTCGCAAGATTAAAACTCAAAGAAATTGACGGG GACCCGCACAAGCGGTGGAGTATGTGGCTTAATTCGATGCAACGCGAAGAACCTTA CCTGGGCTTGACATGTAATGAACAACATGTGAAAGCATGCGACTCTTCGGAGGCGT TACACAGGTGCTGCATGGCCGTCGTCAGCTCGTGTCGTGAGATGTTTGGTTAAGTC CAGCAACGAGCGCAACCCCTGTTGCCAGTTACCAGCACGTAAAGGTGGGGACTCT GGCGAGACTGCCCAGATCAACTGGGAGGAAGGTGGGGACGACGTCAGGTCAGTAT GGCCCTTATGCCCAGGGCTGCACACGTACTACAATGCCCAGTACAGAGGGGGCCG AAGCCGCGAGGCGGAGGAAATCCTAAAAACTGGGCCCAGTTCGGACTGTAGGCTG CAACCCGCCTACACGAAGCCGGAATCGCTAGTAATGGCGCATCAGCTACGGCGCC GTGAATACGTTCCCGGGTCTTGTACACACCGCCCGTCACATCATGGAAGCCGGTCG CACCCGAAGTATCTGAAGCCAACCGCAAGGAGGCAGGGTCCTAAGGTGAGACTGG TAACTGGGATGAAGTCGTAACAAGGTAGCCGTAGGGGAACCTGCGGCTGGATCAC CTCCTTT |
| SEQ ID NO: 38 *Barnesiella intestinihomins* Strain 38 GATGAACGCTAGCGACAGGCCTAACACATGCAAGTCGAGGGGCAGCGAAGAGGTA GCAATACCTCTGTCGGCGACCGGCGCACGGGTGAGTAACACGTATGCAATCCACCT GTAACAGGGGGATAACCCGGAGAAATCCGGACTAATACCCCATAATATGGGCGCTC CGCATGGAGAGTTCATTAAAGAGAGCAATTTTGGTTACAGACGAGCATGCGCTCCA TTAGCCAGTTGGGGGGGTAACGGCCCACCAAAGCGACGATGGATAGGGGTTCTGA GAGGAAGGTCCCCCACATTGGAACTGAGACACGGTCCAAACTCCTACGGGAGGCA |

-continued

| SEQUENCES |
| --- |

GCAGTGAGGAATATTGGTCAATGGTCGGCAGACTGAACCAGCCAAGTCGCGTGAG
GGAAGACGGCCCTACGGGTTGTAAACCTCTTTTGTCGGAGAGTAAAGTACGCTACG
TGTAGCGTATTGCAAGTATCCGAAGAAAAAGCATCGGCTAACTCCGTGCCAGCAGC
CGCGGTAATACGGAGGATGCGAGCGTTATCCGGATTTATTGGGTTTAAAGGGTGCG
TAGGCGGCACGCCAAGTCAGCGGTGAAATTTCCGGGCTCAACCCGGAGTGTGCCG
TTGAAACTGGCGAGCTAGAGTGCACAAGAGGCAGGCGGAATGCGTGGTGTAGCGG
TGAAATGCATAGATATCACGCAGAACCCCGATTGCGAAGGCAGCCTGCTAGGGTGA
AACAGACGCTGAGGCACGAAAGCGTGGGTATCGAACAGGATTAGATACCCTGGTAG
TCCACGCAGTAAACGATGAATACTAACTGTTTGCGATACAATGTAAGCGGTACAGCG
AAAGCGTTAAGTATTCCACCTGGGGAGTACGCCGGCAACGGTGAAACTCAAAGGAA
TTGACGGGGGCCCGCACAAGCGGAGGAACATGTGGTTTAATTCGATGATACGCGA
GGAACCTTACCCGGGCTCAAACGCAGGGGGAATGTCGGTGAAAGCCGGCAGCTAG
TAATAGTCACCTGCGAGGTGCTGCATGGTTGTCGTCAGCTCGTGCCGTGAGGTGTC
GGCTTAAGTGCCATAACGAGCGCAACCCCTATCGACAGTTACTAACGGGTGAAGCC
GAGGACTCTGTCGAGACTGCCGGCGCAAGCCGCGAGGAAGGTGGGGATGACGTCA
AATCAGCACGGCCCTTACGTCCGGGGCGACACACGTGTTACAATGGCAGGTACAGA
AGGCAGCCAGTCAGCAATGACGCGCGAATCCCGAAAACCTGTCTCAGTTCGGATTG
GAGTCTGCAACCCGACTCCATGAAGCTGGATTCGCTAGTAATCGCGCATCAGCCAT
GGCGCGGTGAATACGTTCCCGGGCCTTGTACACACCGCCCGTCAAGCCATGGAAG
CCGGGAGTACCTGAAGCATGCAACCGCAAGGAGCGTACGAAGGTAATACCGGTAA
CTGGGGCTAAGTCGTAACAAGGTAGCCGTACCGGAAGG

SEQ ID NO: 39 *Bilophila wadsworthia* Strain 39
AGAGTTTGATTCTGGCTCAGATTGAACGCTGGGGGCGTGCTTAACACATGCAAGTC
GAACGTGAAAG-TCCTTCGGGGC-
GAGTAAAGTGGCGCACGGGTGAGTAACGCGTGGATAATCTACCCTTAAGATGGGGA
TAACGGCTGGAAACGGTCGCTAATACCGAATACGCTCCCGATTTTATCGTTGGGGG
GAAAGATGGCCTCTGCTTGCAAGCTATCGCTTAAGGATGAGTCCGCGTCCCATTAG
CTAGTTGGCGGGGTAACGGCCCACCAAGGCAACGATGGGTAGCCGGTCTGAGAGG
ATGACCGGCCACACTGGAACTGGAACACGGTCCAGACTCCTACGGGAGGCAGCAG
TGGGGAATATTGCGCAATGGGCGAAAGCCTGACGCAGCGACGCCGCGTGAGGGAT
GAAGGTTCTCGGATCGTAAACCTCTGTCAGGGGGGAAGAAACCCCCTCGTGTGAAT
AATGCGAG-
GGCTTGACGGTACCCCCAAAGGAAGCACCGGCTAACTCCGTGCCAGCAGCCGCGG
TAATACGGAGGGTGCAAGCGTTAATCGGAATCACTGGGCGTAAAGCGCACGTAGGC
GGCTTG-
GTAAGTCAGGGGTGAAATCCCACAGCCCAACTGTGGAACTGCCTTTGATACTGC-
CAGGCTTGAGTACCGGAGAGGGTGGCGGAATTCCAGGTGTAGGAGTGAAATCCGT
AGATATCTGGAGGAACACCGGTGGCGAAGGCGGCCACCTGGAC-
GGTAACTGACGCTGAGGTGCGAAAGCGTGGGTAGCAAACAGGATTAGATACCCTG
GTAGTCCACGCTGTAAACGATGGGTGCTGGGTG-CTGGGATGTATGTC-
TCGGTGCCGTAGCTAACGCGATAAGCACCCCGCCTGGGGAGTACGGTCGCAAGGC
TGAAACTCAAAGAAATTGACGGGGGCCCGCACAAGCGGTGGAGTATGTGGTTTAAT
TCGATGCAACGCGAAGAACCTTACCCAGGCTTGACATCTAGGGAACCCTTCGGAAA
TGAAGGGGTGCCCTTCGGGGAGCCCTAAGACAGGTGCTGCATGGCTGTCGTCAGC
TCGTGCCGTGAGGTGTTGGGTTAAGTCCCGCAACGAGCGCAACCCCTATCTTCAGT
TGCCAGCAGGTAAGGCTGGGCACTCTGGAGAGACCGCCCCGGTCAACGGGGAGGA
AGGTGGGGACGACGTCAAGTCATCATGGCCCTTACGCCTGGGGCTACACACGTACT
ACAATGGCGCGCACAAAGGGTAGCGAGACCGCGAGGTGGAGCCAATCCCAAAAAA
CGCGTCCCAGTCCGGATTGGAGTCTGCAACTCGACTCCATGAAGTCGGAATCGCTA
GTAATTCGAGATCAGCATGCTCGGGTGAATGCGTTCCCGGGCCTTGTACACACCGC
CCGTCACACCACGAAAGTCGGTTTTACCCGAAGCCGGTGAGCTAACTCGCAAGAGA
AGCAGCCGTCTACGGTAGGGCCGATGATTGGGGTGAAGTCGTAACAAGGTAGCCG
TAGGGGAACCTGCGGCTGGATCACCTCCTT SEQ ID NO: 40 *Blautia faecis* Strain 40
AGAGTTTGATCCTGGCTCAGGATGAACGCTGGCGGCGTGCTTAACACATGCAAGTC
GAACGGGAAATACTTTATTGAAACTTCGGTCGATTTAATTTATTTCTAGTGGCGGAC
GGGTGAGTAACGCGTGGGTAACCTGCCTTATACCGGGGGATAACAGCCAGAAATG
GCTGCTAATACCGCATAAGCGCACAGAACCGCATGGTTCGGTGTGAAAAACTCCGG
TGGTATAAGATGGACCCGCGTTGGATTAGCTAGTTGGCAGGGCAGCGGCCTACCAA
GGCGACGATCCATAGCCGGCCTGAGAGGGTGAACGGCCACATTGGGACTGAGACA
CGGCCCAGACTCCTACGGGAGGCAGCAGTGGGGAATATTGCACAATGGGGGAAAC
CCTGATGCAGCGACGCCGCGTGAAGGAAGAAGTATCTCGGTATGTAAACTTCTATC
AGCAGGGAAGATAATGACGGTACCTGACTAAGAAGCCCCGGCTAACTACGTGCCAG
CAGCCGCGGTAATACGTAGGGGGCAAGCGTTATCCGGATTTACTGGGTGTAAAGG
GAGCGTAGACGGCGCAGCAAGTCTGATGTGAAAGGCAGGGGCTTAACCCCTGGAC
TGCATTGGAAACTGCTGTGCTTGAGTGCCGGAGGGGTAAGCGGAATTCCTAGTGTA
GCGGTGAAATGCGTAGATATTAGGAGGAACACCAGTGGCGAAGGCGGCTTACTGG
ACGGTAACTGACGTTGAGGCTCGAAAGCGTGGGGAGCAAACAGGATTAGATACCCT
GGTAGTCCACGCCGTAAACGATGAATACTAGGTGTCAGGGAGCACAGCTCTTTGGT
GCCGCCGCAAACGCATTAAGTATTCCACCTGGGGAGTACGTTCGCAAGAATGAAAC
TCAAAGGAATTGACGGGGACCCGCACAAGCGGTGGAGCATGTGGTTTAATTCGAAG
CAACGCGAAGAACCTTACCAAATCTTGACATCCCTCTGACCGGGACTTAACCGTCC
CTTTCCTTCGGGACAGGGGAGACAGGTGGTGCATGGTTGTCGTCAGCTCGTGTCGT
GAGATGTTGGGTTAAGTCCCGCAACGAGCGCAACCCCTATCCTTAGTAGCCAGCAC
G-

-continued

| SEQUENCES |
| --- |

ATGGTGGGCACTCTGAGGAGACTGCCAGGGATAACCTGGAGGAAGGCGGGGATGA
CGTCAAATCATCATGCCCCTTATGATTTGGGCTACACACGTGCTACAATGGCGTAAA
CAAAGGGAAGCGAACCTGTGAGGGGGCAAATCTCAAAAATAACGTCCCAGTTCG
GACTGCAGTCTGCAACTCGACTGCACGAAGCTGGAATCGCTAGTAATCGCGGATCA
GAATGCCGCGGTGAATACGTTCCCGGGTCTTGTACACACCGCCCGTCACACCATGG
GAGTCAGTAACGCCCGAAGTCAGTGACCTAACCGCAAGGGAGGAGCTGCCGAAGG
CGGGACCGATGACTGGGGTGAAGTCGTAACAAGGTA

SEQ ID NO: 41 *Blautia wexlerae* Strain 41
AGAGTTTGATCCTGGCTCAGGATGAACGCTGGGGGCGTGCTTAACACATGCAAGTC
GAACGGGAATTACTTTATTGAAGCTTCGGCAGATTTAGCTGGTTTCTAGTGGCGGAC
GGGTGAGTAACGCGTGGGTAACCTGCCTTGTACAGGGGGATAACAGTCAGAAATGA
CTGCTAATACCGCATAAGCGCACAGGACCGCATGGTCCGGTGTGAAAAACTCCGGT
GGTATAAGATGGACCCGCGTTGGATTAGCTTGTTGGTGGGGTAACGGCCCACCAAG
GCGACGATCCATAGCCGGCCTGAGAGGGTGAACGGCCACATTGGGACTGAGACAC
GGCCCAGACTCCTACGGGAGGCAGCAGTGGGGAATATTGCACAATGGGGGAAACC
CTGATGCAGCGACGCCGCGTGAAGGAAGAAGTATCTCGGTATGTAAACTTCTATCA
GCAGGGAAGAAAATGACGGTACCTGACTAAGAAGCCCCGGCTAACTACGTGCCAG
CAGCCGCGGTAATACGTAGGGGGCAAGCGTTATCCGGATTTACTGGGTGTAAAGG
GAGCGTAGACGGATGGA-
CAAGTCTGATGTGAAAGGCTGGGGCTCAACCCCGGGACTGCATTGGAAACTGCCC
GTCTTGAGTGCCGGAGAGGTAAGCGGAATTCCTAGTGTAGCGGTGAAATGCGTAGA
TATTAGGAGGAACACCAGTGGCGAAGGCGGCTTACTGGACGGTAACTGACGTTGAG
GCTCGAAAGCGTGGGGAGCAAACAGGATTAGATACCCTGGTAGTCCACGCGGTAAA
CGATGAATGCTAGGTGTCGGGTGACAAAGTCATTCGGTGCCGCCGCAAACGCATTA
AGCATTCCACCTGGGGAGTACGTTCGCAAGAATGAAACTCAAAGGAATTGACGGGG
ACCCGCACAAGCGGTGGAGCATGTGGTTTAATTCGAAGCAACGCGAAGAACCTTAC
CAAGTCTTGACATCCCTCTGACCGGAACTTAACCGTTCCTTCCCTTCGGGGCAGAG
GAGACAGGTGGTGCATGGTTGTCGTCAGCTCGTGTCGTGAGATGTTGGGTTAAGTC
CCGCAACGAGCGCAACCCCTATCCCCAGTAGCCAGCATTTAAGGTGGGCACTCTGG
GGAGACTGCCAGGGATAACCTGGAGGAAGGGGGGGATGACGTCAAATCATCATGC
CCCTTATGATTTGGGCTACACACGTGCTACAATGGCGTAAACAAAGGGAAGCGAAC
CCGCGAGGGTGGGCAAATCCCAAAAATAACGTCCCAGTTCGGACTGTAGTCTGCAA
CCCGACTACACGAAGCTGGAATCGCTAGTAATCGCGGATCAGAATGCCGCGGTGAA
TACGTTCCCGGGTCTTGTACACACCGCCCGTCACACCATGGGAGTCAGTAACGCCC
GAAGTCAGTGACCTAACCGTAAGGAGGGAGCTGCCGAAGGCGGGACCGATGACTG
GGGTGAAGTCGTAACAAGGTA SEQ ID NO: 42 *Blautia luti* Strain 42
CTGGCTCAGGATGAACGCTGGGGGCGTGCTTAACACATGCAAGTCGAACGGGAAAT
ATTTCATTGAGACTTCGGTGGATTTGATCTATTTCTAGTGGGGGACGGGTGAGTAAC
GCGTGGGTAACCTGCCTTATACAGGGGGATAACAGTCAGAAATGGCTGCTAATACC
GCATAAGCGCACAGAGCTGCATGGCTCAGTGTGAAAAACTCCGGTGGTATAAGATG
GACCCGCGTTGGATTAGCTGGTTGGTGGGGTAACGGCCCACCAAGGCGACGATCC
ATAGCCGGCCTGAGAGGGTGAACGGCCACATTGGGACTGAGACACGGCCCAGACT
CCTACGGGAGGCAGCAGTGGGGAATATTGCACAATGGGGGAAACCCTGATGCAGC
GACGCCGCGTGAAGGAAGAAGTATCTCGGTATGTAAACTTCTATCAGCAGGGAAGA
TAGTGACGGTACCTGACTAAGAAGCCCCGGCTAACTACGTGCCAGCAGCCGCGGT
AATACGTAGGGGGCAAGCGTTATCCGGATTTACTGGGTGTAAAGGGAGCGTAGACG
GTGTGGCAAGTCTGATGTGAAAGGCATGGGCTCAACCTGTGGACTGCATTGGAAAC
TGTCATACTTGAGTGCCGGAGGGGTAAGCGGAATTCCTAGTGTAGCGGTGAAATGC
GTAGATATTAGGAGGAACACCAGTGGCGAAGGCGGCTTACTGGACGGTAACTGAC
GTTGAGGCTCGAAAGCGTGGGGAGCAAACAGGATTAGATACCCTGGTAGTCCACG
CCGTAAACGATGAATACTAGGTGTCGGGGAGTATGGCTCTTCGGTGCCGTCGCAAA
CGCAGTAAGTATTCCACCTGGGGAGTACGTTCGCAAGAATGAAACTCAAAGGAATT
GACGGGGACCCGCACAAGCGGTGGAGCATGTGGTTTAATTCGAAGCAACGCGAAG
AACCTTACCAAGTCTTGACATCCGCCTGACCGGTCCTTAACCGGACCTTTCCTTCGG
GACAGGAGAGACAGGTGGTGCATGGTTGTCGTCAGCTCGTGTCGTGAGATGTTGG
GTTAAGTCCCGCAACGAGCGCAACCCCTATCCTCAGTAGCCAGCAT-
TTAAGGTGGGCACTCTGGGGAGACTGCCAGGGATAACCTGGAGGAAGGCGGGGAT
GACGTCAAATCATCATGCCCCTTATGATTTGGGCTACACACGTGCTACAATGGCGTA
AACAAAGGGAAGCGAGATCGTGAGATGGAGCAAATCCCAAAAATAACGTCCCAGTT
CGGACTGTAGTCTGCAACCCGACTACACGAAGCTGGAATCGCTAGTAATCGCGGAT
CAGAATGCCGCGGTGAATACGTTCCCGGGTCTTGTACACACCGCCCGTCACACCAT
GGGAGTCAGTAACGCCCGAAGTCAGTGACCTAACTGCAAAGAAGGAGCTGCCGAA
GGCGGGACCGATGACTGGGGTGAAGTCGTAACAAGGTA SEQ ID NO: 43 *Butyricimonas synergistica* Strain 43
AGAGTTTGATCCTGGCTCAGGATGAACGCTAGCGACAGGCTTAACACATGCAAGTC
GAGGGGCAGCACGGTGTAGCAATACACTGGTGGCGACCGGCGCACGGGTGAGTAA
CACGTGTGCAACCAACCCCGTACCGGGAGATAACCCGCGGAAACGTGGACTAACAT
CCCATAAGACTCTAGAGCCGCATGGCTCTGGATTTAAAATTCCGGTGGTACGGGAC
GGGCACGCGCGACATTAGGTAGTTGGCGGGGTAACGGCCCACCAAGCCGACGATG
TCTAGGGGTTCTGAGAGGAAGGTCCCCCACACTGGAACTGAGACACGGTCCAGACT
CCTACGGGAGGCAGCAGTGAGGAATATTGGTCAATGGGCGCGAGCCTGAACCAGC
CAAGTCGCGTGAGGGAAGAATGGTCTATGGCCTGTAAACCTCTTTTGTCAAGGAAG
AATAAAAGGT-ACGTGTACCTTC- -continued

SEQUENCES

TTGCCAGTACTTGACGAATAAGCATCGGCTAACTCCGTGCCAGCAGCCGCGGTAAT
ACGGGGGATGCGAGCGTTATCCGGATTTATTGGGTTTAAAGGGCGCGTAGGGGGG
ACGCCAAGTCAGCGGTAAAAGACTGCAGCTAAACTGTAGCACGCCGTTGAAACTGG
CGACCTGGAGACGAGACGAGGGAGGCGGAACAAGTGAAGTAGCGGTGAAATGCTT
AGATATCACTTGGAACCCCGATAGCGAAGGCAGCTTCCCAGGCTCGATCTGACGCT
GATGCGCGAGAGCGTGGGTAGCGAACAGGATTAGATACCCTGGTAGTCCACGCCG
TAAACGATGCTCACTGGATCTTGGCGATACACTGCCAGGGTTCAAGCGAAAGTATT
AAGTGAGCCACCTGGGGAGTACGTCGGCAACGATGAAACTCAAAGGAATTGACGG
GGGCCCGCACAAGCGGAGGAACATGTGGTTTAATTCGATGATACGCGAGGAACCTT
ACCCGGGTTTAAATGTATTTTGCATTTCTTGGAAACAGGAATTCCCTTCGGGGCTAG
ATACAAGGTGCTGCATGGTTGTCGTCAGCTCGTGCCGTGAGGTGTCGGGTTAAGTC
CCATAACGAGCGCAACCCCTATCGCCAGTTGCCATCGGTTGAAGCCGGGCACTCTG
TCGAGACTGCCACCGTAAGGTGCGAGGAAGGGGGGGATGACGTCAAATCAGCACG
GCCCTTACACCCGGGGCGACACACGTGTTACAATGGCCGGTACAGAGGGCAGCCA
CGGGGTGACCCGGAGCGAATCTCTAAAGCCGGTCGTAGTTCGGACTGGAGTCTGC
AACCCGACTCCACGAAGTTGGATTCGCTAGTAATCGCGCATCAGCCATGGCGCGGT
GAATACGTTCCCGGGCCTTGTACACACCGCCCGTCAAGCCATGGAAGCCGGGAGT
ACCTGAAGATCGTGACCGCGAGGAACGGGCTAGGGTAATACCGGTAACTGGGGCT
AAGTCGTAACAAGGTA

SEQ ID NO: 44 *Clostridium bolteae* Strain 44
AGAGTTTGATCCTGGCTCAGGATGAACGCTGGCGGCGTGCCTAACACATGCAAGTC
GAACGAAGCAATT-AAAGGAAGTTTTCGGATGGA-
ATTTGATTGACTGAGTGGCGGACGGGTGAGTAACGCGTGGATAACCTGCCTCACAC
TGGGGGATAACAGTTAGAAATGACTGCTAATACCGCATAAGCGCACAGTACCGCAT
GGTACGGTGTGAAAAACTCCGGTGGTGTGAGATGGATCCGCGTCTGATTAGCCAGT
TGGCGGGGTAACGGCCCACCAAAGCGACGATCAGTAGCCGACCTGAGAGGGTGAC
CGGCCACATTGGGACTGAGACACGGCCCAAACTCCTACGGGAGGCAGCAGTGGGG
AATATTGCACAATGGGCGAAAGCCTGATGCAGCGACGCCGCGTGAGTGAAGAAGTA
TTTCGGTATGTAAAGCTCTATCAGCAGGGAAGAAAATGACGGTACCTGACTAAGAA
GCCCCGGCTAACTACGTGCCAGCAGCCGCGGTAATACGTAGGGGGCAAGCGTTAT
CCGGATTTACTGGGTGTAAAGGGAGCGTAGACGGCGAAGCAAGTCTGAAGTGAAAA
CCCAGGGCTCAACCCTGGGACTGCTTTGGAAACTGTTTTGCTAGAGTGTCGGAGAG
GTAAGTGGAATTCCTAGTGTAGCGGTGAAATGCGTAGATATTAGGAGGAACACCAG
TGGCGAAGGCGGCTTACTGGACGATAACTGACGTTGAGGCTCGAAAGCGTGGGGA
GCAAACAGGATTAGATACCCTGGTAGTCCACGCCGTAAACGATGAATGCTAGGTGT
TGGGGGGCAAAGCCCTTCGGTGCCGTCGCAAACGCAGTAAGCATTCCACCTGGGG
AGTACGTTCGCAAGAATGAAACTCAAAGGAATTGACGGGGACCCGCACAAGCGGTG
GAGCATGTGGTTTAATTCGAAGCAACGCGAAGAACCTTACCAAGTCTTGACATCCTC
TTGGCCGGCGTGTAACGGCGCCTTCCCTTCGGGGCAAGAGAGACAGGTGGTGCAT
GGTTGTCGTCAGCTCGTGTCGTGAGATGTTGGGTTAAGTCCCGCAACGAGCGCAAC
CCTTATCCTTAGTAGCCAGCAGGTAGAGCTGGGCACTCTAGGGAGACTGCCAGGGA
TAACCTGGAGGAAGGTGGGGATGACGTCAAATCATCATGCCCCTTATGATTTGGGC
TACACACGTGCTACAATGGCGTAAACAAAGGGAAGCAAGACAGTGATGTGGAGCAA
ATCCCAAAAATAACGTCCCAGTTCGGACTGTAGTCTGCAACCCGACTACACGAAGC
TGGAATCGCTAGTAATCGCGAATCAGAATGTCGCGGTGAATACGTTCCCGGGTCTT
GTACACACCGCCCGTCACACCATGGGAGTCAGCAACGCCCGAAGTCAGTGACCCA
ACTCGCAAGAGAGGGAGCTGCCGAAGGCGGGGCAGGTAACTGGGGTGAAGTCGTA
ACAAGGTAGCCGTA SEQ ID NO: 45 *Parasutterella excrementihominis* Strain 45
ATTGAACGCTGGCGGAACGCTTTACACATGCAAGTCGAACGGTAACGTGGGGAGGA
GCTTGCTCCACCCCGACGACGAGTGGCGAACGGGTGAGTAATACATCGGAACGTG
TCCGCTTGTGGGGGACAACCAGCCGAAAGGTTGGCTAATACCGCATGAGTTCTACG
GAAGAAAGAGGGGGACCCGCAAGGGCCTCTCGCGAGCGGAGCGGCCGATGACTG
ATTAGCCGGTTGGTGAGGTAACGGCTCACCAAAGCAACGATCAGTAGCTGGTCTGA
GAGGACGACCAGCCACACTGGGACTGAGACACGGCCCAGACTCCTACGGGAGGCA
GCAGTGGGGAATTTTGGACAATGGGCGCAAGCCTGATCCAGCTATTCCGCGTGTGG
GATGAAGGCCCTCGGGTTGTAAACCACTTTTGTAGAGAACGAAAAGACACCATCGA
ATAAATGGTGTTGCTGACGGTACTCTAAGAATAAGCACCGGCTAACTACGTGCCAG
CAGCCGCGGTAATACGTAGGGTGCGAGCGTTAATCGGAATTACTGGGCGTAAAGG
GTGCGCAGGCGGTTGAGTAAGACAGATGTGAAATCCCCGAGCTTAACTCGGGAATG
GCATATGTGACTGCTCGACTAGAGTGTGTCAGAGGGAGGTGGAATTCCACGTGTAG
CAGTGAAATGCGTAGATATGTGGAAGAACACCGATGGCGAAGGCAGCCTCCTGGG
ACATAACTGACGCTCAGGCACGAAAGCGTGGGGAGCAAACAGGATTAGATACCCTG
GTAGTCCACGCCCTAAACGATGTTAACTAGTTGTTGGGATGTAACAATCTCAGTAAC
GCAGCCAACGCGAGAAGTTAACCGCCTGGGAAGTACGGTCGCAAGACTAAAACTCA
AAGGAATTGACGGGGACCCGCACAAGCGGTGGATGATGTGGATTAATTCGATGCAA
CGCGAAAAACCTTACCTACCCTTGACATGTCAGGAAGCTCTTGTAATGAGAGCGTG
CCCGCAAGGGAGCCTGAACACAGGTGCTGCATGGCTGTCGTCAGCTCGTGTCGTG
AGATGTTGGGTTAAGTCCCGCAACGAGCGCAACCCTTGTCACTAGTTGCTACGAAA
GGGCACTCTAGTGAGACTGCCGGTGACAAACCGGAGGAAGGTGGGGATGACGTCA
AGTCCTCATGGCCCTTATGGGTAGGGCTTCACACGTCATACAATGGTCGGAACAGA
GGGCAGCGAAGCCGTGAGGCGGAGCCAATCCCAGAAAACCGATCGTAGTCCGGAT -continued

| SEQUENCES |
|---|
| TGCAGTCTGCAACTCGACTGCATGAAGTCGGAATCGCTAGTAATCGCGGATCAGCA<br>TGCCGCGGTGAATACGTTCCCGGGTCTTGTACACACCGCCCGTCAAACAATGGGAG<br>TGGTGTTTACCAGAAGTCGTTAGCCTAACCGCAAGGAGGGCGGCGACCACGGTGA<br>GCACCGTGACTAATGTTAAGTCGTAACAAGGTAGCCGTACCGGAAGG |
| SEQ ID NO: 46 *Prevotella copri* Strain 46<br>AGAGTTTGATCCTGGCTCAGGATGAACGCTAGCTACAGGCTTAACACATGCAAGTC<br>GAGGGGAAACGATATTGGAAGCTTGCTTCCGATAGGCGTCGACCGGCGCACGGGT<br>GAGTAACGCGTATCCAACCTGCCCACCACTTGGGGATAACCTTGCGAAAGTAAGAC<br>TAATACCCAATGATATCTCTAGAAGACATCTGAAAGAGATTAAAGATTTATCGGTGAT<br>GGATGGGGATGCGTCTGATTAGCTTGTTGGCGGGGTAACGGCCCACCAAGGCGAC<br>GATCAGTAGGGGTTCTGAGAGGAAGGTCCCCCACATTGGAACTGAGACACGGTCCA<br>AACTCCTACGGGAGGCAGCAGTGAGGAATATTGGTCAATGGGCGAGAGCCTGAAC<br>CAGCCAAGTAGCGTGCAGGATGACGGCCCTATGGGTTGTAAACTGCTTTTATAAGG<br>GAATAAAGTGAGAGTCGTGACTCTTTTTGCATGTACCTTATGAATAAGGACCGGCTA<br>ATTCCGTGCCAGCAGCCGCGGTAATACGGAAGGTCCGGGCGTTATCCGGATTTATT<br>GGGTTTAAAGGGAGCGTAGGCCGGAGATTAAGCGTGTTGTGAAATGTAGACGCTCA<br>ACGTCTGCACTGCAGCGCGAACTGGTTTCCTTGAGTACGCACAAAGTGGGCGGAAT<br>TCGTGGTGTAGCGGTGAAATGCTTAGATATCACGAAGAACTCCGATTGCGAAGGCA<br>GCTCACTGGAGCGCAACTGACGCTGAAGCTCGAAAGTGCGGGTATCGAACAGGATT<br>AGATACCCTGGTAGTCCGCACGGTAAACGATGGATGCCCGCTGTTGGTCTGAATAG<br>GTCAGCGGCCAAGCGAAAGCATTAAGCATCCCACCTGGGGAGTACGCCGGCAACG<br>GTGAAACTCAAAGGAATTGACGGGGGCCCGCACAAGCGGAGGAACATGTGGTTTAA<br>TTCGATGATACGCGAGGAACCTTACCCGGGCTTGAATTGCAGAGGAAGGATTTGGA<br>GACAATGACGCCCTTCGGGGCCTCTGTGAAGGTGCTGCATGGTTGTCGTCAGCTCG<br>TGCCGTGAGGTGTCGGCTTAAGTGCCATAACGAGCGCAACCCCTCTCCTTAGTTGC<br>CATCAGGTTAAGCTGGGCACTCTGGGGGCACTGCCACCGTAAGGTGTGAGGAAGG<br>TGGGGATGACGTCAAATCAGCACGGCCCTTACGTCCGGGGCTACACACGTGTTACA<br>ATGGCAGGTACAGAGAGATGGTCCCTTGCAAAACGGATCAAATCCTTAAAGCCTGT<br>CTCAGTTCGGACTGGGGTCTGCAACCCGACCCCACGAAGCTGGATTCGCTAGTAAT<br>CGCGCATCAGCCATGGCGCGGTGAATACGTTCCCGGGCCTTGTACACACCGCCCG<br>TCAAGCCATGAAAGCCGGGGGCGCCTAAAGTCCGTGACCGTAAGGAGCGGCCTAG<br>GGCGAAACTGGTAATTGGGGCTAAGTCGTAACAAGGTA |
| SEQ ID NO: 47 *Ruminococcus faecis* Strain 47<br>TTTGATCCTGGCTCAGGATGAACGCTGGGGGCGTGCTTAACACATGCAAGTCGAAC<br>GAAGCACCTTGATTTGA-TTCTTCGG-<br>ATGAAGATCCTGGTGACTGAGTGGCGGACGGGTGAGTAACGCGTGGGTAACCTGC<br>CTCATACAGGGGGATAACAGTTAGAAATGACTGCTAATACCGCATAAGACCACAGC<br>ACCGCATGGTGCAGGGGTAAAAACTCCGGTGGTATGAGATGGACCCGCGTCTGATT<br>AGGTAGTTGGTGGGGTAACGGCCTACCAAGCCGACGATCAGTAGCCGACCTGAGA<br>GGGTGACCGGCCACATTGGGACTGAGACACGGCCCAAACTCCTACGGGAGGCAGC<br>AGTGGGGAATATTGCACAATGGGGGAAACCCTGATGCAGCGACGCCGCGTGAGCG<br>ATGAAGTATTTCGGTATGTAAAGCTCTATCAGCAGGGAAGAAAATGACGGTACCTGA<br>CTAAGAAGCACCGGCTAAATACGTGCCAGCAGCCGCGGTAATACGTATGGTGCAAG<br>CGTTATCCGGATTTACTGGGTGTAAAGGGAGCGTAGACGGAGTGGCAAGTCTGATG<br>TGAAAACCCGGGGCTCAACCCCGGGACTGCATTGGAAACT--<br>GTCAATCTAGAGTACCGGAGAGGTAAGCGGAATTCCTAGTGTAGCGGTGAAATGCG<br>TAGATATTAGGAGGAACACCAGTGGCGAAGGCGGCTTACTGGACGGTAACTGACGT<br>TGAGGCTCGAAAGCGTGGGGAGCAAACAGGATTAGATACCCTGGTAGTCCACGCC<br>GTAAACGATGACTACTAGGTGTCGGGCAGCAAAGCTGTTCGGTGCCGCAGCAAACG<br>CAATAAGTAGTCCACCTGGGGAGTACGTTCGCAAGAATGAAACTCAAAGGAATTGA<br>CGGGGACCCGCACAAGCGGTGGAGCATGTGGTTTAATTCGAAGCAACGCGAAGAA<br>CCTTACCTGCTCTTGACATCTCCCTGACCGGCAAGTAATGTTGCCTTTCCTTCGGGA<br>CAG-<br>GGATGACAGGTGGTGCATGGTTGTCGTCAGCTCGTGTCGTGAGATGTTGGGTTAAG<br>TCCCGCAACGAGCGCAACCCCTATCTTTAGTAGCCAGCGGTCAGGCCGGGCACTCT<br>AGAGAGACTGCCAGGGATAACCTGGAGGAAGGTGGGGATGACGTCAAATCATCAT<br>GCCCCTTATGAGCAGGGCTACACACGTGCTACAATGGCGTAAACAAAGGGAGGCA<br>GAACCGCGAGGTCGAGCAAATCCCAAAAATAACGTCTCAGTTCGGATTGTAGTCTG<br>CAACTCGACTACATGAAGCTGGAATCGCTAGTAATCGCGAATCAGAATGTCGCGGT<br>GAATACGTTCCCGGGTCTTGTACACACCGCCCGTCACACCATGGGAGTCAGTAACG<br>CCCGAAGTCAGTGACCCAACCGTAAGGAGGGAGCTGCCGAAGGTGGGACCGATAA<br>CTGGGGTGAAGTCGTAACAAGGTAGCCGTATCGGAAGGTGCGGCTGGATCACCTC<br>CTTT |
| SEQ ID NO: 48 *Bacteroides caccae*<br>TGGCTCAGGATGAACGCTAGCTACAGGCTTAACACATGCAAGTCGAGGGGCATCAG<br>TTTGGTTTGCTTGCAAACCAAAGCTGGCGACCGGCGCACGGGTGAGTAACACGTAT<br>CCAACCTGCCTCATACTCGGGGATAGCCTTTCGAAAGAAAGATTAATATCCGATAGC<br>ATATATTTCCCGCATGGGTTTTATATTAAAGAAATTCGGTATGAGATGGGGATGCGT<br>TCCATTAGTTTGTTGGGGGGGTAACGGCCCACCAAGACTACGATGGATAGGGGTTC<br>TGAGAGGAAGGTCCCCCACATTGGAACTGAGACACGGTCCAAACTCCTACGGGAG<br>GCAGCAGTGAGGAATATTGGTCAATGGACGCGAGTCTGAACCAGCCAAGTAGCGTG<br>AAGGATGACTGCCCTATGGGTTGTAAACTTCTTTTATATGGGAATAAAGTTGTCCAC<br>GTGTGGATTTTTGTATGTACCATATGAATAAGGATCGGCTAACTCCGTGCCAGCAGC<br>CGCGGTAATACGGAGGATCCGAGCGTTATCCGGATTTATTGGGTTTAAAGGGAGCG |

-continued

| SEQUENCES |
|---|

TAGGCGGATTGTTAAGTCAGTTGTGAAAGTTTGCGGCTCAACCGTAAAATTGCAGTT
GATACTGGCAGTCTTGAGTGCAGTAGAGGTGGGCGGAATTCGTGGTGTAGCGGTG
AAATGCTTAGATATCACGAAGAACTCCGATTGCGAAGGCAGCCACTGGAGTGTAAC
TGACGCTGATGCTCGAAAGTGTGGGTATCAAACAGGATTAGATACCCTGGTAGTCC
ACACAGTAAACGATGAATACTCGCTGTTTGCGATATACAGTAAGCGGCCAAGCGAA
AGCATTAAGTATTCCACCTGGGGAGTACGCCGGCAACGGTGAAACTCAAAGGAATT
GACGGGGGCCCGCACAAGCGGAGGAACATGTGGTTTAATTCGATGATACGCGAGG
AACCTTACCCGGGCTTAAATTGCAAATGAATTATGGGGAAACCCATAGGCCGCAAG
GCATTTGTGAAGGTGCTGCATGGTTGTCGTCAGCTCGTGCCGTGAGGTGTCGGCTT
AAGTGCCATAACGAGCGCAACCCTTATCTTCAGTTACTAACAGGTCATGCTGAGGA
CTCTGGAGAGACTGCCGTCGTAAGATGTGAGGAAGGTGGGGATGACGTCAAATCA
GCACGGCCCTTACGTCCGGGGCTACACACGTGTTACAATGGGGGGTACAGAAGGC
CGCTACCTGGTGACAGGATGCCAATCCCAAAAACCTCTCTCAGTTCGGATCGAAGT
CTGCAACCCGACTTCGTGAAGCTGGATTCGCTAGTAATCGCGCATCAGCCATGGCG
CGGTGAATACGTTCCCGGGCCTTGTACACACCGCCCGTCAAGCCATGAAAGCCGG
GGGTACCTGAAGTACGTAACCGCAAGGAGCGTCCTAGGGTAAAACTGGTAATTGGG
GCTAAGTCGTAACAAGGTA

SEQ ID NO: 49 *Bacteroides cellulosilyticus/ Bacteroides intestinalis*
AGAGTTTGATCCTGGCTCAGGATGAACGCTAGCTACAGGCTTAACACATGCAAGTC
GAGGGGCAGCATGACCTAGCAATAGGTTGATGGCGACCGGCGCACGGGTGAGTAA
CACGTATCCAACCTACCGGTTATTCCGGGATAGCCTTTCGAAAGAAAGATTAATACC
GGATAGTATAACGAGAAGGCATCTTTTTGTTATTAAAGAATTTCGATAACCGATGGG
GATGCGTTCCATTAGTTTGTTGGCGGGGTAACGGCCCACCAAGACATCGATGGATA
GGGGTTCTGAGAGGAAGGTCCCCCACATTGGAACTGAGACACGGTCCAAACTCCTA
CGGGAGGCAGCAGTGAGGAATATTGGTCAATGGACGAGAGTCTGAACCAGCCAAG
TAGCGTGAAGGATGACTGCCCTATGGGTTGTAAACTTCTTTTATATGGGAATAAAGT
GAGCCACGTGTGGCTTTTTGTATGTACCATACGAATAAGGATCGGCTAACTCCGTG
CCAGCAGCCGCGGTAATACGGAGGATCCGAGCGTTATCCGGATTTATTGGGTTTAA
AGGGAGCGTAGGCGGACTATTAAGTCAGCTGTGAAAGTTTGCGGCTCAACCGTAAA
ATTGCAGTTGATACTGGTCGTCTTGAGTGCAGTAGAGGTAGGCGGAATTCGTGGTG
TAGCGGTGAAATGCTTAGATATCACGAAGAACTCCGATTGCGAAGGCAGCTTACTG
GACTGTAACTGACGCTGATGCTCGAAAGTGTGGGTATCAAACAGGATTAGATACCC
TGGTAGTCCACACAGTAAACGATGAATACTCGCTGTTTGCGATATACGGCAAGCGG
CCAAGCGAAAGCATTAAGTATTCCACCTGGGGAGTACGCCGGCAACGGTGAAACTC
AAAGGAATTGACGGGGGCCCGCACAAGCGGAGGAACATGTGGTTTAATTCGATGAT
ACGCGAGGAACCTTACCCGGGCTTAAATTGCAAATGAATATAGTGGAAACATTATAG
CCGCAAGGCATTTGTGAAGGTGCTGCATGGTTGTCGTCAGCTCGTGCCGTGAGGTG
TCGGCTTAAGTGCCATAACGAGCGCAACCCTTATCTTTAGTTACTAACAGGTCATGC
TGAGGACTCTAGAGAGACTGCCGTCGTAAGATGTGAGGAAGGTGGGGATGACGTC
AAATCAGCACGGCCCTTACGTCCGGGGCTACACACGTGTTACAATGGGGGGTACAG
AAGGCAGCTACACAGCGATGTGATGCTAATCCCAAAAGCCTCTCTCAGTTCGGATT
GGAGTCTGCAACCCGACTCCATGAAGCTGGATTCGCTAGTAATCGCGCATCAGCCA
CGGCGCGGTGAATACGTTCCCGGGCCTTGTACACACCGCCCGTCAAGCCATGAAA
GCCGGGGGTACCTGAAGTCCGTAACCGTAAGGAGCGGCCTAGGGTAAAACTGGTA
ATTGGGGCTAAGTCGTA SEQ ID NO: 50 *Bacteroides faecis*
CTCAGGATGAACGCTAGCTACAGGCTTAACACATGCAAGTCGAGGGGCAGCATTTC
AGTTTGCTTGCAAACTGGAGATGGCGACCGGCGCACGGGTGAGTAACACGTATCCA
ACCTGCCGATAACTCGGGGATAGCCTTTCGAAAGAAAGATTAATACCCGATGGCAT
AATAGAACCGCATGGTTTTTTTATTAAAGAATTTCGGTTATCGATGGGGATGCGTTC
CATTAGGCAGTTGGTGAGGTAACGGCTCACCAAACCTTCGATGGATAGGGGTTCTG
AGAGGAAGGTCCCCCACATTGGAACTGAGACACGGTCCAAACTCCTACGGGAGGC
AGCAGTGAGGAATATTGGTCAATGGACGAGAGTCTGAACCAGCCAAGTAGCGTGAA
GGATGACTGCCCTATGGGTTGTAAACTTCTTTTATATGGGAATAAAGTTTTCCACGT
GTGGAATTTTGTATGTACCATATGAATAAGGATCGGCTAACTCCGTGCCAGCAGCC
GCGGTAATACGGAGGATCCGAGCGTTATCCGGATTTATTGGGTTTAAAGGGAGCGT
AGGTGGACAGTTAAGTCAGTTGTGAAAGTTTGCGGCTCAACCGTAAAATTGCAGTT
GATACTGGCTGTCTTGAGTACAGTAGAGGTGGGGGGAATTCGTGGTGTAGCGGTGA
AATGCTTAGATATCACGAAGAACTCCGATTGCGAAGGCAGCTCACTGGACTGCAAC
TGACACTGATGCTCGAAAGTGTGGGTATCAAACAGGATTAGATACCCTGGTAGTCC
ACACAGTAAACGATGAATACTCGCTGTTTGCGATATACAGTAAGCGGCCAAGCGAA
AGCATTAAGTATTCCACCTGGGGAGTACGCCGGCAACGGTGAAACTCAAAGGAATT
GACGGGGGCCCGCACAAGCGGAGGAACATGTGGTTTAATTCGATGATACGCGAGG
AACCTTACCCGGGCTTAAATTGCATTTGAATATATTGGAAACAGTATAGTCGTAAGA
CAAATGTGAAGGTGCTGCATGGTTGTCGTCAGCTCGTGCCGTGAGGTGTCGGCTTA
AGTGCCATAACGAGCGCAACCCTTATCTTTAGTTACTAACAGGTCATGCTGAGGACT
CTAGAGAGACTGCCGTCGTAAGATGTGAGGAAGGTGGGGATGACGTCAAATCAGCA
CGGCCCTTACGTCCGGGGCTACACACGTGTTACAATGGGGGGTACAGAAGGCAGC
TACCTGGTGACAGGATGCTAATCCCAAAAGCCTCTCTCAGTTCGGATCGAAGTCTG
CAACCCGACTTCGTGAAGCTGGATTCGCTAGTAATCGCGCATCAGCCATGGCGCGG
TGAATACGTTCCCGGGCCTTGTACACACCGCCCGTCAAGCCATGAAAGCCGGGGG
TACCTGAAGTACGTAACCGCAAGGAGCGTCCTAGGGTAAAACTGGTAATTGGGGCT
AAGTCGTAACAAGGTA -continued

| SEQUENCES |
|---|

SEQ ID NO: 51 *Bacteroides ovatus*
CGATATCCGGATTTATTGGAGTTT-
AAGGGAGCGTAGGTGGATTGTTAAGTCAGTTGTGAAAGTTTGCGGCTCAACCGTAA
AATTGCAGTTGAAACTGGCAGTCTTGAGTACAGTAGAGGTGGGCGGAATTCGTGGT
GTAGCGGTGAAATGCTTAGATATCACGAAGAACTCCGATTGCGAAGGCAGCTCACT
AGACTGTCACTGACACTGATGCTCGAAAGTGTGGGTATCAAACAGGATTAGATACC
CTGGTAGTCCACACAGTAAACGATGAATACTCGCTGTTTGCGATATACAGTAAGCG
GCCAAGCGAAAGCATTAAGTATTCCACCTGGGGAGTACGCCGGCAACGGTGAAACT
CAAAGGAATTGACGGGGGCCCGCACAAGCGGAGGAACATGTGGTTTAATTCGATGA
TACGCGAGGAACCTTACCCGGGCTTAAATTGCAACAGAATATATTGGAAACAGTATA
GCCGTAAGGCTGTTGTGAAGGTGCTGCATGGTTGTCGTCAGCTCGTGCCGTGAGGT
GTCGGCTTAAGTGCCATAACGAGCGCAACCCTTATCTTTAGTTACTAACAGGTKATG
CTGAGGACTCTAGAGAGACTGCCGTCGTAAGATGTGAGGAAGGTGGGGATGACGT
CAAATCAGCACGGCCCTTACGTCCGGGGCTACACACGTGTTACAATGGGGGGTACA
GAAGGCSGCTACCTGGTGACAGGATGCTAATCCCAAAAACCTCTCTCAGTTCGGAT
CGAAGTCTGCAACCCGACTTCGTGAAGCTGGATTCGCTAGTAATCGCGCATCAGCC
ATGGCGCGGTGAATACGTTCCCGGGCCTTGTACACACCGCCCGTCAAGCCATGAAA
GCCGGGGGTACCTGAAGTACGTAACCGCAAGGAGCGTCCTAGGGGTAAAACTGGT
AATTGGGGC SEQ ID NO: 52 *Bacteroides thetaiotaomicron*
TTTAAGGGAGCGTAGGTGGACAGTTAAGTCAGTTGTGAAAGTTTGCGGCTCAACCG
TAAAATTGCAGTTGATACTGGCTGTCTTGAGTACAGTAGAGGTGGGCGGAATTCGT
GGTGTAGCGGTGAAATGCTTAGATATCACGAAGAACTCCGATTGCGAAGGCAGCTC
ACTGGACTGCAACTGACACTGATGCTCGAAAGTGTGGGTATCAAACAGGATTAGAT
ACCCTGGTAGTCCACACAGTAAACGATGAATACTCGCTGTTTGCGATATACAGTAAG
CGGCCWAGCGAAAGCATTAAGTATTCCACCTGGGGAGTACGCCGGCAACGGTGAA
ACTCAAAGGAATTGACGGGGGCCCGCACAAGCGGAGGAACATGTGGTTTAATTCGA
TGATACGCGAGGAACCTTACCCGGGCTTAAATTGCAWWTGAATAWWYTGGAAACA
GKWTAGYCGYAAGRCAWWTGTGAAGGTGCTGCATGGTTGTCGTCAGCTCGTGCCG
TGAGGTGTCGGCTTAAGTGCCATAACGAGCGCAACCCTTATCTTTAGTTACTAACAG
GTCATGCTGAGGACTCTAGAGAGACTGCCGTCGTAAGATGTGAGGAAGGTGGGGA
TGACGTCAAATCAGCACGGCCCTTACGTCCGGGGCTACACACGTGTTACAATGGGG
GGTACAGAAGGCAGCTACCTGGTGACAGGATGCTAATCCCAAAAGCCTCTCTCAGT
TCGGATCGAAGTCTGCAACCCGACTTCGTGAAGCTGGATTCGCTAGTAATCGCGCA
TCAGCCATGGCGCGGTGAATACGTTCCCGGGCCTTGTACACACCGCCCGTCAAGC
CATGAAAGCCGGGGGTACCTGAAGTACGTAACCGCA SEQ ID NO: 53 *Bacteroides uniformis*
CTGGCTCAGGATGAACGCTAGCTACAGGCTTAACACATGCAAGTCGAGGGGCAGCA
TGAACTTAGCTTGCTAAGTTTGATGGCGACCGGCGCACGGGTGAGTAACACGTATC
CAACCTGCCGATGACTCGGGGATAGCCTTTCGAAAGAAAGATTAATACCCGATGGC
ATAGTTCTTCCGCATGGTAGAACTATTAAAGAATTTCGGTCATCGATGGGGATGCGT
TCCATTAGGTTGTTGGCGGGGTAACGGCCCACCAAGCCTTCGATGGATAGGGGTTC
TGAGAGGAAGGTCCCCCACATTGGAACTGAGACACGGTCCAAACTCCTACGGGAG
GCAGCAGTGAGGAATATTGGTCAATGGACGAGAGTCTGAACCAGCCAAGTAGCGTG
AAGGATGACTGCCCTATGGGTTGTAAACTTCTTTTATACGGGAATAAAGTGAGGCAC
GTGTGCCTTTTTGTATGTACCGTATGAATAAGGATCGGCTAACTCCGTGCCAGCAGC
CGCGGTAATACGGAGGATCCGAGCGTTATCCGGATTTATTGGGTTTAAAGGGAGCG
TAGGCGGACGCTTAAGTCAGTTGTGAAAGTTTGCGGCTCAACCGTAAAATTGCAGT
TGATACTGGGTGTCTTGAGTACAGTAGAGGCAGGCGGAATTCGTGGTGTAGCGGTG
AAATGCTTAGATATCACGAAGAACTCCGATTGCGAAGGCAGCTTGCTGGACTGTAA
CTGACGCTGATGCTCGAAAGTGTGGGTATCAAACAGGATTAGATACCCTGGTAGTC
CACACAGTAAACGATGAATACTCGCTGTTTGCGATATACAGTAAGCGGCCAAGCGA
AAGCGTTAAGTATTCCACCTGGGGAGTACGCCGGCAACGGTGAAACTCAAAGGAAT
TGACGGGGGCCCGCACAAGCGGAGGAACATGTGGTTTAATTCGATGATACGCGAG
GAACCTTACCCGGGCTTGAATTGCAACTGAATGATGTGGAGACATGTCAGCCGCAA
GGCAGTTGTGAAGGTGCTGCATGGTTGTCGTCAGCTCGTGCCGTGAGGTGTCGGC
TTAAGTGCCATAACGAGCGCAACCCTTATCGATAGTTACCATCAGGTTATGCTGGG
GACTCTGTCGAGACTGCCGTCGTAAGATGTGAGGAAGGTGGGGATGACGTCAAATC
AGCACGGCCCTTACGTCCGGGGCTACACACGTGTTACAATGGGGGGTACAGAAGG
CAGCTACACGGCGACGTGATGCTAATCCCTAAAGCCTCTCTCAGTTCGGATTGGAG
TCTGCAACCCGACTCCATGAAGCTGGATTCGCTAGTAATCGCGCATCAGCCACGGC
GCGGTGAATACGTTCCCGGGCCTTGTACACACCGCCCGTCAAGCCATGAAAGCCG
GGGGTACCTGAAGTGCGTAACCGCGAGGAGCGCCCTAGGGTAAAACTGGTGATTG
GGGCTAAGTCGTAACAAGGTA SEQ ID NO: 54 *Bacteroides vulgatus*
ATGAAGAGTTTGATCCTGGCTCAGGATGAACGCTAGCTACAGGCTTAACACATGCA
AGTCGAGGGGCAGCATGGTCTTAGCTTGCTAAGGCCGATGGCGACCGGCGCACGG
GTGAGTAACACGTATCCAACCTGCCGTCTACTCTTGGACAGCCTTCTGAAAGGAAG
ATTAATACAAGATGGCATCATGAGTTCACATGTTCACATGATTAAAGGTATTCCGGT
AGACGATGGGGATGCGTTCCATTAGATAGTAGGGGGGGTAACGGCCCACCTAGTCT
TCGATGGATAGGGGTTCTGAGAGGAAGGTCCCCCACATTGGAACTGAGACACGGTC
CAAACTCCTACGGGAGGCAGCAGTGAGGAATATTGGTCAATGGGCGAGAGCCTGA
ACCAGCCAAGTAGCGTGAAGGATGACTGCCCTATGGGTTGTAAACTTCTTTTATAAA
GGAATAAAGTCGGGTATGCATACCCGTTTGCATGTACTTTATGAATAAGGATCGGCT -continued

| SEQUENCES |
|---|
| AACTCCGTGCCAGCAGCCGCGGTAATACGGAGGATCCGAGCGTTATCCGGATTTAT<br>TGGGTTTAAAGGGAGCGTAGATGGATGTTTAAGTCAGTTGTGAAAGTTTGCGGCTC<br>AACCGTAAAATTGCAGTTGATACTGGATATCTTGAGTGCAGTTGAGGCAGGCGGAA<br>TTCGTGGTGTAGCGGTGAAATGCTTAGATATCACGAAGAACTCCGATTGCGAAGGC<br>AGCCTGCTAAGCTGCAACTGACATTGAGGCTCGAAAGTGTGGGTATCAAACAGGAT<br>TAGATACCCTGGTAGTCCACACGGTAAACGATGAATACTCGCTGTTTGCGATATACG<br>GCAAGCGGCCAAGCGAAAGCGTTAAGTATTCCACCTGGGGAGTACGCCGGCAACG<br>GTGAAACTCAAAGGAATTGACGGGGGCCCGCACAAGCGGAGGAACATGTGGTTTAA<br>TTCGATGATACGCGAGGAACCTTACCCGGGCTTAAATTGCAGATGAATTACGGTGA<br>AAGCCGTAAGCCGCAAGGCATCTGTGAAGGTGCTGCATGGTTGTCGTCAGCTCGTG<br>CCGTGAGGTGTCGGCTTAAGTGCCATAACGAGCGCAACCCTTGTTGTCAGTTACTA<br>ACAGGTTCCGCTGAGGACTCTGACAAGACTGCCATCGTAAGATGTGAGGAAGGTGG<br>GGATGACGTCAAATCAGCACGGCCCTTACGTCCGGGGCTACACACGTGTTACAATG<br>GGGGGTACAGAGGGCCGCTACCACGCGAGTGGATGCCAATCCCAAAAACCTCTCT<br>CAGTTCGGACTGGAGTCTGCAACCCGACTCCACGAAGCTGGATTCGCTAGTAATCG<br>CGCATCAGCCACGGCGCGGTGAATACGTTCCCGGGCCTTGTACACACCGCCCGTC<br>AAGCCATGGGAGCCGGGGGTACCTGAAGTGCGTAACCGCGAGGAGCGCCCTAGG<br>GTAAAACTGGTGACTGGGGCTAAGTCGTAACAAGGTAGCCGTACCGGAAG |
| SEQ ID NO: 55 *Bifidobacterium adolescentis*<br>GGGCTCGTAGKCGGTTCGTCGCGTCCGGTGTGAAAGTCCAYCGCTTAACGGTGGA<br>TCCGCGCCGGGTACGGGCGGGCTTGAGTGCGGTAGGGGAGACTGGAATTCCCGGT<br>GTAACGGTGGAATGTGTAGATATCGGGAAGAACACCAATGGCGAAGGCAGGTCTCT<br>GGGCCGTCACTGACGCTGAGGAGCGAAAGCGTGGGGAGCGAACAGGATTAGATAC<br>CCTGGTAGTCCACGCCGTAAACGGTGGATGCTGGATGTGGGGACCATTCCACGGT<br>CTCCGTGTCGGAGCCAACGCGTTAAGCATCCCGCCTGGGGAGTACGGCCGCAAGG<br>CTAAAACTCAAAGAAATTGACGGGGGCCCGCACAAGCGGCGGAGCATGCGGATTA<br>ATTCGATGCAACGCGAAGAACCTTACCTGGGCTTGACATGTTCCCGACAGCCCCAG<br>AGATGGGGCCTCCCTTCGGGGGGGTTCACAGGTGGTGCATGGTCGTCGTCAGCT<br>CGTGTCGTGAGATGTTGGGTTAAGTCCCGCAACGAGCGCAACCCTCGCCCTGTGTT<br>GCCAGCACGTCGTGGTGGGAACTCACGGGGGACCGCCGGGGTCAACTCGGAGGA<br>AGGTGGGGATGACGTCAGATCATCATGCCCCTTACGTCCAGGGCTTCACGCATGCT<br>ACAATGGCCGGTACAACGGGATGCGACACT-<br>GTGAGGTGGAGCGGATCCCTTAAAACCGGTCTCAGTTCGGATTGGAGTCTGCAACC<br>CGACTCCATGAAGGCGGAGTCGCTAGTAATCGCGGATCAGCAACGCCGCGGTGAA<br>TGCGTTCCCGGGCCTTGTACACACCGCCCGTCAAGTCATGAAAGTGGGTAGCACCC<br>GAAGCCGGTGGCCCATCCTTTTTGGGG |
| SEQ ID NO: 56 *Bifidobacterium longum*<br>TGGCTCAGGATGAACGCTGGGGGCGTGCTTAACACATGCAAGTCGAACGGGATCC<br>ATCAGGCTTTGCTTGGTGGTGAGAGTGGCGAACGGGTGAGTAATGCGTGACCGAC<br>CTGCCCCATACACCGGAATAGCTCCTGGAAACGGGTGGTAATGCCGGATGCTCCAG<br>TTGATCGCATGGTCTTCTGGGAAAGCTTTCGCGGTATGGGATGGGGTCGCGTCCTA<br>TCAGCTTGACGGGGGGGTAACGGCCCACCGTGGCTTCGACGGGTAGCCGGCCTGA<br>GAGGGCGACCGGCCACATTGGGACTGAGATACGGCCCAGACTCCTACGGGAGGCA<br>GCAGTGGGGAATATTGCACAATGGGCGCAAGCCTGATGCAGCGACGCCGCGTGAG<br>GGATGGAGGCCTTCGGGTTGTAAACCTCTTTTATCGGGGAGCAAGCGAGAGTGAGT<br>TTACCCGTTGAATAAGCACCGGCTAACTACGTGCCAGCAGCCGCGGTAATACGTAG<br>GGTGCAAGCGTTATCCGGAATTATTGGGCGTAAAGGGCTCGTAGGCGGTTCGTCGC<br>GTCCGGTGTGAAAGTCCATCGCTTAACGGTGGATCCGCGCCGGGTACGGGGGGGC<br>TTGAGTGCGGTAGGGGAGACTGGAATTCCCGGTGTAACGGTGGAATGTGTAGATAT<br>CGGGAAGAACACCAATGGCGAAGGCAGGTCTCTGGGCCGTTACTGACGCTGAGGA<br>GCGAAAGCGTGGGGAGCGAACAGGATTAGATACCCTGGTAGTCCACGCCGTAAAC<br>GGTGGATGCTGGATGTGGGGCCCGTTCCACGGGTTCCGTGTCGGAGCTAACGCGT<br>TAAGCATCCCGCCTGGGGAGTACGGCCGCAAGGCTAAAACTCAAAGAAATTGACGG<br>GGGCCCGCACAAGCGGCGGAGCATGCGGATTAATTCGATGCAACGCGAAGAACCT<br>TACCTGGGCTTGACATGTTCCCGACGGTCGTAGAGATACGGCTTCCCTTCGGGGCG<br>GGTTCACAGGTGGTGCATGGTCGTCGTCAGCTCGTGTCGTGAGATGTTGGGTTAAG<br>TCCCGCAACGAGCGCAACCCTCGCCCCGTGTTGCCAGCGGATTATGCCGGGAACT<br>CACGGGGGACCGCCGGGGTTAACTCGGAGGAAGGTGGGGATGACGTCAGATCATC<br>ATGCCCCTTACGTCCAGGGCTTCACGCATGCTACAATGGCCGGTACAACGGGATGC<br>GACGCGGCGACGCGGAGCGGATCCCTGAAAACCGGTCTCAGTTCGGATCGCAGTC<br>TGCAACTCGACTGCGTGAAGGCGGAGTCGCTAGTAATCGCGAATCAGCAACGTCGC<br>GGTGAATGCGTTCCCGGGCCTTGTACACACCGCCCGTCAAGTCATGAAAGTGGGCA<br>GCACCCGAAGCCGGTGGCCTAACCCCTTGTGGGATGGAGCCGTCTAAGGTGAGGC<br>TCGTGATTGGGACTAAGTCGTAACAAGGTAGCCGTACCGGAAGGTGCGGCTGG |
| SEQ ID NO: 57 *Bifidobacterium pseudocatenulatum*<br>GGTTCGTCGCGTCCGGTGTGAAAGTCCATCGTTTAACGGTGGATCTGCGCCGGGTA<br>CGGGGGGGCTGGAGTGCGGTAGGGGAGACTGGAATTCCCGGTGTAACGGTGGAAT<br>GTGTAGATATCGGGAAGAACACCAATGGCGAAGGCAGGTCTCTGGGCCGTTACTGA<br>CGCTGAGGAGCGAAAGCGTGGGGAGCGAACAGGATTAGATACCCTGGTAGTCCAC<br>GCCGTAAACGGTGGATGCTGGATGTGGGGCCCGTTCCACGGGTTCCGTGWCGGAG<br>CTAACGCGTTAAGCATCCCGCCTGGGGAGTACGGCCGCAAGGCTAAAACWMAAAK<br>AAATTGACGGGGGCCCGCACAAGCGGCGGAGCATGCGGATTAATTCGATGCAACG<br>CGAAGAACCTTACCTGGGCTTGACATGTTCCCGACAGCCGTAGAGATATGGCCTCC<br>CTTCGGGGGGGGTTCACAGGTGGTGCATGGTCGTCGTCAGCTCGTGTCGTGAGAT |

-continued

| SEQUENCES |
|---|
| GTTGGGTTAAGTCCCGCAACGAGCGCAACCCTCGCCCTGTGTTGCCAGCACGTCAT GGTGGGAACTCACGGGGGACCGCCGGGGTCAACTCGGAGGAAGGTGGGGATGAC GTCAGATCATCATGCCCCTTACGTTCAGGGCTTCACGCATGCTACAATGGCCGGTA CAACGGGATGCGACACGGCGACGTG |
| SEQ ID NO: 58 *Blautia coccoides/ Blautia producta* TGTGACTGAGCGGCGGACGGGTGAGTAACGCGTGGGTAACCTGCCTCATACAGGG GGATAACAGTTAGAAATGACTGCTAATACCGCATAAGCGCACAGGACCGCATGGTC TGGTGTGAAAAACTCCGGTGGTATGAGATGGACCCGCGTCTGATTAGCTAGTTGGA GGGGTAACGGCCCACCAAGGCGACGATCAGTAGCCGGCCTGAGAGGGTGAACGG CCACATTGGGACTGAGACACGGCCCAGACTCCTACGGGAGGCAGCAGTGGGGAAT ATTGCACAATGGGGGAAACCCTGATGCAGCGACGCCGCGTGAAGGAAGAAGTATCT CGGTATGTAAACTTCTATCAGCAGGGAAGAAAATGACGGTACCTGACTAAGAAGCC CCGGCTAACTACGTGCCAGCAGCCGCGGTAATACGTAGGGGGCAAGCGTTATCCG GATTTACTGGGTGTAAAGGGAGCGTAGACGGAAGAGCAAGTCTGATGTGAAAGGCT GGGGCTTAACCCCAGGACTGCATTGGAAACTGTTGTTCTAGAGTGCCGGAGAGGTA AGCGGAATTCCTAGTGTAGCGGTGAAATGCGTAGATATTAGGAGGAACACCAGTGG CGAAGGCGGCTTACTGGACGGTAACTGACGTTGAGGCTCGAAAGCGTGGGGAGCA AACAGGATTAGATACCCTGGTAGTCCACGCCGTAAACGATGAATACTAGGTGTCGG GTGGCAAAGCCATTCGGTGCCGCAGCAAACGCAATAAGTATTCCACCTGGGGAGTA CGTTCGCAAGAATGAAACTCAAAGGAATTGACGGGGACCCGCACAAGCGGTGGAG CATGTGGTTTAATTCGAAGCAACGCGAAGAACCTTACCAAGTCTTGACATCCCTCTG ACCGTCCCGTAACGGGGCTTCCCTTCGGGGCAGAGGAGACAGGTGGTGCATGGT TGTCGTCAGCTCGTGTCGTGAGATGTTGGGTTAAGTCCCGCAACGAGCGCAACCCT TATCCTTAGTAGCCAGCACATGATGGTGGGCACTCTAGGGAGACTGCCGGGGATAA CCCGGAGGAAGGCGGGGACGACGTCAAATCATCATGCCCCTTATGATTTGGGCTAC ACACGTGCTACAATGGCGTAAACAAAGGGAAGCGAGACAGCGATGTTGAGCGAATC CCAAAAATAACGTCCCAGTTCGGACTGCAGTCTGCAACTCGACTGCACGAAGCTGG AATCGCTAGTAATCGCGGATCAGAATGCCGCGGTGAATACGTTCCCGGGTCTTGTA CACACCGCCCGTCACACCATGGGAGTCAGTAACGCCCGAAGTCAGTGACCTAACC GAAAGGAAGGAGCTGCCGAAGGGGGGACCGATAACTGGGGTGAAGTCGTAACAAG GTA |
| SEQ ID NO: 59 *Clostridium citroniae* TCCGGATTTACTGGAGTAGT- AAGGGAGCGTAGACGGCGAAGCAAGTCTGGAGTGAAAACCCAGGGCTCAACCCTG GGACTGCTTTGGAAACTGTTTTGCTAGAGTGTCGGAGAGGTAAGTGGAATTCCTAG TGTAGCGGTGAAATGCGTAGATATTAGGAGGAACACCAGTGGCGAAGGGGCTTAC TGGACGATAACTGACGTTGAGGCTCGAAAGCGTGGGGAGCAAACAGGATTAGATAC CCTGGTAGTCCACGCCGTAAACGATGAATGCTAGGTGTTGGGGGGCAAAGCCCTTC GGTGCCGTCGCAAACGCAATAAGCATTCCACCTGGGGAGTACGTTCGCAAGAATGA AACTCAAAGGAATTGACGGGGACCCGCACAAGCGGTGGAGCATGTGGTTTAATTCG AAGCAACGCGAAGAACCTTACCAAGTCTTGACATCCCCCTGACCGGTCAGTAAAGT GACCTTTCCTTCGGGACAGGGGAGACAGGTGGTGCATGGTTGTCGTCAGCTCGTGT CGTGAGATGTTGGGTTAAGTCCCGCAACGAGCGCAACCCTTATCCTTAGTAGCCAG CAGGTAAAGCTGGGCACTCTAGGGAGACTGCCAGGGATAACCTGGAGGAAGGTGG GGATGACGTCAAATCATCATGCCCCTTATGATTTGGGCTACACACGTGCTACAATGG CGTAAACAAAGGGAAGCGACCCTGCGAAGGCAAGCAAATCCCAAAAATAACGTCCC AGTTCGGACTGTAGTCTGCAACCCGACTACACGAAGCTGGAATCGCTAGTAATCGC GAATCAGAATGTCGCGGTGAATACGTTCCCGGGTCTTGTACACACCGCCCGTCACA CCATGGGAGTCAGCAACGCCCGAAGTCAGTGACCCAACCGAAAGGAGGGAGCTGC CGAA |
| SEQ ID NO: 60 *Clostridium clostridioforme* TAATACCGCATAAGCGCACAGTGCCGCATGGCAGTGTGTGAAAAACTCCGGTGGTG TGAGATGGATCCGCGTCTGATTAGCCAGTTGGGGGGGTAACGGCCCACCAAAGCG ACGATCAGTAGCCGACCTGAGAGGGTGACCGGCCACATTGGGACTGAGACACGGC CCAAACTCCTACGGGAGGCAGCAGTGGGGAATATTGCACAATGGGCGAAAGCCTG ATGCAGCGACGCCGCGTGAGTGAAGAAGTATTTCGGTATGTAAAGCTCTATCAGCA GGGAAGAAAATGACGGTACCTGACTAAGAAGCCCCGGCTAACTACGTGCCAGCAG CCGCGGTAATACGTAGGGGGCAAGCGTTATCCGGATTTACTGGGTGTAAAGGGAG CGTAGACGGCGAAGCAAGTCTGAAGTGAAAACCCGGGGCTCAACCCTGGGACTGC TTTGGAAACTGTTTTGCTAGAGTGTCGGAGAGGTAAGTGGAATTCCTAGTGTAGCG GTGAAATGCGTAGATATTAGGAGGAACACCAGTGGCGAAGGCGGCTTACTGGACGA TAACTGACGTTGAGGCTCGAAAGCGTGGGGAGCAAACAGGATTAGATACCCTGGTA GTCCACGCCGTAAACGATGAATGCTAGGTGTTGGGGGGCAAAGCCCTTCGGTGCC GCCGCAAACGCAGTAAGCATTCCACCTGGGGAGTACGTTCGCAAGAATGAAACTCA AAGGAATTGACGGGGACCCGCACAAGCGGTGGAGCATGTGGTTTAATTCGAAGCAA CGCGAAGAACCTTACCAAGTCTTGACATCCCCCTGACGGGCCGGTAACGCGGCCTT TCCTTCGGGACAGGGGAGACAGGTGGTGCATGGTTGTCGTCAGCTCGTGTCGTGA GATGTTGGGTTAAGTCCCGCAACGAGCGCAACCCTTATCCTTAGTAGCCAGCAGGT AGAGCCGGGCACTCTAGGGAGACTGCCAGGGATAACCTGGAGGAAGGTGGGGATG ACGTCAAATCATCATGCCCCTTATGATTTGGGCTACACACGTGCTACAATGGCGTAA |

-continued

| SEQUENCES |
|---|

ACAAAGGGAAGCGAGACAGTGATGTGGAGCAAATCCCAAAAATAACGTCCCAGTTC
GGACTGTAGTCTGCAACCCGACTACACGAAGCTGGAATCGCTAGTAATCGCGAATC
AGAATGTCGCGGTGAATACGTTCCCGGGTCTTGTACACACCGCCCGTCACACCATG
GGAGTCAGCAACGCCCGAAGTCAGTGACCCAACCGAAAGGAGGGAGCTGCCGAAG
GCGGGGCAGGTAACTGGGGTGAAGTCGT

SEQ ID NO: 61 *Clostridium innocuum*
ATGGAGAGTTTGATCCTGGCTCAGGATGAACGCTGGCGGCATGCCTAATACATGCA
AGTCGAACGAAGT-
TTCGAGGAAGCTTGCTTCCAAAGAGACTTAGTGGCGAACGGGTGAGTAACACGTAG
GTAACCTGCCCATGTGTCCGGGATAACTGCTGGAAACGGTAGCTAAAACCGGATAG
GTATACAGAGCGCATGCTCAGTATATTAAAGCGCCCATCAAGGCGTGAACATGGAT
GGACCTGCGGCGCATTAGCTAGTTGGTGAGGTAACGGCCCACCAAGGCGATGATG
CGTAGCCGGCCTGAGAGGGTAAACGGCCACATTGGGACTGAGACACGGCCCAAAC
TCCTACGGGAGGCAGCAGTAGGGAATTTTCGTCAATGGGGGAAACCCTGAACGAG
CAATGCCGCGTGAGTGAAGAAGGTCTTCGGATCGTAAAGCTCTGTTGTAAGTGAAG
AACGGCTCATAGAGGAAATGCTATGGGAGTGACGGTAGCTTACCAGAAAGCCACGG
CTAACTACGTGCCAGCAGCCGCGGTAATACGTAGGTGGCAAGCGTTATCCGGAATC
ATTGGGCGTAAAGGGTGCGTAGGTGGCGTACTAAGTCTGTAGTAAAAGGCAATGGC
TCAACCATTGTAAGCTATGGAAACTGGTATGCTGGAGTGCAGAAGAGGGCGATGGA
ATTCCATGTGTAGCGGTAAAATGCGTAGATATATGGAGGAACACCAGTGGCGAAGG
CGGTCGCCTGGTCTGTAACTGACACTGAGGCACGAAAGCGTGGGGAGCAAATAGG
ATTAGATACCCTAGTAGTCCACGCCGTAAACGATGAGAACTAAGTGTTGGAGGAATT
CAGTGCTGCAGTTAACGCAATAAGTTCTCCGCCTGGGGAGTATGCACGCAAGTGTG
AAACTCAAAGGAATTGACGGGGGCCCGCACAAGCGGTGGAGTATGTGGTTTAATTC
GAAGCAACGCGAAGAACCTTACCAGGCCTTGACATGGAAACAAATACCCTAGAGAT
AGGGGGATAATTATGGATCACACAGGTGGTGCATGGTTGTCGTCAGCTCGTGTCGT
GAGATGTTGGGTTAAGTCCCGCAACGAGCGCAACCCTTGTCGCATGTTACCAGCAT
CAAGTTGGGGACTCATGCGAGACTGCCGGTGACAAACCGGAGGAAGGTGGGGATG
ACGTCAAATCATCATGCCCCTTATGGCCTGGGCTACACACGTACTACAATGGCGGC
CACAAAGAGCAGCGACACAGTGATGTGAAGCGAATCTCATAAAGGTCGTCTCAGTT
CGGATTGAAGTCTGCAACTCGACTTCATGAAGTCGGAATCGCTAGTAATCGCAGAT
CAGCATGCTGCGGTGAATACGTTCTCGGGCCTTGTACACACCGCCCGTCAAACCAT
GGGAGTCAGTAATACCCGAAGCCGGTGGCATAACCGTAAGGAGTGAGCCGTCGAA
GGTAGGACCGA SEQ ID NO: 62 *Clostridium innocuum / Erysipelotrichaceae bacterium* 6_1_45
ATGGAGAGTTTGATCCTGGCTCAGGATGAACGCTGGGGGCATGCCTAATACATGCA
AGTCGAACGAAGT-
TTCGAGGAAGCTTGCTTCCAAAGAGACTTAGTGGCGAACGGGTGAGTAACACGTAG
GTAACCTGCCCATGTGTCCGGGATAACTGCTGGAAACGGTAGCTAAAACCGGATAG
GTATACAGAGCGCATGCTCAGTATATTAAAGCGCCCATCAAGGCGTGAACATGGAT
GGACCTGCGGCGCATTAGCTAGTTGGTGAGGTAACGGCCCACCAAGGCGATGATG
CGTAGCCGGCCTGAGAGGGTAAACGGCCACATTGGGACTGAGACACGGCCCAAAC
TCCTACGGGAGGCAGCAGTAGGGAATTTTCGTCAATGGGGGAAACCCTGAACGAG
CAATGCCGCGTGAGTGAAGAAGGTCTTCGGATCGTAAAGCTCTGTTGTAAGTGAAG
AACGGCTCATAGAGGAAATGCTATGGGAGTGACGGTAGCTTACCAGAAAGCCACGG
CTAACTACGTGCCAGCAGCCGCGGTAATACGTAGGTGGCAAGCGTTATCCGGAATC
ATTGGGCGTAAAGGGTGCGTAGGTGGCGTACTAAGTCTGTAGTAAAAGGCAATGGC
TCAACCATTGTAAGCTATGGAAACTGGTATGCTGGAGTGCAGAAGAGGGCGATGGA
ATTCCATGTGTAGCGGTAAAATGCGTAGATATATGGAGGAACACCAGTGGCGAAGG
CGGTCGCCTGGTCTGTAACTGACACTGAGGCACGAAAGCGTGGGGAGCAAATAGG
ATTAGATACCCTAGTAGTCCACGCCGTAAACGATGAGAACTAAGTGTTGGAGGAATT
CAGTGCTGCAGTTAACGCAATAAGTTCTCCGCCTGGGGAGTATGCACGCAAGTGTG
AAACTCAAAGGAATTGACGGGGGCCCGCACAAGCGGTGGAGTATGTGGTTTAATTC
GAAGCAACGCGAAGAACCTTACCAGGCCTTGACATGGAAACAAATACCCTAGAGAT
AGGGGGATAATTATGGATCACACAGGTGGTGCATGGTTGTCGTCAGCTCGTGTCGT
GAGATGTTGGGTTAAGTCCCGCAACGAGCGCAACCCTTGTCGCATGTTACCAGCAT
CAAGTTGGGGACTCATGCGAGACTGCCGGTGACAAACCGGAGGAAGGTGGGGATG
ACGTCAAATCATCATGCCCCTTATGGCCTGGGCTACACACGTACTACAATGGCGAC
CACAAAGAGCAGCGACACAGTGATGTGAAGCGAATCTCATAAAGGTCGTCTCAGTT
CGGATTGAAGTCTGCAACTCGACTTCATGAAGTCGGAATCGCTAGTAATCGCAGAT
CAGCATGCTGCGGTGAATACGTTCTCGGGCCTTGTACACACCGCCCGTCAAACCAT
GGGAGTCAGTAATACCCGAAGCCGGTGGCATAACCGTAAGGAGTGAGCCGTCGAA
GGTAGGACCGA SEQ ID NO: 63 *Clostridium sordellii*
ACACATGCAAGTCGAGCGAACCCTTCGGGGTGAGCGGCGGACGGGTGAGTAACGC
GTGGGTAACCTGCCCTGTACACACGGATAACATACCGAAAGGTATGCTAATACGGG
ATRAYATATGAGAGTCGCATGGCTTTTGTATCAAAGCTCCGGCGGTACAGGATGGA
CCCGCGTCTGATTAGCTAGTTGGTAAGGTAACGGCTTACCAAGGCAACGATCAGTA
GCCGACCTGAGAGGGTGATCGGCCACATTGGAACTGAGACACGGTCCAAACTCMT
ACGGGAGGCAGCAGTGGGGAATATTGCACAATGGGCGAAAGCCTGATGCAGCAAC
GCCGCGTGAGCGATGAAGGCCTTCGGGTCGTAAAGCTCTGTCCTCAAGGAAGATAA
TGACGGTACTTGAGGAGGAAGCCCCGGCTAACTACGTGCCAGCAGCCGCGGTAAT
ACGTAGGGGGCTAGCGTTATCCGGAATTACTGGGCGTAAAGGGTGCGTAGGCGGT
CTTTCAAGCCAGAAGTGAAAGGCTACGGCTCAACCGTAGTAAGCTTTTGGAACTGT -continued

| SEQUENCES |
|---|
| AGGACTTGAGTGCAGGAGAGGAGAGTGGAATTCCTAGTGTAGCGGTGAAATGCGTA<br>GATATTAGGAGGAACACCAGTAGCGAAGGCGGCTCTCTGGACTGTAACTGACGCTG<br>AGGCACGAAAGCGTGGGGAGCAAACAGGATTAGATACCCTGGTAGTCCACGCCGT<br>AAACGATGAGTACTAGGTGTCGGGGGTTACCCCCCTCGGTGCCGCAGCTAACGCAT<br>TAAGTACTCCGCCTGGGAAGTACGCTCGCAAGAGTGAAACTCAAAGGAATTGACGG<br>GGACCCGCACAAGTAGCGGAGCATGTGGTTTAATTCGAAGCAACGCGAAGAACCTT<br>ATCTAARCTTGACATC |
| SEQ ID NO: 64 *Coprococcus comes*<br>ACRGGAGGCAGCAGTGGGGAATATTGCACAATGGGGGAAACCCTGATGCAGCGAC<br>GCCRCGTGAGCGAAGAAGTATTKCGGTATGTAAAGCTCTATCAGCAGGGAAGAAAA<br>TGACGGTACCTGACTAAGAAGCACCGGCTAAATACGTGCCAGCAGCCGCGGTAATA<br>CGTATGGTGCAAGCGTTATCCGGATTTACTGGGTGTAAAGGGAGCGTAGACGGCTG<br>TGTAAGTCTGAAGTGAAAGGGGGGGGCTCCCCCCCGGGGACTGCTTTGGAAACTAT<br>GCAGCTAGACTGTCGGACAGGTAAGTGGAATTCCCAGTGTAGCGGTGAAATGCGTA<br>GATATTGGGAGGAACAGCAKTGGGTAAGGCTSCTTACAGGACRAT |
| SEQ ID NO: 65 *Dorea longicatena*<br>TAACGCGTGGGTAACCTGCCTCATACAGGGGGATAACAGTTAGAAATGACTGCTAA<br>TACCGCATAAGACCACGGTACCGCATGGTACAGTGGTAAAAACTCCGGTGGTATGA<br>GATGGACCCGCGTCTGATTAGGTAGTTGGTGGGGTAACGGCCTACCAAGCCGACG<br>ATCAGTAGCCGACCTGAGAGGGTGACCGGCCACATTGGGACTGAGACACGGCCCA<br>GACTCCTACGGGAGGCAGCAGTGGGGAATATTGCACAATGGAGGAAACTCTGATGC<br>AGCGACGCCGCGTGAAGGATGAAGTATTTCGGTATGTAAACTTCTATCAGCAGGGA<br>AGAAAATGACGGTACCTGACTAAGAAGCCCCGGCTAACTACGTGCCAGCAGCCGC<br>GGTAATACGTAGGGGGCAAGCGTTATCCGGATTTACTGGGTGTAAAGGGAGCGTAG<br>ACGGCACGGCAAGCCAGATGTG-<br>AAAGCCCGGGGCTCAACCCCGGGACTGCATTTGGAACTGCTGAGCTAGAGTGTCG<br>GAGAGGCAAGTGGAATTCCTAGTGTAGCGGTGAAATGCGTAGATATTAGGAGGAAC<br>ACCAGTGGCGAAGGCGGCTTGCTGGACGATGACTGACGTTGAGGCTCGAAAGCGT<br>GGGGAGCAAACAGGATTAGATACCCTGGTAGTCCACGCCGTAAACGATGACTGCTA<br>GGTGTCGGGTGGCAAAGCCATTCGGTGCCGCAGCTAACGCAATAAGCAGTCCACC<br>TGGGGAGTACGTTCGCAAGAATGAAACTCAAAGGAATTGACGGGGACCCGCACAAG<br>CGGTGGAGCATGTGGTTTAATTCGAAGCAACGCGAAGAACCTTACCTGATCTTGAC<br>ATCCCGATGACCGCTTCGTAATGGAAGCTTTTCTTCGGAACATCGGTGACAGGTGG<br>TGCATGGTTGTCGTCAGCTCGTGTCGTGAGATGTTGGGTTAAGTCCCGCAACGAGC<br>GCAACCCCTATCTTCAGTAGCCAGCAGGTTAAGCTGGGCACTCTGGAGAGACTGCC<br>AGGGATAACCTGGAGGAAGGTGGGGATGACGTCAAATCATCATGCCCCTTATGACC<br>AGGGCTACACACGTGCTACAATGGCGTAAACAAAGAGAAGCGAACTCGCGAGGGTA<br>AGCAAATCTCAAAAATAACGTCTCAGTTCGGATTGTAGTCTGCAACTCGACTACATG<br>AAGCTGGAATCGCTAGTAATCGCAGATCAGAATGCTGCGGTGAATACGTTCCCGGG<br>TCTTGTACACACCGCCCGTCACACCATGGGAGTCAGTAACGCCCGAAGTCAGTGAC<br>CCAACCGTAAGG |
| SEQ ID NO: 66 *Erysipelatoclostridium ramosum*<br>GAGGGAGCAGGCGGCAGCAAGGGTCTGTGGTGAAAGCCTGAAGTTAAACTTCAGT<br>AAGCCATAGAAACCAGGCAGCTAGAGTGCAGGAGAGGAKCGTGGAATTCCATGTGT<br>AGCGGTGAAATGCGTAGATATATGGAGGAACACCAGTGGCGAAGGCGACGATCTG<br>GCCTGCAACTGACGCTCAGTCCCGAAAGCGTGGGGAGCAAATAGGATTAGATACCC<br>TAGTAGTCCACGCCGTAAACGATGAGTACTRAGTGTTGGATGTCAAAGTTCAGTGCT<br>GCAGTTAACGCAATAAGTACTCCGCCTGAGTAGTACGTTCGCAAGAATGAAACTCAA<br>AGGAATTGACGGGGGCCCGCACAAGCGGTGGAGCATGTGGTTTAATTCGAAGCAA<br>CGCGAAGAACCTTACCAGGTCTTGACATACTCATAAAGGCTCCAGAGATGGAGAGA<br>TAGCTATATGAGATACAGGTGGTGCATGGTTGTCGTCAGCTCGTGTCGTGAGATGT<br>TGGGTTAAGTCCCGCAACGAGCGCAACCCTTATCGTTAGTTACCATCATTAAGTTGG<br>GGACTCTAGCGAGACTGCCAGTGACAAGCTGGAGGAARGCGGGGATGACGTCAAA<br>TCATCATGCCCCTTATGACCTGGGCTACACACGTGCTACAATGGATGGTGCAGAGG<br>GAAGCGAAGCCGCGAGGTGAAGCAAAACCCATAAAACCATTCTCAGTTCGGATTGT<br>AGTCTGCARCTCGACTACATGAAGTTGGAATCGCTAGTAATCGCGAATCARCATGTC<br>GCGATGAATAMGTTCTCGGGCCTT |
| SEQ ID NO: 67 *Eubacterium rectale*<br>AGAGTTTGATCCTGGCTCAGGATGAACGCTGGCGGCGTGCTTAACACATGCAAGTC<br>GAACGAAGCACTTTATTTGATTTCCTTCGGGACTGATTATTTTGTGACTGAGTGGCG<br>GACGGGTGAGTAACGCGTGGGTAACCTGCCTTGTACAGGGGGATAACAGTTGGAA<br>ACGGCTGCTAATACCGCATAAGCGCACGGCATCGCATGATGCAGTGTGAAAAACTC<br>CGGTGGTATAAGATGGACCCGCGTTGGATTAGCTAGTTGGTGAGGTAACGGCCCAC<br>CAAGGCGACGATCCATAGCCGACCTGAGAGGGTGACCGGCCACATTGGGACTGAG<br>ACACGGCCCAAACTCCTACGGGAGGCAGCAGTGGGGAATATTGCACAATGGGCGA<br>AAGCCTGATGCAGCGACGCCGCGTGAGCGAAGAAGTATTTCGGTATGTAAAGCTCT<br>ATCAGCAGGGAAGATAATGACGGTACCTGACTAAGAAGCACCGGCTAAATACGTGC<br>CAGCAGCCGCGGTAATACGTATGGTGCAAGCGTTATCCGGATTTACTGGGTGTAAA<br>GGGAGCGCAGGCGGTGCGGCAAGTCTGATGTGAAAGCCCGGGGCTCAACCCCGG<br>TACTGCATTGGAAACTGTCGTACTAGAGTGTCGGAGGGGTAAGCGGAATTCCTAGT<br>GTAGCGGTGAAATGCGTAGATATTAGGAGGAACACCAGTGGCGAAGGCGGCTTACT<br>GGACGATAACTGACGCTGAGGCTCGAAAGCGTGGGGAGCAAACAGGATTAGATAC<br>CCTGGTAGTCCACGCCGTAAACGATGAATACTAGGTGTTGGGAAGCATTGCTTCTC |

-continued

| SEQUENCES |
| --- |
| GGTGCCGTCGCAAACGCAGTAAGTATTCCACCTGGGGAGTACGTTCGCAAGAATGA<br>AACTCAAAGGAATTGACGGGGACCCGCACAAGCGGTGGAGCATGTGGTTTAATTCG<br>AAGCAACGCGAAGAACCTTACCAAGTCTTGACATCCTTCTGACCGGTACTTAACCGT<br>ACCTTCTCTTCGGAGCAGGAGTGACAGGTGGTGCATGGTTGTCGTCAGCTCGTGTC<br>GTGAGATGTTGGGTTAAGTCCCGCAACGAGCGCAACCCTTATCTTTAGTAGCCAGC<br>GGTTCGGCCGGGCACTCTAGAGAGACTGCCAGGGATAACCTGGAGGAAGGCGGGG<br>ATGACGTCAAATCATCATGCCCCTTATGACTTGGGCTACACACGTGCTACAATGGC<br>GTAAACAAAGGGAAGCAAAGCTGTGAAGCCGAGCAAATCTCAAAAATAACGTCTCA<br>GTTCGGACTGTAGTCTGCAACCCGACTACACGAAGCTGGAATCGCTAGTAATCGCA<br>GATCAGAATGCTGCGGTGAATACGTTCCCGGGTCTTGTACACACCGCCCGTCACAC<br>CATGGGAGTTGGGAATGCCCGAAGCCAGTGACCTAACCGAAAGGAAGGAGCTGTC<br>GAAGGCAGGCTCGATAACTGGGGTGAAGTCGTAACAAGGTAGCCGTATCGGAAGG<br>TGCGGCTGGATCACCT |
| SEQ ID NO: 68 *Odoribacter splanchnicus*<br>AGAGTTTGATCCTGGCTCAGGATGAACGCTAGCGACAGGCTTAACACATGCAAGTC<br>GAGGGGCATCATGAGGTAGCAATACCTTGATGGCGACCGGCGCACGGGTGAGTAA<br>CGCGTATGCAACCTGCCCGATACCGGGGTATAGCCCATGGAAACGTGGATTAACAC<br>CCCATAGTACTTTTATCCTGCATGGGATGTGAGTTAAATGTTTAAGGTATCGGATGG<br>GCATGCGTCCTATTAGTTAGTTGGCGGGGTAACAGCCCACCAAGACGATGATAGGT<br>AGGGGTTCTGAGAGGAAGGTCCCCCACATTGGAACTGAGACACGGTCCAAACTCCT<br>ACGGGAGGCAGCAGTGAGGAATATTGGTCAATGGACGAGAGTCTGAACCAGCCAA<br>GTCGCGTGAGGGAAGACTGCCCTATGGGTTGTAAACCTCTTTTATAAGGGAAGAAT<br>AAGTTCTACGTGTAGAATGATGCCTGTACCTTATGAATAAGCATCGGCTAACTCCGT<br>GCCAGCAGCCGCGGTAATACGGAGGATGCGAGCGTTATCCGGATTTATTGGGTTTA<br>AAGGGTGCGTAGGCGGTTTATTAAGTTAGTGGTTAAATATTTGAGCTAAACTCAATT<br>GTGCCATTAATACTGGTAAACTGGAGTACAGACGAGGTAGGCGGAATAAGTTAAGT<br>AGCGGTGAAATGCATAGATATAACTTAGAACTCCGATAGCGAAGGCAGCTTACCAG<br>ACTGTAACTGACGCTGATGCACGAGAGCGTGGGTAGCGAACAGGATTAGATACCCT<br>GGTAGTCCACGCCGTAAACGATGCTCACTGGTTCTGTGCGATATATTGTACGGGAT<br>TAAGCGAAAGTATTAAGTGAGCCACCTGGGGAGTACGTCGGCAACGATGAAACTCA<br>AAGGAATTGACGGGGGCCCGCACAAGCGGAGGAACATGTGGTTTAATTCGATGATA<br>CGCGAGGAACCTTACCTGGGTTTAAATGGGAAATGTCGTATTTGGAAACAGATATTC<br>TCTTCGGAGCGTTTTTCAAGGTGCTGCATGGTTGTCGTCAGCTCGTGCCGTGAGGT<br>GTCGGGTTAAGTCCCATAACGAGCGCAACCCTTACCGTTAGTTGCTAGCATGTAAT<br>GATGAGCACTCTAACGGGACTGCCACCGTAAGGTGAGAGGAAGGCGGGGATGACG<br>TCAAATCAGCACGGCCCTTACACCCAGGGCTACACACGTGTTACAATGGCCGGTAC<br>AGAGGGCCGCTACCAGGTGACTGGATGCCAATCTCAAAAGCCGGTCGTAGTTCGG<br>ATTGGAGTCTGTAACCCGACTCCATGAAGTTGGATTCGCTAGTAATCGCGCATCAG<br>CCATGGCGCGGTGAATACGTTCCCGGGCCTTGTACACACCGCCCGTCAAGCCATG<br>GAAGCCGGGGGTGCCTGAAGTCCGTAACCGCGAGGATCGGCCTAGGGCAAAACTG<br>GTAACTGGGGCTAAGTCGTAACAAGGTA |
| SEQ ID NO: 69 Parabacteroides distasonis<br>CGAGGGGCAGCRCAGGAGT-TAGCAATAC-<br>CSGGTGGCGACCGGCGCACGGGTGAGTAACGCGTATGCAACTTRCCTATCAGAGG<br>GGGATAACCCGGCGAAAGTCGGACTAATACCGCATGAAGCAGGGATYCCGCATGG<br>GRATATTTGCTAAAGATTCATCGCTGATAGATAGGCATGCGTTCCATTAGGCAGTTG<br>GCGGGGTAACRGCCCACCAAACCGACGATGGATAGGGGTTCTGAGAGGAAGGTCC<br>CCCACATTGGTACTGAGACACGGACCAAACTCCTACGGGAGGCAGCAGTGAGGAAT<br>ATTGGTCAATGGSCGWRAGSCTGAACCAGCCAAGTCGCGTGAGGGATGAAGGTTC<br>TATGGATCGTAAACCTCTTTTATAAGGGAATAAAGTGCGGGACGTGTCCYRTTTTGT<br>ATGTACCTTATGAATAAGGATCGGCTAACTCCGTGCCAGCAGCCGCGGTAATACGG<br>AGGATCCGAGCGTTATCCGGATTTATTGGGTTTAAAGGGTGCGTAGGCGGCCTTTT<br>AAGTCAGCGGTGAAAGTCTGTGGCTCAACCATAGAATTGCCGTTGAAACTGGGGGG<br>CTTGAGTATGTTTGAGGCAGGCGGAATGCGTGGTGTAGCGGTGAAATGCATAGATA<br>TCACGCAGAACCCCGWTTGCGAAGGCAGCCTGCCAAGCCGTAACTGACGCGGATG<br>CACGAAAGCGTGGGGATCAAACAGGATTAGATACCCTGGTA |
| SEQ ID NO: 70 *Parabacteroides merdae*<br>CATGCAAGTCGAGGGGCAGCATGATTTGTAGCAATACAGATTGATGGCGACCGGCG<br>CACGGGTGAGTAACGCGTATGCAACTTACCTATCAGAGGGGGATAGCCCGGCGAA<br>AGTCGGATTAATACCCCATAAAACAGGGGTCCCGCATGGGAATATTTGTTAAAGATT<br>CATCGCTGATAGATAGGCATGCGTTCCATTAGGCAGTTGGCGGGGTAACGGCCCAC<br>CAAACCGACGATGGATAGGGGTTCKGAGAGGAAGGTCCCCCACATTGGTACTGAGA<br>CACGGACCAAACTCCTACGGGAGGCAGCAGTGAGGAATATTGGTCAATGGCCGAG<br>AGGCTGAACCAGCCAAGTCGCGTGAAGGAAGAAGGATCTATGGTTTGTAAACTTCT<br>TTTATAGGGGAATAAAGTGGAGGACGTGTCCTTTTTTGTATGTACCCTATGAATAAG<br>CATCGGCTAACTCCGTGMSARCMGCCGCGGGAATACGGAAGATGCAGAGCGTTAT<br>CCGGATWTATTGGGGTTA |
| SEQ ID NO: 71 *Bacteroides xylanisolvens*<br>CATGCAAGTCGAGGGGCAGCATTTTAGTTTGCTTGCAAACTAAAGATGGCGACCGG<br>CGCACGGGTGAGTAACACGTATCCAACCTGCCGATAACTCGGGGATAGCCTTTCGA<br>AAGAAAGATTAATATCCGATAGTATATTAAAACCGCATGGTTTTACTATTAAAGAATT<br>TCGGTTATCGATGGGGATGCGTTCCATTAGTTTGTTGGCGGGGTAACGGCCCACCA<br>AGACTACGATGGATAGGGGTTCTGAGAGGAAGGTCCCCCACATTGGAACTGAGACA |

-continued

| SEQUENCES |
| --- |

CGGTCCAAACTCCTACGGGAGGCAGCAGTGAGGAATATTGGTCAATGGACGAGAGT
CTGAACCAGCCAAGTAGCGTGAAGGATGACTGCCCTATGGGTTGTAAACTTCTTTTA
TATGGGAATAAAGTATTCCACGTGTGGGATTTTGTATGTACCATATGAATAAGGATC
GGCTAACTCCGTGCCAGCAGCCGCGGTAATACGGAGGATCCGAGCGTTATCCGGA
TTTATTGGGTTTAAAGGGAGCGTAGGTGGATTGTTAAGTCAGTTGTGAAAGTTTGCG
GCTCAACCGTAAAATTGCAGTTGAAACTGGCAGTCTTGAGTACAGTAGAGGTGGGC
GGAATTCGTGGTGTAGCGGTGAAATGCTTAGATATCACGAAGAACTCCGATTGCGA
AGGCAGCTCACTAGACTGCAACTGACACTGATGCTCGAAAGTGTGGGTATCAAACA
GGATTAGATACCCTGGTAGTCCACACAGTAAACGATGAATACTCGCTGTTTGCGATA
TACAGTAAGCGGCCAAGCGAAAGCATTAAGTATTCCACCTGGGGAGTACGCCGGCA
ACGGTGAAACTCAAAGGAATTGACGGGGGCCCGCACAAGCGGAGGAACATGTGGT
TTAATTCGATGATACGCGAGGAACCTTACCCGGGCTTAAATTGCATTTGAATAATCT
GGAAACAGGTTAGCCGCAAGGCAAATGTGAAGGTGCTGCATGGTTGTCGTCAGCTC
GTGCCGTGAGGTGTCGGCTTAAGTGCCATAACGAGCGCAACCCTTATCTTTAGTTA
CTAACAGGTTATGCTGAGGACTCTAGAGAGACTGCCGTCGTAAGATGTGAGGAAGG
TGGGGATGACGTCAAATCAGCACGGCCCTTACGTCCGGGGCTACACACGTGTTACA
ATGGGGGGTACAGAAGGCAGCTACCTGGCGACAGGATGCTAATCCCAAAAACCTCT
CTCAGTTCGGATCGAAGTCTGCAACCCGACTTCGTGAAGCTGGATTCGCTAGTAAT
CGCGCATCAGCCATGGCGCGGTGAATACGTTCCCGGGCCTTGTACACACCGCCCG
TCAAGCCATGAAAGCCGGGG

SEQ ID NO: 72 *Blautia obeum*
GGCGTGCTTAACACATGCAAGTCGAACGGGAAACCTTTTATTGAAGCTTCGGCAGA
TTTAG-
CTGGTTTCTAGTGGCGGACGGGTGAGTAACGCGTGGGTAACCTGCCTTATACAGGG
GGATAACAACCAGAAATGGTTGCTAATACCGCATAAGCGCACAGGACCGCATGGTC
CGGTGTGAAAAACTCCGGTGGTATAAGATGGACCCGCGTTGGATTAGCTAGTTGGC
AGGGTAACGGCCTACCAAGGCGACGATCCATAGCCGGCCTGAGAGGGTGAACGGC
CACATTGGGACTGAGACACGGCCCAGACTCCTACGGGAGGCAGCAGTGGGGAATA
TTGCACAATGGGGGAAACCCTGATGCAGCGACGCCGCGTGAAGGAAGAAGTATCT
CGGTATGTAAACTTCTATCAGCAGGGAAGATAGTGACGGTACCTGACTAAGAAGCC
CCGGCTAACTACGTGCCAGCAGCCGCGGTAATACGTAGGGGGCAAGCGTTATCCG
GATTTACTGGGTGTAAAGGGAGCGTAGACGGACTGGCAAGTCTGATGTGAAAGGCG
GGGGCTCAACCCCTGGACTGCATTGGAAACTGTTAGTCTTGAGTGCCGGAGAGGTA
AGCGGAATTCCTAGTGTAGCGGTGAAATGCGTAGATATTAGGAGGAACACCAGTGG
CGAAGGCGGCTTACTGGACGGTAACTGACGTTGAGGCTCGAAAGCGTGGGGAGCA
AACAGGATTAGATACCCTGGTAGTCCACGCCGTAAACGATGAATACTAGGTGTTGG
GGAGCAAAGCTCTTCGGTGCCGCCGCAAACGCATTAAGTATTCCACCTGGGGAGTA
CGTTCGCAAGAATGAAACTCAAAGGAATTGACGGGGACCCGCACAAGCGGTGGAG
CATGTGGTTTAATTCGAAGCAACGCGAAGAACCTTACCAAGTCTTGACATCCCTCTG
ACCGTTCCTTAACCGGAACTTTCCTTCGGGACAGGGGAGACAGGTGGTGCATGGTT
GTCGTCAGCTCGTGTCGTGAGATGTTGGGTTAAGTCCCGCAACGAGCGCAACCCCT
ATCCCCAGTAGCCAGCAGTCCGGCTGGGCACTCTGAGGAGACTGCCAGGGATAAC
CTGGAGGAAGGCGGGGATGACGTCAAATCATCATGCCCCTTATGATTTGGGCTACA
CACGTGCTACAATGGCGTAAACAAAGGGAAGCAAGCCTGCGAAGGTAAGCAAATCC
CAAAAATAACGTCCCAGTTCGGACTGCAGTCTGCAACTCGACTGCACGAAGCTGGA
ATCGCTAGTAATCGCGGATCAGAATGCCGCGGTGAATACGTTCCCGGGTCTTGTAC
ACACCGCCCGTCACACCATGGGAGTCAGTAACGCCCGAAGTCAGTGACCTAACTGC SEQ ID NO: 73 *Alistipes putredinis*
AGAGTTTGATCCTGGCTCAGGATGAACGCTAGCGGCAGGCTTAACACATGCAAGTC
GAGGGGCAGCATAATGGATAGCAATATCTATGGTGGCGACCGGCGCACGGGTGCG
TAACGCGTATGCAACCTACCTTTAACAGGGGGATAACACTGAGAAATTGGTACTAAT
ACCCCATAATATCATAGAAGGCATCTTTTATGGTTGAAAATTCCGATGGTTAGAGAT
GGGCATGCGTTGTATTAGCTAGTTGGTGGGGTAACGGCTCACCAAGGCGACGATAC
ATAGGGGGACTGAGAGGTTAACCCCCCACACTGGTACTGAGACACGGACCAGACT
CCTACGGGAGGCAGCAGTGAGGAATATTGGTCAATGGACGCAAGTCTGAACCAGC
CATGCCGCGTGCAGGATGACGGCTCTATGAGTTGTAAACTGCTTTTGTACGAGGGT
AAACGCAGATACGTGTATCTGTCTGAAAGTATCGTACGAATAAGGATCGGCTAACTC
CGTGCCAGCAGCCGCGGTAATACGGAGGATTCAAGCGTTATCCGGATTTATTGGGT
TTAAAGGGTGCGTAGGCGGTTTGATAAGTTAGAGGTGAAATTTCGGGGCTCAACCC
TGAACGTGCCTCTAATACTGTTGAGCTAGAGAGTAGTTGCGGTAGGCGGAATGTAT
GGTGTAGCGGTGAAATGCTTAGAGATCATACAGAACACCGATTGCGAAGGCAGCTT
ACCAAACTATATCTGACGTTGAGGCACGAAAGCGTGGGGAGCAAACAGGATTAGAT
ACCCTGGTAGTCCACGCAGTAAACGATGATAACTCGTTGTCGGCGATACACAGTCG
GTGACTAAGCGAAAGCGATAAGTTATCCACCTGGGGAGTACGTTCGCAAGAATGAA
ACTCAAAGGAATTGACGGGGGCCCGCACAAGCGGAGGAACATGTGGTTTAATTCGA
TGATACGCGAGGAACCTTACCCGGGCTTGAAAGTTAGCGACGATTCTTGAAAGAGG
ATTTCCCTTCGGGGCGCGAAACTAGGTGCTGCATGGTTGTCGTCAGCTCGTGCCGT
GAGGTGTCGGGTTAAGTCCCATAACGAGCGCAACCCCTACCGTTAGTTGCCATCAG
GTGAAGCTGGGCACTCTGGGGGGACTGCCGGTGTAAGCCGAGAGGAAGGTGGGG
ATGACGTCAAATCAGCACGGCCCTTACGTCCGGGGCTACACACGTGTTACAATGGT
AGGTACAGAGGGCAGCTACCCAGCGATGGGATGCGAATCTCGAAAGCCTATCTCAG
TTCGGATTGGAGGCTGAAACCCGCCTCCATGAAGTTGGATTCGCTAGTAATCGCGC
ATCAGCCATGGCGCGGTGAATACGTTCCCGGGCCTTGTACACACCGCCCGTCAAG
CCATGGGAGCCGGGGGTGCCTGAAGTTCGTGACCGCAAGGAGCGACCTAGGGCAA
AACTGGTGACTGGGGCTAAGTCGTAACAAGGTA -continued

SEQUENCES

SEQ ID NO: 74 *Collinsella aerofaciens*
AGAGTTCGATCCTGGCTCAGGATGAACGCTGGCGGCGCGCCTAACACATGCAAGT
CGAACGGCACCTATCTTCGGATAGAAGCGAGTGGCGAACGGCTGAGTAACACGTG
GAGAACCTGCCCCCTCCCCCGGGATAGCCGCCCGAAAGGACGGGTAATACCGGAT
ACCCCGGGGTGCCGCATGGCACCCCGGCTAAAGCCCCGACGGGAGGGGATGGCT
CCGCGGCCCATCAGGTAGACGGCGGGGTGACGGCCCACCGTGCCGACAACGGGT
AGCCGGGTTGAGAGACCGACCGGCCAGATTGGGACTGAGACACGGCCCAGACTCC
TACGGGAGGCAGCAGTGGGGAATCTTGCGCAATGGGGGGAACCCTGACGCAGCGA
CGCCGCGTGCGGGACGGAGGCCTTCGGGTCGTAAACCGCTTTCAGCAGGGAAGAG
TCAAGACTGTACCTGCAGAAGAAGCCCCGGCTAACTACGTGCCAGCAGCCGCGGT
AATACGTAGGGGGCGAGCGTTATCCGGATTCATTGGGCGTAAAGCGCGCGTAGGC
GGCCCGGCAGGCCGGGGGTCGAAGCGGGGGGCTCAACCCCCCGAAGCCCCCGGA
ACCTCCGCGGCTTGGGTCCGGTAGGGGAGGGTGGAACACCCGGTGTAGCGGTGG
AATGCGCAGATATCGGGTGGAACACCGGTGGCGAAGGCGGCCCTCTGGGCCGAGA
CCGACGCTGAGGCGCGAAAGCTGGGGGAGCGAACAGGATTAGATACCCTGGTAGT
CCCAGCCGTAAACGATGGACGCTAGGTGTGGGGGGACGATCCCCCCGTGCCGCAG
CCAACGCATTAAGCGTCCCGCCTGGGGAGTACGGCCGCAAGGCTAAAACTCAAAG
GAATTGACGGGGGCCCGCACAAGCAGCGGAGCATGTGGCTTAATTCGAAGCAACG
CGAAGAACCTTACCAGGGCTTGACATATGGGTGAAGCGGGGGAGACCCCGTGGCC
GAGAGGAGCCCATACAGGTGGTGCATGGCTGTCGTCAGCTCGTGTCGTGAGATGTT
GGGTTAAGTCCCGCAACGAGCGCAACCCCCGCCGCGTGTTGCCATCGGGTGATGC
CGGGAACCCACGCGGGACCGCCGCCGTCAAGGCGGAGGAGGGGGGGGACGACGT
CAAGTCATCATGCCCCTTATGCCCTGGGCTGCACACGTGCTACAATGGCCGGTACA
GAGGGATGCCACCCCGCGAGGGGGAGCGGATCCCGGAAAGCCGGCCCCAGTTCG
GATTGGGGGCTGCAACCCGCCCCCATGAAGTCGGAGTTGCTAGTAATCGCGGATC
AGCATGCCGCGGTGAATGCGTTCCCGGGCCTTGTACACACCGCCCGTCACACCAC
CCGAGTCGTCTGCACCCGAAGTCGCCGGCCCAACCGAGAGGGGGGAGGCGCCGA
AGGTGTGGAGGGTGAGGGGGGTGAAGTCGTAACAAGGTA SEQ ID NO: 75 *Bacteroides faecis /Eubacterium hallii*
CTCAGGATGAACGCTAGCTACAGGCTTAACACATGCAAGTCGAGGGGCAGCATTCC
AGTTTGCTTGCAAACTGGAGATGGCGACCGGCGCACGGGTGAGTAACACGTATCCA
ACCTGCCGATAACTCGGGGATAGCCTTTCGAAAGAAAGATTAATACCCGATGGCAT
AATAGAACCGCATGGTTTGATTATTAAAGAATTTCGGTTATCGATGGGGATGCGTTC
CATTAGGCAGTTGGTGGGGTAACGGCCCACCAAACCTTCGATGGATAGGGGTTCTG
AGAGGAAGGTCCCCCACATTGGAACTGAGACACGGTCCAAACTCCTACGGGAGGC
AGCAGTGAGGAATATTGGTCAATGGACGAGAGTCTGAACCAGCCAAGTAGCGTGAA
GGATGACTGCCCTATGGGTTGTAAACTTCTTTTATATGGGAATAAAGTGGTCCACGT
GTGGATTTTTGTATGTACCATATGAATAAGGATCGGCTAACTCCGTGCCAGCAGCCG
CGGTAATACGGAGGATCCGAGCGTTATCCGGATTTATTGGGTTTAAAGGGAGCGTA
GGTGGACAGTTAAGTCAGTTGTGAAAGTTTGCGGCTCAACCGTAAAATTGCAGTTG
ATACTGGCTGTCTTGAGTACAGTAGAGGGGGGGGAATTCGTGGTGTAGCGGTGAA
ATGCTTAGATATCACGAAGAACTCCGATTGCGAAGGCAGCTCACTGGACTGCAACT
GACACTGATGCTCGAAAGTGTGGGTATCAAACAGGATTAGATACCCTGGTAGTCCA
CACAGTAAACGATGAATACTCGCTGTTTGCGATATACAGTAAGCGGCCAAGCGAAA
GCATTAAGTATTCCACCTGGGGAGTACGCCGGCAACGGTGAAACTCAAAGGAATTG
ACGGGGGCCCGCACAAGCGGAGGAACATGTGGTTTAATTCGATGATACGCGAGGA
ACCTTACCCGGGCTTAAATTGCATTTGAATATATTGGAAACAGTATAGTCGTAAGAC
AAATGTGAAGGTGCTGCATGGTTGTCGTCAGCTCGTGCCGTGAGGTGTCGGCTTAA
GTGCCATAACGAGCGCAACCCTTATCTTTAGTTACTAACAGGTCATGCTGAGGACTC
TGGAGAGACTGCCGTCGTAAGATGTGAGGAAGGTGGGGATGACGTCAAATCAGCA
CGGCCCTTACGTCCGGGGCTACACACGTGTTACAATGGGGGGTACAGAAGGCCGC
TACCTGGTGACAGGATGCTAATCCCAAAAGCCTCTCTCAGTTCGGATCGAAGTCTG
CAACCCGACTTCGTGAAGCTGGATTCGCTAGTAATCGCGCATCAGCCATGGCGCGG
TGAATACGTTCCCGGGCCTTGTACACACCGCCCGTCAAGCCATGAAAGCCGGGGG
TACCTGAAGTACGTAACCGCAAGGAGCGTCCTAGGGTAAAACTGGTAATTGGGGCT
AAGTCGTAACAAGGTA SEQ ID NO: 76 *Alistipes shahii*
ACATAGGGGGWSTGWKAGGTTWRCCSCCCACATTSRTACTGAGMCA-
TGAWCMAACTCTMTACGGGARGSAGSAGTGAGGAATATTGGTCRRTGGACGCAAG
TCTGAACCAGCCATGCCGSGTGCRGGAAGACGGCTCKATGAGTKGKAAACTGCTTT
TGTACRARRGTAAACGCTCTTACGTGTAAGAGCCTGAAAGTATSGTACRAATGAGGA
TCGGCTAACTCCGTGCCAGCAGCCGCGGTAATACGGAGGATCCAAGCGTTATCCG
GATTTATTGGGTTTAAAGGGTGCGTAGGGGGGTTGATAAAGTTAGRGG SEQ ID NO: 77 *Anaerostipes caccae*
GCTT-ACACATG-
CAAGTCGAACGAAGCATTTARGATTGAAGTTTTCGGATGGATTTCCTATATGACTGA
GTGGCGGACGGGTGAGTAACGCGTGGGGAACCTGCCCTATACAGGGGGATAACAG
CTGGAAACGGCTGCTAATACCGCATAAGCGCACAGAATCGCATGATTCAGTGTGAA
AAGCCCTGGCAGTATAGGATGGTCCCGCGTCTGATTAGCTGGTTGGTGAGGTAACG
GCTCACCAAGGCGACGATCAGTAGCCGGCTTGAGAGAGTGAACGGCCACATTGGG
ACTGAGACACGGCCCAAACTCCTACGGGAGGCAGCAGTGGGGAATATTGCACAAT
GGGGG-
AAACCCTGATGCAGCGACGCCGCGTGAGTGAAGAAGTATTTCGGTATGTAAAGCTC -continued

| SEQUENCES |
| --- |
| TATCAGCAGGGAAGAAAACAGACGGTACCTGACTAAGAAGCCCCGGCTAACTACGT<br>GCCAGCAGCCGCGGTAATACGTAGGGGGCAAGCGTTATCCGGAATTACTGGGTGT<br>AAAGGGTGCGTAGGTGGCATGGTAAGTCAGAAGTGAAAGCCCGGGGCTTAACCCC<br>GGGACTGCTTTTGAAACTGTCATGCTGGAGTGCAGGAGAGGTAAGCGGAATTCCTA<br>GTGTAGCGGTGAAATGCGTAGATATTAGGAGGAACACCAGTGGCGAAGGCGGCTTA<br>CTGGACTGTCACTGACACTGATGCACGAAAGCGTGGGGAGCAAACAGGATTAGATA<br>CCCTGGTAGTCCACGCCGTAAACGATGAATACTAGGTGTCGGGGCCGTAGAGGCTT<br>CGGTGCCGCAGCAAA |
| SEQ ID NO: 78 *Phascolarctobacterium faecium*<br>CGGAGAATTTTCATTTCGGTAGAATTCTTAGTGGCGAACGGGTGAGTAACGCGTAG<br>GCAACCTGCCCTTTAGACGGGGACAACATTCCGAAAGGAGTGCTAATACCGGATGT<br>GATCATCGTGCCGCATGGCAGGATGAAGAAAGATGGCCTCTACAAGTAAGCTATCG<br>CTAAAGGATGGGCCTGCGTCTGATTAGCTAGTTGGTAGTGTAACGGACTACCAAGG<br>CGATGATCAGTAGCCGGTCTGAGAGGATGAACGGCCACATTGGGACTGAGACACG<br>GCCCAAACTCCTACGGGAGGCAGCAGTGGGGAATCTTCCGCAATGGACGAAAGTC<br>TGACAGAGCAACGCCGCGTGAGTGATGAAGGATTTCGGTCTGTAAAGCTCTGTTGT<br>TTATGACGAACGTGCAGTGTGTGAACAATGCATTGCAATGACGGTAGTAAACGAGG<br>AAGCCACGGCTAACTACGTGCCAGCAGCCGCGGTAATACGTAGGTGGCGAGCGTT<br>GTCCGGAATTATTGGGCGTAAAGAGCATGTAGGCGGCTTAATAAGTCGAGCGTGAA<br>AAATGCGGGGCTCAACCCCGTATGGCGCTGGAAACTGTTAGGCTTGAGTGCAGGA<br>GAGGAAAGGGGAATTCCCAGTGTAGCGGTGAAATGCGTAGATATTGGGAGGAACAC<br>CAGTGGCGAAGGCGCCTTTCTGGACTGTGTTTGACGCTGAGATGCGAAAGCCAGG<br>GTAGC |
| SEQ ID NO: 79 *Agathobaculum butyriciproducens*<br>TAGTGGGGGACGGGTGAGTAACGCGTGAGCAATCTGCCTTTAAGAGGGGGATAAC<br>AGTCGGAAACGGCTGCTAATACCGCATAAAGCATTGAATTCGCATGTTTTCGATGCC<br>AAAGGAGCAATCCGCTTTTAGATGAGCTCGCGTCTGATTAGCTAGTTGGGGGGTA<br>ACGGCCCACCAAGGCGACGATCAGTAGCCGGACTGAGAGGTTGAACGGCCACATT<br>GGGACTGAGACACGGCCCAGACTCCTACGGGAGGCAGCAGTGGGGAATATTGCGC<br>AATGGGGGRAACCCTGACGCAGCAACGCCGCGTGATTGAAGAAGGCCTTCGGGTT<br>GTAAAGATCTTTAATCAGGGACGAA--<br>AMATGACGGTACCTGAAGAATAAGCTCCGGCTAACTACGTGCCAGCAGCCGCGGTA<br>ATACGTAGGGAGCAAGCGTTATCCGGATTTACTGGGTGTAAAGGGCGCGCAGGCG<br>GGCCGGCAAGTTGGAAGTGAAATCCGGGGGCTTAACCCCCGAACTGCTTTCAAAAC<br>TGCTGGTCTTGAGTGATGGAGAGGCAGGCGGAATTCCGTGTGTAGCGGTGAAATG<br>CGTAGATATACGGAGGAACACCAGTGGCGAAGGCGGCCTGCTGGACATTAACTGA<br>CGCTGAGGCGCGAAAGCGTGGGGAGCAAACAGGATTAGATACCCTGGTAGTCCAC<br>GCCGTAAACGATGGATA |
| SEQ ID NO: 80 *Bacteroides fragilis*<br>ATGAAGAGTTTGATCCTGGCTCAGGATGAACGCTAGCTACAGGCTTAACACATGCA<br>AGTCGAGGGGCATCAGGAAGAAAGCTTGCTTTCTTTGCTGGCGACCGGCGCACGG<br>GTGAGTAACACGTATCCAACCTGCCCTTTACTCGGGGATAGCCTTTCGAAAGAAAG<br>ATTAATACCCGATGGCATAATGATTCCGCATGGTTTCATTATTAAAGGATTCCGGTA<br>AAGGATGGGGATGCGTTCCATTAGGTTGTTGGTGAGGTAACGGCTCACCAAGCCTT<br>CGATGGATAGGGGTTCTGAGAGGAAGGTCCCCCACATTGGAACTGAGACACGGTC<br>CAAACTCCTACGGGAGGCAGCAGTGAGGAATATTGGTCAATGGGCGCTAGCCTGAA<br>CCAGCCAAGTAGCGTGAAGGATGAAGGCTCTATGGGTCGTAAACTTCTTTTATATAA<br>GAATAAAGTGCAGTATGTATACTGTTTTGTATGTATTATATGAATAAGGATCGGCTAA<br>CTCCGTGCCAGCAGCCGCGGTAATACGGAGGATCCGAGCGTTATCCGGATTTATTG<br>GGTTTAAAGGGAGCGTAGGTGGACTGGTAAGTCAGTTGTGAAAGTTTGCGGCTCAA<br>CCGTAAAATTGCAGTTGATACTGTCAGTCTTGAGTACAGTAGAGGTGGGCGGAATT<br>CGTGGTGTAGCGGTGAAATGCTTAGATATCACGAAGAACTCCGATTGCGAAGGCAG<br>CTCACTGGACTGCAACTGACACTGATGCTCGAAAGTGTGGGTATCAAACAGGATTA<br>GATACCCTGGTAGTCCACACAGTAAACGATGAATACTCGCTGTTTGCGATATACAGT<br>AAGCGGCCAAGCGAAAGCATTAAGTATTCCACCTGGGGAGTACGCCGGCAACGGT<br>GAAACTCAAAGGAATTGACGGGGGCCCGCACAAGCGGAGGAACATGTGGTTTAATT<br>CGATGATACGCGAGGAACCTTACCCGGGCTTAAATTGCAGTGGAATGATGTGGAAA<br>CATGTCAGTGAGCAATCACCGCTGTGAAGGTGCTGCATGGTTGTCGTCAGCTCGTG<br>CCGTGAGGTGTCGGCTTAAGTGCCATAACGAGCGCAACCCTTATCTTTAGTTACTAA<br>CAGGTTATGCTGAGGACTCTAGAGAGACTGCCGTCGTAAGATGTGAGGAAGGTGG<br>GGATGACGTCAAATCAGCACGGCCCTTACGTCCGGGGCTACACACGTGTTACAATG<br>GGGGGTACAGAAGGCAGCTAGCGGGTGACCGTATGCTAATCCCAAAAGCCTCTCTC<br>AGTTCGGATCGAAGTCTGCAACCCGACTTCGTGAAGCTGGATTCGCTAGTAATCGC<br>GCATCAGCCACGGCGCGGTGAATACGTTCCCGGGCCTTGTACACACCGCCCGTCA<br>AGCCATGGGAGCCGGGGGTACCTGAAGTACGTAACCGCAAGGATCGTCCTAGGGT<br>AAAACTGGTGACTGGGGCTAAGTCGTAACAAGGTAGCCGTACCGGAAGGTGCGGC<br>TGGAACACCTCCTT |
| SEQ ID NO: 81 *Fusobacterium mortiferum*<br>TGGCTCAGGATGAACGCTGACAGAATGCTTAACACATGCAAGTCTACTTGATCCTTC<br>GGGTGATGGTGGCGGACGGGTGAGTAACGCGTAAAGAACTTGCCCTGCAGTCTGG<br>GACAACATTTGGAAACGAATGCTAATACCGGATATTATGT-<br>ATTTCTCGCATGAGTTTTACATGAAAGCTATATGCGCTGCAGGAGAGCTTTGCGTCC<br>TATTAGCTAGTTGGTGAGGTAACGGCTCACCAAGGCCATGATAGGTAGCCGGCCTG |

-continued

| SEQUENCES |
| --- |
| AGAGGGTGAACGGCCACAAGGGGACTGAGACACGGCCCTTACTCCTACGGGAGGC<br>AGCAGTGGGGAATATTGGACAATGGACCAAAAGTCTGATCCAGCAATTCTGTGTGC<br>ACGATGAAGTTTTTCGGAATGTAAAGTGCTTTCAGTTGGGACGAAGTAAGTGACGGT<br>ACCAACAGAAGAAGCGACGGCTAAATACGTGCCAGCAGCCGCGGTAATACGTATGT<br>CGCAAGCGTTATCCGGATTTATTGGGCGTAAAGCGCGTCTAGGCGGTTTGGTAAGT<br>CTGATGTGAAAATGCGGGGCTCAACTCCGTATTGCGTTGGAAACTGCTAAACTAGA<br>GTACTGGAGAGGTGGGGGGAACTACAAGTGTAGAGGTGAAATTCGTAGATATTTGT<br>AGGAATGCCGATGGGGAAGCCAGCCCACTGGACAGATACTGACGCTAAAGCGCGA<br>AAGCGTGGGTAGCAAACAGGATTAGATACCCTGGTAGTCCACGCCGTAAACGATGA<br>TTACTAGGTGTTGGGGGTCGAACCTCAGCGCCCAAGCTAACGCGATAAGTAATCCG<br>CCTGGGGAGTACGTACGCAAGTATGAAACTCAAAGGAATTGACGGGGACCCGCACA<br>AGCGGTGGAGCATGTGGTTTAATTCGACGCAACGCGAGGAACCTTACCAGCGTTTG<br>ACATCCTAAGAAATTAGCAGAGATGCTTTTGTGCCCCTTCGGGGGAACTTAGTGACA<br>GGTGGTGCATGGCTGTCGTCAGCTCGTGT |
| SEQ ID NO: 82 Paraclostridium benzoelyticum/ *Clostridium bifermantans*<br>AGAGTTTGATCCTGGCTCAGGATGAACGCTGGGGGCGTGCCTAACACATGCAAGTC<br>GAGCGATCTCTTCGGAGAGAGCGGCGGACGGGTGAGTAACGCGTGGGTAACCTGC<br>CCTGTACACACGGATAACATACCGAAAGGTATACTAATACGGGATAACATACGAAAG<br>TCGCATGGCTTTTGTATCAAAGCTCCGGGGGTACAGGATGGACCCGCGTCTGATTA<br>GCTAGTTGGTAAGGTAATGGCTTACCAAGGCAACGATCAGTAGCCGACCTGAGAGG<br>GTGATCGGCCACACTGGAACTGAGACACGGTCCAGACTCCTACGGGAGGCAGCAG<br>TGGGGAATATTGCACAATGGGCGAAAGCCTGATGCAGCAACGCCGCGTGAGCGAT<br>GAAGGCCTTCGGGTCGTAAAGCTCTGTCCTCAAGGAAGATAATGACGGTACTTGAG<br>GAGGAAGCCCCGGCTAACTACGTGCCAGCAGCCGCGGTAATACGTAGGGGGCTAG<br>CGTTATCCGGAATTACTGGGCGTAAAGGGTGCGTAGGTGGTTTTTTAAGTCAGAAG<br>TGAAAGGCTACGGCTCAACCGTAGTAAGCTTTTGAAACTAGAGAACTTGAGTGCAG<br>GAGAGGAGAGTAGAATTCCTAGTGTAGCGGTGAAATGCGTAGATATTAGGAGGAAT<br>ACCAGTAGCGAAGGCGGCTCTCTGGACTGTAACTGACACTGAGGCACGAAAGCGT<br>GGGGAGCAAACAGGATTAGATACCCTGGTAGTCCACGCCGTAAACGATGAGTACTA<br>GGTGTCGGGGGTTACCCCCCTCGGTGCCGCAGCTAACGCATTAAGTACTCCGCCT<br>GGGAAGTACGCTCGCAAGAGTGAAACTCAAAGGAATTGACGGGGACCCGCACAAG<br>TAGCGGAGCATGTGGTTTAATTCGAAGCAACGCGAAGAACCTTACCTAAGCTTGAC<br>ATCCCACTGACCTCTCCCTAATCGGAGATTTCCCTTCGGGGACAGTGGTGACAGGT<br>GGTGCATGGTTGTCGTCAGCTCGTGTCGTGAGATGTTGGGTTAAGTCCCGCAACGA<br>GCGCAACCCTTGCCTTTAGTTGCCAGCATTAAGTTGGGCACTCTAGAGGGACTGCC<br>GAGGATAACTCGGAGGAAGGTGGGGATGACGTCAAATCATCATGCCCCTTATGCTT<br>AGGGCTACACACGTGCTACAATGGGTGGTACAGAGGGTTGCCAAGCCGCGAGGTG<br>GAGCTAATCCCTTAAAGCCATTCTCAGTTCGGATTGTAGGCTGAAACTCGCCTACAT<br>GAAGCTGGAGTTACTAGTAATCGCAGATCAGAATGCTGCGGTGAATGCGTTCCCGG<br>GTCTTGTACACACCGCCCGTCACACCATGGAAGTTGGGGGCGCCCGAAGCCGGTT<br>AGCTAACCTTTTAGGAAGCGGCCGTCGAAGGTGAAACCAATGACTGGGGTGAAGTC<br>GTAACAAGGTAGCCGTATCGGAAGGTGCGGCTGGATCACCT |
| SEQ ID NO: 83 *Escherichia fergusonii* / *Escherichia coli*<br>TTGAAGAGTTTGATCATGGCTCAGATTGAACGCTGGCGGCAGGCCTAACACATGCA<br>AGTCGAACGGTAACAGGAAGCAGCTTGCTGCTTTGCTGACGAGTGGCGGACGGGT<br>GAGTAATGTCTGGGAAACTGCCTGATGGAGGGGGATAACTACTGGAAACGGTAGCT<br>AATACCGCATAACGTCGCAAGACCAAAGAGGGGGACCTTCGGGCCTCTTGCCATCG<br>GATGTGCCCAGATGGGATTAGCTAGTAGGTGGGGTAACGGCTCACCTAGGCGACG<br>ATCCCTAGCTGGTCTGAGAGGATGACCAGCCACACTGGAACTGAGACACGGTCCAG<br>ACTCCTACGGGAGGCAGCAGTGGGGAATATTGCACAATGGGCGCAAGCCTGATGC<br>AGCCATGCCGCGTGTATGAAGAAGGCCTTCGGGTTGTAAAGTACTTTCAGCGGGGA<br>GGAAGGGAGTAAAGTTAATACCTTTGCTCATTGACGTTACCCGCAGAAGAAGCACC<br>GGCTAACTCCGTGCCAGCAGCCGCGGTAATACGGAGGGTGCAAGCGTTAATCGGA<br>ATTACTGGGCGTAAAGCGCACGCAGGCGGTTTGTTAAGTCAGATGTGAAATCCCCG<br>GGCTCAACCTGGGAACTGCATCTGATACTGGCAAGCTTGAGTCTCGTAGAGGGGG<br>GTAGAATTCCAGGTGTAGCGGTGAAATGCGTAGAGATCTGGAGGAATACCGGTGGC<br>GAAGGCGGCCCCCTGGACGAAGACTGACGCTCAGGTGCGAAAGCGTGGGGAGCAA<br>ACAGGATTAGATACCCTGGTAGTCCACGCCGTAAACGATGTCGACTTGGAGGTTGT<br>GCCCTTGAGGCGTGGCTTCCGGAGCTAACGCGTTAAGTCGACCGCCTGGGGAGTA<br>CGGCCGCAAGGTTAAAACTCAAATGAATTGACGGGGGCCCGCACAAGCGGTGGAG<br>CATGTGGTTTAATTCGATGCAACGCGAAGAACCTTACCTGGTCTTGACATCCACGGA<br>AGTTTTCAGAGATGAGAATGTGCCTTCGGGAACCGTGAGACAGGTGCTGCATGGCT<br>GTCGTCAGCTCGTGTTGTGAAATGTTGGGTTAAGTCCCGCAACGAGCGCAACCCTT<br>ATCCTTTGTTGCCAGCGGTCCGGCCGGGAACTCAAAGGAGACTGCCAGTGATAAAC<br>TGGAGGAAGGTGGGGATGACGTCAAGTCATCATGGCCCTTACGACCAGGGCTACA<br>CACGTGCTACAATGGCGCATACAAAGAGAAGCGACCTCGCGAGAGCAAGCGGACC<br>TCATAAAGTGCGTCGTAGTCCGGATTGGAGTCTGCAACTCGACTCCATGAAGTCGG<br>AATCGCTAGTAATCGTGGATCAGAATGCCACGGTGAATACGTTCCCGGGCCTTGTA<br>CACACCGCCCGTCACACCATGGGAGTGGGTTGCAAAAGAAGTAGGTAGCTTAACCT<br>TCGGGAGGGCGCTTACCACTTTGTGATTCATGACTGGGGTGAAGTCGTAACAAGGT<br>AACCGTAGGGGAACCTGCGGTTGGATCACCTCCTT |

The invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Efficacy of Bacterial Compositions to Decolonize ESBL

As shown in FIG. 1, mice were treated with antibiotics (e.g., 0.5 g/L ampicillin) for 7 days prior to challenge with CRE or ESBL-producing *Enterobacteriaceae* challenge (*Escherichia coli* ATCC BAA-2777, "ESBL"). On day-3, mice were challenged with CRE or ESBL. On days 0.1, and 2, mice were administered treatment (e.g., PBS (control), a 36-mix live biotherapeutic product (36-mix), or stool fraction library from a human donor (Donor 1 SFL)). Fecal samples (pellets) were collected at various time points post-treatment to quantify colony forming units (CFU) as measure of ESBL colonization levels. The efficacy of a treatment in reducing CRE or ESBL colonization was assessed.

Figure 2:
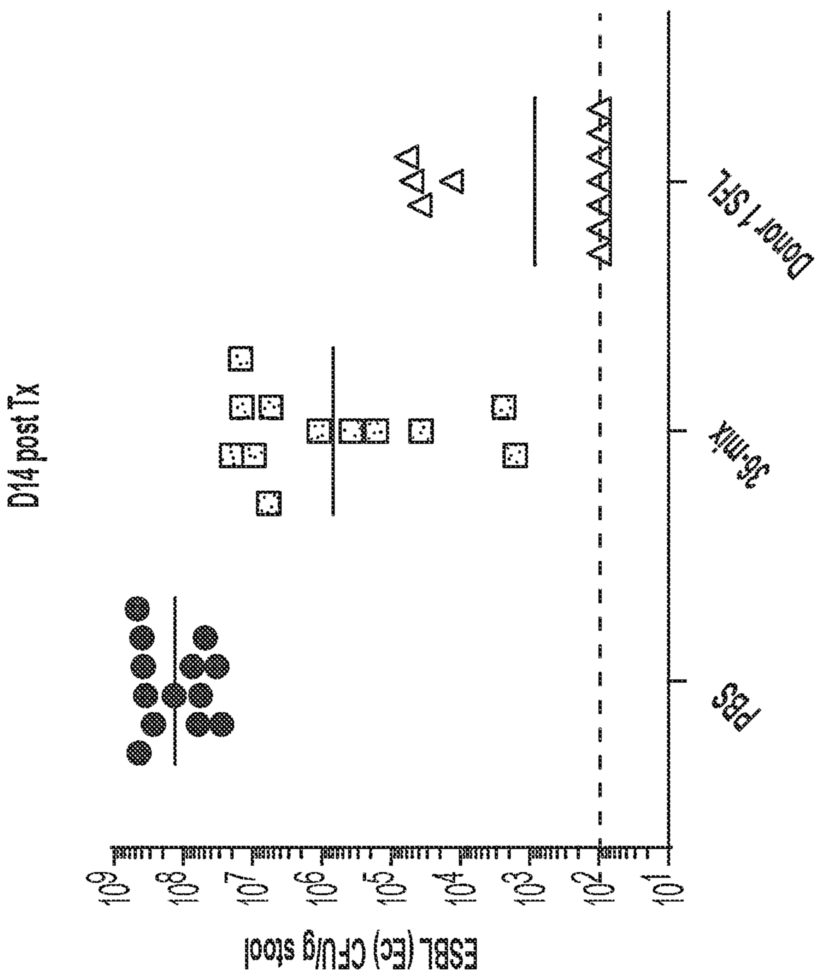
FIG. 2 shows extended spectrum beta-lactamase (ESBL) producing Enterobacteriaceae colonization (colony forming units, "CFU") levels in mice at 14 days post-treatment ("D14 post Tx"). From left to right, control (PBS), a composition of 36 bacterial strains ("36-mix"), or stool fraction from a human donor (Donor 1 "SFL"). Dashed line represents the limit of detection.

As shown in FIG. 2, the 36-mix and SFL derived from Donor 1 were capable of reducing ESBL colonization levels, however the SFL derived from Donor 1 reduce ESBL colonization to lower levels. Several of the mice treated with the 35-mix exhibited a greater reduction in ESBL colonization. Stools from the mice treated with the 36-mix and having the lowest levels of ESBL colonization were subjected to metagenomic sequencing, which identified several mouse-derived taxa that were present in these mice compared to mice that received the 36-mix and higher levels of ESBL colonization.

Additional bacterial strains were evaluated for combination with strains of the 36-mix. A bacterial mixture comprising the strains present in the 36-mix and 11 additional strains, for a total of 47 bacterial strains (47-mix), was prepared. See, FIG. 3 and Table 1.

Example 2: Efficacy of Bacterial Compositions Comprising 47 Bacterial Strains to Decolonize CRE and ESBL Mice were treated with antibiotics (e.g., 0.5 g/L ampicillin) for 7 days prior to challenge with carbapenem-resistant *Klebsiella pneumoniae* challenge (*Klebsiella pneuomoniae* ATCC BAA-2814, "CRE") or ESBL-producing *Enterobacteriaceae* challenge (*Escherichia coli* ATCC BAA-2777, "ESBL") (FIG. 1). On day-3, mice were challenged with CRE or ESBL. On days 0, 1, and 2, mice were administered treatment (e.g., PBS (control), or the 47-mix live biotherapeutic product (47-mix). Fecal samples (pellets) were collected at various time points post-treatment to quantify colony forming units (CFU) as measure of CRE or ESBL colonization levels.

Colonization levels of CRE and ESBL in mice are shown in FIG. 4. Administration of the 47-mix bacterial composition resulted in a reduction of both CRE and ESBL by at least 3-logs as compared to mice that received the control (PBS).

Example 3: Efficacy of Bacterial Compositions Comprising 47 Bacterial Strains to Decolonize ESBL or CRE Mice were treated with antibiotics (e.g., 0.5 g/L ampicillin) for 7 days prior to challenge with carbapenem-resistant *Klebsiella pneumoniae* challenge (*Klebsiella pneuomoniae* ATCC BAA-2814, "CRE") or ESBL-producing *Enterobacteriaceae* challenge (*Escherichia coli* ATCC BAA-2777, "ESBL") (FIG. 1). On day-3, mice were challenged with CRE or ESBL. On days 0, 1, and 2, mice were administered treatment (e.g., PBS (control), the 47-mix live biotherapeutic product (47-mix), stool fraction library derived by culturing stool from a second human donor (Donor 2 SFL), or a bacterial mixture obtained by introducing fecal matter from a first human donor (Donor 1) into a mouse and obtaining stool from the mouse to prepare a fecal matter transplant (Donor 1-inoculated mouse FMT).

Figure 5A:
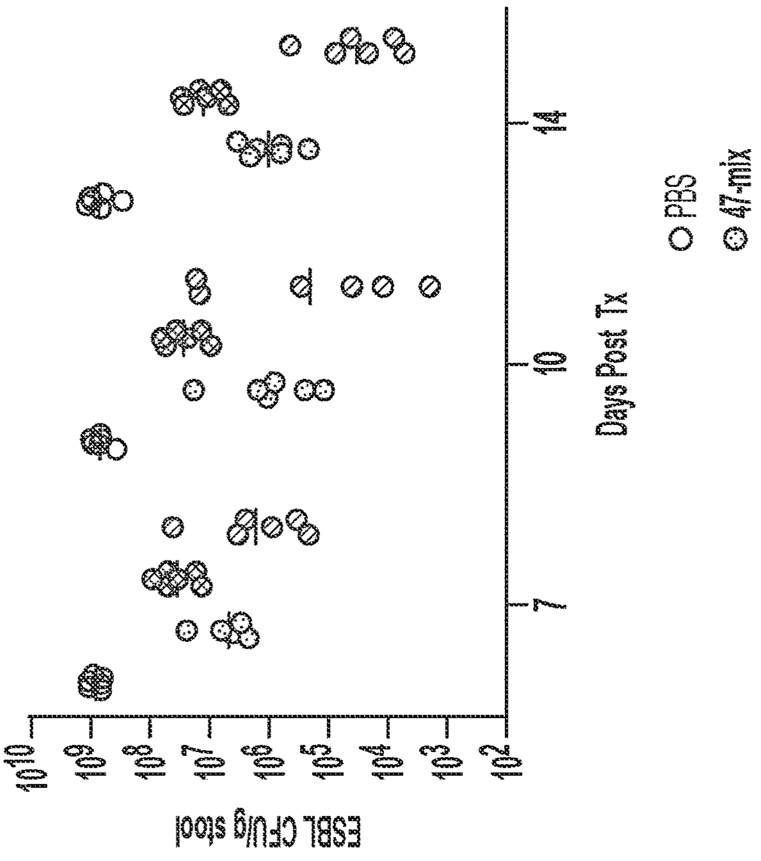
FIGS. 5A and 5B show ESBL-producing Enterobacteriaceae and carbapenem-resistant *Klebsiella pneumoniae* (CRE) colonization in mice treated with the indicated compositions.
Figure 5B:
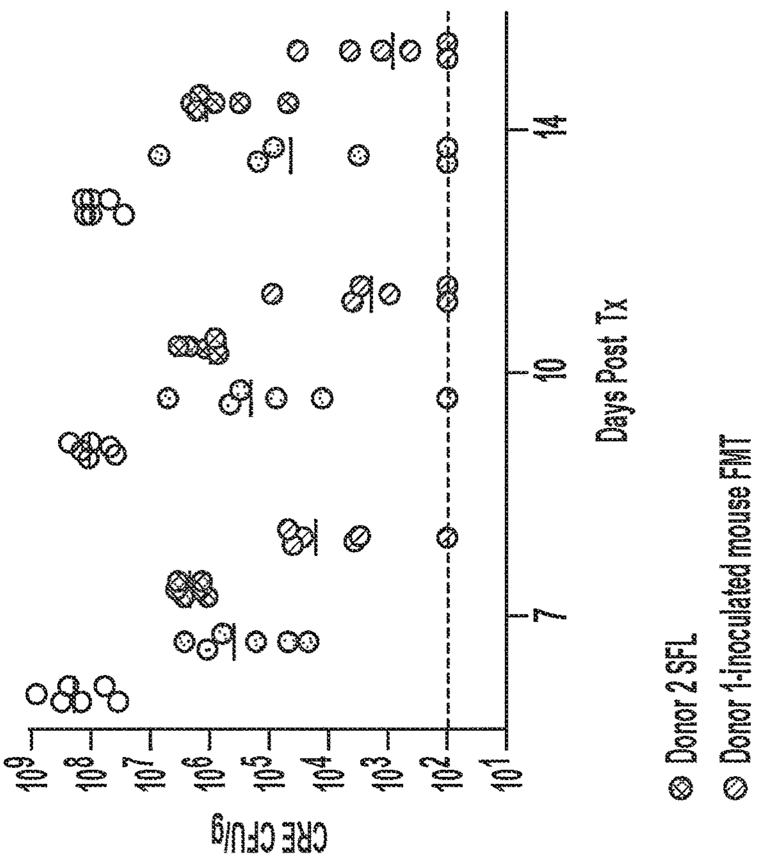

Fecal samples (pellets) were collected at various time points post-treatment to quantify colony forming units (CFU) as measure of CRE or ESBL colonization levels. Colonization levels of ESBL and CRE in mice are shown in FIGS. 5A and 5B, respectively.

Administration of the 47-mix bacterial composition resulted in a reduction in both ESBL and CRE colonization by at least 2-logs by day 7. Colonization of both ESBL and CRE were further reduced at both 10 days and 14 days post treatment.

Example 4: Efficacy of Bacterial Compositions Comprising Bacterial Strains and Taurine to Decolonize ESBL or CRE Mice are treated with antibiotics (e.g., 0.5 g/L ampicillin) for 7 days prior to challenge with carbapenem-resistant *Klebsiella pneumoniae* challenge (*Klebsiella pneuomoniae*

ATCC BAA-2814, "CRE") or ESBL-producing *Enterobacteriaceae* challenge (*Escherichia coli* ATCC BAA-2777, "ESBL"). On day-3, mice are challenged with CRE or ESBL. Mice are administered the following treatment conditions:

- PBS (control),
- PBS+taurine (taurine only),
- live biotherapeutic product (any of the compositions described herein), and
- live biotherapeutic product+taurine (any of the compositions described herein+taurine).

Taurine may be administered in the same composition with the live biotherapeutic product or in a separate composition, which may be administered prior to, at the same time, or after administration of the live biotherapeutic product.

Fecal samples (pellets) are collected at various time points post-treatment to quantify colony forming units (CFU) as measure of CRE or ESBL colonization levels.

What is claimed is:

1. A composition comprising (i)-(xv):

(i) an isolated bacterial strain belonging to the species *Collinsella aerofaciens;*

(ii) an isolated bacterial strain belonging to the species *Bifidobacterium longum;*

(iii) an isolated bacterial strain belonging to the species *Bacteroides ovatus;*

(iv) an isolated bacterial strain belonging to the species *Bacteroides_B vulgatus;*

(v) an isolated bacterial strain belonging to the species *Alistipes putredinis;*

(vi) an isolated bacterial strain belonging to the species *Clostridium_M citroniae;*

(vii) an isolated bacterial strain belonging to the species *Clostridium_M clostridioforme;*

(viii) an isolated bacterial strain belonging to the species *Clostridium ramosum;*

(ix) an isolated bacterial strain belonging to the species *Absiella innocuum;*

(x) an isolated bacterial strain belonging to the species *Blautia_A obeum;*

(xi) an isolated bacterial strain belonging to the species *Blautia coccoides;*

(xii) an isolated bacterial strain belonging to the species *Dorea longicatena_B;*

(xiii) an isolated bacterial strain belonging to the species *Phascolarctobacterium faecium;*

(xiv) an isolated bacterial strain belonging to the species *Escherichia coli*; and (XV) an isolated bacterial strain belonging to the species genus *Fusobacterium_A;* wherein the composition further comprises one or more of (1)-(11):

(1) an isolated bacterial strain belonging to the species *Barnesiella intestinihominis;*

(2) an isolated bacterial strain belonging to the species *Blautia luti;*

(3) an isolated bacterial strain belonging to the species *Blautia faecis;*

(4) an isolated bacterial strain belonging to the species *Blautia wexlerae;*

(5) an isolated bacterial strain belonging to the species *Ruminococcus faecis;*

(6) an isolated bacterial strain belonging to the species *Clostridium bolteae;*

(7) an isolated bacterial strain belonging to the species *Butyricimonas synergistica;*

(8) an isolated bacterial strain belonging to the species *Bilophila wadsworthia;*

(9) an isolated bacterial strain belonging to the species *Akkermansia muciniphila;*

(10) an isolated bacterial strain belonging to the species *Parasuterella excrementinihominis*; and

(11) an isolated bacterial strain belonging to the species *Prevotella copri.*

2. The composition of claim 1, wherein the composition comprises 6 or more of the isolated bacterial strains of (1)-(11).

3. The composition of claim 2, wherein the composition inhibits replication or survival of a pathogenic organism belonging the species *Escherichia coli.*

4. The composition of claim 3, wherein the pathogenic organism is *Escherichia coli* strain ATCC BAA-2777.

5. The composition of claim 4, wherein the composition inhibits replication or survival of a pathogenic organism belonging to the species *Klebsiella pneumoniae.*

6. The composition of claim 1, comprising at least 47 isolated bacterial strains, each of the at least 47 isolated bacterial strains belonging to a different species of *Collinsella aerofaciens, Bifidobacterium longum, Bifidobacterium pseudocatenulatum, Bifidobacterium adolescentis, Bacteroides caccae, Bacteroides xylanisolvens, Bacteroides cellulosilyticus, Bacteroides uniformis, Bacteroides_B vulgatus, Bacteroides fragilis, Bacteroides thetaiotaomicron, Bacteroides faecis, Bacteroides ovatus, Odoribacter splanchnicus, Parabacteroides distasonis, Parabacteroides merdae, Alistipes putredinis, Alistipes shahii, Paraclostridium massiliensis, Paeniclostridium sordellii, Absiella innocuum, Absiella innocuum, Clostridium ramosum, Clostridium_M citroniae, Clostridium_M clostridioforme, Eubacterium_E hallii, Agathobacter rectale, Blautia coccoides, Blautia_A obeum, Dorea longicatena_B, Coprococcus_B comes, Anaerostipes caccae, Agathobaculum* sp., *Phascolarctobacterium faecium, Escherichia coli*, a species in the genus *Fusobacterium_A, Barnesiella intestinihominis, Blautia luti, Blautia faecis, Blautia wexlerae, Ruminococcus faecis, Clostridium bolteae, Butyricimonas synergistica, Bilophila*

*wadsworthia, Akkermansia muciniphila, Parasuterella excrementinihominis*, and *Prevotella copri*.

7. The composition of claim 1, wherein the bacterial strains are lyophilized.

8. The composition of claim 1, wherein the composition comprises a pH-sensitive enteric coating with a pH of decomposition between about 6.8 and about 7.5.

9. The composition of claim 1, wherein the composition is in the form of a capsule.

* * * * *